United States Patent
Zhang et al.

(10) Patent No.: US 9,902,712 B2
(45) Date of Patent: Feb. 27, 2018

(54) NITROGENOUS HETEROCYCLIC DERIVATIVES AND THEIR APPLICATION IN DRUGS

(71) Applicant: Sunshine Lake Pharma Co., Ltd., Dongguan, Guangdong (CN)

(72) Inventors: Jiancun Zhang, Dongguan (CN); Xiaojun Wang, Dongguan (CN); Yingjun Zhang, Dongguan (CN); Runfeng Lin, Dongguan (CN); Yi Yu, Dongguan (CN); Liang Chen, Dongguan (CN); Jihua Lin, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/034,546

(22) PCT Filed: Dec. 19, 2014

(86) PCT No.: PCT/CN2014/094424
§ 371 (c)(1),
(2) Date: May 4, 2016

(87) PCT Pub. No.: WO2015/090232
PCT Pub. Date: Jun. 25, 2015

(65) Prior Publication Data
US 2016/0355501 A1    Dec. 8, 2016

(30) Foreign Application Priority Data

Dec. 19, 2013 (CN) .......................... 2013 1 0713840
Mar. 21, 2014 (CN) .......................... 2014 1 0109513

(51) Int. Cl.
| | | |
|---|---|---|
| *C07D 401/10* | (2006.01) | |
| *C07D 405/14* | (2006.01) | |
| *C07D 413/14* | (2006.01) | |
| *C07D 409/14* | (2006.01) | |
| *C07D 417/14* | (2006.01) | |
| *C07D 401/14* | (2006.01) | |

(52) U.S. Cl.
CPC ......... *C07D 401/10* (2013.01); *C07D 401/14* (2013.01); *C07D 405/14* (2013.01); *C07D 409/14* (2013.01); *C07D 413/14* (2013.01); *C07D 417/14* (2013.01)

(58) Field of Classification Search
CPC   C07D 401/10; C07D 405/114; C07D 413/14; C07D 417/14
USPC ....................................................... 514/269
See application file for complete search history.

(56) References Cited

U.S. PATENT DOCUMENTS

| | | |
|---|---|---|
| 3,185,689 A | 5/1965 | Ruschig |
| 4,411,691 A | 10/1983 | Rohr et al. |
| 4,523,946 A | 6/1985 | Parg et al. |
| 4,990,512 A | 2/1991 | Perrior et al. |
| 5,079,251 A | 1/1992 | Fitzjohn |
| 5,104,878 A | 4/1992 | Whittle et al. |
| 5,149,810 A | 9/1992 | Perrior et al. |
| 5,470,975 A | 11/1995 | Atwal |
| 5,518,994 A | 5/1996 | Kawamura et al. |
| 5,532,208 A | 7/1996 | Nagano et al. |
| 5,869,476 A | 2/1999 | Paik et al. |
| 5,877,121 A | 3/1999 | Andree et al. |
| 6,369,067 B1 | 4/2002 | Gurram et al. |
| 6,649,604 B2 | 11/2003 | Spohr et al. |
| 7,012,041 B2 | 3/2006 | Linker et al. |
| 7,166,595 B2 | 1/2007 | Zhou et al. |
| 7,732,456 B2 | 6/2010 | Otake et al. |
| 7,790,734 B2 | 9/2010 | Cao et al. |
| 7,790,736 B2 | 9/2010 | Feng et al. |
| 7,795,271 B2 | 9/2010 | Durley |
| 7,998,968 B2 | 8/2011 | Kuroita et al. |

(Continued)

FOREIGN PATENT DOCUMENTS

| | | |
|---|---|---|
| CN | 1386737 A | 12/2002 |
| DE | 4343528 A1 | 6/1995 |

(Continued)

OTHER PUBLICATIONS

William Gattrell et al , 2012, An example of designed multiple ligands spanning protein classes, Dual MCH-!R antagonist/DPPIV inhibitors.*

Eng_Abstract.

ISR of PCT/CN2014/094424.

Written Opinion of PCT/CN2014/094424.

*Primary Examiner* — Rita J Desai
(74) *Attorney, Agent, or Firm* — Kam W. Law; Squire Patton Boggs (US) LLP

(57) ABSTRACT

The present invention relates to the field of medicine, provided herein are novel nitrogenous heterocyclic compounds, their preparation methods and their uses as drugs, especially for treatment and prevention of tissue fibrosis. Also provided herein are pharmaceutically acceptable compositions comprising the nitrogenous heterocyclic compounds and the uses of the compositions in the treatment of human or animal tissue fibrosis, especially for human or animal renal interstitial fibrosis, glomerular sclerosis, liver fibrosis, pulmonary fibrosis, IPF, peritoneal fibrosis, myocardial fibrosis, dermatofibrosis, postsurgical adhesion, benign prostatic hyperplasia, skeletal muscle fibrosis, scleroderma, multiple sclerosis, pancreatic fibrosis, cirrhosis, myosarcoma, neurofibroma, pulmonary interstitial fibrosis, diabetic nephropathy, alzheimer disease or vascular fibrosis.

16 Claims, No Drawings

(56) References Cited

U.S. PATENT DOCUMENTS

| | | |
|---|---|---|
| 8,198,276 B2 | 6/2012 | Liang |
| 8,232,408 B2 | 7/2012 | Chen et al. |
| 8,324,230 B2 | 12/2012 | Selbo |
| 8,377,932 B2 | 2/2013 | Hu et al. |
| 8,426,407 B2 | 4/2013 | Hu et al. |
| 2005/0256122 A1 | 11/2005 | Hepperle et al. |
| 2007/0129379 A1 | 6/2007 | Naidu et al. |
| 2007/0270446 A1 | 11/2007 | Marquis, Jr. et al. |
| 2009/0137557 A1 | 5/2009 | Ku |
| 2009/0258911 A1 | 10/2009 | Tao |
| 2010/0056526 A1 | 3/2010 | Kuroita et al. |
| 2010/0190731 A1 | 7/2010 | Olgin |
| 2011/0218515 A1 | 9/2011 | Olgin |
| 2012/0010185 A1 | 1/2012 | Stenkamp et al. |
| 2012/0088795 A1 | 4/2012 | Song et al. |
| 2013/0143906 A1 | 6/2013 | Selness et al. |
| 2013/0158053 A1 | 6/2013 | Selbo |
| 2013/0196002 A1 | 8/2013 | Wolkenberg |
| 2013/0303551 A1 | 11/2013 | Adams |
| 2014/0235637 A1 | 8/2014 | Kossen et al. |

FOREIGN PATENT DOCUMENTS

| | | |
|---|---|---|
| EP | 0481604 A1 | 9/1991 |
| EP | 0481448 A1 | 10/1991 |
| WO | 9511235 A1 | 4/1995 |
| WO | 9608151 A1 | 3/1996 |
| WO | 9824782 A2 | 6/1998 |
| WO | 2007141200 A1 | 12/2007 |
| WO | 2007142217 A1 | 12/2007 |
| WO | 2008156607 A1 | 12/2008 |
| WO | 2010142143 A1 | 12/2010 |
| WO | 2012011592 A1 | 1/2012 |
| WO | 2012011707 A2 | 1/2012 |
| WO | 2014012360 A1 | 1/2014 |

* cited by examiner

NITROGENOUS HETEROCYCLIC DERIVATIVES AND THEIR APPLICATION IN DRUGS

CROSS-REFERENCE TO RELATED APPLICATIONS

This is a U.S. national stage application of the International Patent Application No. PCT/CN2014/094424, filed 19 Dec. 2014, which claims priorities to Chinese Patent Application No. 201310713840.8, filed 19 Dec. 2013, and No. 201410109513.6, filed 21 Mar. 2014, all of which are incorporated herein by reference in their entirety.

FIELD

The present invention relates to the field of medicine. Provided herein are novel nitrogenous heterocyclic compounds, their combinations, their methods of preparation and their uses as drugs, especially for treatment and prevention of tissue fibrosis.

BACKGROUND

Slight fibrosis of organ or tissue be called fibrosis, severe fibrosis can cause damage of tissues leading to organ scarring. Tissue fibrosis is not only in lung and liver, but in all the organs and systems of the human body. A variety of factors (such as inflammation, immune response, poison, ischemia and changes of hemodynamics, and so on) cause parenchymal cellular damage. This leads to parenchymal cells inflammation, deformation, necrosis, and activates the corresponding macrophages to release cytokines and growth factors which in turn activate the resting extracellular matrix (ECM) to produce cells, and then transform the cells into myofibroblasts. Myofibroblasts proliferate and secrete cytokines which act on macrophages through paracrine. Myofibroblasts can synthesize a lot of collagen of ECM. ECM degradation is decreased at the same time causing organ and tissue fibrosis. Therefore, the occurrence and development of organ and tissue fibrosis is a result of the interactions between multiple factors, such as cell, cytokine and ECM. Cell produced by ECM is important for the formation of organ or tissue fibrosis. Therefore, one of the drug targets for treating organ and tissue fibrosis is the cell produced by ECM. Therapeutic goal can be achieved by inhibiting the cell proliferation, activation and inducing the cell apoptosis.

It is because each organ or tissue has different functions, morphologies and different main component cells, different organ or tissue fibrosis have commonness and individuality in the pathogenesises. Cells can be produced by ECM, while hepatic stellate cells are produced in liver, glomerular mesangial cells are produced in glomerulus, renal interstitial fibroblasts are produced in renal interstitium, lung fibroblasts are produced in lung, cardiac fibroblasts are produced in heart and peritoneal mesothelial cells are produced in peritoneal. Therefore, there are some differences in the pathogenesises and therapeutic targets of different organs or tissues fibrosis.

An anti-fibrotic drug named pirfenidone (PFD, 5-methyl-1-phenyl-2-(1H)-pyridone) was disclosed in patent EP1138329A. Experiments show that PFD could prevent ECM gathering, or even reverse it in animal experiments of renal fibrosis, pulmonary fibrosis, and in clinical trials of patients with specific lung fibrosis.

SUMMARY

Provided herein are novel compounds or pharmaceutical compositions that may be more effective to prevent or treat human or animal tissue fibrosis. The compounds of the present invention compared with pirfenidone does not exist pyridone structure, does not occur double aggregation by pyridone, and does not exist risk of phototoxicity.

In one aspect, provided herein are compounds having Formula (I) as shown below, or a stereoisomer, a geometric isomer, a tautomer, an N-oxide, a hydrate, a solvate, a metabolite, a pharmaceutically acceptable salt or a prodrug thereof,

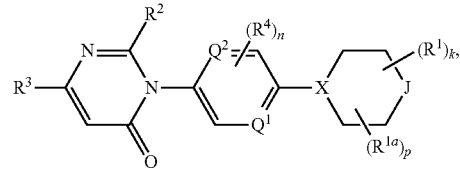

wherein, each of $Q^1$ and $Q^2$ is independently N or CH;
X is N or CH;
J is —O—, —C(=S)—, —(CH$_2$)$_m$—O—, —C(=O)—, —C(=O)O—, —S(=O)$_t$—, —(CH$_2$)$_m$—N(R$^6$)—, —N(R$^6$)—, —S(=O)$_t$N(R$^6$)—, —CH=CH—, —N(R$^6$)C(=O)— or —(CH$_2$)$_m$—;
each $R^1$ is independently —Y—R$^5$, wherein each Y is independently —O—, —C(=S)—, —(CH$_2$)$_m$—O—, —C(=O)—, —C(=O)O—, —S(=O)$_t$—, —(CH$_2$)$_m$—N(R$^6$)—, —N(R$^6$)—, —S(=O)$_t$N(R$^6$)—, —CH=CH—, —N(R$^6$)C(=O)— or —(CH$_2$)$_m$—;
each $R^{1a}$ is independently H, F, Cl, Br, I, cyano, hydroxy, amino, carboxy, alkyl, haloalkyl, alkoxy, alkylamino, alkylthio, alkenyl, alkynyl, nitro, mercapto, hydroxyalkoxy, hydroxyalkyl, aminoalkoxy, alkyl-O—C(=O)—, aryl, arylalkyl, heteroaryl, heteroarylalkyl, heterocyclyl, heterocyclylalkyl, cycloalkyl, aryloxy, heteroaryloxy, haloalkoxy or cycloalkylalkyl;
each of $R^2$ and $R^3$ is independently H, F, Cl, Br, I, cyano, hydroxy, carboxy, alkyl, haloalkyl, alkoxy, hydroxyalkoxy, hydroxyalkyl, aminoalkoxy, haloalkoxy, aryl, arylalkyl, heteroaryl, heteroarylalkyl, heterocyclyl, heterocyclylalkyl, cycloalkyl or cycloalkylalkyl;
each $R^4$ is independently H, hydroxy, carboxy, amino, F, Cl, Br, I, cyano, nitro, mercapto, alkyl, haloalkyl, alkoxy, alkylamino, alkylthio, aryl, arylalkyl, heteroaryl, heteroarylalkyl, heterocyclyl, heterocyclylalkyl, cycloalkyl or cycloalkylalkyl;
each $R^5$ is independently bridged heterobicyclyl, bridged bicyclyl, fused bicyclyl, fused heterobicyclyl, aryl, arylalkyl, heteroaryl, heteroarylalkyl, heterocyclyl, heterocyclylalkyl, cycloalkyl or cycloalkylalkyl;
each $R^6$ is independently H, hydroxy, amino, alkyl, haloalkyl, alkoxy, alkylamino, alkylthio, aryl, arylalkyl or heteroaryl;
each t is independently 0, 1 or 2;
each m is independently 1, 2, 3 or 4;
each of n and p is independently 0, 1, 2, 3 or 4; and
k is 1, 2, 3 or 4;
wherein each of —(CH$_2$)$_m$—O—, —(CH$_2$)$_m$—N(R$^6$)—, —N(R$^6$)—, —S(=O)$_t$N(R$^6$)—, —CH=CH—, —N(R$^6$)C(=O)—, —(CH$_2$)$_m$—, alkyl, alkenyl, alkynyl, haloalkyl, alkoxy, hydroxyalkoxy, hydroxyalkyl, aminoalkoxy, alkyl- O—C(=O)—, aryl, aryloxy, heteroaryloxy, haloalkoxy, arylalkyl, heteroaryl, heteroarylalkyl, heterocyclyl, heterocyclylalkyl, cycloalkyl, cycloalkylalkyl, bridged heterobicyclyl, bridged bicyclyl, fused bicyclyl, fused heterobicyclyl, alkylamino and alkylthio is independently and optionally substituted with one or more substituents independently selected from H, oxo (=O), F, Cl, Br, I, alkyl —O—C(=O)—, alkyl, alkenyl, alkynyl, alkoxy, haloalkyl, cyano, nitro, amino, alkylamino, mercapto, alkylthio, aryl, aryloxy, heteroaryl, heteroaryloxy and haloalkoxy.

In some embodiments, each $R^5$ is independently $C_{5-12}$ bridged heterobicyclyl, $C_{5-12}$ bridged bicyclyl, $C_{5-12}$ fused bicyclyl, $C_{5-12}$ fused heterobicyclyl, $C_{6-10}$ aryl, $C_{6-10}$ aryl-$C_{1-4}$-alkyl, $C_{1-9}$ heteroaryl, $C_1$-9 heteroarylaryl-$C_{1-4}$-alkyl, $C_{2-10}$ heterocyclyl, $C_{2-10}$ heterocyclyl-$C_{1-4}$-alkyl, $C_{3-10}$ cycloalkyl or $C_{3-10}$ cycloalkyl-$C_{1-4}$-alkyl; and each $R^6$ is independently H, hydroxy, amino, $C_{1-4}$ alkyl, $C_{1-4}$ haloalkyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl or $C_{1-9}$ heteroaryl;

wherein each of —$(CH_2)_m$—O—, —$(CH_2)_m$—N($R^6$)—, —N($R^6$)—, —S(=O)$_t$N($R^6$)—, —CH=CH—, —N($R^6$)C(=O)—, —$(CH_2)_m$—, $C_{1-4}$ alkyl, $C_{1-4}$ haloalkyl, $C_{1-4}$ alkoxy, $C_{5-12}$ bridged heterobicyclyl, $C_{5-12}$ bridged bicyclyl, $C_{5-12}$ fused bicyclyl, $C_{5-12}$ fused heterobicyclyl, $C_{6-10}$ aryl, $C_{6-10}$ aryl-$C_{1-4}$-alkyl, $C_{1-9}$ heteroaryl, $C_{1-9}$ heteroaryl-$C_{1-4}$-alkyl, $C_{2-10}$ heterocyclyl, $C_{2-10}$ heterocyclyl-$C_{1-4}$-alkyl, $C_{3-10}$ cycloalkyl, $C_{3-10}$ cycloalkyl-$C_{1-4}$-alkyl, $C_{1-4}$ alkylamino and $C_{1-4}$ alkylthio is independently and optionally substituted with one or more substituents independently selected from H, oxo (=O), F, Cl, Br, I, $C_{1-4}$ alkyl-O—C(=O)—, $C_{1-4}$ alkyl, $C_{2-4}$ alkenyl, $C_{2-4}$ alkynyl, $C_{1-4}$ alkoxy, $C_{1-4}$ haloalkyl, cyano, nitro, amino, $C_{1-4}$ alkylamino, mercapto, $C_{1-4}$ alkylthio, $C_{6-10}$ aryl, $C_{6-10}$ aryloxy, $C_{1-9}$ heteroaryl, $C_{1-9}$ heteroaryloxy and $C_{1-4}$ haloalkoxy.

In other embodiments, each $R^{1a}$ is independently H, F, Cl, Br, I, cyano, hydroxy, amino, carboxy, $C_{1-4}$ alkyl, $C_{1-4}$ haloalkyl, $C_{1-4}$ alkoxy, $C_{1-4}$ alkylamino, $C_{1-4}$ alkylthio, $C_{2-4}$ alkenyl, $C_{2-4}$ alkynyl, nitro, mercapto, $C_{1-4}$ hydroxyalkoxy, $C_{1-4}$ hydroxyalkyl, $C_{1-4}$ aminoalkoxy, $C_{1-4}$ alkyl-O—C(=O)—, $C_{6-10}$ aryl, $C_{6-10}$ aryl-$C_{1-4}$-alkyl, $C_{1-9}$ heteroaryl, $C_{1-9}$ heteroaryl-$C_{1-4}$-alkyl, $C_{2-10}$ heterocyclyl, $C_{2-10}$ heterocyclyl-$C_{1-4}$-alkyl, $C_{3-10}$ cycloalkyl, $C_{6-10}$ aryloxy, $C_{1-9}$ heteroaryloxy, $C_{1-4}$ haloalkoxy or $C_{3-10}$ cycloalkyl-$C_{1-4}$-alkyl;

each of $R^2$ and $R^3$ is independently H, F, Cl, Br, I, cyano, carboxy, hydroxy, $C_{1-6}$ alkyl, $C_{1-6}$ haloalkyl, $C_{1-6}$ alkoxy, $C_{1-6}$ hydroxyalkoxy, $C_{1-6}$ hydroxyalkyl, $C_{1-6}$ aminoalkoxy, $C_{1-6}$ haloalkoxy, $C_{6-10}$ aryl, $C_{6-10}$ aryl-$C_{1-6}$-alkyl, $C_{1-9}$ heteroaryl, $C_{1-9}$ heteroaryl-$C_{1-6}$-alkyl, $C_{2-10}$ heterocyclyl, $C_{2-10}$ heterocyclyl-$C_{1-6}$-alkyl, $C_{3-10}$ cycloalkyl or $C_{3-10}$ cycloalkyl-$C_{1-6}$-alkyl; and each $R^4$ is independently H, hydroxy, carboxyl, amino, F, Cl, Br, I, cyano, nitro, mercapto, $C_{1-4}$ alkyl, $C_{1-6}$ haloalkyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl, $C_{1-9}$ heteroaryl, $C_{1-9}$ heteroaryl-$C_{1-6}$-alkyl, $C_{2-10}$ heterocyclyl, $C_{2-10}$ heterocyclyl-$C_{1-6}$-alkyl, $C_{3-10}$ cycloalkyl or $C_{3-10}$ cycloalkyl-$C_{1-6}$-alkyl.

In some embodiments, provided herein are compounds having Formula (II), or a stereoisomer, a geometric isomer, a tautomer, an N-oxide, a hydrate, a solvate, a metabolite, a pharmaceutically acceptable salt or a prodrug thereof,

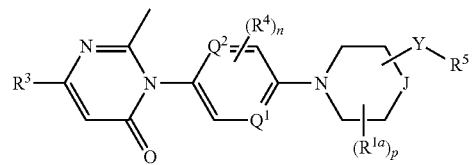

(II)

wherein, each of $Q^1$ and $Q^2$ is independently N or CH;

J is —O— or —$(CH_2)_m$—; and

Y is —O—, —$(CH_2)_m$—O—, —$(CH_2)_m$—N($R^6$)—, —N($R^6$)— or —$(CH_2)_m$—;

wherein, each $R^5$, $R^3$, $R^4$, n, m, $R^6$, $R^{1a}$ and p is as defined herein.

In other embodiments, each Y is independently —O—, —$(CH_2)_m$—O—, —$(CH_2)_m$—N($R^6$)—, —N($R^6$)— or —$(CH_2)_m$—;

each $R^5$ is independently

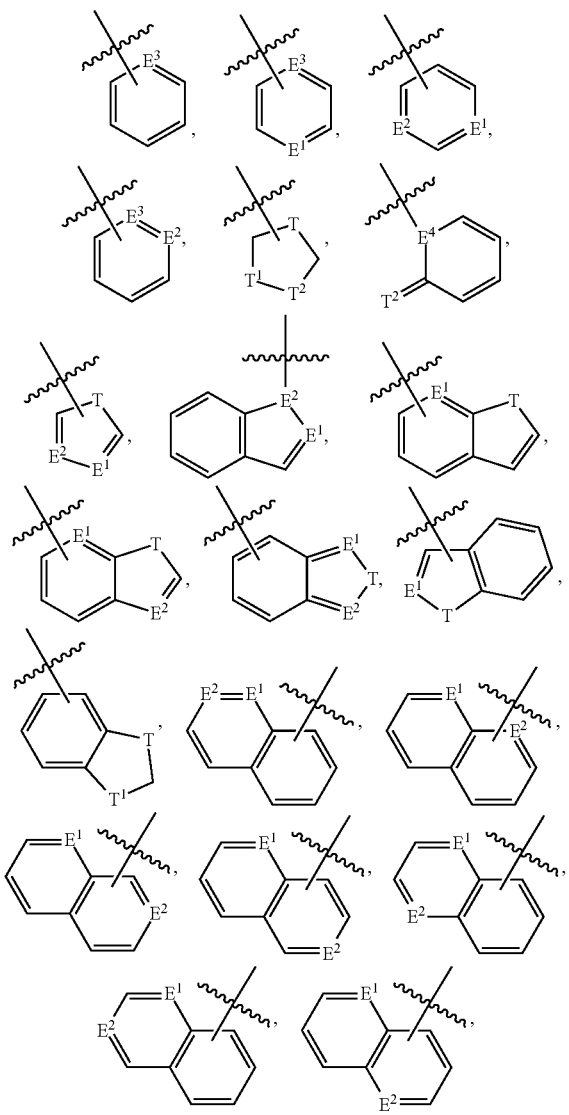

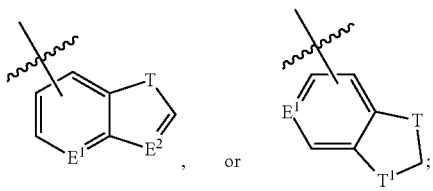

wherein, each $E^1$, $E^2$, $E^3$ and $E^4$ is independently N or $CR^7$;

each T, $T^1$ and $T^2$ is independently —$NR^8$—, —O—, —S— or —$CR^7R^{7a}$—;

each $R^7$ and $R^{7a}$ is independently H, F, Cl, Br, I, $C_{1-4}$ alkyl-O—C(=O)—, $C_{1-4}$ alkyl, $C_{2-4}$ alkenyl, $C_{2-4}$ alkynyl, $C_{1-4}$ alkoxy, $C_{1-4}$ haloalkyl, cyano, nitro, amino, $C_{1-4}$ alkylamino, mercapto, $C_{1-4}$ alkylthio, $C_{6-10}$ aryl, $C_{6-10}$ aryloxy, $C_{1-9}$ heteroaryl, $C_{1-9}$ heteroaryloxy or $C_{1-4}$ haloalkoxy;

wherein, each $R^5$ is independently and optionally substituted with one or more substituents independently selected from H, oxo (=O), F, Cl, Br, I, $C_{1-4}$ alkyl —O—C(=O)—, $C_{1-4}$ alkyl, $C_{2-4}$ alkenyl, $C_{2-4}$ alkynyl, $C_{1-4}$ alkoxy, $C_{1-4}$ haloalkyl, cyano, nitro, amino, $C_{1-4}$ alkylamino, mercapto, $C_{1-4}$ alkylthio, $C_{6-10}$ aryl, $C_{6-10}$ aryloxy, $C_{1-9}$ heteroaryl, $C_{1-9}$ heteroaryloxy and $C_{1-4}$ haloalkoxy;

each $R^6$ is independently H, hydroxy, amino, $C_{1-4}$ alkyl, $C_{1-4}$ haloalkyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl or $C_{1-9}$ heteroaryl;

each $R^8$ is independently H, $C_{1-4}$ alkyl-O—C(=O)—, $C_{1-4}$ alkyl, $C_{2-4}$ alkenyl, $C_{2-4}$ alkynyl, $C_{1-4}$ alkoxy, $C_{1-4}$ haloalkyl, amino, $C_{1-4}$ alkylamino, $C_{1-4}$ alkylthio, $C_{6-10}$ aryl or $C_{1-9}$ heteroaryl; and m is as define herein.

In other embodiments, each $R^5$ is independently

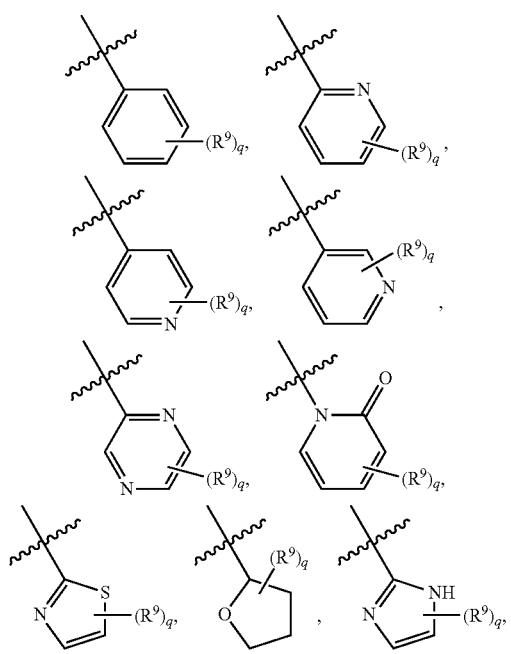

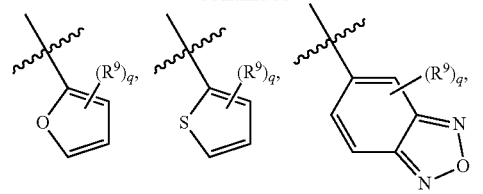

wherein, each $R^9$ is independently H, oxo (=O), F, Cl, Br, I, $C_{1-4}$ alkyl-O—C(=O)—, $C_{1-4}$ alkyl, $C_{2-4}$ alkenyl, $C_{2-4}$ alkynyl, $C_{1-4}$ alkoxy, $C_{1-4}$ haloalkyl, cyano, nitro, amino, $C_{1-4}$ alkylamino, mercapto, $C_{1-4}$ alkylthio, $C_{6-10}$ aryl, $C_{6-10}$ aryloxy, $C_{1-9}$ heteroaryl, $C_{1-9}$ heteroaryloxy or $C_{1-4}$ haloalkyloxy; and each q is independently 0, 1, 2, 3, 4, 5, 6 or 7.

In other embodiments, each $R^9$ is independently H, oxo (=O), F, Cl, Br, I, methyl-O—C(=O)—, ethyl-O—C(=O)—, propyl-O—C(=O)—, butyl-O—C(=O)—, tert-butyl —O—C(=O)—, isopropyl-O—C(=O)—, methyl, ethyl, propyl, butyl, tert-butyl, isopropyl, ethenyl, 3-propenyl, propenyl, $C_{2-4}$ alkynyl, methoxy, ethoxy, propoxy, butoxy, trifluoromethyl, chloromethyl, trifluoroethyl, 1-fluoroethyl, cyano, nitro, amino, methylamino, dimethylamino, ethylamino, diethylamino, mercapto, methylthio, ethylthio, propylthio, $C_{6-10}$ aryl, phenoxy, $C_{1-9}$ heteroaryl, $C_{1-9}$ heteroaryloxy, trifluoroethoxy or trifluoromethoxy.

In other embodiments, each $R^{1a}$ is independently H, F, Cl, Br, I, cyano, hydroxy, amino, carboxyl, methyl, ethyl, propyl, butyl, tert-butyl, isopropyl, trifluoromethyl, trifluoroethyl, 1-fluoromethyl, 1-chloroethyl, methoxy, propoxy, ethoxy, methylamino, ethylamino, dimethylamino, diethylamino, methylthio, ethylthio, $C_{2-4}$ alkenyl, $C_{2-4}$ alkynyl, nitro, mercapto, $C_{1-4}$ hydroxyalkoxy, $C_{1-4}$ hydroxyalkyl, $C_{1-4}$ aminoalkoxy, $C_{1-4}$ alkyl-O—C(=O)— or phenyl;

each of $R^2$ and $R^3$ is independently H, F, Cl, Br, I, cyano, carboxyl, hydroxy, methyl, ethyl, propyl, butyl, tert-butyl, trifluoromethyl, chloromethyl, trifluoroethyl, 1-chloroethyl, methoxy, ethoxy, propoxy, $C_{1-4}$hydroxyalkoxy, $C_{1-4}$ hydroxyalkyl, $C_{1-4}$aminoalkoxy, trifluoromethoxy, 1-chloroethoxy, phenyl or phenyl-$C_{1-4}$-alkyl; and each $R^4$ is independently H, F, Cl, Br, I, cyano, carboxyl, hydroxy, methyl, ethyl, propyl, butyl, tert-butyl, trifluoromethyl, chloromethyl, trifluoroethyl, 1-chloroethyl, methoxy, ethoxy, propoxy, $C_{1-4}$ hydroxyalkoxy, $C_{1-4}$ hydroxyalkyl, $C_{1-4}$ aminoalkoxy, trifluoromethoxy, 1-chloroethoxy, phenyl or phenyl-$C_{1-4}$-alkyl.

In one aspect, provided herein are pharmaceutical compositions comprising a compound of Formula (I) or Formula (II) disclosed herein, or a stereoisomer, geometric isomer, tautomer, nitrogen oxide, hydrate, solvate, metabolite, pharmaceutically acceptable salt or prodrug thereof; and an optionally pharmaceutically acceptable carrier, excipient, diluent, adjuvant, vehicle or a combination thereof.

In one aspect, provided herein is use of the compound or pharmaceutical composition of Formula (I) or Formula (II) disclosed herein in the manufacture of a medicament for preventing, managing, treating or lessening the severity of a tissue or organ fibrosis.

In some embodiments, the tissue or organ fibrosis is renal interstitial fibrosis, glomerulosclerosis, liver fibrosis, pulmonary fibrosis, IPF, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

In one aspect, provided herein is the compound or pharmaceutical composition of Formula (I) or Formula (II) disclosed herein for use in preventing, managing, treating or lessening the severity of tissue or organ fibrosis.

In some embodiments, the tissue or organ fibrosis is renal interstitial fibrosis, glomerulosclerosis, liver fibrosis, pulmonary fibrosis, IPF, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

In one aspect, provided herein is a method for preventing, managing, treating or lessening the severity of tissue or organ fibrosis comprising administering to a patient a therapeutically effective amount of the compound or the pharmaceutical composition.

In some embodiments, the tissue or organ fibrosis is renal interstitial fibrosis, glomerulosclerosis, liver fibrosis, pulmonary fibrosis, IPF, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

In one aspect, provided herein are methods for preventing, managing, treating or lessening the severity of tissue or organ fibrosis, which comprises administering a pharmaceutically effective amount of the compound or the pharmaceutical composition disclosed herein to a patient.

In some embodiments, the tissue or organ fibrosis is renal interstitial fibrosis, glomerulosclerosis, liver fibrosis, pulmonary fibrosis, IPF, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

In another aspect, provided herein is use of the compound of Formula (I) or Formula (II) or pharmaceutical composition disclosed herein for preventing, managing, treating or lessening the severity of a tissue or organ fibrosis.

In one aspect, provided herein are methods for preventing, managing, treating or lessening the severity of tissue or organ fibrosis, which comprises administering a pharmaceutically acceptable effective amount of the compound disclosed herein to a patient.

In another aspect, provided herein is use of the pharmaceutical composition of Formula (I) or Formula (II) disclosed herein in the manufacture of a medicament for preventing, managing, treating or lessening the severity of a tissue or organ fibrosis.

In another aspect, provided herein is use of the compound or pharmaceutical composition of Formula (I) or Formula (II) disclosed herein for preventing, managing, treating or lessening the severity of a tissue or organ fibrosis in human or animal, which comprises administering a pharmaceutically effective amount of the (a) compound or pharmaceutical composition disclosed herein to a patient.

In another aspect, provided herein include methods of preparing, methods of separating, and methods of purifying compounds of Formula (I) or Formula (II).

The foregoing merely summarizes certain aspects disclosed herein and is not intended to be limiting in nature. These aspects and other aspects and embodiments are described more fully below.

DETAILED DESCRIPTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and *the Handbook of Chemistry and Physics, 75th Ed. 1994*. Additionally, general principles of organic chemistry are described in Sorrell et al., "*Organic Chemistry*", University Science Books, Sausalito: 1999, and Smith et al., "*March's Advanced Organic Chemistry*", John Wiley & Sons, Inc., New York: 2007, all of which are incorporated herein by reference in their entireties.

As described herein, compounds may optionally be substituted with one or more substituents, such as those illustrated above, or as exemplified by particular classes, subclasses, and species disclosed herein. It will be appreciated that the phrase "optionally substituted" is used interchangeably with the phrase "substituted or unsubstituted". In general, the term "substituted" whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure may be substituted with more than one substituents selected from a specified group, the substituents may be either the same or different at each position. Wherein the substituents include, but are not limited to, H, oxo (=O), F, Cl, Br, I, alkyl —O—C(=O)—, alkyl, alkenyl, alkynyl, alkoxy, haloalkyl, cyano, nitro, amino, alkylamino, mercapto, alkylthio, aryl, aryloxy, heteroaryl, heteroaryloxy, haloalkoxy, hydroxy, heterocyclyl, carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "aliphatic" or "aliphatic group" refers to a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms. In yet other embodiments, aliphatic groups contain 1-4 carbon atoms and in yet other embodiments, aliphatic groups contain 1-3 carbon atoms. Suitable aliphatic groups include, but are not limited to, linear or branched, substituted or unsubstituted alkyl, alkenyl, or alkynyl groups, such as methyl, ethyl, propyl, isopropyl, butyl, tert-butyl, hexyl, isobutyl, s-butyl, ethenyl, and the like.

The term "alkyl" refers to a saturated linear or branched-chain monovalent hydrocarbon radical of 1-20 carbon atoms, 1-10 carbon atoms, 1-6 carbon atoms, 1-4 carbon atoms, or 1-3 carbon atoms, wherein the alkyl radical is independently and optionally substituted with one or more substituents described herein. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like. The terms "alkyl" and the prefix "alk-" are inclusive of both straight chain and branched saturated carbon chain. The term "alkylene", as used herein, represents a saturated divalent hydrocarbon group derived from a straight or branched chain saturated hydrocarbon by the removal of two hydrogen atoms, and is exemplified by methylene, ethylene, isopropylene, and the like.

The term "alkenyl" refers to a linear or branched-chain monovalent hydrocarbon radical of 2-12 carbon atoms, 2-8 carbon atoms, 2-6 carbon atoms, or 2-4 carbon atoms, with at least one site of unsaturation, i.e., a carbon-carbon, sp$^2$ double bond, wherein the alkenyl radical may be independently and optionally substituted with one or more substituents described herein, including "cis" and "trans" orientations, or alternatively, "E" and "Z" orientations. Some non-limiting examples include ethenyl or vinyl (—CH=CH$_2$), allyl (—CH$_2$CH=CH$_2$), butenyl (—CH$_2$CH$_2$CH=CH$_2$), and the like.

The term "alkynyl" refers to a linear or branched-chain monovalent hydrocarbon radical of 2-12 carbon atoms, 2-8 carbon atoms, 2-6 carbon atoms, or 2-4 carbon atoms, with at least one site of unsaturation, i.e., a carbon-carbon, sp triple bond, wherein the alkynyl radical may be optionally and independently substituted with one or more substituents described herein. Some non-limiting examples include ethynyl (—C≡CH), propargyl (—CH$_2$C≡CH), and the like.

The term "hydroxyalkyl" or "hydroxy-substituted alkyl" refers to an alkyl group substituted with one or more hydroxy groups, wherein the alkyl group is as defined herein. Some non-limiting examples include hydroxymethyl, hydroxyethyl, 1,2-dihydroxyethyl, and the like.

The term "heteroatom" refers to oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl); or —CH$_2$— in a heterocyclic ring was oxidized to form —C(=O)—.

The term "halogen" refers to F, Cl, Br or I.

The term "unsaturated" refers to a moiety having one or more units of unsaturation.

The term "alkoxy" or "alkyloxy" refers to an alkyl group, as previously defined, attached to the principal carbon chain through an oxygen atom. Some non-limiting examples include methoxy, ethoxy, propoxy, butoxy, and the like. And the alkoxy defined above may be substituted or unsubstituted, wherein the substituents may be, but are not limited to, H, oxo (=O), F, Cl, Br, I, alkyl —O—C(=O)—, alkyl, alkenyl, alkynyl, alkoxy, haloalkyl, cyano, nitro, amino, alkylamino, mercapto, alkylthio, aryl, aryloxy, heteroaryl, heteroaryloxy, haloalkoxy, hydroxy, heterocyclyl, carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "haloalkyl", "haloalkenyl" or "haloalkoxy" refers to an alkyl group, alkenyl group or alkoxy group substituted with one or more halogen atoms. Some non-limiting examples include trifluoromethyl, 2-chloro-ethenyl, trifluoromethoxy, and the like.

The term "hydroxyalkoxy" refers to an alkoxy group substituted with one or more hydroxy groups, wherein the alkoxy group is as defined above. Some non-limiting examples include hydroxymethoxy, hydroxyethoxy, 1,2-dihydroxyethoxy, and the like.

The term "alkamino" or "alkylamino" refers to "N-alkylamino" and "N,N-dialkylamino", wherein the amino groups are independently substituted with one or two alkyl groups. In some embodiments, the alkylamino group is lower alkylamino group having one or two alkyl groups of 1 to 6 carbon atoms attached to nitrogen atom. In other embodiments, the alkylamino group is lower alkylamino group having 1 to 3 carbon atoms. Some non-limiting examples of the alkylamino group include monoalkylamino or dialkylamino such as N-methylamino, N-ethylamino, N,N-dimethylamino, N,N-diethylamino, and the like.

The term "cycloaliphatic", "carbocycle", "carbocyclyl" or "cycloalkyl" refers to a monovalent or multivalent, non-aromatic, saturated or partially unsaturated ring, and not containing heteroatoms, having 3 to 12 carbon atoms as a monocyclic ring or 7 to 12 carbon atoms as a bicyclic ring or a tricyclic ring. Bicyclic carbocycles having 7 to 12 ring atoms can be arranged as a bicyclo [4,5], [5,5], [5,6] or [6,6] system, and bicyclic carbocycles having 9 or 10 ring atoms can be arranged as a bicyclo [5,6] or [6,6] system. Some non-limiting examples of cycloaliphatic groups include cycloalkyl, cycloalkenyl, and cycloalkynyl. Further examples of cycloaliphatic groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, adamantyl, and the like. And "cycloaliphatic", "carbocycle", "carbocyclyl", or "cycloalkyl" may be substituted or unsubstituted, wherein the substituents may be, but are not limited to, H, oxo (=O), F, Cl, Br, I, alkyl —O—C(=O)—, alkyl, alkenyl, alkynyl, alkoxy, haloalkyl, cyano, nitro, amino, alkylamino, mercapto, alkylthio, aryl, aryloxy, heteroaryl, heteroaryloxy, haloalkyloxy, hydroxy, heterocyclyl, carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "cycloalkyloxy" or "carbocyclyloxy" refers to an optionally substituted cycloalkyl radical or carbocyclyl radical, as defined herein, attached to an oxygen atom, which is connected to the rest of the molecule. Some non-limiting examples include cyclopropyloxy, cyclopentyloxy, cyclohexyloxy, hydroxy-substituted cyclopropyloxy, and the like.

The term "cycloalkylaliphatic" or "carbocyclylaliphatic" refers to an aliphatic group substituted with one or more cycloalkyl groups or carbocyclyl groups, wherein the carbocyclyl group, cycloalkyl group and aliphatic group are as defined herein. Some non-limiting examples include cyclopropylmethyl, cyclopropylethyl, cyclopropylpropyl, cyclopentylmethyl, cyclohexylethyl, and the like.

The term "cycloalkylalkoxy" ("carbocyclylalkoxy") refers to an alkoxy group substituted with one or more cycloalkyl groups or carbocyclyl groups, wherein the carbocyclyl group, cycloalkyl group and alkoxy group are as defined herein. Some non-limiting examples include cyclopropylmethoxy, cyclopropylethoxy, cyclopentylethoxy, cyclohexylethoxy, cyclohexylmethoxy, cyclopropylpropoxy, and the like.

The term "heterocycle", "heterocyclyl", "heterocycloaliphatic", or "heterocyclic" as used interchangeably herein refers to a monocyclic, bicyclic, or tricyclic ring system in which one or more ring members are an independently selected heteroatom and that is completely saturated or that contains one or more units of unsaturation, but not aromatic having a single point of attachment to the rest of the molecule. One or more ring atoms are optionally and independently substituted with one or more substituents described herein. In some embodiments, the "heterocycle", "heterocyclyl", "heterocycloaliphatic" or "heterocyclic" group is a monocycle having 3 to 7 ring members (e.g., 1 to 6 carbon atoms and 1 to 3 heteroatoms selected from N, O, P or S, wherein the S or P is optionally substituted with one or more oxo to provide the group SO or SO$_2$, PO or PO$_2$, with the proviso that when the ring is a 3-membered ring, there is only one heteroatom) or a bicycle having 7 to 10 ring members (e.g., 4 to 9 carbon atoms and 1 to 3 heteroatoms selected from N, O, P or S, wherein the S or P is optionally substituted with one or more oxo to provide the group SO or SO$_2$, PO or PO$_2$).

The heterocyclyl may be a carbon radical or heteroatom radical. "heterocyclyl" also includes radicals where heterocycle radicals are fused with a saturated, partially unsaturated ring, or heterocyclic ring. Some non-limiting examples of heterocyclic rings include pyrrolidinyl, tetrahydrofuranyl, dihydrofuranyl, tetrahydrothienyl, tetrahydropyranyl, dihydropyranyl, tetrahydrothiopyranyl, tetrahydropyrrolyl, piperidino, morpholino, thiomorpholino, thioxanyl, piperazinyl, homopiperazinyl, azetidinyl, oxetanyl, thietanyl, piperidino, homopiperidinyl, epoxypropyl, azepanyl, oxepanyl, thiepanyl, 4-methoxy-piperidin-1-yl, 1,2,3,6-tetrahydropyridin-1-yl, oxazepinyl, diazepinyl, thiazepinyl, pyrrolin-1-yl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydrothienyl, thiazolidinyl, pyrazolidinyl, imidazolinyl, imidazolidinyl, 1,2,3,4-tetrahydroisoquinolinyl, 1,2,6-thiadiazine-1-1-dioxo-2-yl, 4-hydroxy-1,4-azaphosphine-4-oxide-1-yl, 2-hydroxy-1-(piperazin-1-yl)ethanon-4-yl, 2-hydroxy-1-(5,6-dihydro-1,2,4-triazin-1(4H)-yl)ethanon-4-yl, 5,6-dihydro-4H-1,2,4-oxadiazin-4-yl, 2-hydroxy-1-(5,6-dihydropyridin-1 (2H)-yl)ethanon-4-yl, 3-azabicyco[3.1.0]hexanyl, 3-azabicyclo[4.1.0]heptanyl, azabicyclo[2.2.2]hexanyl, 2-methyl-5,6,7,8-tetrahydro-[1,2,4]triazolo[1,5-c]pyrimidin-6-yl, 4,5,6,7-tetrahydroisoxazol[4,3-c]pyridin-5-yl, 3H-indolyl-2-oxo-5-azabicyclo[2.2.1]heptan-5-yl, 2-oxo-5-azabicyclo[2.2.2]octan-5-yl, quinolizinyl and N-pyridyl urea. Some non-limiting examples of a heterocyclic ring further include 1,1-dioxothiomorpholinyl, heterocyclic group wherein 2 carbon atoms on the ring are substituted with oxo (=O) moieties are pyrimidindionyl and 2-oxo-pyridinyl. The heterocyclic group herein may be substituted or unsubstituted, wherein the substituents may be, but are not limited to, H, oxo (=O), F, Cl, Br, I, alkyl —O—C(=O)—, alkyl, alkenyl, alkynyl, alkoxy, haloalkyl, cyano, nitro, amino, alkylamino, thiol, alkylthio, aryl, aryloxy, heteroaryl, heteroaryloxy, haloalkyloxy, hydroxy, heterocyclyl, carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "heterocyclylalkyl" refers to heterocyclic-substituted alkyl radical. The term "heterocyclylalkoxy" refers to heterocyclic-substituted alkoxy radical wherein oxygen atom serves as the attaching point to the rest of the molecule.

The term "heterocyclylalkylamino" refers to heterocyclic-substituted alkylamino radical wherein nitrogen atom serves as the attaching point to the rest of the molecule. Some non-limiting examples of heterocyclyl, alkyl, alkoxy and alkylamino include pyrrol-2-ylmethyl, morpholin-4-ylethyl, morpholin-4-ylethoxy, piperazin-4-ylethoxy, piperidin-4-ylethylamino, and the like.

The term "heterocyclylaliphatic" refers to heterocyclic-substituted aliphatic group, wherein the heterocyclic radical and aliphatic group are as defined herein. Some non-limiting examples include pyrrol-2-ylmethyl, piperidin-2-ylethyl, piperazin-2-ylethyl, piperidin-2-ylmethyl, and the like.

The term "aryl" used alone or as part of a larger moiety in "aralkyl", "arylalkoxy" or "aryloxyalkyl" refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Some non-limiting examples of aryl rings include phenyl, naphthyl, and anthracene. And the aryl defined herein may be substituted or unsubstituted, wherein the substituents may be, but are not limited to, H, oxo (=O), F, Cl, Br, I, alkyl —O—C(=O)—, alkyl, alkenyl, alkynyl, alkoxy, haloalkyl, cyano, nitro, amino, alkylamino, mercapto, alkylthio, aryl, aryloxy, heteroaryl, heteroaryloxy, haloalkyloxy, hydroxy, heterocyclyl, carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "aralkyl" or "arylalkyl" refers to an alkyl group substituted with one or more aryl-substituted groups, wherein the alkyl group and aryl-substituted group are as defined herein. Some non-limiting examples include phenylethyl, benzyl, p-tolylethyl, and the like.

The term "aryloxy" refers to optionally substituted aryl radicals, as defined herein, attached to an oxygen atom, wherein the oxygen atom serves as the attaching point to the rest of the molecule. Wherein the aryl radical is as defined herein. Some non-limiting examples include phenyloxy, methylphenyloxy, ethylphenyloxy, and the like.

The term "heteroaryl" used alone or as part of a larger moiety in "heteroaralkyl" or "heteroarylalkoxy" refers to monocyclic, bicyclic, and tricyclic ring systems having a total of five to fourteen ring members, wherein at least one ring in the system is aromatic, at least one ring in the system contains one or more heteroatoms (heteroatoms selected from —C(=O)—, N, O, P, S, wherein the S or P is optionally substituted with one or more oxo to provide the group SO, SO$_2$, PO or PO$_2$), wherein each ring in the system contains 3 to 7 ring members and that has a single point of attachment to the rest of the molecule, wherein bicyclic or tricyclic ring system is fused to form ring. The heteroaryl may be attached to the main structure at any heteroatom or carbon atom which results in the creation of a stable compound. The heteroaryl group may be 3-7 membered monocyclic ring, 7-10 membered bicyclic ring or 10-15 membered tricyclic ring. And the heteroaryl or heteroaryl rings defined herein may be substituted or unsubstituted, wherein the substituents may be, but is not limited to, H, oxo (=O), F, Cl, Br, I, alkyl —O—C(=O)—, alkyl, alkenyl, alkynyl, alkoxy, haloalkyl, cyano, nitro, amino, alkylamino, mercapto, alkylthio, aryl, aryloxy, heteroaryl, heteroaryloxy, haloalkyloxy, hydroxy, heterocyclyl, carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

Some non-limiting examples of the suitable heteroaryl group include the following monocycles: 2-furanyl, 3-furanyl, thienyl, N-imidazolyl, pyrazolyl, 2-imidazolyl, 4-imidazolyl, 5-imidazolyl, methylimidazolyl, 3-isoxazolyl, 4-isoxazolyl, 5-isoxazolyl, 2-oxazolyl, 4-oxazolyl, 5-oxazolyl, 4-methylisoxazol-5-yl, N-pyrrolyl, 2-pyrrolyl, 3-pyrrolyl, 2-pyridyl, 3-pyridyl, 4-pyridyl, 2-oxo-pyridinyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, 1,3,4-thiadiazol-2-yl, pyrazinyl, 2-pyrazinyl, 1,3,5-triazinyl; and the following bicycles: benzimidazolyl, benzofuryl, quinazolinyl, benzothiophenyl, benzothiazolyl, benzo[d]thiazol-2-yl, imidazo[1,5-a]pyridin-6-yl, 1,7-naphthyridinyl, 1,5-naphthyridinyl, 2H-isoindolyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), benzo[c][1,2,5]oxadiazolyl, benzo[d][1,3] dioxolyl, benzo[d]isothiazolyl, quinazolinyl, 6H-cyclopenta[b]furyl, 5H-cyclopenta[c]pyridyl, 5H-cyclopenta[c]pyrazinyl, 7H-cyclopenta[c]pyridyl, 7H-cyclopenta[d]pyrimidinyl, benzo[d][1,3]dioxolyl, benzo[c]isoxazolyl, benzo[d] isoxazolyl, phthalazinyl, 2,3-dihydro-1H-pyrrolo[2,3-c]pyridyl, 1H-pyrrolo[3,2-b]pyridyl, 7H-cyclopenta[b]pyridyl, isobenzofuryl, 2H-isoindolyl, 1H-isoindolyl, dihydrobenzofuryl, dihydrobenzothienyl, dihydroindolyl, dihydro-1H-pyrrolopyridyl, 7H-pyrrolo[3,4-b]pyridyl, cyclopenta[b]pyrazinyl, 1H-benzo[d]imidazolyl, benzo[c]thienyl, 7H-pyrazolo[3,4-b] pyridyl, and the like.

The term "heteroaryoxy" or "heteroaryloxy" refers to optionally substituted aryl radicals, as defined herein, attached to an oxygen atom, wherein the oxygen atom serves as the attaching point to the rest of the molecule. Some non-limiting examples include pyrid-2-yloxy, thiazol-2-yloxy, imidazol-2-yloxy, pyrimidin-2-yloxy, and the like.

The term "sulfamyl", "aminosulfonyl" or "sulfonamidyl" refers to a sulfonyl radical substituted with an amine radical, forming a sulfonamide (—SO$_2$NH$_2$).

The term "carboxy" or "carboxyl", whether used alone or with other terms, refers to —CO$_2$H; such as "carboxyalkyl", refers to CH$_2$CO$_2$H. The term "carbonyl", whether used alone or with other terms, such as "aminocarbonyl" or "carbonyloxy", refers to —(C=O)—.

The term "carboxyalkoxy" refers to an alkoxy group substituted with one or more carboxy groups, wherein the alkoxy group and the carboxy group are as defined herein. Some non-limiting examples include carboxymethoxy, carboxyethoxy, and the like.

The term "aminoalkoxy" refers to an alkoxy group substituted with one or more amino groups, wherein the alkoxy group and the amino group are as defined above. Some non-limiting examples include aminomethoxy, aminoethoxy, and the like.

The term "alkyl-C(=O)—" refers to optionally substituted alkyl radicals, as defined herein, connected to a carbonyl (—C(=O)—) radical and the carbonyl radical connected to the rest of the molecule, wherein alkyl is as defined above. Some non-limiting examples include methylcarbonyl, ethylcarbonyl, and the like.

The term "alkyl-O—C(=O)—" refers to optionally substituted alkyl radicals, as defined herein, connected to a —O—C(=O)— radical and the carbonyl radical connected to the rest of the molecule, wherein alkyl is as defined above. Some non-limiting examples include methyl —O—C(=O)—, ethyl-O—C(=O)—, and the like.

The term "hydroxyalkylcarbonyl" refers to hydroxy-substituted alkyl connected to a carbonyl —C(=O)—) radical, and the carbonyl radical connected to the rest of the molecule, wherein alkyl is as defined above. Some non-limiting examples include hydroxymethylcarbonyl, 1,2-dihydroxyethylcarbonyl, and the like.

The term "alkylthio" refers to radicals containing a linear or branched alkyl radical, of one to ten carbon atoms, attached to a divalent sulfur atom. In some embodiments, alkylthio radicals are lower alkylthio radicals having one to three carbon atoms. Some non-limiting examples of "alkylthio" include methylthio ($CH_3S$—).

The term "haloalkylthio" refers to radicals containing a haloalkyl radical, of one to ten carbon atoms, attached to a divalent sulfur atom. In other embodiments, haloalkylthio radicals are lower haloalkylthio radicals having one to three carbon atoms. Some non-limiting examples of "haloalkylthio" include trifluoromethylthio.

The term "heteroarylalkyl" refers to alkyl groups substituted with one or more heteroaryl radicals, wherein the heteroaryl radical and the alkyl group are as defined herein. Some non-limiting examples of heteroarylalkyl include imidazol-2-methyl, furan-2-ethyl, indole-3-methyl, and the like.

The term "aminoalkyl" refers to a linear or branched alkyl radical having one to ten carbon atoms, substituted with one or more amino radicals. In some embodiments, aminoalkyl radicals are "lower aminoalkyl" radicals having one to six carbon atoms and one or more amino radicals. Some non-limiting examples of such radicals include aminomethyl, aminoethyl, aminopropyl, aminobutyl or aminohexyl.

The term "carboxyalkyl" refers to a linear or branched alkyl radical having one to ten carbon atoms, substituted with one or more carboxy radicals. Some non-limiting examples of such radicals include carboxymethyl, carboxypropyl, and the like.

The term "heteroarylalkoxy" refers to oxy-containing heteroarylalkyl radicals attached through an oxygen atom to other radicals, wherein the heteroarylalkyl radical is as defined herein. Some non-limiting examples of such radicals include pyridin-2-ylmethoxy, thiazol-2-ylethoxy, imidazol-2-ylethoxy, pyrimidin-2-ylpropoxy, pyrimidin-2-ylmethoxy, and the like.

The term "cycloalkylalkyl" refers to cycloalkyl-substituted alkyl radicals. Some non-limiting examples of such radicals include cyclohexylmethyl. The cycloalkyl in the radicals may be additionally substituted with halo, alkyl, alkoxy or hydroxy.

The term "fused bicyclic", "fused cyclic", "fused bicyclyl" or "fused cyclyl" refers to saturated or unsaturated fused ring system, which refers to a bicyclic ring system that is not aromatic. Such a system may contain isolated or conjugated unsaturation, but not aromatic or heteroaromatic rings in its core structure (but may have aromatic substitution thereon). Each cyclic ring in the fused bicyclyl can be either a carbocyclic or a heteroalicyclic. Some non-limiting examples of fused bicyclic ring system include hexahydro-furo[3,2-b]furan, 2,3,3a,4,7,7a-hexahydro-1H-indene, 7-azabicyclo[2.3.0]heptane, fused bicyclo[3.3.0]octane, fused bicyclo[3.1.0]hexane, 1,2,3,4,4a,5,8,8a-octahydronaphthalene, and the like. And the fused bicyclyl defined herein may be substituted or unsubstituted, wherein the substituents include, but are not limited to, H, oxo (=O), F, Cl, Br, I, alkyl —O—C(=O)—, alkyl, alkenyl, alkynyl, alkoxy, haloalkyl, cyano, nitro, amino, alkylamino, mercapto alkylthio, aryl, aryloxy, heteroaryl, heteroaryloxy, haloalkyloxy, hydroxy, heterocyclyl, carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "fused heterobicyclyl" refers to saturated or unsaturated fused ring system, which refers to a bicyclic ring system that is not aromatic. Such a system may contain isolated or conjugated unsaturation, but not aromatic or heteroaromatic rings in its core structure (but may have aromatic substitution thereon). Wherein at least one ring in the system contains one or more heteroatoms, wherein each ring in the system contains 3 to 7 ring members and that contains one to six carbon atoms and one to three heteroatoms selected from N, O, P, S, wherein the S or P is optionally substituted with one or more oxo to provide the group SO, $SO_2$, PO or $PO_2$. Some non-limiting examples of fused heterobicyclic ring system include hexahydro-furo[3,2-b]furan, 7-azabicyclo[2.3.0]heptane, and the like. And the fused heterobicyclyl defined herein may be substituted or unsubstituted, wherein the substituents include, but are not limited to, H, oxo (=O), F, Cl, Br, I, alkyl —O—C(=O)—, alkyl, alkenyl, alkynyl, alkoxy, haloalkyl, cyano, nitro, amino, alkylamino, mercapto, alkylthio, aryl, aryloxy, heteroaryl, heteroaryloxy, haloalkyloxy, hydroxy, heterocyclyl, carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "fused bicyclylalkyl" refers to alkyl groups substituted with one or more fused bicyclyl groups, wherein the alkyl group and the fused bicyclyl group are as defined herein. Some non-limiting examples include 1,2,3,4,4a,5,8,8a-octahydro-naphthylethyl, 1,2,3,4,4a,5,8,8a-octahydro-naphthylmethyl, 1,2,3,4,4a,5,8,8a-octahydro-naphthylpropyl, fused bicyclo[3.3.0]octylmethyl, fused bicyclo[3.1.0]hexylethyl, and the like.

The term "fused heterobicyclylalkyl" refers to alkyl groups substituted with one or more fused heterobicyclyl groups, wherein the alkyl group and the fused heterobicyclyl group are as defined herein. Some non-limiting examples include hexahydro-furo[3,2-b]furanylpropyl, 7-azabicyclo[2.3.0]heptylethyl, and the like.

The term "bridged heterobicyclyl" refers to saturated or unsaturated bridged ring system, which refers to a bicyclic ring system that is not aromatic. Such a system may contain isolated or conjugated unsaturation, but not aromatic or heteroaromatic rings in its core structure (but may have aromatic substitution thereon). Wherein at least one ring in the system contains one or more heteroatoms, wherein each ring in the system contains 3 to 7 ring members and that contains one to six carbon atoms and one to three heteroatoms selected from N, O, P, S, wherein the S or P is optionally substituted with one or more oxo to provide the group SO, $SO_2$, PO or $PO_2$. Some non-limiting examples of bridged heterobicyclic ring system include 2-oxo-5-azabicyclo[2.2.1]heptyl, 2-thio-5-azabicyclo[2.2.1]heptyl, 2,5-diazabicyclo[2.2.1] heptyl, 2-methyl-2,5-diazabicyclo[2.2.1] heptyl, and the like. And the bridged heterobicyclyl defined herein may be substituted or unsubstituted, wherein the substituents include, but are not limited to, H, oxo (=O), F, Cl, Br, I, alkyl —O—C(=O)—, alkyl, alkenyl, alkynyl, alkoxy, haloalkyl, cyano, nitro, amino, alkylamino, mercapto, alkylthio, aryl, aryloxy, heteroaryl, heteroaryloxy, haloalkyloxy, hydroxy, heterocyclyl, carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "bridged bicyclyl" refers to saturated or unsaturated bridged ring system, which refers to a bicyclic ring system that is not aromatic. Such a system may contain isolated or conjugated unsaturation, but not aromatic or heteroaromatic rings in its core structure (but may have aromatic substitution thereon). Wherein each ring in the system contains 3 to 7 ring members. Some non-limiting examples of bridged bicyclic ring system include, bicyclo [2.2.1] heptyl, 2-methyl-bicyclo [2.2.1] heptyl, and the like. And the bridged bicyclyl defined herein may be substituted or unsubstituted, wherein the substituents include, but are not limited to, H, oxo (=O), F, Cl, Br, I, alkyl —O—C (=O)—, alkyl, alkenyl, alkynyl, alkoxy, haloalkyl, cyano, nitro, amino, alkylamino, mercapto, alkylthio, aryl, aryloxy, heteroaryl, heteroaryloxy, haloalkyloxy, hydroxy, heterocyclyl, carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "bridged bicyclylalkyl" refers to alkyl groups substituted with one or more bridged bicyclyl groups, wherein the alkyl group and the bridged bicyclyl group are as defined herein. Some non-limiting examples include bicyclo [2.2.1] heptylmethyl, 2-methyl-heterobicyclo [2.2.1] heptylethyl, and the like.

The term "bridged heterobicyclylalkyl" refers to alkyl groups substituted with one or more bridged heterobicyclyl groups, wherein the alkyl group and the bridged heterobicyclyl group are as defined herein. Some non-limiting examples include, 2-oxy-5-azabicyclo[2.2.1]heptylethyl, 2-thio-5-azabicyclo[2.2.1]heptylpropyl, 2,5-diazabicyclo [2.2.1]heptylmethyl, 2-methyl-2,5-diazabicyclo[2.2.1]heptylbutyl, and the like.

As described herein, a bond drawn from a substituent to the center of one ring within a ring system (as shown below) represents substitution of R at any substitutable position on the ring A and ring B. For example, Figure a represents possible substitution of R in any of the positions on the A ring and B ring shown in Figure b, c, d, e, f, g and h.

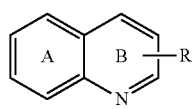

Figure a

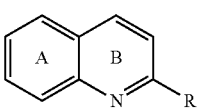

Figure b

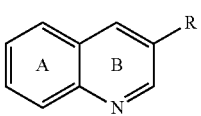

Figure c

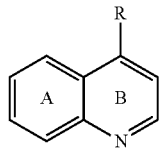

Figure d

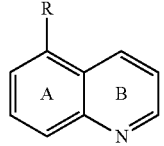

Figure e

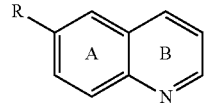

Figure f

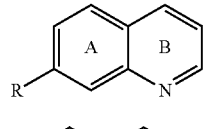

Figure g

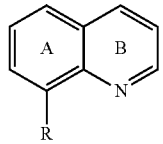

Figure h

As described herein, a bond drawn from a substituent to the center of one ring within a ring system (as shown below) represents substitutions of one or more R at any substitutable position on the ring A and ring B. For example, Figure i or j represents possible substitutions of one or more R in any of the position on the A ring or B ring.

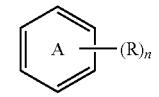

Figure i

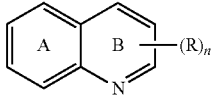

Figure j

As described herein, a connection bond to the center of one ring within a ring system (as shown in Figure k) represents connection of the connection bond at any substitutable position on the A ring or B ring attached to the rest of the molecule. For example, Figure k represents possible substitution attached to the rest of the molecule in any of the position A ring or on the B ring.

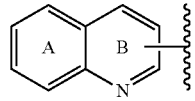

Figure k

As described herein, a bond drawn from a substituent to the center of one ring within a ring system (as shown below) represents substitutions of one or more $R^1$ at any substitutable position on the ring. For example, Figure n represents possible substitutions of one or more $R^1$ in any of the position on the ring shown in Figure m.

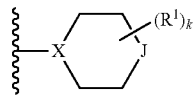

Figure n

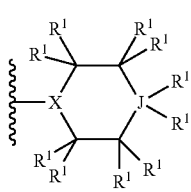

Figure m

As described herein, two attaching points within a ring system may be attach to the rest of the molecule, For example, as shown in —$(CH_2)_m$—O—, —$(CH_2)_m$—O— can also be expressed by —O—$(CH_2)_m$—, i.e., both end of —$(CH_2)_m$—O— may be used interchangeably with each other; as shown in Formula p, either E or E' can attach to the rest of the molecule and be used interchangeably with each other.

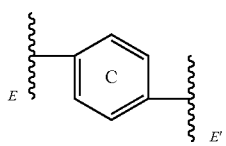

Figure p

Furthermore, what need to be explained is that the phrases "each . . . and . . . is independently", "each of . . . and . . . is independently" are used interchangeably. It should be broadly understood that the specific options expressed by the same symbol are variable independently of each other in different groups; or the specific options expressed by the same symbol are variable independently of each other in same groups. For example, specific options of $E^1$ between figure t and figure r are variable independently of each other; at the same time, in the same structure, as shown in figure s, specific options of multiple $R^9$ are variable independently each other, and specific options of multiple q are variable independently of each other.

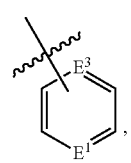

Figure t

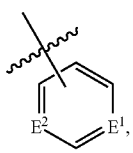

Figure r

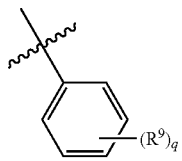

Figure s

Unless otherwise stated, structures depicted herein are also meant to include all isomeric (e.g., enantiomeric, diastereomeric, geometric or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, geometric or conformational mixtures of the present compounds are within the scope disclosed herein.

Unless otherwise stated, structures and compounds depicted herein are also meant to include all isomeric (e.g., enantiomeric, diastereomeric, geometric or conformational), N-oxide, hydrate, solvate, metabolite, pharmaceutically acceptable salt or prodrug thereof. Therefore, single stereochemical isomers, enantiomeric, diastereomeric, geometric, conformational, N-oxide, hydrate, solvate, metabolite, pharmaceutically acceptable salt or prodrug thereof are within the scope disclosed herein. Additionally, unless otherwise stated, structures depicted herein are also meant to include compounds that differ only in the presence of one or more isotopically enriched atoms.

A "metabolite" depicted herein which show the similar active with Form (I) or Form (II) analogue in vivo or in vitro is a product produced through metabolism in the body of a specified compound or pharmaceutically acceptable salt, analogue or ramification thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

Stereochemical definitions and conventions used herein generally follow Parker et al., McGraw-Hill Dictionary of Chemical Terms (1984) McGraw-Hill Book Company, New York and Eliel et al., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in *J. Pharmacol Sci,* 1977, 66, 1-19, which is incorporated herein by reference. Some non-limiting examples of pharmaceutically acceptable salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, malic acid salt, 2-hydracrylic acid salt, alginate, ascorbate, aspartate, benzenesulfonate, benzoate, bisulfate, borate, butyrate, camphanic acid salt, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "hydrate" refers to the complex where the solvent molecule is water.

A "solvate" refers to an association or complex of one or more solvent molecules and a compound disclosed herein. Some non-limiting examples of solvents that form solvates include water, isopropanol, ethanol, methanol, DMSO, ethyl acetate, acetic acid, and ethanolamine.

An "ester" refers to an in vivo hydrolysable ester of a compound of the Formula (I) or (II) containing hydroxy group, for example, a pharmaceutically acceptable ester which is hydrolysed in the human or animal body to produce the parent alcohol. Some non-limiting examples of in vivo hydrolysable ester forming groups for hydroxy include phosphate, acetoxymethoxy, 2,2-dimethylpropionyloxymethoxy, alkanoyl, benzoyl, phenylacetyl, alkoxycarbonyl, dialkylcarbamoyl, N-(dialkylaminoethyl)-N-alkylcarbamoyl, and the like.

A "N-oxide" refers to one or more than one nitrogen atoms oxidised to form an N-oxide, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g. a peroxycarboxylic acid) (See, *Advanced Organic Chemistry*, by Jerry March, 4$^{th}$ Edition, Wiley Interscience, pages). More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The term "prodrug" refers to a compound that is transformed in vivo into a compound of Formula (I) or Formula (II). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in Higuchi et al., *Pro-drugs as Novel Delivery Systems*, Vol. 14, A.C.S. Symposium Series; Roche et al., ed., *Bioreversible Carriers in Drug Design*, American Pharmaceutical Association and Pergamon Press, 1987; Rautio et al., Prodrugs: Design and Clinical Applications, *Nature Reviews Drug Discovery*, 2008, 7, 255-270, and Hecker et al., Prodrugs of Phosphates and Phosphonates, *J Med. Chem.*, 2008, 51, 2328-2345, all of which are incorporated herein by reference.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (Boc), benzyloxycarbonyl (Cbz) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include acetyl and silyl. A "carboxy-protecting group" refers to a substituent of the carboxy group that blocks or protects the carboxy functionality. Some non-limiting examples of common carboxy-protecting groups include —$CH_2CH_2SO_2Ph$, cyanoethyl, 2-(trimethylsilyl) ethyl, 2-(trimethylsilyl) ethoxymethyl, 2-(p-toluenesulfonyl) ethyl, 2-(p-nitrophenylsulfonyl) ethyl, 2-(diphenyl phosphino)-ethyl, nitroethyl, and the like. For a general description of protecting groups and their use, see Greene et al., *Protective Groups in*

DESCRIPTION OF COMPOUNDS OF THE INVENTION

Provided herein are new compounds or pharmaceutical compositions that may be more effective to prevent or treat human or animal tissue fibrosis.

In one aspect, provided herein are compounds having Formula (I) as shown below, or a stereoisomer, a geometric isomer, a tautomer, an N-oxide, a hydrate, a solvate, a metabolite, a pharmaceutically acceptable salt or a prodrug thereof, $$\text{(I)}$$

wherein, each of $Q^1$ and $Q^2$ is independently N or CH; X is N or CH;

J is —O—, —C(=S)—, —(CH$_2$)$_m$—O—, —C(=O)—, —C(=O)O—, —S(=O)$_t$—, —(CH$_2$)$_m$—N(R$^6$)—, —N(R$^6$)—, —S(=O)$_t$N(R$^6$)—, —CH=CH—, —N(R$^6$)C(=O)— or —(CH$_2$)$_m$—;

each $R^1$ is independently —Y—R$^5$, wherein each Y is independently —O—, —C(=S)—, —(CH$_2$)$_m$—O—, —C(=O)—, —C(=O)O—, —S(=O)$_t$—, —(CH$_2$)$_m$—N(R$^6$)—, —N(R$^6$)—, —S(=O)$_t$N(R$^6$)—, —CH=CH—, —N(R$^6$)C(=O)— or —(CH$_2$)$_m$—;

each $R^{1a}$ is independently H, F, Cl, Br, I, cyano, hydroxy, amino, carboxy, alkyl, haloalkyl, alkoxy, alkylamino, alkylthio, alkenyl, alkynyl, nitro, mercapto, hydroxyalkoxy, hydroxyalkyl, aminoalkoxy, alkyl-O—C(=O)—, aryl, arylalkyl, heteroaryl, heteroarylalkyl, heterocyclyl, heterocyclylalkyl, cycloalkyl, aryloxy, heteroaryloxy, haloalkoxy or cycloalkylalkyl;

each of $R^2$ and $R^3$ is independently H, F, Cl, Br, I, cyano, hydroxy, carboxy, alkyl, haloalkyl, alkoxy, hydroxyalkoxy, hydroxyalkyl, aminoalkoxy, haloalkoxy, aryl, arylalkyl, heteroaryl, heteroarylalkyl, heterocyclyl, heterocyclylalkyl, cycloalkyl or cycloalkylalkyl;

each $R^4$ is independently H, hydroxy, carboxy, amino, F, Cl, Br, I, cyano, nitro, mercapto, alkyl, haloalkyl, alkoxy, alkylamino, alkylthio, aryl, arylalkyl, heteroaryl, heteroarylalkyl, heterocyclyl, heterocyclylalkyl, cycloalkyl or cycloalkylalkyl;

each $R^5$ is independently bridged heterobicyclyl, bridged bicyclyl, fused bicyclyl, fused heterobicyclyl, aryl, arylalkyl, heteroaryl, heteroarylalkyl, heterocyclyl, heterocyclylalkyl, cycloalkyl or cycloalkylalkyl;

each $R^6$ is independently H, hydroxy, amino, alkyl, haloalkyl, alkoxy, alkylamino, alkylthio, aryl, arylalkyl or heteroaryl;

each t is independently 0, 1 or 2;
each m is independently 1, 2, 3 or 4;
each of n and p is independently 0, 1, 2, 3 or 4; and
k is 1, 2, 3 or 4;

wherein each of —(CH$_2$)$_m$—O—, —(CH$_2$)$_m$—N(R$^6$)—, —N(R$^6$)—, —S(=O)$_t$N(R$^6$)—, —CH=CH—, —N(R$^6$)C(=O)—, —(CH$_2$)$_m$—, alkyl, alkenyl, alkynyl, haloalkyl, alkoxy, hydroxyalkoxy, hydroxyalkyl, aminoalkoxy, alkyl-O—C(=O)—, aryl, aryloxy, heteroaryloxy, haloalkoxy, arylalkyl, heteroaryl, heteroarylalkyl, heterocyclyl, heterocyclylalkyl, cycloalkyl, cycloalkylalkyl, bridged heterobicyclyl, bridged bicyclyl, fused bicyclyl, fused heterobicyclyl, alkylamino and alkylthio is independently and optionally substituted with one or more substituents independently selected from H, oxo (=O), F, Cl, Br, I, alkyl —O—C(=O)—, alkyl, alkenyl, alkynyl, alkoxy, haloalkyl, cyano, nitro, amino, alkylamino, mercapto, alkylthio, aryl, aryloxy, heteroaryl, heteroaryloxy and haloalkoxy.

In some embodiments,
each $R^5$ is independently $C_{5-12}$ bridged heterobicyclyl, $C_{5-12}$ bridged bicyclyl, $C_{5-12}$ fused bicyclyl, $C_{5-12}$ fused heterobicyclyl, $C_{6-10}$ aryl, $C_{6-10}$ aryl-$C_{1-4}$-alkyl, $C_{1-9}$ heteroaryl, $C_{1-9}$ heteroaryl-$C_{1-4}$-alkyl, $C_{2-10}$ heterocyclyl, $C_{2-10}$ heterocyclyl-$C_{1-4}$-alkyl, $C_{3-10}$ cycloalkyl or $C_{3-10}$ cycloalkyl-$C_{1-4}$-alkyl; and each $R^6$ is independently H, hydroxy, amino, $C_{1-4}$ alkyl, $C_{1-4}$ haloalkyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl or $C_{1-9}$ heteroaryl;

wherein each of —(CH$_2$)$_m$—O—, —(CH$_2$)$_m$—N(R$^6$)—, —N(R$^6$)—, —S(=O)$_t$N(R$^6$)—, —CH=CH—, —N(R$^6$)C(=O)—, —(CH$_2$)$_m$—, $C_{1-4}$ alkyl, $C_{1-4}$ haloalkyl, $C_{1-4}$ alkoxy, $C_{5-12}$ bridged heterobicyclyl, $C_{5-12}$ bridged bicyclyl, $C_{5-12}$ fused bicyclyl, $C_{5-12}$ fused heterobicyclyl, $C_{6-10}$ aryl, $C_{6-10}$ aryl-$C_{1-4}$-alkyl, $C_{1-9}$ heteroaryl, $C_{1-9}$ heteroaryl-$C_{1-4}$-alkyl, $C_{2-10}$ heterocyclyl, $C_{2-10}$ heterocyclyl-$C_{1-4}$-alkyl, $C_{3-10}$ cycloalkyl, $C_{3-10}$ cycloalkyl-$C_{1-4}$-alkyl, $C_{1-4}$ alkylamino and $C_{1-4}$ alkylthio is independently and optionally substituted with one or more substituents independently selected from H, oxo (=O), F, Cl, Br, I, $C_{1-4}$ alkyl-O—C(=O)—, $C_{1-4}$ alkyl, $C_{2-4}$ alkenyl, $C_{2-4}$ alkynyl, $C_{1-4}$ alkoxy, $C_{1-4}$ haloalkyl, cyano, nitro, amino, $C_{1-4}$ alkylamino, mercapto, $C_{1-4}$ alkylthio, $C_{6-10}$ aryl, $C_{6-10}$ aryloxy, $C_{1-9}$ heteroaryl, $C_{1-9}$ heteroaryloxy and $C_{1-4}$ haloalkoxy.

In other embodiments,
each $R^{1a}$ is independently H, F, Cl, Br, I, cyano, hydroxy, amino, carboxy, $C_{1-4}$ alkyl, $C_{1-4}$ haloalkyl, $C_{1-4}$ alkoxy, $C_{1-4}$ alkylamino, $C_{1-4}$ alkylthio, $C_{2-4}$ alkenyl, $C_{2-4}$ alkynyl, nitro, mercapto, $C_{1-4}$ hydroxyalkoxy, $C_{1-4}$ hydroxyalkyl, $C_{1-4}$ aminoalkoxy, $C_{1-4}$ alkyl-O—C(=O)—, $C_{6-10}$ aryl, $C_{6-10}$ aryl-$C_{1-4}$-alkyl, $C_{1-9}$ heteroaryl, $C_{1-9}$ heteroaryl-$C_{1-4}$-alkyl, $C_{2-10}$ heterocyclyl, $C_{2-10}$ heterocyclyl-$C_{1-4}$-alkyl, $C_{3-10}$ cycloalkyl, $C_{6-10}$ aryloxy, $C_{1-9}$ heteroaryloxy, $C_{1-4}$ haloalkoxy or $C_{3-10}$ cycloalkyl-$C_{1-4}$-alkyl;

each of $R^2$ and $R^3$ is independently H, F, Cl, Br, I, cyano, carboxy, hydroxy, $C_{1-6}$ alkyl, $C_{1-6}$ haloalkyl, $C_{1-6}$ alkoxy, $C_{1-6}$ hydroxyalkoxy, $C_{1-6}$ hydroxyalkyl, $C_{1-6}$ aminoalkoxy, $C_{1-6}$ haloalkoxy, $C_{6-10}$ aryl, $C_{6-10}$ aryl-$C_{1-6}$-alkyl, $C_{1-9}$ heteroaryl, $C_{1-9}$ heteroaryl-$C_{1-6}$-alkyl, $C_{2-10}$ heterocyclyl, $C_{2-10}$ heterocyclyl-$C_{1-6}$-alkyl, $C_{3-10}$ cycloalkyl or $C_{3-10}$ cycloalkyl-$C_{1-6}$-alkyl; and each $R^4$ is independently H, hydroxy, carboxyl, amino, F, Cl, Br, I, cyano, nitro, mercapto, $C_{1-4}$ alkyl, $C_{1-6}$ haloalkyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl, $C_{1-9}$ heteroaryl, $C_{1-9}$ heteroaryl-$C_{1-6}$-alkyl, $C_{2-10}$ heterocyclyl, $C_{2-10}$ heterocyclyl-$C_{1-6}$-alkyl, $C_{3-10}$ cycloalkyl or $C_{3-10}$ cycloalkyl-$C_{1-6}$-alkyl.

In some embodiments, provided herein are compounds having Formula (II), or a stereoisomer, a geometric isomer, a tautomer, an N-oxide, a hydrate, a solvate, a metabolite, a pharmaceutically acceptable salt or a prodrug thereof,

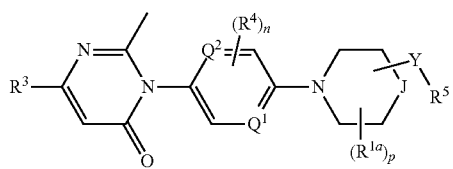

(II)

wherein, each of $Q^1$ and $Q^2$ is independently N or CH;
J is —O— or —(CH$_2$)$_m$—; and
Y is —O—, —(CH$_2$)$_m$—O—, —(CH$_2$)$_m$—N(R$^6$)—, —N(R$^6$)— or —(CH$_2$)$_m$—;

Wherein, each $R^5$, $R^3$, $R^4$, n, m, $R^6$, $R^{1a}$ and p is as defined herein.

In other embodiments, each Y is independently —O—, —(CH$_2$)$_m$—O—, —(CH$_2$)$_m$—N(R$^6$)—, —N(R$^6$)— or —(CH$_2$)$_m$—;

each $R^5$ is independently

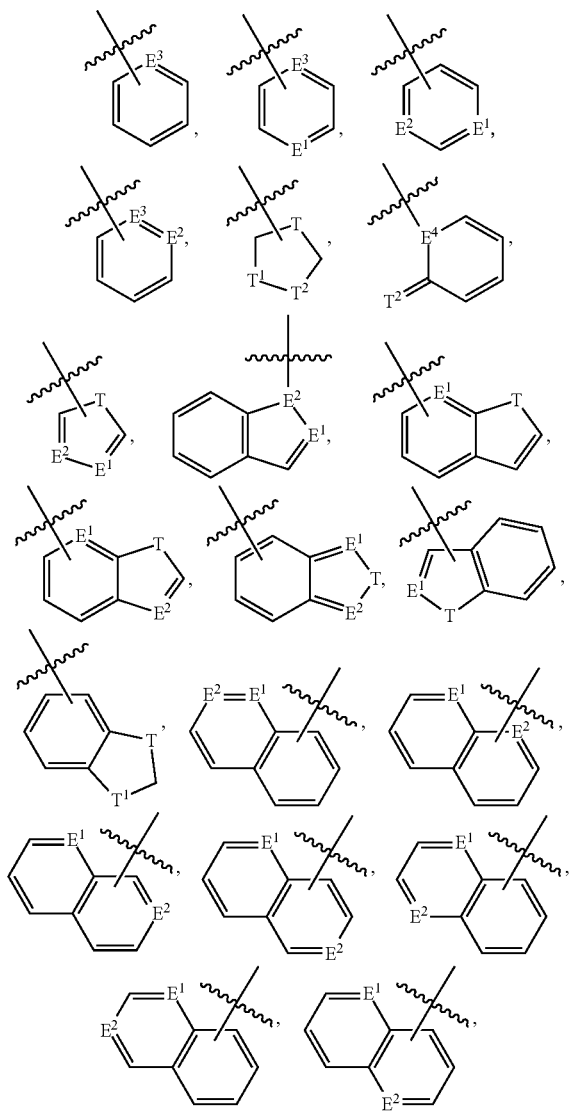

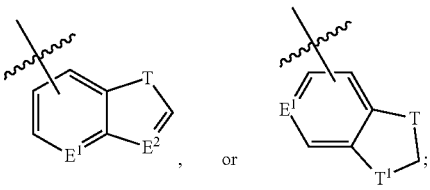

wherein, each $E^1$, $E^2$, $E^3$ and $E^4$ is independently N or $CR^7$;

each T, $T^1$ and $T^2$ is independently —NR$^8$—, —O—, —S— or —CR$^7$R$^{7a}$;

each $R^7$ and $R^{7a}$ is independently H, F, Cl, Br, I, $C_{1-4}$ alkyl-O—C(=O)—, $C_{1-4}$ alkyl, $C_{2-4}$ alkenyl, $C_{2-4}$ alkynyl, $C_{1-4}$ alkoxy, $C_{1-4}$ haloalkyl, cyano, nitro, amino, $C_{1-4}$ alkylamino, mercapto, $C_{1-4}$ alkylthio, $C_{6-10}$ aryl, $C_{6-10}$ aryloxy, $C_{1-9}$ heteroaryl, $C_{1-9}$ heteroaryloxy or $C_{1-4}$ haloalkoxy;

wherein, each $R^5$ is independently and optionally substituted with one or more substituents independently selected from H, oxo (=O), F, Cl, Br, I, $C_{1-4}$ alkyl —O—C(=O)—, $C_{1-4}$ alkyl, $C_{2-4}$ alkenyl, $C_{2-4}$ alkynyl, $C_{1-4}$ alkoxy, $C_{1-4}$ haloalkyl, cyano, nitro, amino, $C_{1-4}$ alkylamino, mercapto, $C_{1-4}$ alkylthio, $C_{6-10}$ aryl, $C_{6-10}$ aryloxy, $C_{1-9}$ heteroaryl, $C_{1-9}$ heteroaryloxy and $C_{1-4}$ haloalkoxy;

each $R^6$ is independently H, hydroxy, amino, $C_{1-4}$ alkyl, $C_{1-4}$ haloalkyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl or $C_{1-9}$ heteroaryl;

each $R^8$ is independently H, $C_{1-4}$ alkyl-O—C(=O)—, $C_{1-4}$ alkyl, $C_{2-4}$ alkenyl, $C_{2-4}$ alkynyl, $C_{1-4}$ alkoxy, $C_{1-4}$ haloalkyl, amino, $C_{1-4}$ alkylamino, $C_{1-4}$ alkylthio, $C_{6-10}$ aryl or $C_{1-9}$ heteroaryl; and each m is as define herein.

In other embodiments, each $R^5$ is independently

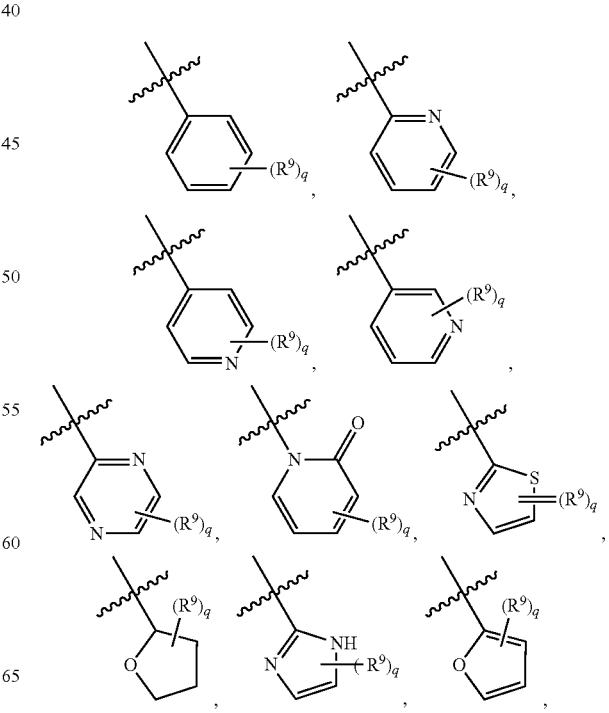

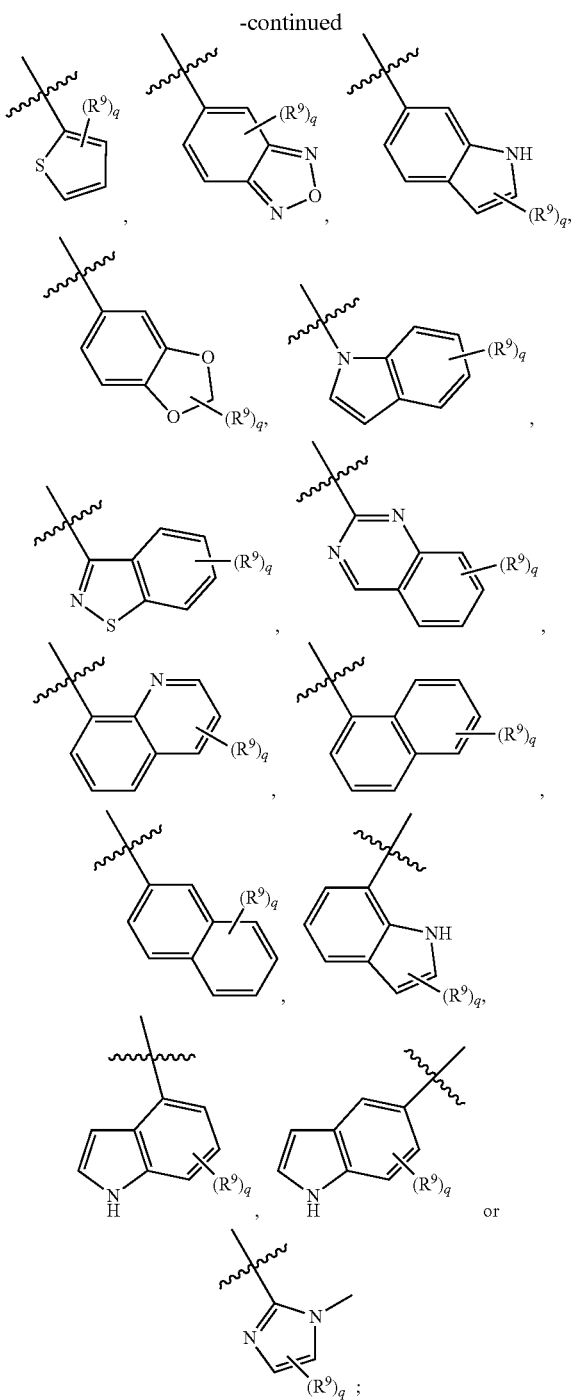

wherein, each $R^9$ is independently H, oxo (=O), F, Cl, Br, I, $C_{1-4}$ alkyl-O—C(=O)—, $C_{1-4}$ alkyl, $C_{2-4}$ alkenyl, $C_{2-4}$ alkynyl, $C_{1-4}$ alkoxy, $C_{1-4}$ haloalkyl, cyano, nitro, amino, $C_{1-4}$ alkylamino, mercapto, $C_{1-4}$ alkylthio, $C_{6-10}$ aryl, $C_{6-10}$ aryloxy, $C_{1-9}$ heteroaryl, $C_{1-9}$ heteroaryloxy or $C_{1-4}$ haloalkyloxy; and each q is independently 0, 1, 2, 3, 4, 5, 6 or 7.

In other embodiments, each $R^9$ is independently H, oxo (=O), F, Cl, Br, I, methyl-O—C(=O)—, ethyl-O—C(=O)—, propyl-O—C(=O)—, butyl-O—C(=O)—, tert-butyl—O—C(=O)—, isopropyl-O—C(=O)—, methyl, ethyl, propyl, butyl, tert-butyl, isopropyl, ethenyl, 3-propenyl, propenyl, $C_{2-4}$ alkynyl, methoxy, ethoxy, propoxy, butoxy, trifluoromethyl, chloromethyl, trifluoroethyl, 1-fluoroethyl, cyano, nitro, amino, methylamino, dimethylamino, ethylamino, diethylamino, mercapto, methylthio, ethylthio, propylthio, $C_{6-10}$ aryl, phenoxy, $C_{1-9}$ heteroaryl, $C_{1-9}$ heteroaryloxy, trifluoroethoxy or trifluoromethoxy.

In other embodiments, each $R^{1a}$ is independently H, F, Cl, Br, I, cyano, hydroxy, amino, carboxyl, methyl, ethyl, propyl, butyl, tert-butyl, isopropyl, trifluoromethyl, trifluoroethyl, 1-fluoromethyl, 1-chloroethyl, methoxy, propoxy, ethoxy, methylamino, ethylamino, dimethylamino, diethylamino, methylthio, ethylthio, $C_{2-4}$ alkenyl, $C_{2-4}$ alkynyl, nitro, mercapto, $C_{1-4}$ hydroxyalkoxy, $C_{1-4}$ hydroxyalkyl, $C_{1-4}$ aminoalkoxy, $C_{1-4}$ alkyl-O—C(=O)— or phenyl;

each of $R^2$ and $R^3$ is independently H, F, Cl, Br, I, cyano, carboxyl, hydroxy, methyl, ethyl, propyl, butyl, tert-butyl, trifluoromethyl, chloromethyl, trifluoroethyl, 1-chloroethyl, methoxy, ethoxy, propoxy, $C_{1-4}$ hydroxyalkoxy, $C_{1-4}$ hydroxyalkyl, $C_{1-4}$ aminoalkoxy, trifluoromethoxy, 1-chloroethoxy, phenyl or phenyl-$C_{1-4}$-alkyl; and each $R^4$ is independently H, F, Cl, Br, I, cyano, carboxyl, hydroxy, methyl, ethyl, propyl, butyl, tert-butyl, trifluoromethyl, chloromethyl, trifluoroethyl, 1-chloroethyl, methoxy, ethoxy, propoxy, $C_{1-4}$ hydroxyalkoxy, $C_{1-4}$ hydroxyalkyl, $C_{1-4}$ aminoalkoxy, trifluoromethoxy, 1-chloroethoxy, phenyl or phenyl-$C_{1-4}$-alkyl.

In some embodiments, provided herein are one of the compounds as follows, or a stereoisomer, a geometric isomer, a tautomer, an N-oxide, a solvate, a hydrate, a metabolite, an ester, a pharmaceutically acceptable salt or a prodrug, and not limited to

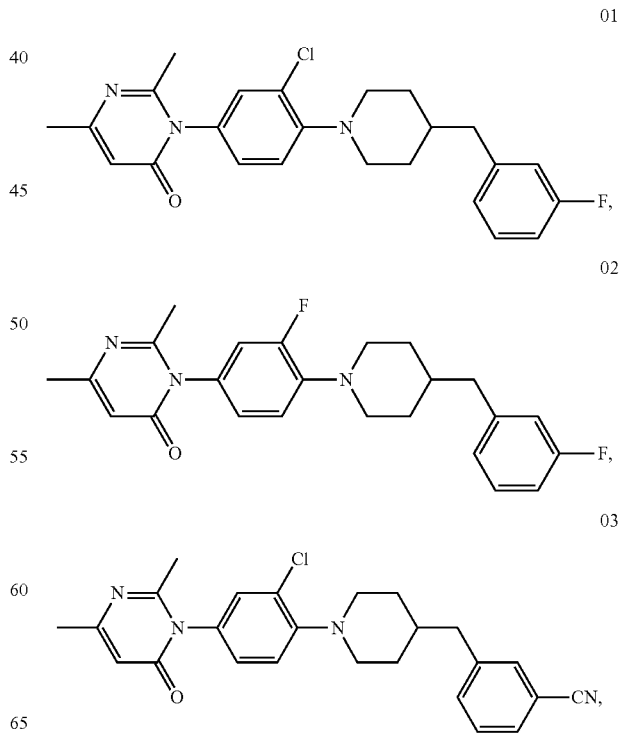

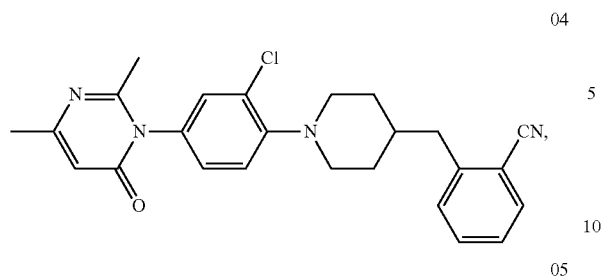
04
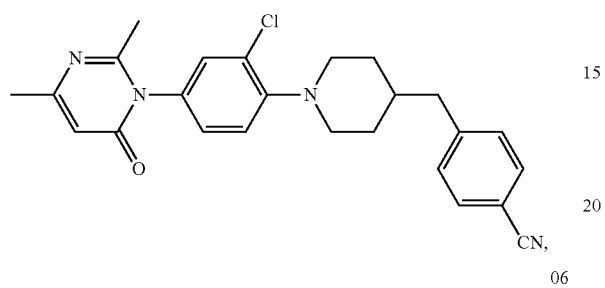
05
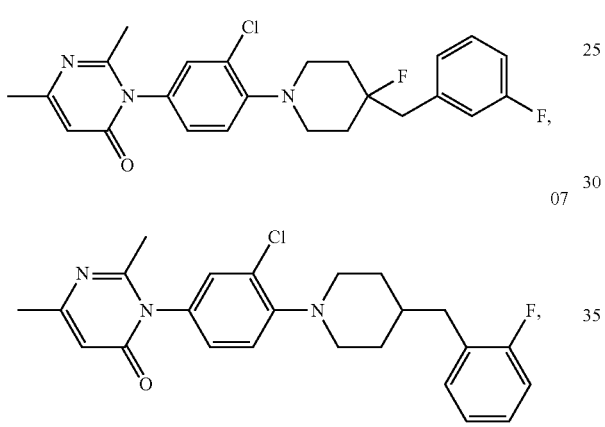
06
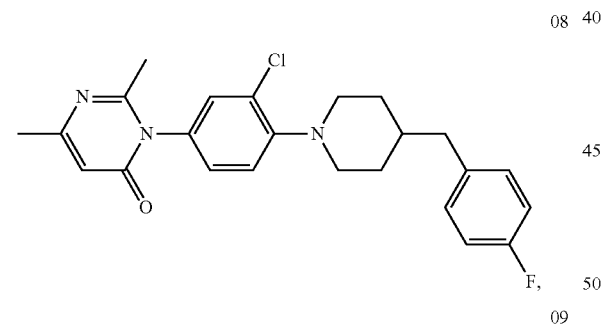
07
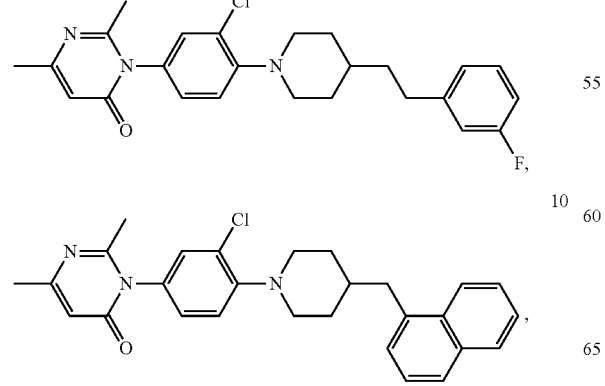
08
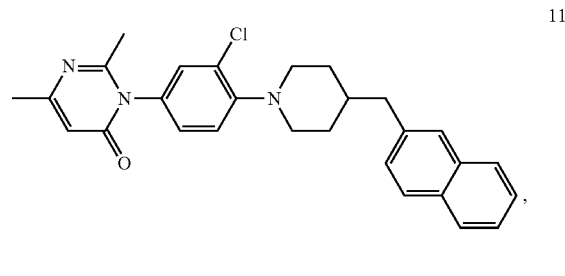
09
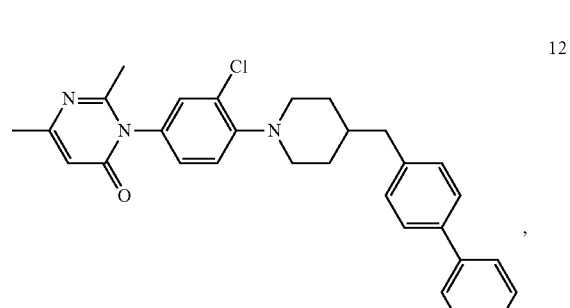
10
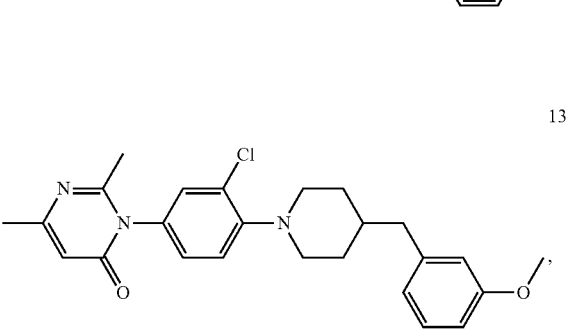
11
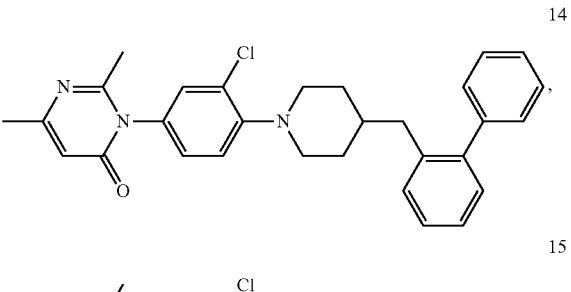
12
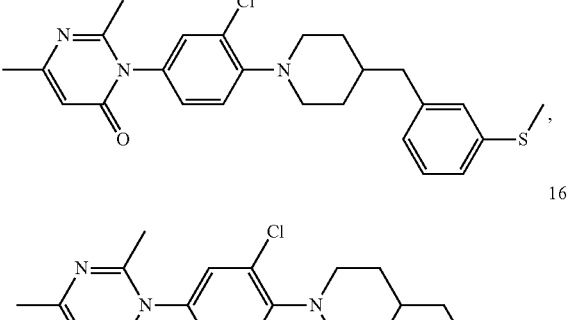
13
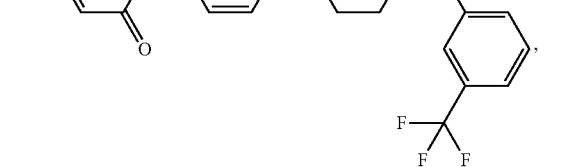
14
15
16

-continued
17
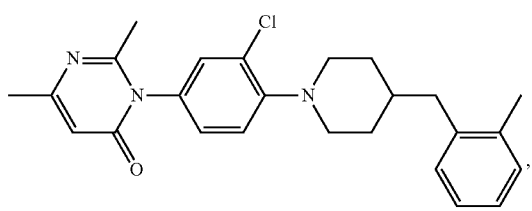
18
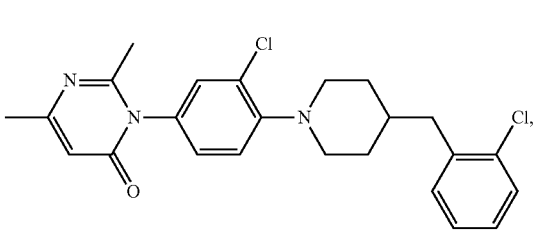
19
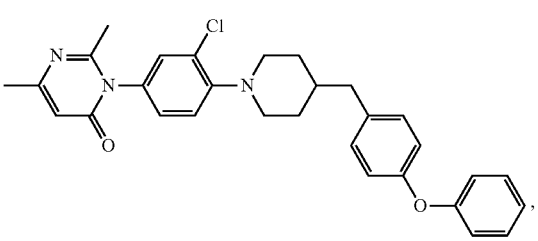
20
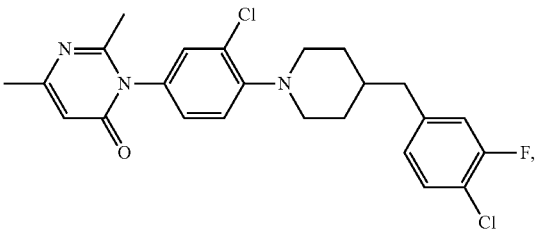
21
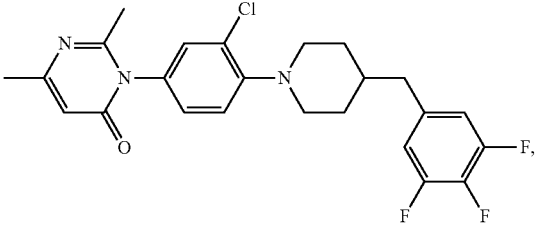
22
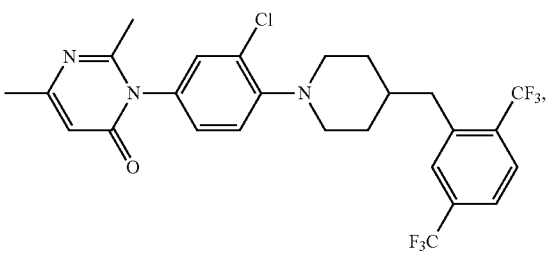
-continued
23
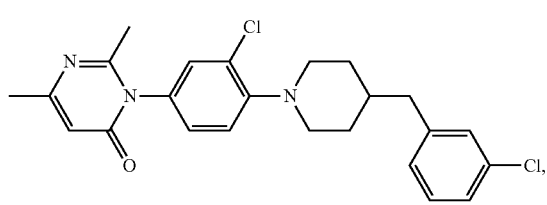
24
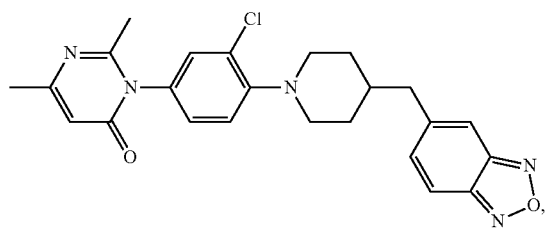
25
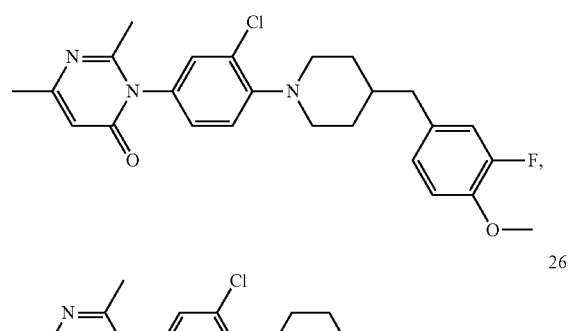
26
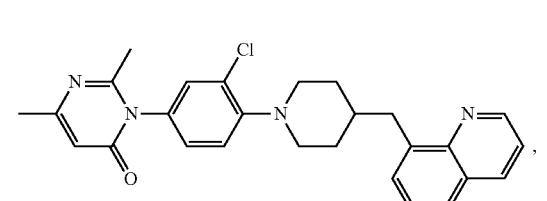
27
28
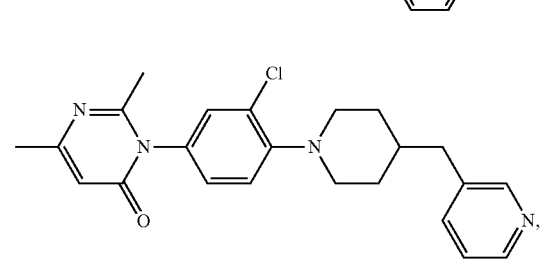
29
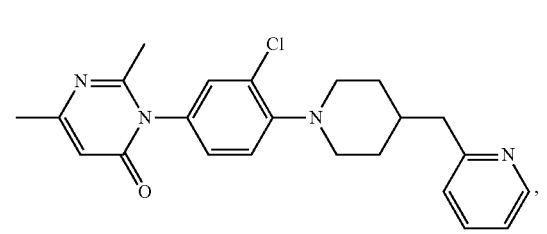

-continued

30

31

32

33

34

35

36

-continued

37

38

39

40

41

42

43

44
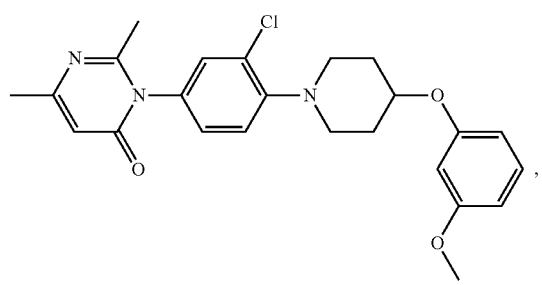
45
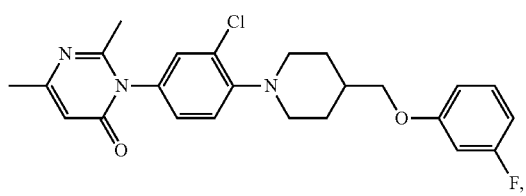
46
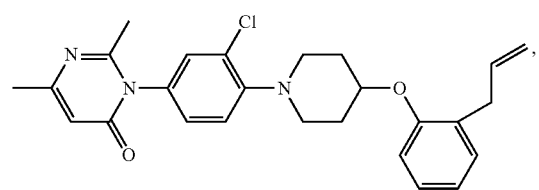
47
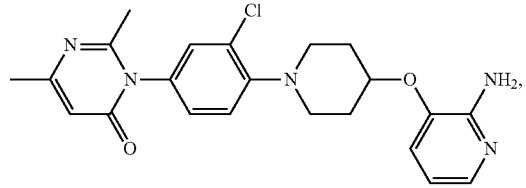
48
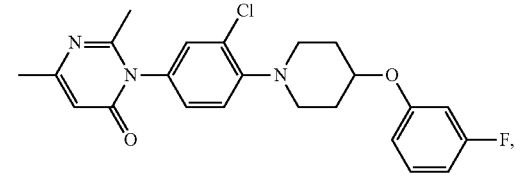
49
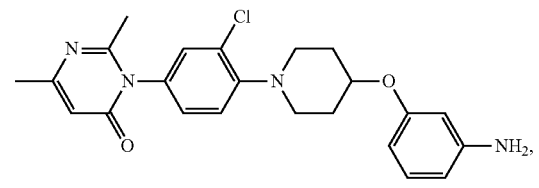
50
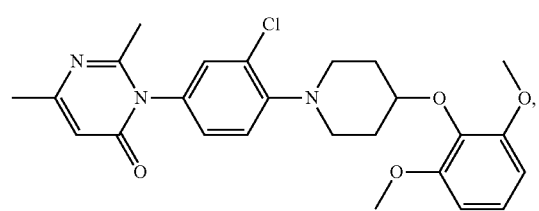
51
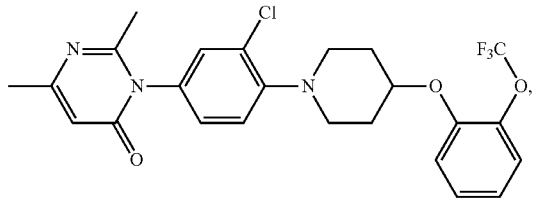
52
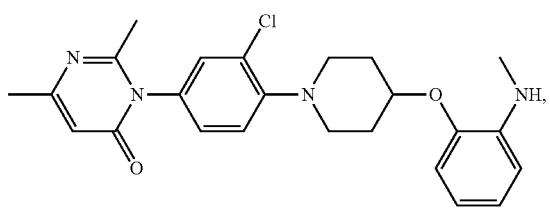
53
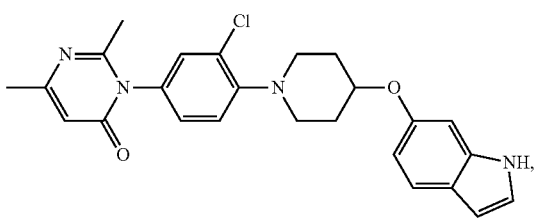
54
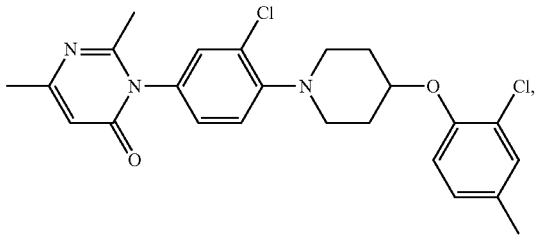
55
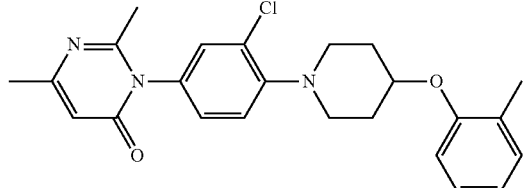
56
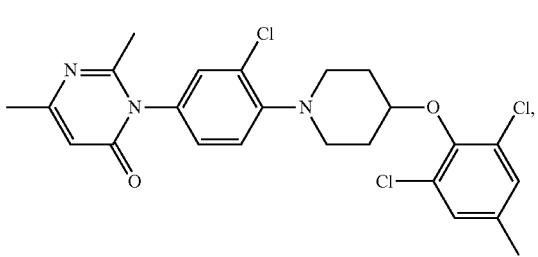

-continued

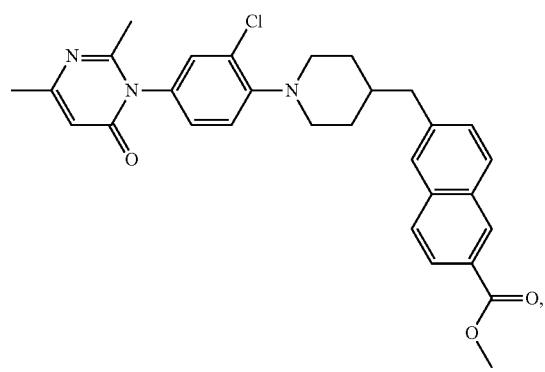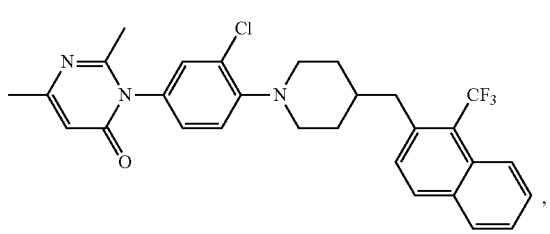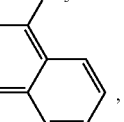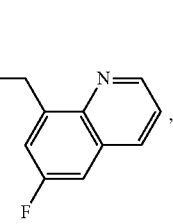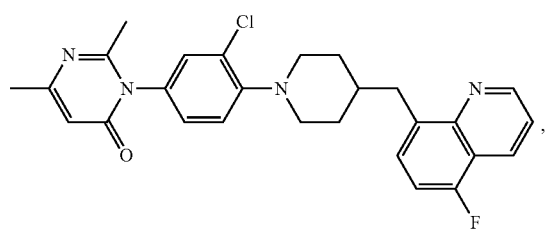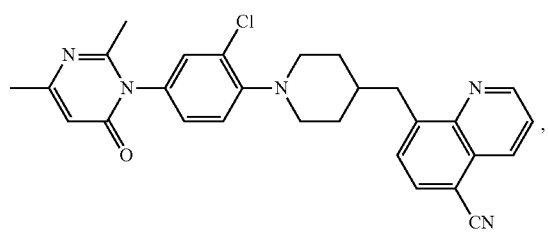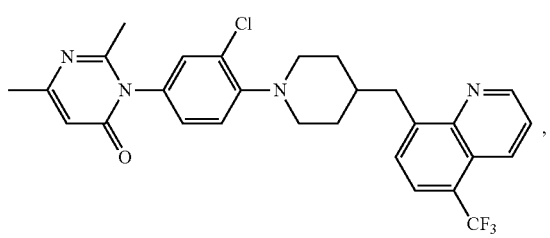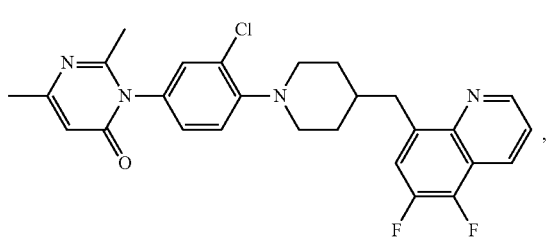

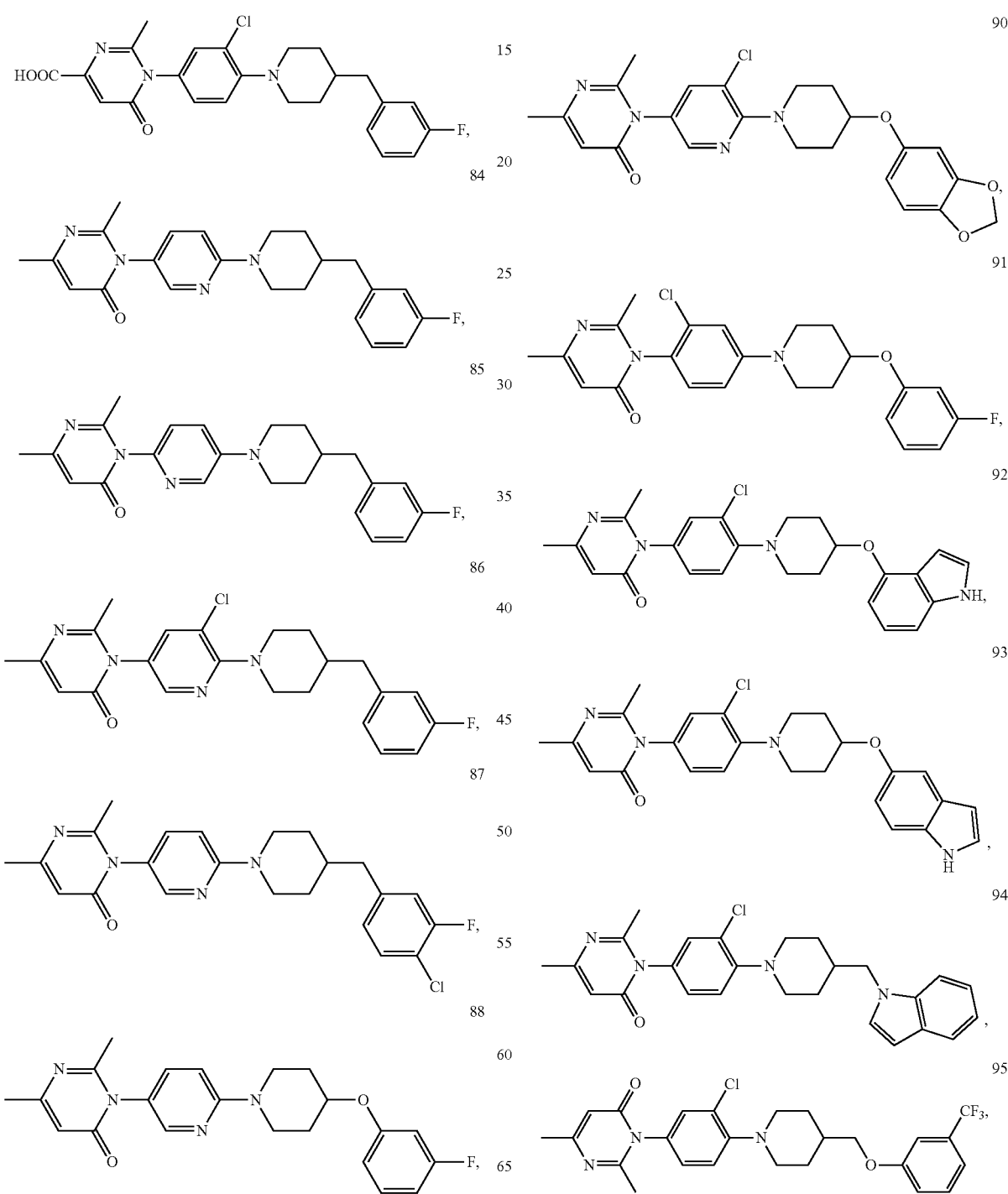

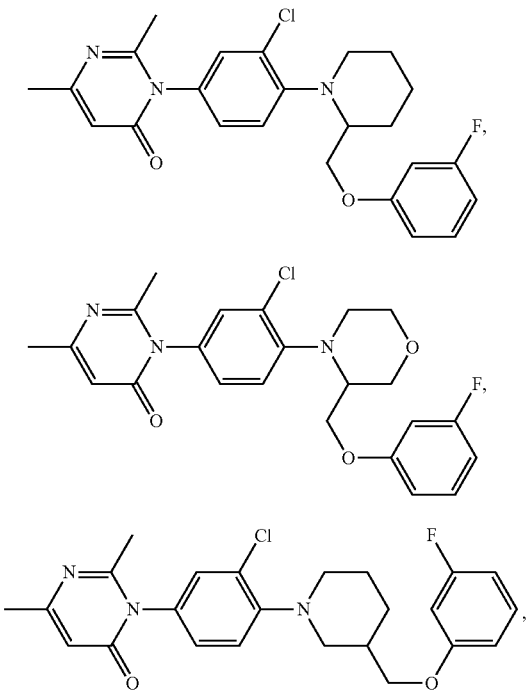

In one aspect, provided herein are pharmaceutical compositions comprising a compound of Formula (I) or Formula (II) disclosed herein, or a stereoisomer, geometric isomer, tautomer, nitrogen oxide, hydrate, solvate, metabolite, pharmaceutically acceptable salt or prodrug thereof; and an optionally pharmaceutically acceptable carrier, excipient, diluent, adjuvant, vehicle or a combination thereof.

In one aspect, provided herein is use of the compound of Formula (I) or Formula (II) disclosed herein in the manufacture of a medicament for preventing, managing, treating or lessening the severity of a tissue or organ fibrosis.

In some embodiments, the tissue or organ fibrosis is renal interstitial fibrosis, glomerulosclerosis, liver fibrosis, pulmonary fibrosis, IPF, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

In one aspect, provided herein is the compound or pharmaceutical composition of Formula (I) or Formula (II) disclosed herein for use in preventing, managing, treating or lessening the severity of tissue or organ fibrosis.

In some embodiments, the tissue or organ fibrosis is renal interstitial fibrosis, glomerulosclerosis, liver fibrosis, pulmonary fibrosis, IPF, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

In one aspect, provided herein is a method for preventing, managing, treating or lessening the severity of tissue or organ fibrosis comprising administering to a patient a therapeutically effective amount of the compound or the pharmaceutical composition.

In some embodiments, the tissue or organ fibrosis is renal interstitial fibrosis, glomerulosclerosis, liver fibrosis, pulmonary fibrosis, IPF, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

In one aspect, provided herein are methods for preventing, managing, treating or lessening the severity of tissue or organ fibrosis, which comprises administering a pharmaceutically effective amount of the compound or a pharmaceutical composition disclosed herein to the patient.

In some embodiments, the tissue or organ fibrosis is renal interstitial fibrosis, glomerulosclerosis, liver fibrosis, pulmonary fibrosis, IPF, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

In another aspect, provided herein is use of the compound of Formula (I) or Formula (II) or pharmaceutical composition disclosed herein in the manufacture of a medicament for preventing, managing, treating or lessening the severity of a tissue or organ fibrosis.

In one aspect, provided herein are methods for preventing, managing, treating or lessening the severity of tissue or organ fibrosis, which comprises administering a pharmaceutically effective amount of the compound disclosed herein to a patient.

In another aspect, provided herein is use of the pharmaceutical composition of Formula (I) or Formula (II) disclosed herein in the manufacture of a medicament for preventing, managing, treating or lessening the severity of a tissue or organ fibrosis.

In another aspect, provided herein is use of the compound of Formula (I) or Formula (II) or pharmaceutical composition disclosed herein for preventing, managing, treating or lessening the severity of a tissue or organ fibrosis in human or animal, which comprises administering a pharmaceutically effective amount of the (a) compound or pharmaceutical composition disclosed herein to a patient.

In another aspect, provided herein include methods of preparing, methods of separating, and methods of purifying compounds of Formula (I) or Formula (II).

Unless otherwise stated, all stereoisomers, geometric isomers, tautomers, nitrogen oxides, hydrates, solvates, metabolites, salts, and pharmaceutically acceptable prodrugs of the compounds disclosed herein are within the scope of the invention.

In certain embodiments, the salt is a pharmaceutically acceptable salt. The phrase "pharmaceutically acceptable" refers to that the substance or composition must be compatible chemically and/or toxicologically, with the other ingredients comprising a Formulation, and/or the mammal being treated therewith.

The compounds disclosed herein also include salts of such compounds which are not necessarily pharmaceutically acceptable salts, and which may be useful as intermediates for preparing and/or purifying compounds of Formula (I), or (II) and/or for separating enantiomers of compounds of Formula (I), or (II).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like. Or with an organic acid, such as acetic acid, maleic acid, succinic acid, mandelic acid, fumaric acid, malonic acid, pyruvic acid, oxalic acid, glycolic acid, salicylic acid; a pyranosidyl acid, such as glucuronic acid or galacturonic acid; an alpha hydroxy acid, such as citric acid or tartaric acid; an amino acid, such as aspartic acid or glutamic acid; an aromatic acid, such as benzoic acid or cinnamic acid, a sulfonic acid, such as p-toluenesulfonic acid or ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or alkaline earth metal hydroxide, and the like. Some non-limiting examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum, lithium, and the like.

Composition, Formulations and Administration of Compounds of the Invention

According to another aspect, the features of pharmaceutical compositions disclosed herein include a compound of Formula (I) or (II), a compound listed herein, or a compound named in Examples 1-68, and a pharmaceutically acceptable carrier, adjuvant, or vehicle. The amount of the compound in the compositions disclosed herein is such that is effective to detectably treat or lessen the severity of a tissue or organ fibrosis.

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable compositions disclosed herein additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Troy et al., *Remington: The Science and Practice of Pharmacy,* 21st ed., 2005, Lippincott Williams & Wilkins, Philadelphia and Swarbrick et al., Encyclopedia of Pharmaceutical Technology, eds., 1988-1999, Marcel Dekker, New York, all of which are herein incorporated by reference in their entireties, are disclosed various carriers used in Formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

Some non-limiting examples of materials which can serve as pharmaceutically acceptable carriers include ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The compositions disclosed herein may be administered orally, parenterally, by inhalation spray, topically, rectally, nasally, buccally, vaginally or via an implanted reservoir. The pharmaceutically acceptable compositions disclosed herein include orally administered in any orally acceptable dosage form including, but not limited to, capsules, tablets, pills, powders, granules, aqueous suspensions or solutions.

The compositions disclosed herein can be orally administered in the following dosage forms: tablets, pellets, capsules, dispensable powders, particles or suspensions, syrup, and elixirs. Alternatively, the compositions disclosed herein can be for external use in the form of ointment, gel, or medicated patch; or they can be administered parenterally in the form of sterile injectable solution or suspension.

The compounds disclosed herein may be administered parenterally or intraperitoneally. The compounds disclosed herein (as free bases or pharmaceutically acceptable salt) may be formulated into solutions or suspensions in water suitably mixed with surfactant (e.g. hydroxypropyl cellulose, polyvinyl pyrrolidone). Dispersion can also be prepared from a mixture of the active compounds in glycerin, liquid, polyethylene glycol and oil. In the normal condition of storage and usage, these preparations may contain preservatives to prevent the growth of microorganisms.

The pharmaceutical forms suitable for injection include sterile water or dispersion and sterile powder (used for the temporary preparation of sterile injectable solutions or dispersions). In all the cases, these forms must be sterile, and they must be fluidic to allow their discharge from the injection syringe. These forms must be stable in the condition of production and storage, and they must prevent from the pollution of microorganisms (such as bacteria and fungi). The carriers may be solvents or dispersion media, including, for example, water, alcohols (such as glycerin, propylene glycol and liquid polyethylene glycol), plant oil and combinations thereof.

The compounds disclosed herein can be administered in a local rather than systemic manner, for example, via injection of the compound directly into organ, often in a depot or sustained release formulation. Furthermore, the pharmaceutical composition comprising a compound disclosed herein can be administered in a targeted drug delivery system, for example, in a liposome coated with organ-specific antibody.

The liposomes may be targeted to and taken up selectively by the organ. In addition, the pharmaceutical compositions comprising a compound disclosed herein may be provided in the form of a rapid release formulation, in the form of an extended release formulation, or in the form of an intermediate release formulation.

For administration by inhalation, the compounds disclosed herein may be in a form as an aerosol, a mist or a powder. The pharmaceutical compositions comprising a compound disclosed herein may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a value to deliver a metered amount. Capsules and cartridges, such as, by way of example only, gelatin for use in an inhaler or insufflators maybe formulated containing a powder mix of the compound disclosed herein and a suitable powder base such as lactose or starch.

The compounds disclosed herein may also be formulated in rectal compositions such as enemas, rectal gels, rectal foams, rectal aerosol, suppositories, jelly suppositories, or retention enemas, containing conventional suppository bases such as cocoa butter or other glycerides, as well as any synthetic polymers suitable for preparing suppository bases such as polyvinylpyrrolidone, PEG, and the like. In suppository forms of the compositions, a low-melting wax such as, but not limited to, a mixture of fatty acid glycerides, optionally in combination with cocoa butter is first melted.

Additionally, the compound disclosed herein may be used in combination with other agents of treating fibrosis, such as, but not limited to, ivacaftor, roflumilast, pirfenidone, miglustat, losartan, ACTIMMUNE® (interferon gamma-1B), dornase alfa, VELDONA® (interferon alfa), ataluren, cortical hormone, methotrexate, tacrolimus, and the like.

The pharmaceutical compositions disclosed herein may be formulated in conventional manner using one or more physiologically acceptable carriers comprising excipients and auxiliaries which facilitate processing of the active compounds into preparations which may be used pharmaceutically. Proper formulation is dependent upon the route of administration chosen. Any of the well-known techniques, carriers, and excipients may be used as suitable and as understood in the art. The pharmaceutical compositions comprising a compound disclosed herein may be manufactured in a conventional manner, such as, by way of example, by means of conventional mixing, dissolving, granulating, dragee-making, levigating, emulsifying, encapsulating, entrapping, or compression processes. The pharmaceutical compositions containing a compound of the invention may be administered in therapeutically effective amounts as pharmaceutical compositions by any conventional form and route known the art including, but not limited to: intravenous, oral, rectal, aerosol, parenteral, ophthalmic, pulmonary, transdermal, vaginal, otic, nasal, and topical administration.

The pharmaceutical compositions disclosed herein include at least one pharmaceutically acceptable carrier, diluent or excipient and a compound disclosed herein as an active ingredient in free-acid or free-base form, or in a pharmaceutically acceptable salt form. In addition, the pharmaceutical compositions disclosed herein include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions contain other therapeutically valuable substances.

The pharmaceutical compositions disclosed herein include at least one pharmaceutically acceptable carrier, diluent or excipient and a compound disclosed herein as an active ingredient in free-acid or free-base form, or in a pharmaceutically acceptable salt form. In addition, the pharmaceutical compositions disclosed herein include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions contain other therapeutically valuable substances.

Methods for the preparation of the pharmaceutical compositions disclosed herein include formulating the compounds disclosed herein with one or more inert, pharmaceutically acceptable excipients or carriers to form a solid, semi-solid or liquid. Some non-limiting examples of solid compositions include powders, tablets, dispersible granules, capsules, cachets, and suppositories. Some non-limiting examples of liquid compositions include solutions in which a compound is dissolved, emulsions comprising a compound, or a solution containing liposomes, micelles, or nanoparticles comprising a compound as disclosed herein. Some non-limiting examples of semi-solid compositions include gels, suspensions and creams. The compositions may be in liquid solutions or suspensions, solid forms suitable for solution or suspension in a liquid prior to use, or as emulsions. The pharmaceutical compositions disclosed herein may also contain minor amounts of nontoxic, auxiliary substances, such as wetting or emulsifying agents, pH buffering agents, and so forth.

The compounds disclosed herein are preferably formulated in dosage unit form for ease of administration and uniformity of dosage. The expression "dosage unit form" refers to a physically discrete unit of agent appropriate for the patient to be treated. It will be understood, however, that the total daily usage of the compounds and compositions disclosed herein will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The effective dose of the active ingredients used may vary with the compound used, the administration mode and the severity of the disease to be treated. However, typically, a desirable result can be achieved when the compound disclosed herein is administered at a dose of about 0.25-1000 mg/kg animal body weight per day. More preferably, it is administered in 2-4 separated dosages per day, or in the form of slow release. For most of the large mammals, the total dose per day is about 1-100 mg/kg, more preferably about 2-80 mg/kg. The dosage form suitable for inner use comprises about 0.25-500 mg active compound sufficiently mixed with a solid or liquid pharmaceutically acceptable carrier. The dosage may be adjusted to provide the best treatment response. In addition, upon urgent requirement of the condition to be treated, several separate dosages per day may be administered, or the dosage may be reduced in proportion.

The selective biological properties of the compounds may be enhanced through being modified by additional appropriate functional groups. Such modification is known in the field herein and includes the modification of penetrate to biological cavities (such as blood, lymphatic system, central nervous system), improves oral effectiveness and improves the solubility so that it can be administered by injection, alter metabolism and change the excretion.

The compound, compositions or pharmaceutically acceptable salt or hydrate disclosed herein may be used effectively for preventing, managing, treating or lessening the severity of tissue or organ fibrosis in a patient, especially in renal interstitial fibrosis, glomerulosclerosis, liver fibrosis, pulmonary fibrosis, peritoneum fibrosis, myocardial fibrosis, dermatofibrosis, postsurgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

General Synthetic Procedures

Generally, the compounds disclosed herein may be prepared by methods described herein, wherein the substituents are as defined for Formulas (I) or (II) above, except further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF dioxane, toluene, and ether were obtained by refluxing the solvent with sodium. Anhydrous $CH_2Cl_2$ and $CHCl_3$ were obtained by refluxing the solvent with $CaH_2$. EtOAc, petroleum ether, hexane, N,N-dimethyl acetamide and N,N-dimethyl formamide were treated with anhydrous $Na_2SO_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1H$ NMR spectra were recorded with a Bruker 400 MHz or 600 MHz spectrometer at ambient temperature. $^1H$ NMR spectra were obtained as $CDCl_3$, $d_6$-DMSO, $CD_3OD$ or $d_6$-acetone solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), q (quartet), dt (doublet of triplets), tt (triplet of triplets), dddd (doublet of doublet of doublet of doublets), qd (quartet of doublets), ddd (doublet of doublet of doublets), td (triplet of doublets), dq (doublet of quartets), ddt (doublet of doublet of triplets), tdd (triplet of doublet of doublets), dtd (doublet of triplet of doublets). Coupling constants, when given, are reported in Hertz (Hz).

Low-resolution mass spectral (MS) data were also determined on an Agilent 6320 series LC-MS spectrometer equipped with G1312A binary pumps, a G1316A TCC (Temperature Control of Column, maintained at 30° C.), a G1329A autosampler and a G1315B DAD detector were used in the analysis, An ESI source was used on the LC-MS spectrometer.

Low-resolution mass spectral (MS) data were also determined on an Agilent 6120 series LC-MS spectrometer equipped with G1311A Quaternary pump, a G1316A TCC (Temperature Control of Column, maintained at 30° C.), a G1329A autosampler and a G1315D DAD detector were used in the analysis, An ESI source was used on the LC-MS spectrometer.

Both LC-MS spectrometers were equipped with an Agilent Zorbax SB-C18, 2.1×30 mm, 3.5 m column, 6 min, and detected with UV wavelength at 210/254 nm using electrospray ionization (ESI). The flow rate was 0.6 mL/min. The mobile phase was 5% to 95% (0.1% formic acid in acetonitrile) and (0.1% formic acid in ultrapure water). The HPLC peaks were recorded by UV-vis wavelength at 210 nm and 254 nm. The gradient condition is shown in Table 1:

TABLE 1

| time(min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were also assessed by Agilent 1260 Series preparative high performance liquid chromatography (pre-HPLC) or Calesep Pump 250 Series preparative high performance liquid chromatography (Pre-HPLC) with UV detection at 210 nm and 254 nm (Zorbax SB-C18, 2.1×30 mm, 4 micron, 10 min, 0.6 mL/min flow rate, 5 to 95% (0.1% formic acid in $CH_3CN$) in (0.1% formic acid in $H_2O$). Column was operated at 40° C.

The following abbreviations are used throughout the specification:
BOC, Boc tert-butyloxycarbonyl
$CHCl_3$ chloroform
$CDCl_3$ chloroform deuterated
DMF dimethylformamide
DCM dichloromethane
DMAP dimethylaminopyridine
$SOCl_2$ sulfoxide chloride DMSO dimethylsulfoxide
DMF N,N-dimethyl formamide
DMSO-$d_6$ dimethylsulfoxide-D6
$CD_3OD$ methanol-D4
Fe iron
mL, ml milliliter
$N_2$ nitrogen
NaOH sodium hydroxide
Pd/C palladium on carbon
Pd(OAc)$_2$ palladium acetate
$K_2CO_3$ potassium carbonate
RT, rt room temperature
NaCl sodium chloride
$Na_2SO_4$ sodium sulfate
HCl hydrochloric acid
t-Bu tertiary butyl
Me —$CH_3$ methyl
MeOH methanol
THF tetrahydrofuran
Et —$CH_2CH_3$ ethyl
OTf trifluoromethylsulfonyl
TsOCl tosyl chloride
$H_2O$ water
TEA triethylamine
EtOAc ethyl acetate
PE petroleum ether
Pd(dppf)Cl$_2$ [1,1'-Bis(diphenylphosphino)ferrocene]dichloropalladium(II)

General Synthetic Scheme

The following synthetic schemes and examples are given by way of illustrating the specific implementation scheme only, and in no way should not be construed as limitations. Experimental procedure for the generated data will be discussed in detail below.

Scheme 1

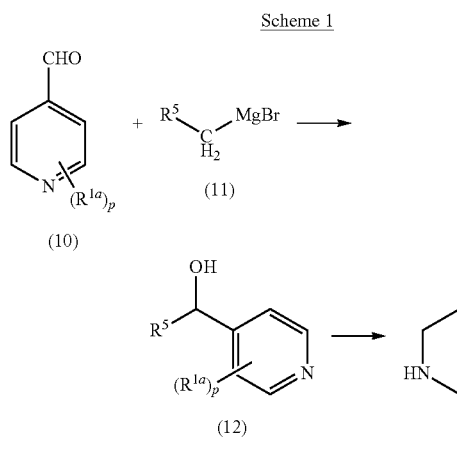

Compound (13) can be prepared by a general synthetic procedure illustrated in Scheme 1, wherein each $R^{1a}$, $R^5$ and p is as defined herein. Optionally substituted aldehyde (10) can be treated with Grignard reagent (11) to afford a compound (12). Subsequently, the compound (12) can be reduced to give the target compound (13).

Scheme 2

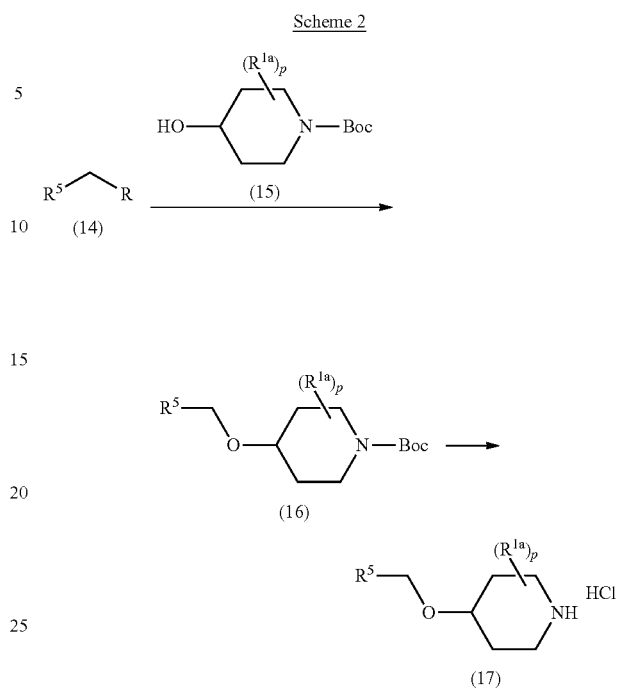

Compound (17) can be prepared by a general synthetic procedure illustrated in Scheme 2, wherein R is —OTf, F, Cl, or Br; each $R^{1a}$, $R^5$ and p is as defined herein. Compound (14) can react with compound (15) to afford a compound (16). Subsequently, deprotection of compound (16) affords the target compound (17).

Scheme 3

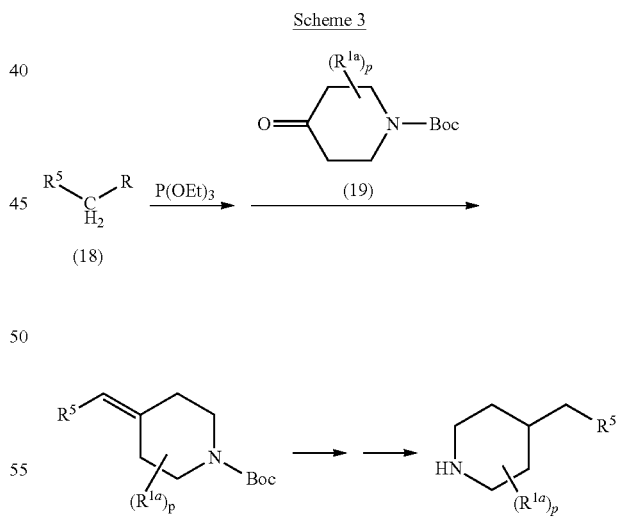

Compound (13) can be prepared by a general synthetic procedure illustrated in Scheme 3, wherein R is —OTf, F, Cl, or Br; each $R^{1a}$, $R^5$ and p is as defined herein. Compound (18) can react with P(OEt)$_3$ to give witting reagent, and then react with compound (19) to afford compound (20). Compound (20) can be converted to compound (13) by the reaction of reduction and deprotection.

Scheme 4

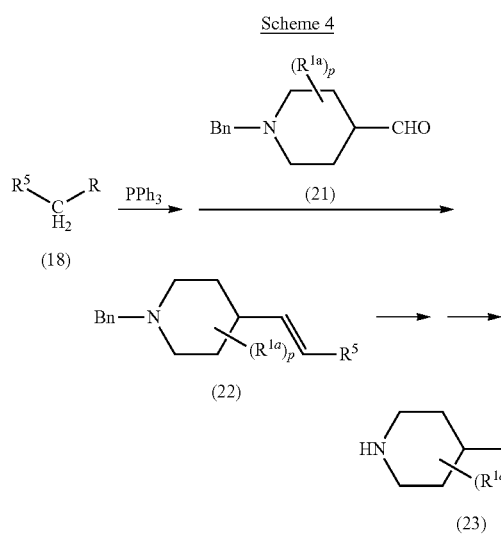

Compound (23) can be prepared by a general synthetic procedure illustrated in Scheme 4, wherein R is —OTf, F, Cl, or Br; each $R^{1a}$, $R^5$ and p is as defined herein. Compound (18) can react with PPh₃ to give witting reagent, and then react with compound (21) to afford compound (22). Compound (22) can be converted to compound (23) by the reaction of reduction and deprotection.

Scheme 5

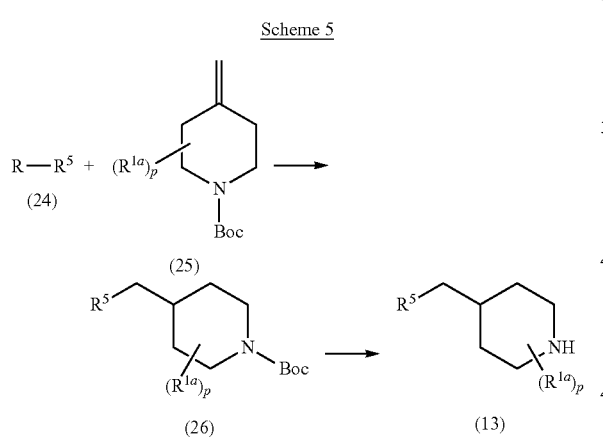

Compound (13) can be prepared by a general synthetic procedure illustrated in Scheme 5, wherein R is —OTf, F, Cl, or Br; each $R^{1a}$, $R^5$ and p is as defined herein. Suzuki reaction of compound (24) with compound (25) can yield compound (26). Subsequently, compound (26) can be converted to compound (13) by the reaction of deprotection.

Scheme 6

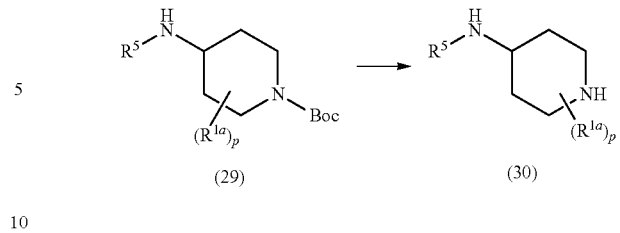

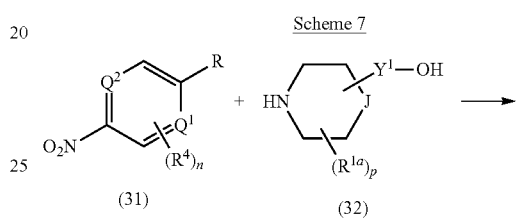

Compound (30) can be prepared by a general synthetic procedure illustrated in Scheme 6, wherein each $R^{1a}$, $R^5$ and p is as defined herein. Compound (27) can react with compound (28) to afford compound (29). Subsequently, compound (29) can be converted to compound (30) by the reaction of deprotection.

Scheme 7

Compound (1) can be prepared by a general synthetic procedure illustrated in Scheme 7, wherein R is —OTf, F, Cl, or Br; each $Y^1$ is independently a bond, —O—, —C(=S)—, —C(=O)—, —C(=O)O—, —NH—, —S(=O)₂NH—, —CH=CH—, —NHC(=O)—, or —(CH₂)$_m$—; each $Q^1$, $Q^2$, $R^{1a}$, $R^4$, m, n, J and p is as defined herein. Compound (31) can react with compound (32) to afford compound (33). Reaction of compound (33) with TsOCl can yield compound 1 which is used for next step.

Scheme 8

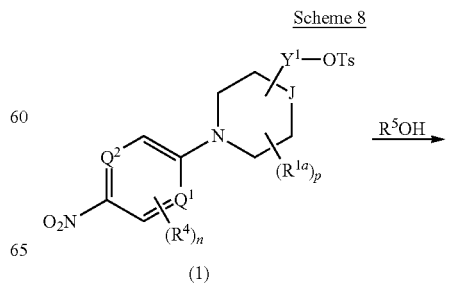

-continued

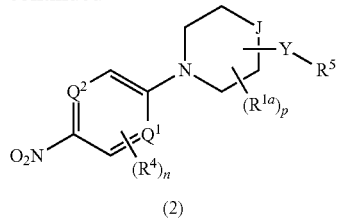

(2)

Compound (2) can be prepared by a general synthetic procedure illustrated in Scheme 8, wherein each $Y^1$ is independently a bond, —O—, —C(=S)—, —C(=O)—, —C(=O)O—, —NH—, —S(=O)$_2$NH—, —CH=CH—, —NHC(=O)—, or —(CH$_2$)$_m$—; each $Q^1$, $Q^2$, m, $R^{1a}$, $R^4$, n, J, Y, $R^5$ and p is as defined herein. Compound (1) can react with $R^5$OH to give intermediate (2)

Scheme 9

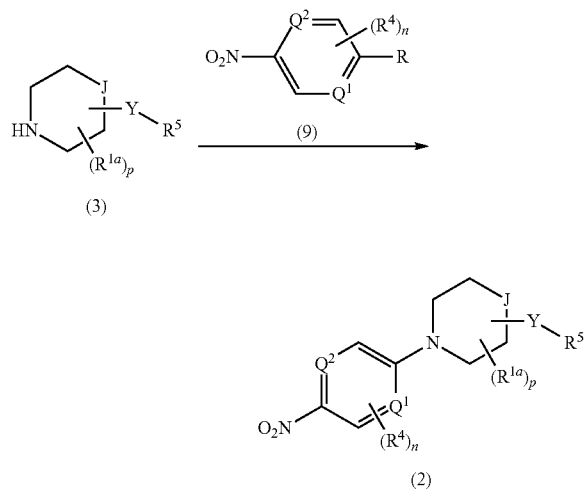

Compound (2) can be prepared by a general synthetic procedure illustrated in Scheme 9, wherein R is independently -OTf, F, Cl, or Br, each $Q^1$, $Q^2$, $R^{1a}$, $R^4$, n, J, Y, $R^5$ and p is as defined herein. Compound (3) can react with compound 9 to give intermediate (2).

Scheme 10

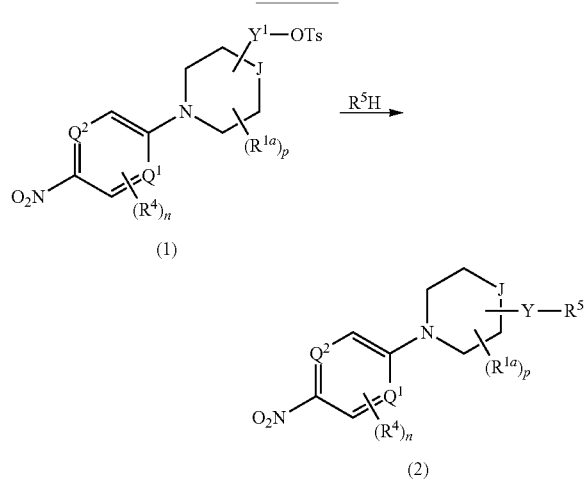

Compound (2) can be prepared by a general synthetic procedure illustrated in Scheme 10, wherein each $Y^1$ is independently a bond, —O—, —C(=S)—, —C(=O)—, —C(=O)O—, —NH—, —S(=O)$_2$NH—, —CH=CH—, —NHC(=O)—, or —(CH$_2$)$_m$—; each $Q^1$, $Q^2$, m, $R^{1a}$, $R^4$, n, J, Y, $R^5$ and p is as defined herein. Compound (1) can react with $R^5$H to give intermediate (2).

Scheme 11

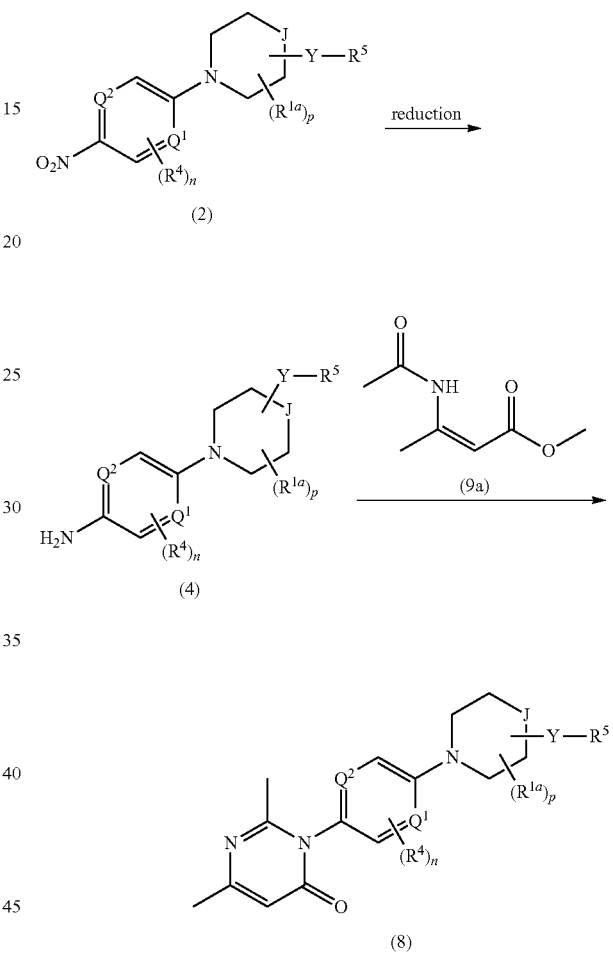

Compound (8) can be prepared by a general synthetic procedure illustrated in Scheme 11, wherein each $Q^1$, $Q^2$, $R^{1a}$, $R^4$, n, J, Y, $R^5$ and p is as defined herein. Intermediate (2) can be reduced to afford intermediate (4), and intermediate (4) can react with compound (9a) to give compound (8).

Scheme 12

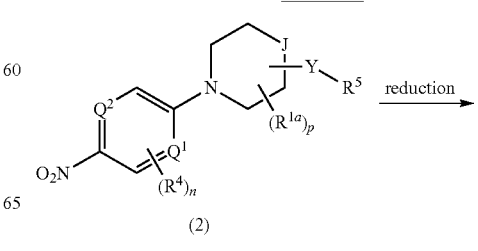

57
-continued

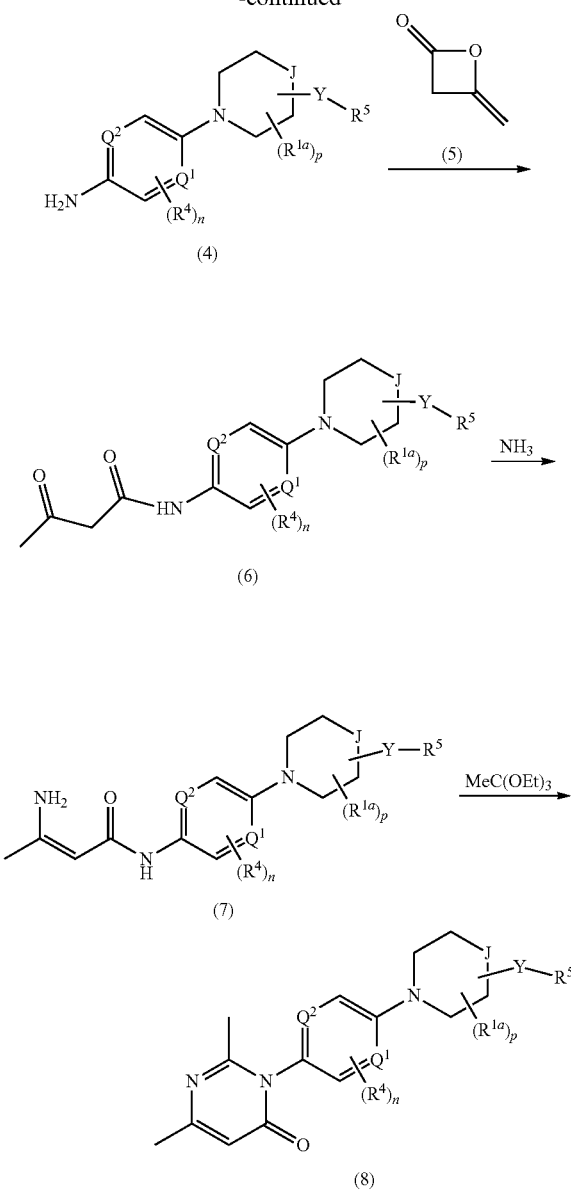

Compound (8) can be prepared by a general synthetic procedure illustrated in Scheme 12, wherein each $Q^1$, $Q^2$, $R^{1a}$, $R^4$, n, J, Y, $R^5$ and p is as defined herein. Intermediate (2) can be reduced to afford intermediate (4). Intermediate (4) can be converted to compound (6) by reacting with compound (5). Compound (6) can react with $NH_3$ to give compound (7), and compound (7) can react with $MeC(OEt)_3$ to give compound (8) by cyclization.

In a synthesis method or intermediate synthesis scheme, the acid salt of the compound can be prepared by adding acid, as described in the invention, including adding excess acid to free alkali.

It should be understood that the above details and embodiments of the invention are given by way of illustration only, and should not be construed as limiting the subject scope of the present application. Various changes and modifications to the disclosed embodiment described herein will be apparent to those skilled person in the art.

58
EXAMPLES

Example 1: 3-(3-chloro-4-(4-(3-fluorobenzyl)piperidin-1-yl)phenyl)-2,6-dimethylpyrimidin-4(3H)-one

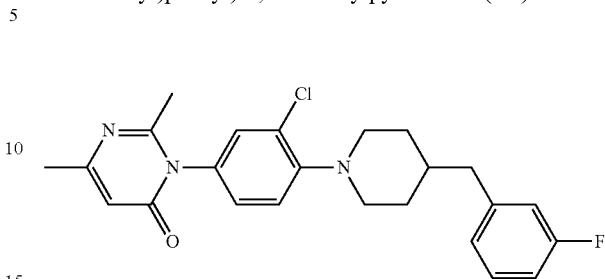

Step 1: (3-fluorophenyl)(pyridin-4-yl)methanol

To a cooled −78° C. solution of (3-fluorophenyl)magnesium bromide in THF (90 mL, 90.0 mmol, 1.0 mol/L) was added a solution of isonicotinaldehyde (9.10 g, 85.00 mmol) in 50 mL of THF. The resulted mixture was stirred at this temperature for 1 hour, then heated to rt and stirred for 12 hours. After the reaction was finished, the mixture was quenched with saturated aqueous ammonium chloride solution (100 mL), and then filtered. The filtrate was concentrated in vacuo. The residue was dissolved in 100 mL DCM, and the resulted mixture was washed with $H_2O$ (100 mL×2). The organic phase was dried over anhydrous $Na_2SO_4$ (20 g), filtered and concentrated in vacuo. The crude was purified by silica column chromatography (PE/EtOAc (v/v)=4/1) to give the title compound as a white solid (10.28 g, 59.5%). The compound was characterized by the following spectroscopic data:

MS (ESI, pos. ion) m/z: 204.1 (M+1); exact mass of $C_{12}H_{10}FNO$: 203.07.

Step 2: 4-(3-fluorobenzyl)piperidine

A mixture of (3-fluorophenyl)(pyridin-4-yl)methanol (10.28 g, 50.59 mmol), 30 mL of acetic acid and 10% Pa/C (1.10 g) was stirred under $H_2$ (3 MPa) at 80° C. for 18 hours. After the reaction was finished, the mixture was cooled to rt and falled down to atmospheric pressure. The mixture was filtered. The filtrate was concentrated in vacuo. The crude was purified by silica column chromatography (PE/EtOAc (v/v)=4/1) to give the title compound as yellow oil (4.94 g, 50.5%). The compound was characterized by the following spectroscopic data:

MS (ESI, pos. ion) m/z: 194.1 (M+1); exact mass of $C_{12}H_{16}FN$: 193.13.

Step 3:1-(2-chloro-4-nitrophenyl)-4-(3-fluorobenzyl)piperidine

A mixture of 4-(3-fluorobenzyl)piperidine (9.78 g, 50.59 mmol), 2-chloro-1-fluoro-4-nitrobenzene (13.32 g, 75.89 mmol), TEA (15.0 mL, 107.62 mmol) and EtOAc (50 mL) was heated at 50° C. overnight. After the reaction was finished, the mixture was cooled to rt, and then filtered. The filtrate was concentrated in vacuo to remove the solvent. The crude was purified by silica column chromatography (PE/EtOAc (v/v)=10/1) to give the title compound as yellow oil (14.20 g, 80.5%). The compound was characterized by the following spectroscopic data:

MS (ESI, pos. ion) m/z: 349.1 (M+1); exact mass of $C_{18}H_{18}ClFN_2O_2$: 348.10.

Step 4: 3-chloro-4-(4-(3-fluorobenzyl)piperidin-1-yl)aniline

To a mixture of $H_2O$ (50 mL) and concentrated hydrochloric acid (1.0 mL) was added iron powder (4.80 g, 86.00 mmol). The mixture was heated to 65° C. and stirred for 15 minutes, and then removed the water phase. Then to the activated iron power was added a solution of 1-(2-chloro-4-nitrophenyl)-4-(3-fluorobenzyl)piperidine (3.00 g, 8.60 mmol) in MeOH (50 mL), and the mixture was adjusted to pH 3 with concentrated hydrochloric acid. The resulted mixture was heated at 65° C. overnight. After the reaction was finished, the mixture was cooled to rt, and adjusted to pH 10 with TEA. The mixture was filtered. The filtrate was concentrated in vacuo. The crude was purified by silica column chromatography (PE/EtOAc (v/v)=4/1) to give the title compound as a light yellow solid (20.32 g, 74.1%). The compound was characterized by the following spectroscopic data:

MS (ESI, pos. ion) m/z: 319.2 (M+1); exact mass of $C_{18}H_{20}ClFN_2$: 318.13.

Step 5 N-(3-chloro-4-(4-(3-fluorobenzyl)piperidin-1-yl)phenyl)-3-oxobutanamide To a solution of 3-chloro-4-(4-(3-fluorobenzyl)piperidin-1-yl)aniline (2.00 g, 6.27 mmol) in EtOAc (30 mL) was added 4-methyleneoxetan-2-one (1.58 g, 18.82 mmol). The reaction mixture was heated at 90° C. overnight. After the reaction was finished, the mixture was cooled to rt and concentrated in vacuo. The crude was purified by silica column chromatography (PE/EtOAc (v/v)=2/1) to give the title compound as light yellow oil (1.62 g, 64.1%). The compound was characterized by the following spectroscopic data:

MS (ESI, pos. ion) m/z: 403.2 (M+1); exact mass of $C_{22}H_{24}ClFN_2O_2$: 402.15.

Step 6: (Z)-3-amino-N-(3-chloro-4-(4-(3-fluorobenzyl)piperidin-1-yl)phenyl)but-2-enamide A mixture of N-(3-chloro-4-(4-(3-fluorobenzyl)piperidin-1-yl)phenyl)-3-oxobutanamide (1.00 g, 2.48 mmol), MeOH (10 mL) and ammonium hydroxide (10 mL) was stirred at rt overnight. After the reaction was finished, the mixture was concentrated in vacuo to remove the solvent. The crude product was used directly for the next step without purification.

Step 7: 3-(3-chloro-4-(4-(3-fluorobenzyl)piperidin-1-yl)phenyl)-2,6-dimethylpyrimidin-4(3H)-one A solution of (Z)-3-amino-N-(3-chloro-4-(4-(3-fluorobenzyl)piperidin-1-yl)phenyl)but-2-enamide in triethyl orthoacetate (10 mL) was stirred under $N_2$ at 150° C. for 18 hours. After the reaction was finished, the mixture was cooled to rt and concentrated in vacuo. The residue was purified by silica column chromatography (PE/EtOAc (v/v)=1/1) to give the title compound as a light yellow solid (565 mg, 53.1%). The compound was characterized by the following spectroscopic data:

MS (ESI, pos. ion) m/z: 426.1 (M+1); exact mass of $C_{24}H_{25}ClFN_3O$: 425.17; and $^1$H NMR (600 MHz, CDCl$_3$) δ 7.27 (dd, J=13.5, 7.1 Hz, 1H), 7.21 (d, J=2.4 Hz, 1H), 7.13 (d, J=8.5 Hz, 1H), 7.04 (dd, J=8.5, 2.4 Hz, 1H), 6.97 (d, J=7.6 Hz, 1H), 6.92 (dd, J=13.9, 5.5 Hz, 2H), 6.29 (s, 1H), 3.53-3.36 (m, 2H), 2.70 (tt, J=10.2, 5.0 Hz, 1H), 2.65-2.57 (m, 3H), 2.31 (s, 3H), 2.20 (s, 3H), 1.81-1.75 (m, 2H), 1.71 (dddd, J=14.7, 10.9, 7.4, 3.7 Hz, 1H), 1.53 (qd, J=11.8, 3.2 Hz, 2H).

Example 2: 3-(3-fluoro-4-(4-(3-fluorobenzyl)piperidin-1-yl)phenyl)-2,6-dimethylpyrimidin-4(3H)-one

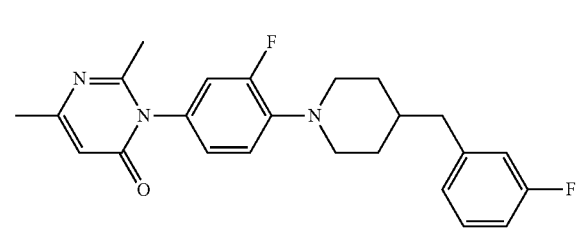 [SMILES: Cc1cc(=O)n(-c2ccc(N3CCC(Cc4cccc(F)c4)CC3)c(Cl)c2)c(C)n1]

Step 1: 1-(2-fluoro-4-nitrophenyl)-4-(3-fluorobenzyl)piperidine

A mixture of 4-(3-fluorobenzyl)piperidine (3.30 g, 17.10 mmol), 1,2-difluoro-4-nitrobenzene (2.29 g, 14.40 mmol), potassium carbonate (5.96 g, 43.10 mmol) and CH$_3$CN (30 mL) was heated at 80° C. overnight. After the reaction was finished, the mixture was cooled to rt and filtered. The filtrate was concentrated in vacuo. The residue was purified by silica column chromatography (PE/EtOAc (v/v)=8/1) to give the title compound as light yellow oil (4.45 g, 93.0%). The compound was characterized by the following spectroscopic data:

MS (ESI, pos. ion) m/z: 333.1 (M+1); exact mass of $C_{18}H_{18}F_2N_2O_2$: 332.13.

Step 2: 3-fluoro-4-(4-(3-fluorobenzyl)piperidin-1-yl)aniline

A mixture of 1-(2-fluoro-4-nitrophenyl)-4-(3-fluorobenzyl)piperidine (4.40 g, 13.20 mmol), 10% Pa/C (0.44 g), a mixture of MeOH and THF (v/v=15 mL/15 mL) was bubbled with $H_2$ and stirred at rt for 6 hours. After the reaction was finished, the mixture was filtered. The filtrate was concentrated in vacuo. The crude was purified by silica column chromatography (PE/EtOAc (v/v)=4/1) to give the title compound as yellow oil (3.20 g, 80.0%). The compound was characterized by the following spectroscopic data:

MS (ESI, pos. ion) m/z: 303.2 (M+1); exact mass of $C_{18}H_{20}F_2N_2$: 302.16.

Step 3: 3-(3-fluoro-4-(4-(3-fluorobenzyl)piperidin-1-yl)phenyl)-2,6-dimethylpyrimidin-4(3H)-one To a mixture of 3-fluoro-4-(4-(3-fluorobenzyl)piperidin-1-yl)aniline (3.20 g, 10.60 mmol) in DCM (30 mL) was added trimethylaluminium (20.0 mL, 40.00 mmol, 2.0 mol/L in toluene). After the addition, the mixture was stirred at rt for 30 minutes, and to the mixture was added a solution of methyl 3-acetamidobut-2-enoate (2.00 g, 12.70 mmol) in DCM (10 mL) dropwise. The resulted mixture was stirred at rt for 72 hours. After the reaction was finished, the reaction was quenched with saturated aqueous ammonium chloride solution (100 mL), and the resulted mixture was extracted with DCM (100 mL×3). The combined organic phases were washed with water (100 mL×2) and saturated brine (100 mL), dried over anhydrous $Na_2SO_4$ (20 g), filtered and concentrated in vacuo. The crude was purified by silica column chromatography (PE/EtOAc (v/v)=1/1) to give the title compound as yellow powder (1.30 g, 30.0%). The compound was characterized by the following spectroscopic data:

MS (ESI, pos. ion) m/z: 410.1 (M+1); exact mass of $C_{24}H_{25}F_2N_3O$: 409.20; and $^1$H NMR (400 MHz, DMSO-$d_6$) δ 7.33 (dd, J=14.3, 7.8 Hz, 1H), 7.22 (dd, J=13.1, 2.1 Hz, 1H), 7.15-6.95 (m, 5H), 6.22 (s, 1H), 2.75-2.63 (m, 2H), 2.60 (d, J=6.8 Hz, 2H), 2.50 (s, 2H), 2.19 (s, 3H), 2.07 (s, 3H), 1.67 (d, J=12.3 Hz, 3H), 1.37 (d, J=12.0 Hz, 2H).

Example 3: 3-((1-(2-chloro-4-(2,4-dimethyl-6-oxopyrimidin-1 (6H)-yl)phenyl)piperidin-4-yl)methyl)benzonitrile

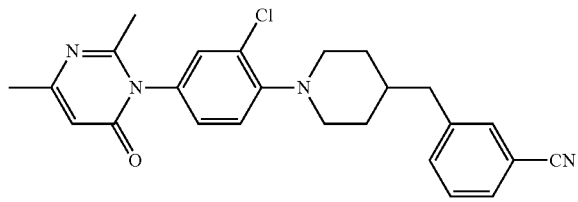 [SMILES: Cc1cc(=O)n(-c2ccc(N3CCC(Cc4cccc(C#N)c4)CC3)c(Cl)c2)c(C)n1]

Step 1: diethyl 3-cyanobenzylphosphonate

A mixture of triethyl phosphite (9.55 g, 57.50 mmol) and 3-(bromomethyl)benzonitrile (9.80 g, 50.00 mmol) was stirred at 87° C. overnight. After the reaction was finished, the mixture was cooled to room temperature. The reaction mixture was used directly for the next step without further operation. The compound was characterized by the following spectroscopic data:

MS (ESI, pos. ion) m/z: 507.2 (2M+1); exact mass of $C_{12}H_{16}NO_3P$: 253.09.

Step 2: tert-butyl 4-(3-cyanobenzylidene)piperidine-1-carboxylate

To a suspension of 60% NaH (2.00 g, 50.00 mmol) in anhydrous THF (50 mL) was added a solution of diethyl 3-cyanobenzylphosphonate (12.66 g, 50.00 mmol) and 15-crown-5 (0.1 mL) in anhydrous THF (25 mL) dropwise at ice bath. After the addition, the mixture was stirred at rt for 30 minutes. Then the mixture was cooled at ice bath again and to the mixture was added a solution of tert-butyl 4-oxopiperidine-1-carboxylate (8.30 g, 42.00 mmol) in THF (25 mL). After the addition, the mixture was stirred at rt overnight, then diluted with water (70 mL), and extracted with EtOAc (100 mL×2). The combined organic phases were washed with water (100 mL×2) and saturated brine (100 mL), dried over anhydrous $Na_2SO_4$ (20 g), filtered and concentrated in vacuo. The crude was purified by silica column chromatography (PE/EtOAc (v/v)=6/1) to give the title compound as a white solid (6.00 g, 48.3%). The compound was characterized by the following spectroscopic data:

MS (ESI, pos. ion) m/z: 243.2 (M+1-t-Bu); exact mass of $C_{18}H_{22}N_2O_2$: 298.1; and $^1$H NMR (400 MHz, CDCl$_3$) δ 7.54-7.46 (m, 2H), 7.45-7.38 (m, 2H), 6.32 (s, 1H), 3.56-3.47 (m, 2H), 3.47-3.36 (m, 2H), 2.48-2.38 (m, 2H), 2.37-2.30 (m, 2H), 1.48 (s, 9H).

Step 3: tert-butyl 4-(3-cyanobenzyl)piperidine-1-carboxylate

To a solution of tert-butyl 4-(3-cyanobenzylidene)piperidine-1-carboxylate (1.49 g, 5.00 mmol) in a mixture of THF and MeOH (v/v=25 mL/25 mL) was added 10% Pa/C (0.08 g). The resulted mixture was bubbled with $H_2$ and stirred at rt overnight. After the reaction was finished, the mixture was filtered. The filtrate was concentrated in vacuo to give the title compound as a white solid (1.53 g, 101.9%). The crude product was used directly for the next step without purification. The compound was characterized by the following spectroscopic data:

MS (ESI, pos. ion) m/z: 245.2 (M+1-t-Bu); exact mass of $C_{18}H_{24}N_2O_2$: 300.18.

Step 4: 3-(piperidin-4-ylmethyl)benzonitrile hydrochloride

To a solution of tert-butyl 4-(3-cyanobenzyl)piperidine-1-carboxylate (1.53 g, 5.09 mmol) in EtOAc (50 mL) was added a solution of HCl in EtOAc (4.3 mol/L, 8.0 mL, 34.38 mmol). The reaction was stirred at rt overnight. After completion, the mixture was concentrated in vacuo to give the crude product as yellow oil (1.53 g, 127.0%). The crude product was used directly for the next step without further purification. The compound was characterized by the following spectroscopic data:

MS (ESI, pos. ion) m/z: 201.2 (M+1-HCl); exact mass of $C_{13}H_{17}ClN_2$: 236.11.

Step 5: 3-((1-(2-chloro-4-nitrophenyl)piperidin-4-yl)methyl)benzonitrile

To a solution of 2-chloro-1-fluoro-4-nitrobenzene (1.53 g, 6.46 mmol) in DMF (25 mL) was added potassium carbonate (4.47 g, 32.31 mmol) and 3-(piperidin-4-ylmethyl)benzonitrile hydrochloride (1.53 g, 6.46 mmol). The mixture was stirred at 90° C. under $N_2$ overnight. After the reaction was finished, the mixture was cooled to rt overnight, and then poured in DCM (100 mL). The resulted mixture was washed with water (100 mL×2) and brine (100 mL). The organic phase was dried over anhydrous $Na_2SO_4$ (10 g), filtered and concentrated in vacuo. The crude was purified by silica column chromatography (PE/EtOAc (v/v)=10/1) to give the title compound as a yellow solid (1.10 g, 47.8%). The compound was characterized by the following spectroscopic data:

MS (ESI, pos. ion) m/z: 356.1 (M+1); exact mass of $C_{19}H_{18}ClN_3O_2$: 355.11.

Step 6: 3-((1-(4-amino-2-chlorophenyl)piperidin-4-yl)methyl)benzonitrile

To a mixture of $H_2O$ (50 mL) and concentrated hydrochloric acid (0.2 mL) was added iron powder (1.73 g, 30.90 mol) The mixture was heated to 65° C. and stirred for 15 minutes to activate the iron powder, and then removed the water phase. Then to the activated iron powder was added a solution of 3-((1-(2-chloro-4-nitrophenyl)piperidin-4-yl)methyl)benzonitrile (1.10 g, 3.09 mmol) in a mixture of MeOH and THF (v/v=25 mL/25 mL), and the mixture was adjusted to pH 3 with concentrated hydrochloric acid. The resulted mixture was heated to 65° C. overnight. After the reaction was finished, the mixture was cooled to rt, and adjusted to pH 10 with TEA. The mixture was filtered. The filtrate was concentrated in vacuo. The crude was diluted in DCM (100 mL). The resulted mixture was washed with water (100 mL×2) and saturated brine (100 mL). The organic phase was dried over anhydrous $Na_2SO_4$ (10 g), filtered and concentrated in vacuo. The crude was purified by silica column chromatography (PE/EtOAc (v/v)=4/1) to give the title compound as a light yellow solid (334 mg, 33.2%). The compound was characterized by the following spectroscopic data:

MS (ESI, pos. ion) m/z: 326.1 (M+1); exact mass of $C_{19}H_{20}ClN_3$:325.13.

Step 7: 3-((1-(2-chloro-4-(2,4-dimethyl-6-oxopyrimidin-1 (6H)-yl)phenyl)piperidin-4-yl)methyl)benzonitrile The title compound was prepared by the procedure described in step 3 of Example 2 using 3-((1-(4-amino-2-chlorophenyl)piperidin-4-yl)methyl)benzonitrile (334 mg, 1.03 mmol), trimethylaluminium (2.1 mL, 4.20 mmol, 2.0 mol/L in toluene) and a solution of methyl 3-acetamidobut-2-enoate (193 mg, 1.23 mmol) in toluene (2 mL) under $N_2$ to give the title compound as a light yellow solid (147 mg, 33.1%). The compound was characterized by the following spectroscopic data:

MS (ESI, pos. ion) m/z: 433.2 (M+1); exact mass of $C_{25}H_{25}ClN_4O$: 432.1; and $^1$H NMR (400 MHz, CDCl$_3$) δ 7.51 (dd, J=9.7, 6.8 Hz, 2H), 7.41 (d, J=5.5 Hz, 2H), 7.20 (d, J=2.4 Hz, 1H), 7.11 (d, J=8.5 Hz, 1H), 7.03 (dd, J=8.5, 2.4 Hz, 1H), 6.28 (s, 1H), 3.44 (dd, J=35.2, 11.8 Hz, 2H), 2.65 (tt, J=23.7, 11.8 Hz, 4H), 2.29 (d, J=5.3 Hz, 3H), 2.17 (d, J=3.6 Hz, 3H), 1.73 (d, J=12.1 Hz, 3H), 1.53 (d, J=12.0 Hz, 2H).

Example 4: 2-((1-(2-chloro-4-(2,4-dimethyl-6-oxopyrimidin-1 (6H)-yl)phenyl)piperidin-4-yl)methyl)benzonitrile

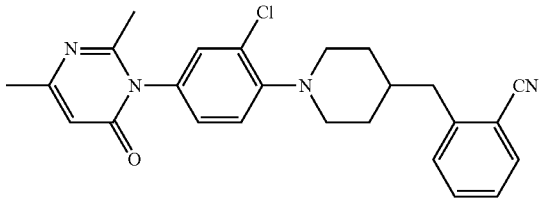

Step 1: diethyl 2-cyanobenzylphosphonate

A mixture of triethyl phosphite (1.91 g, 11.50 mmol) and 2-(bromomethyl)benzonitrile (1.96 g, 10.00 mmol) was stirred under $N_2$ at 87° C. overnight. The mixture was cooled to room temperature. The reaction mixture was used directly for the next step without further operation.

Step 2: tert-butyl 4-(2-cyanobenzylidene)piperidine-1-carboxylate

The title compound was prepared by the procedure described in step 2 of Example 3 using 60% NaH (480 mg, 12.00 mmol), diethyl 2-cyanobenzylphosphonate (2.53 g, 10.00 mmol), 15-crown-5 (0.1 mL) and tert-butyl 4-oxopiperidine-1-carboxylate (1.99 g, 10.00 mmol) to give the title compound as a white solid (1.33 g, 44.6%). The compound was characterized by the following spectroscopic data:

MS (ESI, pos. ion) m/z: 243.0 (M+1-t-Bu); exact mass of $C_{18}H_{22}N_2O_2$: 298.1; and $^1$H NMR (400 MHz, CDCl$_3$) δ 7.65 (d, J=7.8 Hz, 1H), 7.54 (dd, J=7.7, 6.6 Hz, 1H), 7.35-7.28 (m, 2H), 6.50 (s, 1H), 3.59-3.51 (m, 2H), 3.48-3.39 (m, 2H), 2.39 (ddd, J=22.8, 14.2, 5.8 Hz, 4H), 1.48 (s, 9H).

Step 3: tert-butyl 4-(2-cyanobenzyl)piperidine-1-carboxylate

The title compound was prepared by the procedure described in step 3 of Example 3 using tert-butyl 4-(2-cyanobenzylidene)piperidine-1-carboxylate (1.33 g, 4.46 mmol) and 10% Pa/C (0.13 g) to give the title compound as yellow oil (1.35 g, 100.8%). The compound was characterized by the following spectroscopic data:

MS (ESI, pos. ion) m/z: 245.2 (M+1-t-Bu); exact mass of $C_{18}H_{24}N_2O_2$: 300.18.

Step 4: 2-(piperidin-4-ylmethyl)benzonitrile hydrochloride

The title compound was prepared by the procedure described in step 4 of Example 3 using tert-butyl 4-(2-cyanobenzyl)piperidine-1-carboxylate (1.35 g, 4.49 mmol) and a solution of HCl in EtOAc (3.8 mol/L, 10.0 mL, 38.00 mmol) to give the title compound as a white solid (1.32 g, 124%). The compound was characterized by the following spectroscopic data:

MS (ESI, pos. ion) m/z: 201.1 (M+1-HCl); exact mass of $C_{13}H_{17}ClN_2$: 236.11.

Step 5: 2-((1-(2-chloro-4-nitrophenyl)piperidin-4-yl)methyl)benzonitrile

To a solution of 2-chloro-1-fluoro-4-nitrobenzene (979 mg, 5.58 mmol) in EtOAc (30 mL) was added TEA (2.82 g, 27.88 mmol) and 2-(piperidin-4-ylmethyl)benzonitrile hydrochloride (1.32 g, 5.58 mmol). The mixture was stirred at 70° C. under $N_2$ overnight. After the reaction was finished, the mixture was cooled to rt and poured in EtOAc (100 mL). The resulted mixture was washed with water (100 mL×2) and saturated brine (100 mL), dried over anhydrous $Na_2SO_4$ (10 g), filtered and concentrated in vacuo to give the title compound as yellow oil (1.78 g, 92.2%). The compound was characterized by the following spectroscopic data:

MS (ESI, pos. ion) m/z: 356.0 (M+1); exact mass of $C_{19}H_{18}ClN_3O_2$: 355.11.

Step 6: 2-((1-(4-amino-2-chlorophenyl)piperidin-4-yl)methyl)benzonitrile

The title compound was prepared by the procedure described in step 6 of Example 3 starting with a solution of 2-((1-(2-chloro-4-nitrophenyl)piperidin-4-yl)methyl)benzonitrile (1.78 g, 5.00 mmol) in a mixture of THF and MeOH (v/v=25 mL/25 mL) was added in activated iron powder (2.79 g, 50.00 mol) to give a brown solid (680 mg, 41.7%). The compound was characterized by the following spectroscopic data:

MS (ESI, pos. ion) m/z: 326.1 (M+1); exact mass of $C_{19}H_{20}ClN_3$: 325.13.

Step 7: 2-((1-(2-chloro-4-(2,4-dimethyl-6-oxopyrimidin-1 (6H)-yl)phenyl)piperidin-4-yl)methyl)benzonitrile The title compound was prepared by the procedure described in step 3 of Example 2 using 2-((1-(4-amino-2-chlorophenyl)piperidin-4-yl)methyl)benzonitrile (680 mg, 2.09 mmol), trimethylaluminium (4.2 mL, 8.40 mmol, 2.0 mol/L in toluene) and a solution of methyl 3-acetamidobut-2-enoate (394 mg, 2.50 mmol) in toluene (2 mL) under $N_2$ to give the title compound as a light yellow solid (486 mg, 53.8%). The compound was characterized by the following spectroscopic data:

MS (ESI, pos. ion) m/z: 433.2 (M+1); exact mass of $C_{25}H_{25}ClN_4O$: 432.17; and $^1$H NMR (400 MHz, CDCl$_3$) δ 7.68-7.61 (m, 1H), 7.53 (t, J=7.0 Hz, 1H), 7.32 (dd, J=7.2, 5.5 Hz, 2H), 7.20 (d, J=2.4 Hz, 1H), 7.11 (d, J=8.5 Hz, 1H), 7.02 (dd, J=8.5, 2.4 Hz, 1H), 6.28 (s, 1H), 3.44 (dd, J=32.9, 11.9 Hz, 2H), 2.94-2.80 (m, 2H), 2.65 (ddd, J=43.6, 11.7, 9.5 Hz, 2H), 2.29 (s, 3H), 2.18 (s, 3H), 1.81 (dt, J=29.3, 10.6 Hz, 3H), 1.67-1.61 (m, 2H).

Example 5: 4-((1-(2-chloro-4-(2,4-dimethyl-6-oxopyrimidin-1 (6H)-yl)phenyl)piperidin-4-yl)methyl)benzonitrile

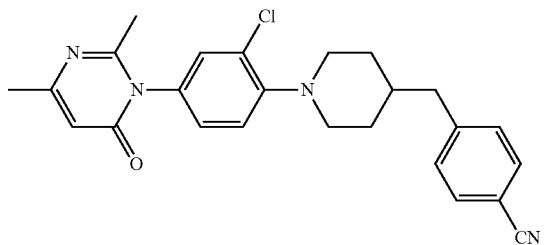 [SMILES: Cc1cc(=O)n(-c2ccc(N3CCC(Cc4ccc(C#N)cc4)CC3)c(Cl)c2)c(C)n1]

Step 1: diethyl 4-cyanobenzylphosphonate

A mixture of triethyl phosphite (1.91 g, 11.50 mmol) and 4-(bromomethyl)benzonitrile (1.96 g, 10.00 mmol) was stirred under $N_2$ at 87° C. overnight. The mixture was cooled to room temperature. The reaction mixture was used directly for the next step without further operation. The compound was characterized by the following spectroscopic data:

MS (ESI, pos. ion) m/z: 254.1 (M+1); exact mass of $C_{12}H_{16}NO_3P$: 253.09.

Step 2: tert-butyl 4-(4-cyanobenzylidene)piperidine-1-carboxylate

The title compound was prepared by the procedure described in step 2 of Example 3 using 60% NaH (480 mg, 12.00 mmol), diethyl 4-cyanobenzylphosphonate (2.53 g, 10.00 mmol), 15-crown-5 (0.1 mL), and tert-butyl 4-oxopiperidine-1-carboxylate (1.99 g, 10.00 mmol) to give the title compound as a white solid (2.38 g, 79.8%). The compound was characterized by the following spectroscopic data:

MS (ESI, pos. ion) m/z: 243.1 (M+1-t-Bu); exact mass of $C_{18}H_{22}N_2O_2$: 298.1.

Step 3: tert-butyl 4-(4-cyanobenzyl)piperidine-1-carboxylate

The title compound was prepared by the procedure described in step 3 of Example 3 using tert-butyl 4-(4-cyanobenzylidene)piperidine-1-carboxylate (2.38 g, 7.98 mmol) and 10% Pa/C (0.12 g) as starting materials to give the title compound as yellow oil (2.41 g, 100.6%). The compound was characterized by the following spectroscopic data:

MS (ESI, pos. ion) m/z: 245.1 (M+1-t-Bu); exact mass of $C_{18}H_{24}N_2O_2$: 300.18.

Step 4: 4-(piperidin-4-ylmethyl)benzonitrile hydrochloride

The title compound was prepared by the procedure described in step 4 of Example 3 using tert-butyl 4-(4-cyanobenzyl)piperidine-1-carboxylate (2.41 g, 8.02 mmol) and a solution of HCl in EtOAc (4.4 mol/L, 10.0 mL, 44.00 mmol) to give the title compound as a white solid (1.63 g, 85.8%). The compound was characterized by the following spectroscopic data:

MS (ESI, pos. ion) m/z: 201.1 (M+1-HCl); exact mass of $C_{13}H_{17}ClN_2$: 236.11.

Step 5: 4-((1-(2-chloro-4-nitrophenyl)piperidin-4-yl)methyl)benzonitrile

The title compound was prepared by the procedure described in step 5 of Example 3 using 2-chloro-1-fluoro-4-nitrobenzene (1.21 g, 6.89 mmol), potassium carbonate (2.85 g, 20.66 mmol) and 4-(piperidin-4-ylmethyl)benzonitrile hydrochloride (1.63 g, 6.89 mmol) to give the title compound as yellow oil (1.78 g, 92.2%). The compound was characterized by the following spectroscopic data:

MS (ESI, pos. ion) m/z: 356.1 (M+1); exact mass of $C_{19}H_{18}ClN_3O_2$: 355.11.

Step 6: 4-((1-(4-amino-2-chlorophenyl)piperidin-4-yl)methyl)benzonitrile

To a solution of 4-((1-(2-chloro-4-nitrophenyl)piperidin-4-yl)methyl)benzonitrile (2.36 g, 6.63 mmol) in a mixture of THF and MeOH (25 mL/25 mL) was added in activated iron powder (3.70 g, 66.33 mmol). Then the title compound was prepared by the procedure described in step 4 of Example 1 to give a brown solid (1.92 g, 88.8%). The compound was characterized by the following spectroscopic data: MS (ESI, pos. ion) m/z: 326.1 (M+1); exact mass of $C_{19}H_{20}ClN_3$: 325.13.

Step 7: 4-((1-(2-chloro-4-(2,4-dimethyl-6-oxopyrimidin-1 (6H)-yl)phenyl)piperidin-4-yl)methyl)benzonitrile The title compound was prepared by the procedure described in step 3 of Example 2 except starting with 4-((1-(4-amino-2-chlorophenyl)piperidin-4-yl)methyl)benzonitrile (1.92 g, 5.89 mmol), trimethylaluminium (12.0 mL, 24.00 mmol, 2.0 mol/L in toluene) and a solution of methyl 3-acetamidobut-2-enoate (1.11 g, 7.07 mmol) in toluene (2 mL) under $N_2$ to give the title compound as a light yellow solid (1.38 g, 54.1%). The compound was characterized by the following spectroscopic data:

MS (ESI, pos. ion) m/z: 433.1 (M+1); exact mass of $C_{25}H_{25}ClN_4O$: 432.17; and ¹H NMR (400 MHz, CDCl₃) δ 7.60 (d, J=8.2 Hz, 2H), 7.32-7.27 (m, 2H), 7.20 (d, J=2.4 Hz, 1H), 7.11 (d, J=8.5 Hz, 1H), 7.03 (dd, J=8.5, 2.4 Hz, 1H), 6.28 (s, 1H), 3.44 (dd, J=34.7, 11.2 Hz, 2H), 2.74-2.64 (m, 3H), 2.59 (t, J=10.9 Hz, 1H), 2.29 (s, 3H), 2.18 (s, 3H), 1.72 (t, J=11.2 Hz, 3H), 1.58-1.49 (m, 2H).

Example 6: 3-(3-chloro-4-(4-(2-fluorobenzyl)piperidin-1-yl)phenyl)-2,6-dimethylpyrimidin-4(3H)-one

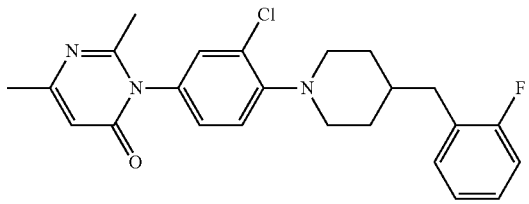 [SMILES: Cc1cc(=O)n(-c2ccc(N3CCC(Cc4ccccc4F)CC3)c(Cl)c2)c(C)n1]

Step 1: diethyl 2-fluorobenzylphosphonate

A mixture of triethyl phosphite (5.73 g, 34.50 mmol) and 1-(bromomethyl)-2-fluorobenzene (5.67 g, 30.00 mmol) was stirred under N₂ at 87° C. overnight. The mixture was cooled to room temperature. The reaction mixture was used directly for the next step without further operation.

Step 2: tert-butyl 4-(2-fluorobenzylidene)piperidine-1-carboxylate

The title compound was prepared by the procedure described in step 2 of Example 3 using 60% NaH (1.20 g, 30.00 mmol), diethyl 2-fluorobenzylphosphonate (7.39 g, 30.00 mmol), 15-crown-5 (0.1 mL) and tert-butyl 4-oxopiperidine-1-carboxylate (4.98 g, 25.00 mmol) in 15 mL of anhydrous THF to give the title compound as a white solid (2.76 g, 37.9%). The compound was characterized by the following spectroscopic data:
MS (ESI, pos. ion) m/z: 236.0 (M+1-t-Bu); exact mass of C₁₇H₂₂FNO₂: 291.16; and
¹H NMR (400 MHz, CDCl₃): δ7.15-7.24 (m, 2H), 7.02-7.10 (m, 2H), 6.27 (s, 1H), 3.51-3.54 (t, J=5.8 Hz, 2H), 3.40-3.43 (t, J=5.8 Hz, 2H), 2.35-2.37 (m, 4H), 1.48 (s, 9H).

Step 3: tert-butyl 4-(2-fluorobenzyl)piperidine-1-carboxylate

The title compound was prepared by the procedure described in step 3 of Example 3 using tert-butyl 4-(2-fluorobenzylidene)piperidine-1-carboxylate (2.76 g, 9.47 mmol) and 10% Pa/C (0.30 g) to give the crude product which was used directly for the next step without further purification. The compound was characterized by the following spectroscopic data:
MS (ESI, pos. ion) m/z: 238.1 (M+1-t-Bu); exact mass of C₁₇H₂₄FNO₂: 291.16.

Step 4: 4-(2-fluorobenzyl)piperidine hydrochloride

The title compound was prepared by the procedure described in step 4 of Example 3 using tert-butyl 4-(2-fluorobenzyl)piperidine-1-carboxylate (2.78 g, 9.47 mmol) and a solution of HCl in EtOAc (4.4 mol/L, 20 mL, 88.00 mmol) to give the crude product which was used directly for the next step without further purification.

Step 5: 1-(2-chloro-4-nitrophenyl)-4-(2-fluorobenzyl)piperidine

The title compound was prepared by the procedure described in step 5 of Example 4 using 2-chloro-1-fluoro-4-nitrobenzene (1.19 g, 6.76 mmol), 4-(2-fluorobenzyl)piperidine hydrochloride (2.18 g, 9.47 mmol), EtOAc (30 mL) and TEA (2.46 g, 24.35 mmol) to give the crude product which was used directly for the next step without further purification.

Step 6: 3-chloro-4-(4-(2-fluorobenzyl)piperidin-1-yl)aniline

A solution of 1-(2-chloro-4-nitrophenyl)-4-(2-fluorobenzyl)piperidine (2.36 g, 6.77 mmol) in a mixture of THF and MeOH (v/v=30 mL/30 mL) was added in activated iron powder (3.78 g, 67.70 mmol). The title compound was prepared by the procedure described in step 6 of Example 3 to give the title compound as yellow oil (2.07 g, 96.0%).

Step 7: 3-(3-chloro-4-(4-(2-fluorobenzyl)piperidin-1-yl)phenyl)-2,6-dimethylpyrimidin-4(3H)-one The title compound was prepared by the procedure described in step 3 of Example 2 starting with 3-chloro-4-(4-(2-fluorobenzyl)piperidin-1-yl)aniline (956 mg, 3.00 mmol), trimethylaluminium (5.0 mL, 10.00 mmol, 2.0 mol/L in toluene) and a solution of methyl 3-acetamidobut-2-enoate (707 mg, 4.50 mmol) in toluene (4 mL) under N₂ to give the title compound as a white solid (938 mg, 73.4%). The compound was characterized by the following spectroscopic data:
MS (ESI, pos. ion) m/z: 426.0 (M+1); exact mass of C₂₄H₂₅ClFN₃O: 425.17; and
¹H NMR (400 MHz, CDCl₃) δ 7.23-7.13 (m, 3H), 7.09 (d, J=5.1 Hz, 1H), 7.06 (d, J=7.4 Hz, 1H), 7.02 (dd, J=8.5, 2.3 Hz, 2H), 6.27 (s, 1H), 3.43 (dd, J=35.9, 10.6 Hz, 2H), 2.76-2.52 (m, 4H), 2.29 (s, 3H), 2.18 (s, 3H), 1.72 (d, J=21.3 Hz, 3H), 1.60-1.50 (m, 2H).

Example 7: 3-(3-chloro-4-(4-(4-fluorobenzyl)piperidin-1-yl)phenyl)-2,6-dimethylpyrimidin-4(3H)-one

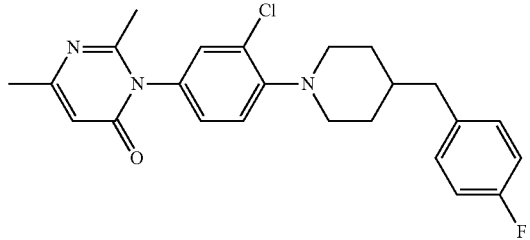 [SMILES: Cc1cc(=O)n(-c2ccc(N3CCC(Cc4ccc(F)cc4)CC3)c(Cl)c2)c(C)n1]

Step 1: diethyl 4-fluorobenzylphosphonate

A mixture of triethyl phosphite (3.03 g, 18.25 mmol) and 1-(bromomethyl)-4-fluorobenzene (3.00 g, 15.87 mmol) was stirred under N₂ at 87° C. overnight. The mixture was cooled to room temperature. The reaction mixture was used directly for the next step without further operation.

Step 2: tert-butyl 4-(4-fluorobenzylidene)piperidine-1-carboxylate

To a mixture of tert-butyl 4-oxopiperidine-1-carboxylate (2.53 g, 12.70 mmol), diethyl 4-fluorobenzylphosphonate (3.91 g, 15.88 mmol) and THF (50 mL) was added a solution of potassium tert-butanolate (1.96 g, 17.47 mmol) in anhydrous THF (20 mL) dropwise at ice bath. After the addition, the mixture was stirred at rt overnight. After the reaction was finished, the mixture was diluted with water (100 mL), and extracted with EtOAc (100 mL×2). The combined organic phases were washed with water (100 mL×2) and saturated brine (100 mL×2), dried over anhydrous $Na_2SO_4$ (20 g), filtered and concentrated in vacuo to give the title compound as yellow oil (4.63 g, 91.0%). The compound was characterized by the following spectroscopic data:

MS (ESI, pos. ion) m/z: 236.2 (M+1-t-Bu); exact mass of $C_{17}H_{22}FNO_2$: 291.16; and $^1$H NMR (400 MHz, $CDCl_3$) δ 7.20-7.08 (m, 2H), 7.04-6.94 (m, 2H), 6.31 (s, 1H), 3.55-3.45 (m, 2H), 3.45-3.35 (m, 2H), 2.42 (t, J=5.6 Hz, 2H), 2.36-2.26 (m, 2H), 1.48 (s, 9H).

Step 3: tert-butyl 4-(4-fluorobenzyl)piperidine-1-carboxylate

The title compound was prepared by the procedure described in step 3 of Example 3 using tert-butyl 4-(4-fluorobenzylidene)piperidine-1-carboxylate (4.63 g, 15.89 mmol) and 10% Pa/C (0.23 g) to give the title compound as white oil (4.66 g, 100%).

Step 4: 4-(4-fluorobenzyl)piperidine hydrochloride

The title compound was prepared by the procedure described in step 4 of Example 3 using tert-butyl 4-(4-fluorobenzyl)piperidine-1-carboxylate (4.66 g, 15.88 mmol) and a solution of HCl in EtOAc (4.4 mol/L, 30 mL, 132.0 mmol) to give the title compound as a white solid (3.65 g, 100%). The compound was characterized by the following spectroscopic data:

MS (ESI, pos. ion) m/z: 194.1 (M+1-HCl); exact mass of $C_{12}H_{17}ClFN$: 229.10.

Step 5: 1-(2-chloro-4-nitrophenyl)-4-(4-fluorobenzyl)piperidine

The title compound was prepared by the procedure described in step 5 of Example 4 using 2-chloro-1-fluoro-4-nitrobenzene (2.79 g, 15.89 mmol), 4-(4-fluorobenzyl) piperidine hydrochloride (3.65 g, 15.89 mmol) and TEA (5.62 g, 9.70 mmol) to give the title compound as a yellow solid (1.05 g, 19.0%). The compound was characterized by the following spectroscopic data:

MS (ESI, pos. ion) m/z: 349.1 (M+1); exact mass of $C_{18}H_{18}ClFN_2O_2$: 348.10.

Step 6: 3-chloro-4-(4-(4-fluorobenzyl)piperidin-1-yl)aniline

The title compound was prepared by the procedure described in step 6 of Example 3 starting with a solution of 1-(2-chloro-4-nitrophenyl)-4-(4-fluorobenzyl)piperidine (1.05 g, 3.01 mmol) in a mixture of THF and MeOH (v/v=15 mL/15 mL) was added in activated iron powder (1.68 g, 30.10 mol) to give the title compound as yellow oil (439 mg, 45.7%). The compound was characterized by the following spectroscopic data:

MS (ESI, pos. ion) m/z: 319.1 (M+1); exact mass of $C_{18}H_{20}ClFN_2$: 318.13.

Step 7: 3-(3-chloro-4-(4-(4-fluorobenzyl)piperidin-1-yl)phenyl)-2,6-dimethylpyrimidin-4(3H)-one The title compound was prepared by the procedure described in step 3 of Example 2 using 3-chloro-4-(4-(4-fluorobenzyl)piperidin-1-yl)aniline (439 mg, 1.38 mmol), trimethylaluminium (2.8 mL, 5.60 mmol, 2.0 mol/L in toluene) and a solution of methyl 3-acetamidobut-2-enoate (259 mg, 1.65 mmol) in toluene (2 mL) under $N_2$ to give the title compound as a yellow solid (85 mg, 14.5%). The compound was characterized by the following spectroscopic data:

MS (ESI, pos. ion) m/z: 426.2 (M+1); exact mass of $C_{24}H_{25}ClFN_3O$: 425.17; and $^1$H NMR (400 MHz, $CDCl_3$) δ 7.19 (d, J=2.4 Hz, 1H), 7.16-7.07 (m, 3H), 7.00 (dt, J=17.5, 5.6 Hz, 3H), 6.27 (s, 1H), 3.43 (dd, J=35.9, 11.0 Hz, 2H), 2.68 (td, J=11.4, 1.9 Hz, 1H), 2.58 (t, J=10.1 Hz, 3H), 2.29 (s, 3H), 2.17 (s, 3H), 1.74 (d, J=12.6 Hz, 2H), 1.55-1.42 (m, 3H).

Example 8: 3-(3-chloro-4-(4-(3-fluorophenethyl)piperidin-1-yl)phenyl)-2,6-dimethylpyrimidin-4(3H)-one

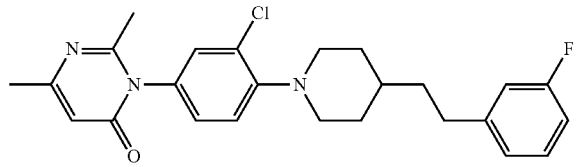

Step 1: (3-fluorobenzyl)triphenylphosphonium bromide

A mixture of 1-(bromomethyl)-3-fluorobenzene (1.89 g, 10.00 mmol), triphenylphosphine (2.75 g, 10.50 mmol) and toluene (50 mL) was heated at 80° C. and stirred for 5 hours. The mixture was cooled to room temperature and filtered. The filter cake was dried under vacuum to give the title compound as a white solid (3.50 g, 75%).

Step 2: (E)-1-benzyl-4-(3-fluorostyryl)piperidine

A mixture of (3-fluorobenzyl)triphenylphosphonium bromide (3.50 g, 7.80 mmol), 1-benzylpiperidine-4-carbaldehyde (1.90 g, 9.36 mmol) and DMF (40 mL) was added 60% NaH (468 mg, 11.70 mmol) at ice bath. The resulted mixture was stirred at rt overnight. After the completion of the reaction, the mixture was diluted with water (100 mL), and extracted with DCM (50 mL×3). The combined organic phases were washed with saturated brine (50 mL×3), dried over anhydrous $Na_2SO_4$ (15 g), filtered and concentrated in vacuo. The crude was purified by silica column chromatography (PE/EtOAc (v/v)=6/1) to give the title compound as colourless oil (1.80 g, 78.1%).

Step 3: 4-(3-fluorophenethyl)piperidine

The title compound was prepared by the procedure described in step 3 of Example 3 using a solution of (E)-1-benzyl-4-(3-fluorostyryl)piperidine (1.80 g, 6.10 mmol) in a mixture of THF and MeOH (v/v=20 mL/20 mL), and 10% Pa/C (0.36 g) to give the crude product which was used directly for the next step without further purification.

Step 4: 1-(2-chloro-4-nitrophenyl)-4-(3-fluorophenethyl)piperidine

The title compound was prepared by the procedure described in step 5 of Example 4 using 2-chloro-1-fluoro-4-nitrobenzene (890 mg, 5.07 mmol), 4-(3-fluorophenethyl)piperidine (1.26 g, 6.08 mmol) and TEA (1.54 g, 15.20 mmol) to give the title compound as a yellow solid (1.14 g, 62.0%). The compound was characterized by the following spectroscopic data:
MS (ESI, pos. ion) m/z: 363.2 (M+1); exact mass of $C_{19}H_{20}ClFN_2O_2$: 362.12.

Step 5: 3-chloro-4-(4-(3-fluorophenethyl)piperidin-1-yl)aniline

A solution of 1-(2-chloro-4-nitrophenyl)-4-(3-fluorophenethyl)piperidine (1.14 g, 3.10 mmol) in a mixture solvent of THF and MeOH (v/v=25 mL/25 mL) was added in activated iron powder (1.75 g, 31.40 mmol). The title compound was prepared by the procedure described in step 6 of Example 3 to give yellow oil (0.93 g, 88.5%). The compound was characterized by the following spectroscopic data:
MS (ESI, pos. ion) m/z: 333.2 (M+1); exact mass of $C_{19}H_{22}ClFN_2$: 332.15.

Step 6: 3-(3-chloro-4-(4-(3-fluorophenethyl)piperidin-1-yl)phenyl)-2,6-dimethylpyrimidin-4(3H)-one The title compound was prepared by the procedure described in step 3 of Example 2 starting with 3-chloro-4-(4-(3-fluorophenethyl)piperidin-1-yl)aniline (925 mg, 2.78 mmol), trimethylaluminium (5.0 mL, 10.00 mmol, 2.0 mol/L in toluene) and a solution of methyl 3-acetamidobut-2-enoate (655 mg, 4.17 mmol) in toluene (5 mL) under $N_2$ to give the title compound as a light yellow solid (776 mg, 63.5%). The compound was characterized by the following spectroscopic data:
MS (ESI, pos. ion) m/z: 440.0 (M+1); exact mass of $C_{25}H_{27}ClFN_3O$: 439.18; and
$^1$H NMR (400 MHz, CDCl$_3$) δ 7.26-7.18 (m, 2H), 7.15-7.08 (m, 1H), 7.03 (dd, J=8.5, 2.4 Hz, 1H), 6.97 (d, J=7.6 Hz, 1H), 6.93-6.85 (m, 2H), 6.28 (s, 1H), 3.46 (dd, J=39.1, 11.3 Hz, 2H), 2.77-2.56 (m, 4H), 2.30 (d, J=4.0 Hz, 3H), 2.18 (s, 3H), 1.85 (d, J=11.8 Hz, 2H), 1.70-1.59 (m, 2H), 1.57-1.40 (m, 3H).

Example 9: 3-(3-chloro-4-(4-(naphthalen-1-ylmethyl)piperidin-1-yl)phenyl)-2,6-dimethylpyrimidin-4(3H)-one

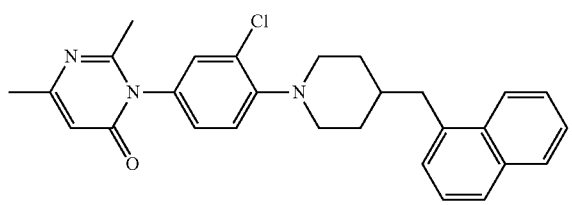 [SMILES: Cc1cc(=O)n(-c2ccc(N3CCC(Cc4cccc5ccccc45)CC3)c(Cl)c2)c(C)n1]

Step 1: diethyl (naphthalen-1-ylmethyl)phosphonate

A mixture of triethyl phosphite (955 mg, 5.75 mmol) and 1-(bromomethyl)naphthalene (1.11 g, 5.00 mmol) was stirred under $N_2$ at 87° C. overnight. The mixture was cooled to room temperature. The reaction mixture was used directly for the next step without further operation. The compound was characterized by the following spectroscopic data:
MS (ESI, pos. ion) m/z: 279.2 (M+1); exact mass of $C_{15}H_{19}O_3P$: 278.11.

Step 2: tert-butyl 4-(naphthalen-1-ylmethylene)piperidine-1-carboxylate

The title compound was prepared by the procedure described in step 2 of Example 7 using potassium tert-butanolate (673 mg, 6.00 mmol), diethyl (naphthalen-1-ylmethyl)phosphonate (1.39 g, 5.00 mmol), 15-crown-5 (0.1 mL) and tert-butyl 4-oxopiperidine-1-carboxylate (797 mg, 4.00 mmol) to give the title compound as yellow oil (865 mg, 62.2%). The compound was characterized by the following spectroscopic data:
$^1$H NMR (400 MHz, CDCl$_3$) δ 7.99 (dd, J=6.1, 3.5 Hz, 1H), 7.85 (dd, J=6.3, 3.2 Hz, 1H), 7.76 (d, J=8.3 Hz, 1H), 7.49 (dd, J=6.3, 3.3 Hz, 2H), 7.46-7.39 (m, 1H), 7.25 (s, 1H), 6.74 (s, 1H), 3.63-3.55 (m, 2H), 3.39-3.32 (m, 2H), 2.47 (t, J=4.6 Hz, 2H), 2.31-2.21 (m, 2H), 1.47 (s, 9H).

Step 3: tert-butyl 4-(naphthalen-1-ylmethyl)piperidine-1-carboxylate

The title compound was prepared by the procedure described in step 3 of Example 3 using tert-butyl 4-(naphthalen-1-ylmethylene)piperidine-1-carboxylate (1.62 g, 5.00 mmol) and 10% Pa/C (0.16 g) to give the title compound as white oil (1.24 g, 76.0%). The compound was characterized by the following spectroscopic data:
MS (ESI, pos. ion) m/z: 270.2 (M+1-t-Bu); exact mass of $C_{21}H_{27}NO_2$: 325.20.

Step 4: 4-(naphthalen-1-ylmethyl)piperidine hydrochloride

The title compound was prepared by the procedure described in step 4 of Example 3 using tert-butyl 4-(naphthalen-1-ylmethyl)piperidine-1-carboxylate (900 mg, 2.77 mmol) and a solution of HCl in EtOAc (4.4 mol/L, 5.2 mL, 22.00 mmol) to give the title compound as a white solid (668 mg, 92.4%). The compound was characterized by the following spectroscopic data:
MS (ESI, pos. ion) m/z: 226.2 (M+1-HCl); exact mass of $C_{16}H_{20}ClN$: 261.13.

Step 5: 1-(2-chloro-4-nitrophenyl)-4-(naphthalen-1-ylmethyl)piperidine

To a suspension of 2-chloro-1-fluoro-4-nitrobenzene (486 mg, 2.77 mmol), 4-(naphthalen-1-ylmethyl)piperidine hydrochloride (725 mg, 2.77 mmol) in CH$_3$CN (15 mL) was added potassium carbonate (1.34 g, 9.70 mmol). The mixture was stirred at 90° C. under $N_2$ overnight. After the reaction was finished, the mixture was concentrated in vacuo. The crude was purified by silica column chromatography (PE/EtOAc (v/v)=30/1) to give the title compound as a yellow solid (600 mg, 56.9%). The compound was characterized by the following spectroscopic data:

MS (ESI, pos. ion) m/z: 381.2 (M+1); exact mass of $C_{22}H_{21}ClN_2O_2$: 380.13.

Step 6: 3-chloro-4-(4-(naphthalen-1-ylmethyl)piperidin-1-yl)aniline

A solution of 1-(2-chloro-4-nitrophenyl)-4-(naphthalen-1-ylmethyl)piperidine (535 mg, 1.40 mmol) in a mixture of THF and MeOH (v/v=6 mL/6 mL) was added in activated iron powder (784 mg, 14.05 mmol). The title compound was prepared by the procedure described in step 6 of Example 3 to give a yellow solid (585 mg, 119.0%). The compound was characterized by the following spectroscopic data:
MS (ESI, pos. ion) m/z: 351.1 (M+1); exact mass of $C_{22}H_{23}ClN_2$: 350.15.

Step 7: 3-(3-chloro-4-(4-(naphthalen-1-ylmethyl)piperidin-1-yl)phenyl)-2,6-methylpyrimidin-4(3H)-one The title compound was prepared by the procedure described in step 3 of Example 2 starting with 3-chloro-4-(4-(naphthalen-1-ylmethyl)piperidin-1-yl)aniline (585 mg, 1.67 mmol), trimethylaluminium (3.3 mL, 6.6 mmol, 2.0 mol/L in toluene) and a solution of methyl 3-acetamidobut-2-enoate (314 mg, 2.00 mmol) in toluene (2 mL) under $N_2$ to give the title compound as a yellow solid (253 mg, 33.1%). The compound was characterized by the following spectroscopic data:
MS (ESI, pos. ion) m/z: 458.1 (M+1); exact mass of $C_{28}H_{28}ClN_3O$: 457.19; and
$^1$H NMR (400 MHz, CDCl$_3$) δ 8.02 (d, J=8.3 Hz, 1H), 7.83 (d, J=8.0 Hz, 1H), 7.70 (d, J=8.2 Hz, 1H), 7.46 (dt, J=14.6, 6.9 Hz, 2H), 7.36 (t, J=7.6 Hz, 1H), 7.26 (d, J=6.9 Hz, 1H), 7.15 (d, J=2.0 Hz, 1H), 6.96 (dt, J=8.5, 5.3 Hz, 2H), 6.24 (s, 1H), 3.36 (dd, J=31.0, 11.3 Hz, 2H), 3.02 (d, J=6.0 Hz, 2H), 2.51 (dt, J=29.2, 11.2 Hz, 2H), 2.24 (s, 3H), 2.11 (s, 3H), 1.74 (d, J=12.2 Hz, 2H), 1.64-1.51 (m, 3H).

Example 10: 3-(3-chloro-4-(4-(naphthalen-2-ylmethyl)piperidin-1-yl)phenyl)-2,6-dimethylpyrimidin-4(3H)-one

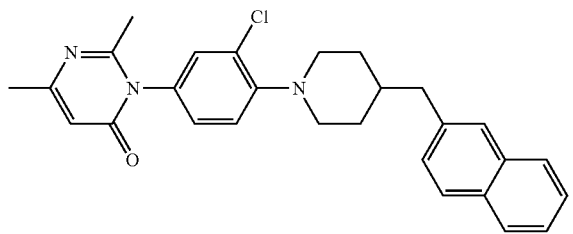 [SMILES: Cc1cc(=O)n(-c2ccc(N3CCC(Cc4ccc5ccccc5c4)CC3)c(Cl)c2)c(C)n1]

Step 1: diethyl (naphthalen-2-ylmethyl)phosphonate

A mixture of triethyl phosphite (1.91 g, 11.50 mmol) and 2-(bromomethyl)naphthalene (2.21 g, 10.00 mmol) was stirred under $N_2$ at 87° C. overnight. The mixture was cooled to room temperature. The reaction mixture was used directly for the next step without further operation.

Step 2: tert-butyl 4-(naphthalen-2-ylmethylene)piperidine-1-carboxylate

The title compound was prepared by the procedure described in step 2 of Example 3 using 60% NaH (480 mg, 12.00 mmol), diethyl (naphthalen-2-ylmethyl)phosphonate (2.78 g, 10.00 mmol), 15-crown-5 (0.1 mL) and tert-butyl 4-oxopiperidine-1-carboxylate (1.99 g, 10.00 mmol) to give the title compound as a white solid (2.21 g, 68.3%). The compound was characterized by the following spectroscopic data:
$^1$H NMR (400 MHz, CDCl$_3$) δ 7.79 (d, J=7.8 Hz, 3H), 7.63 (s, 1H), 7.45 (s, 2H), 7.33 (d, J=8.3 Hz, 1H), 6.51 (s, 1H), 3.54 (s, 2H), 3.43 (s, 2H), 2.54 (s, 2H), 2.39 (s, 2H), 1.48 (s, 9H).

Step 3: tert-butyl 4-(naphthalen-2-ylmethyl)piperidine-1-carboxylate

The title compound was prepared by the procedure described in step 3 of Example 3 using tert-butyl 4-(naphthalen-2-ylmethylene)piperidine-1-carboxylate (2.21 g, 6.83 mmol) and 10% Pa/C (0.22 g) to give the title compound as colourless oil (2.02 g, 90.8%). The compound was characterized by the following spectroscopic data:
MS (ESI, pos. ion) m/z: 270.2 (M+1-t-Bu); exact mass of $C_{21}H_{27}NO_2$: 325.20.

Step 4: 4-(naphthalen-2-ylmethyl)piperidine hydrochloride

The title compound was prepared by the procedure described in step 4 of Example 3 using tert-butyl 4-(naphthalen-2-ylmethyl)piperidine-1-carboxylate (2.02 g, 6.21 mmol) and a solution of HCl in EtOAc (4.3 mol/L, 10 mL, 43.35 mmol) to give the title compound as a white solid (1.39 g, 85.5%). The compound was characterized by the following spectroscopic data:
MS (ESI, pos. ion) m/z: 226.1 (M+1-HCl); exact mass of $C_{16}H_{20}ClN$: 261.13.

Step 5: 1-(2-chloro-4-nitrophenyl)-4-(naphthalen-2-ylmethyl)piperidine

The title compound was prepared by the procedure described in step 5 of Example 3 using 2-chloro-1-fluoro-4-nitrobenzene (1.47 g, 8.39 mmol), potassium carbonate (3.48 g, 25.16 mmol) and 4-(naphthalen-2-ylmethyl)piperidine hydrochloride (1.89 g, 8.39 mmol) to give the title compound as yellow oil (1.05 g, 32.9%). The compound was characterized by the following spectroscopic data:
$^1$H NMR (400 MHz, CDCl$_3$) δ 8.23 (d, J=2.6 Hz, 1H), 8.06 (dd, J=9.0, 2.6 Hz, 1H), 7.85-7.76 (m, 3H), 7.62 (s, 1H), 7.45 (dq, J=6.8, 5.5 Hz, 2H), 7.33 (dd, J=8.3, 1.4 Hz, 1H), 7.00 (d, J=9.0 Hz, 1H), 3.58 (d, J=12.1 Hz, 2H), 2.83-2.67 (m, 4H), 1.84 (dd, J=21.3, 8.5 Hz, 3H), 1.25 (s, 2H).

Step 6: 3-chloro-4-(4-(naphthalen-2-ylmethyl)piperidin-1-yl)aniline

A solution of 1-(2-chloro-4-nitrophenyl)-4-(naphthalen-2-ylmethyl)piperidine (1.05 g, 2.76 mmol) in a mixture of THF and MeOH (v/v=25 mL/25 mL) was added in activated iron powder (1.54 g, 27.60 mmol). The title compound was prepared by the procedure described in step 6 of Example 3 to give yellow oil (909 mg, 94.0%). The compound was characterized by the following spectroscopic data:
MS (ESI, pos. ion) m/z: 351.1 (M+1); exact mass of $C_{22}H_{23}ClN_2$: 350.15.

Step 7: 3-(3-chloro-4-(4-(naphthalen-2-ylmethyl)piperidin-1-yl)phenyl)-2,6-dimethylpyrimidin-4(3H)-one The title compound was prepared by the procedure described in step 3 of Example 2 starting with 3-chloro-4-(4-(naphthalen-2-ylmethyl)piperidin-1-yl)aniline (909 mg, 2.59 mmol), trimethylaluminium (5.2 mL, 10.4 mmol, 2.0 mol/L in toluene) and a solution of methyl 3-acetamidobut-2-enoate (489 mg, 3.11 mmol) in toluene (2 mL) under $N_2$ to give the title compound as a yellow solid (613 mg, 51.7%). The compound was characterized by the following spectroscopic data:

MS (ESI, pos. ion) m/z: 458.2 (M+1); exact mass of $C_{28}H_{28}ClN_3O$: 457.19; and $^1$H NMR (400 MHz, CDCl$_3$) δ 7.80 (t, J=9.4 Hz, 3H), 7.62 (s, 1H), 7.50-7.39 (m, 2H), 7.34 (d, J=6.9 Hz, 1H), 7.19 (d, J=2.4 Hz, 1H), 7.11 (d, J=8.6 Hz, 1H), 7.01 (dd, J=8.5, 2.4 Hz, 1H), 6.27 (s, 1H), 3.44 (dd, J=37.8, 12.0 Hz, 2H), 2.79 (d, J=4.4 Hz, 2H), 2.64 (dt, J=36.3, 10.8 Hz, 2H), 2.28 (s, 3H), 2.17 (s, 3H), 1.80 (d, J=9.5 Hz, 3H), 1.36-1.26 (m, 2H).

Example 11: 3-(4-(4-([1,1'-biphenyl]-4-ylmethyl)piperidin-1-yl)-3-chlorophenyl)-2,6-dimethylpyrimidin-4(3H)-one

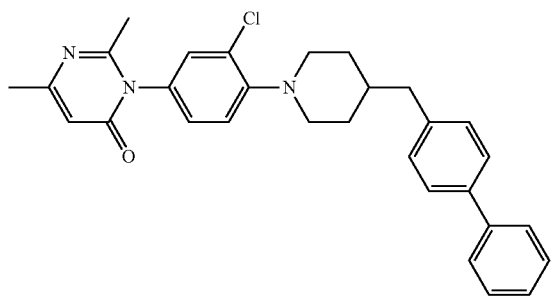 [SMILES: Cc1cc(=O)n(-c2ccc(N3CCC(Cc4ccc(-c5ccccc5)cc4)CC3)c(Cl)c2)c(C)n1]

Step 1: diethyl ([1,1'-biphenyl]-4-ylmethyl)phosphonate

A mixture of triethyl phosphite (2.81 g, 17.00 mmol) and 4-(bromomethyl)-1,1'-biphenyl (2.47 g, 10.00 mmol) was heated to 88° C. overnight. The mixture was cooled to room temperature. The reaction mixture was used directly for the next step without further operation.

Step 2: tert-butyl 4-([1,1'-biphenyl]-4-ylmethylene)piperidine-1-carboxylate The title compound was prepared by the procedure described in step 2 of Example 3 using 60% NaH (0.40 g, 10.00 mmol), diethyl ([1,1'-biphenyl]-4-ylmethyl)phosphonate (3.04 g, 10.00 mmol), 15-crown-5 (0.05 mL) and tert-butyl 4-oxopiperidine-1-carboxylate (1.66 g, 8.33 mmol) to give the title compound as a white solid (1.70 g, 58.4%). The compound was characterized by the following spectroscopic data:

MS (ESI, pos. ion) m/z: 294.2 (M+1-t-Bu); exact mass of $C_{23}H_{27}NO_2$: 349.20.

Step 3: tert-butyl 4-([1,1'-biphenyl]-4-ylmethyl)piperidine-1-carboxylate

The title compound was prepared by the procedure described in step 3 of Example 3 using a solution of tert-butyl 4-([1,1'-biphenyl]-4-ylmethylene)piperidine-1-carboxylate (1.70 g, 4.86 mmol) in a mixture of THF and MeOH (v/v=20 mL/20 mL), and 10% Pa/C (0.20 g) to give the crude product which was used directly for the next step without further purification. The compound was characterized by the following spectroscopic data:

MS (ESI, pos. ion) m/z: 296.2 (M+1-t-Bu); exact mass of $C_{23}H_{29}NO_2$: 351.22.

Step 4: 4-([1,1'-biphenyl]-4-ylmethyl)piperidine hydrochloride

The title compound was prepared by the procedure described in step 4 of Example 3 using tert-butyl 4-([1,1'-biphenyl]-4-ylmethyl)piperidine-1-carboxylate (1.71 g, 4.86 mmol) and a solution of HCl in EtOAc (4.4 mol/L, 10 mL, 44.00 mmol) to give the crude product which was used directly for the next step without further purification.

Step 5: 4-([1,1'-biphenyl]-4-ylmethyl)-1-(2-chloro-4-nitrophenyl)piperidine The title compound was prepared by the procedure described in step 5 of Example 4 using 2-chloro-1-fluoro-4-nitrobenzene (710 mg, 4.04 mmol), 4-([1,1'-biphenyl]-4-ylmethyl)piperidine hydrochloride (1.40 g, 4.85 mmol) and TEA (1.47 g, 14.56 mmol) to give the title compound as a yellow solid (1.04 g, 63.2%).

Step 6: 4-(4-([1,1'-biphenyl]-4-ylmethyl)piperidin-1-yl)-3-chloroaniline

A solution of 4-([1,1'-biphenyl]-4-ylmethyl)-1-(2-chloro-4-nitrophenyl)piperidine (1.04 g, 2.56 mmol) in a mixture of THF and H$_2$O (v/v=40 mL/10 mL) was added in activated iron powder (1.43 g, 25.60 mmol). The title compound was prepared by the procedure described in step 6 of Example 3 to give a yellow solid (868 mg, 90.1%). The compound was characterized by the following spectroscopic data:

MS (ESI, pos. ion) m/z: 377.2 (M+1); exact mass of $C_{24}H_{25}ClN_2$: 376.17.

Step 7: 3-(4-(4-([1,1'-biphenyl]-4-ylmethyl)piperidin-1-yl)-3-chlorophenyl)-2,6-dimethylpyrimidin-4(3H)-one The title compound was prepared by the procedure described in step 3 of Example 2 starting with 4-(4-([1,1'-biphenyl]-4-ylmethyl)piperidin-1-yl)-3-chloroaniline (868 mg, 2.30 mmol), trimethylaluminium (4.0 mL, 8.00 mmol, 2.0 mol/L in toluene) and a solution of methyl 3-acetamidobut-2-enoate (543 mg, 3.45 mmol) in toluene (5 mL) under $N_2$ to give the title compound as a light yellow solid (843 mg, 75.6%). The compound was characterized by the following spectroscopic data:

MS (ESI, pos. ion) m/z: 484.2 (M+1); exact mass of $C_{30}H_{30}ClN_3O$: 483.21; and $^1$H NMR (400 MHz, CDCl$_3$) δ 7.63-7.56 (m, 2H), 7.54 (d, J=8.1 Hz, 2H), 7.43 (t, J=7.6 Hz, 2H), 7.33 (t, J=7.3 Hz, 1H), 7.27 (s, 1H), 7.25 (s, 1H), 7.20 (d, J=2.4 Hz, 1H), 7.12 (d, J=8.5 Hz, 1H), 7.02 (dd, J=8.5, 2.4 Hz, 1H), 6.28 (s, 1H), 3.45 (dd, J=37.7, 11.7 Hz, 2H), 2.76-2.54 (m, 4H), 2.29 (s, 3H), 2.18 (s, 3H), 1.87-1.67 (m, 3H), 1.54 (dt, J=11.5, 8.2 Hz, 2H).

Example 12: 3-(3-chloro-4-(4-(3-methoxybenzyl) piperidin-1-yl)phenyl)-2,6-dimethylpyrimidin-4 (3H)-one

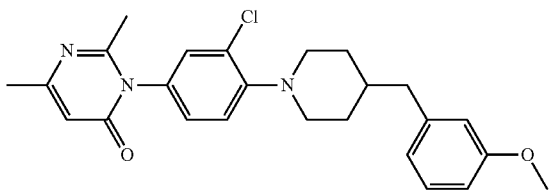

Step 1: diethyl 3-methoxybenzylphosphonate

A mixture of triethyl phosphite (1.45 g, 8.70 mmol) and 1-(bromomethyl)-3-methoxybenzene (1.50 g, 7.50 mmol) was stirred under $N_2$ at 90° C. overnight. The mixture was cooled to room temperature to give yellow oil (1.84 g, 95.9%). The reaction mixture was used directly for the next step without further operation. The compound was characterized by the following spectroscopic data:

MS (ESI, pos. ion) m/z: 259.2 (M+1); exact mass of $C_{12}H_{19}O_4P$: 258.10.

Step 2: tert-butyl 4-(3-methoxybenzylidene)piperidine-1-carboxylate

The title compound was prepared by the procedure described in step 2 of Example 3 using 60% NaH (692 mg, 28.80 mmol), diethyl 3-methoxybenzylphosphonate (1.84 g, 7.20 mmol), 15-crown-5 (0.5 mL) and tert-butyl 4-oxopiperidine-1-carboxylate (1.16 g, 5.80 mmol) to give the title compound as yellow oil (1.65 g, 93.8%). The compound was characterized by the following spectroscopic data:

MS (ESI, pos. ion) m/z: 248.2 (M+1-t-Bu); exact mass of $C_{18}H_{25}NO_3$: 303.18.

Step 3: tert-butyl 4-(3-methoxybenzyl)piperidine-1-carboxylate

The title compound was prepared by the procedure described in step 3 of Example 3 using tert-butyl 4-(3-methoxybenzylidene)piperidine-1-carboxylate (1.65 g, 5.45 mmol) and 10% Pa/C (0.06 g) as starting materials to give the title compound as colourless oil (1.65 g, 99.4%). The compound was characterized by the following spectroscopic data:

MS (ESI, pos. ion) m/z: 250.1 (M+1-t-Bu); exact mass of $C_{18}H_{27}NO_3$: 305.20.

Step 4: 4-(3-methoxybenzyl)piperidine hydrochloride

The title compound was prepared by the procedure described in step 4 of Example 3 using tert-butyl 4-(3-methoxybenzyl)piperidine-1-carboxylate (1.65 g, 5.40 mmol) and a solution of HCl in EtOAc (4.45 mol/L, 13.0 mL, 54.00 mmol) to give the title compound as a colourless solid (1.30 g, 100%). The compound was characterized by the following spectroscopic data:

MS (ESI, pos. ion) m/z: 206.1 (M+1-HCl); exact mass of $C_{13}H_{20}ClNO$: 241.12.

Step 5: 1-(2-chloro-4-nitrophenyl)-4-(3-methoxybenzyl)piperidine

The title compound was prepared by the procedure described in step 5 of Example 3 using 4-(3-methoxybenzyl)piperidine hydrochloride (1.30 g, 5.40 mmol), potassium carbonate (2.56 g, 18.50 mmol) and 2-chloro-1-fluoro-4-nitrobenzene (948 mg, 5.40 mmol) to give the title compound as yellow oil (1.94 g, 99.6%). The compound was characterized by the following spectroscopic data:

MS (ESI, pos. ion) m/z: 361.2 (M+1); exact mass of $C_{19}H_{21}ClN_2O_3$: 360.12.

Step 6: 3-chloro-4-(4-(3-methoxybenzyl)piperidin-1-yl)aniline

A solution of 1-(2-chloro-4-nitrophenyl)-4-(3-methoxybenzyl)piperidine (1.94 g, 5.40 mmol) in a mixture of THF and MeOH (v/v=10 mL/5 mL) was added in activated iron powder (1.80 g, 32.40 mol). The title compound was prepared by the procedure described in step 6 of Example 3 to give yellow oil (1.20 g, 67.4%). The compound was characterized by the following spectroscopic data:

MS (ESI, pos. ion) m/z: 331.0 (M+1); exact mass of $C_{19}H_{23}ClN_2O$: 330.15.

Step 7: N-(3-chloro-4-(4-(3-methoxybenzyl)piperidin-1-yl)phenyl)-3-oxobutanamide The title compound was prepared by the procedure described in step 5 of Example 1 starting with 3-chloro-4-(4-(3-methoxybenzyl)piperidin-1-yl)aniline (1.20 g, 3.62 mmol) and 4-methyleneoxetan-2-one (620 mg, 7.38 mmol) to give the title compound as light yellow oil (1.00 g, 66.7%). The compound was characterized by the following spectroscopic data:

MS (ESI, pos. ion) m/z: 415.2 (M+1); exact mass of $C_{23}H_{27}ClN_2O_3$: 414.17.

Step 8: (Z)-3-amino-N-(3-chloro-4-(4-(3-methoxybenzyl)piperidin-1-yl)phenyl)but-2-enamide A mixture of N-(3-chloro-4-(4-(3-methoxybenzyl)piperidin-1-yl)phenyl)-3-oxobutanamide (1.00 g, 2.41 mmol), MeOH (20 mL) and a solution of $NH_3$ in MeOH (7 mol/L, 2.0 mL, 14.0 mmol) was stirred at rt overnight. After the reaction was finished, the mixture concentrated in vacuo to give the crude product as reddish brown oil (1.00 g, 99.8%) which was used directly for the next step without further purification.

Step 9: 3-(3-chloro-4-(4-(3-methoxybenzyl)piperidin-1-yl)phenyl)-2,6-dimethylpyrimidin-4(3H)-one The title compound was prepared by the procedure described in step 7 of Example 1 starting with a solution of (Z)-3-amino-N-(3-chloro-4-(4-(3-methoxybenzyl)piperidin-1-yl)phenyl)but-2-enamide (1.00 g, 2.41 mmol) in triethyl orthoacetate (10 mL) to give the title compound as a light yellow solid (400 mg, 39.8%). The compound was characterized by the following spectroscopic data:

MS (ESI, pos. ion) m/z: 438.2 (M+1); $C_{25}H_{28}ClN_3O_2$: 437.19; and $^1$H NMR (400 MHz, DMSO-d$_6$) δ 7.46 (d, J=1.8 Hz, 1H), 7.27-7.15 (m, 3H), 6.77 (t, J=7.1 Hz, 3H), 6.22 (s, 1H), 3.74 (s, 3H), 3.27 (s, 2H), 2.66-2.53 (m, 4H), 2.19 (s, 3H), 2.04 (s, 3H), 1.68 (d, J=8.1 Hz, 3H), 1.45-1.31 (m, 2H).

Example 13: 3-(4-(4-([1,1'-biphenyl]-2-ylmethyl) piperidin-1-yl)-3-chlorophenyl)-2,6-dimethylpyrimidin-4(3H)-one

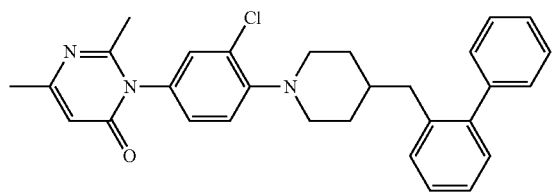 [SMILES: Cc1cc(=O)n(-c2ccc(N3CCC(Cc4ccccc4-c4ccccc4)CC3)c(Cl)c2)c(C)n1]

Step 1: diethyl ([1,1'-biphenyl]-2-ylmethyl)phosphonate

A mixture of triethyl phosphite (1.91 g, 11.50 mmol) and 2-(bromomethyl)-1,1'-biphenyl (2.47 g, 10.00 mmol) was stirred under N$_2$ at 87° C. overnight. The mixture was cooled to room temperature. The reaction mixture was used directly for the next step without further operation. The compound was characterized by the following spectroscopic data:

MS (ESI, pos. ion) m/z: 305.1 (M+1); exact mass of C$_{17}$H$_{21}$O$_3$P: 304.12.

Step 2: tert-butyl 4-([1,1'-biphenyl]-2-ylmethylene) piperidine-1-carboxylate

The title compound was prepared by the procedure described in step 2 of Example 3 using 60% NaH (480 mg, 12.00 mmol), diethyl ([1,1'-biphenyl]-2-ylmethyl)phosphonate (3.04 g, 10.00 mmol), 15-crown-5 (0.1 mL) and tert-butyl 4-oxopiperidine-1-carboxylate (1.99 g, 10.00 mmol) to give the title compound as yellow oil (1.97 g, 56.2%).

Step 3: tert-butyl 4-([1,1'-biphenyl]-2-ylmethyl) piperidine-1-carboxylate

The title compound was prepared by the procedure described in step 3 of Example 3 using a solution of tert-butyl 4-([1,1'-biphenyl]-2-ylmethylene)piperidine-1-carboxylate (1.97 g, 5.62 mmol) in a mixture of THF and MeOH (v/v=25 mL/25 mL), and 10% Pa/C (0.20 g) to give the title compound as yellow oil (1.91 g, 96.6%). The compound was characterized by the following spectroscopic data:

MS (ESI, pos. ion) m/z: 296.0 (M+1-t-Bu); exact mass of C$_{23}$H$_{29}$NO$_2$: 351.22.

Step 4: 4-([1,1'-biphenyl]-2-ylmethyl)piperidine hydrochloride

The title compound was prepared by the procedure described in step 4 of Example 3 using tert-butyl 4-([1,1'-biphenyl]-2-ylmethyl)piperidine-1-carboxylate (1.91 g, 5.47 mmol) and a solution of HCl in EtOAc (4.3 mol/L, 10.0 mL, 43.35 mmol) to give the title compound as a white solid (1.55 g, 112.5%). The compound was characterized by the following spectroscopic data:

MS (ESI, pos. ion) m/z: 252.2 (M+1-HCl); exact mass of C$_{18}$H$_{22}$ClN: 287.14.

Step 5: 4-([1,1'-biphenyl]-2-ylmethyl)-1-(2-chloro-4-nitrophenyl)piperidine

The title compound was prepared by the procedure described in step 5 of Example 3 using 2-chloro-1-fluoro-4-nitrobenzene (1.08 g, 6.17 mmol), potassium carbonate (4.26 g, 30.83 mmol) and 4-([1,1'-biphenyl]-2-ylmethyl) piperidine hydrochloride (1.55 g, 6.17 mmol) to give the title compound as a yellow solid (1.45 g, 57.8%). The compound was characterized by the following spectroscopic data:

$^1$H NMR (400 MHz, CDCl$_3$) δ 8.36 (dd, J=6.3, 2.7 Hz, 1H), 8.23-8.13 (m, 2H), 8.03 (dd, J=9.0, 2.6 Hz, 1H), 7.41 (t, J=7.2 Hz, 2H), 7.32 (ddt, J=9.6, 8.1, 5.8 Hz, 6H), 7.23 (dt, J=8.3, 4.3 Hz, 1H), 6.93 (d, J=9.0 Hz, 1H), 3.44 (d, J=12.1 Hz, 2H), 2.70-2.53 (m, 4H), 1.54-1.44 (m, 1H), 1.35-1.21 (m, 4H).

Step 6: 4-(4-([1,1'-biphenyl]-2-ylmethyl)piperidin-1-yl)-3-chloroaniline

A solution of 4-([1,1'-biphenyl]-2-ylmethyl)-1-(2-chloro-4-nitrophenyl)piperidine (1.45 g, 3.56 mmol) in a mixture of THF and MeOH (v/v=25 mL/25 mL) was added in activated iron powder (1.99 g, 35.63 mmol). The title compound was prepared by the procedure described in step 6 of Example 3 to give light yellow oil (1.25 g, 93.1%). The compound was characterized by the following spectroscopic data:

MS (ESI, pos. ion) m/z: 377.2 (M+1); exact mass of C$_{24}$H$_{25}$ClN$_2$: 376.17.

Step 7: 3-(4-(4-([1,1'-biphenyl]-2-ylmethyl)piperidin-1-yl)-3-chlorophenyl)-2,6-dimethylpyrimidin-4 (3H)-one The title compound was prepared by the procedure described in step 3 of Example 2 starting with 4-(4-([1,1'-biphenyl]-2-ylmethyl)piperidin-1-yl)-3-chloroaniline (1.25 g, 3.32 mmol), trimethylaluminium (6.6 mL, 13.20 mmol, 2.0 mol/L in toluene) and a solution of methyl 3-acetamidobut-2-enoate (522 mg, 3.32 mmol) in toluene (2 mL) under N$_2$ to give the title compound as a light yellow solid (463 mg, 28.8%). The compound was characterized by the following spectroscopic data:

MS (ESI, pos. ion) m/z: 484.2 (M+1); exact mass of C$_{30}$H$_{30}$ClN$_3$O: 483.21; and $^1$H NMR (400 MHz, CDCl$_3$) δ 7.41 (t, J=7.2 Hz, 2H), 7.36 (d, J=7.2 Hz, 1H), 7.33-7.27 (m, 5H), 7.22 (d, J=7.9 Hz, 1H), 7.16 (d, J=2.3 Hz, 1H), 7.05 (d, J=8.5 Hz, 1H), 6.99 (dd, J=8.5, 2.3 Hz, 1H), 6.26 (s, 1H), 3.31 (dd, J=41.3, 12.0 Hz, 2H), 2.64 (d, J=6.9 Hz, 2H), 2.50 (dt, J=21.3, 9.6 Hz, 2H), 2.28 (s, 3H), 2.15 (s, 3H), 1.49 (dd, J=7.1, 3.6 Hz, 1H), 1.37-1.28 (m, 4H).

Example 14: 3-(3-chloro-4-(4-(3-(trifluoromethyl) benzyl)piperidin-1-yl)phenyl)-2,6-dimethylpyrimidin-4(3H)-one

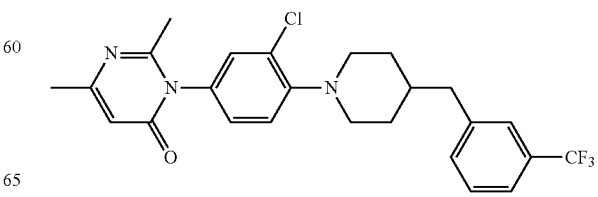

Step 1: diethyl 3-(trifluoromethyl)benzylphosphonate

A mixture of triethyl phosphite (1.60 g, 9.62 mmol) and 1-(bromomethyl)-3-(trifluoromethyl)benzene (2.00 g, 8.37 mmol) was stirred under $N_2$ at 87° C. overnight. The mixture was cooled to room temperature. The reaction mixture was used directly for the next step without further operation. The compound was characterized by the following spectroscopic data:

MS (ESI, pos. ion) m/z: 297.1 (M+1); exact mass of $C_{12}H_{16}F_3O_3P$: 296.08.

Step 2: tert-butyl 4-(3-(trifluoromethyl)benzylidene) piperidine-1-carboxylate The title compound was prepared by the procedure described in step 2 of Example 3 using tert-butyl 4-oxopiperidine-1-carboxylate (1.53 g, 7.67 mmol), diethyl 3-(trifluoromethyl)benzylphosphonate (2.84 g, 9.59 mmol) and potassium tert-butanolate (1.13 g, 10.07 mmol) to give the crude product which was used directly for the next step without further purification. The compound was characterized by the following spectroscopic data:

MS (ESI, pos. ion) m/z: 286.0 (M+1-t-Bu); exact mass of $C_{18}H_{22}F_3NO_2$: 341.16.

Step 3: tert-butyl 4-(3-(trifluoromethyl)benzyl)piperidine-1-carboxylate

The title compound was prepared by the procedure described in step 3 of Example 3 using tert-butyl 4-(3-(trifluoromethyl)benzylidene)piperidine-1-carboxylate (2.54 g, 7.44 mmol) and 10% Pa/C (0.25 g) to give the crude product which was used directly for the next step without further purification. The compound was characterized by the following spectroscopic data:

MS (ESI, pos. ion) m/z: 288.0 (M+1-t-Bu); exact mass of $C_{18}H_{24}F_3NO_2$: 343.18.

Step 4: 4-(3-(trifluoromethyl)benzyl)piperidine hydrochloride

The title compound was prepared by the procedure described in step 4 of Example 3 using a solution of tert-butyl 4-(3-(trifluoromethyl)benzyl)piperidine-1-carboxylate (2.37 g, 6.90 mmol) in EtOAc (50 mL) and a solution of HCl in EtOAc (4.4 mol/L, 15.7 mL, 69.00 mmol) to give the title compound as a white solid (1.76 g, 91.2%). The compound was characterized by the following spectroscopic data:

MS (ESI, pos. ion) m/z: 244.2 (M+1-HCl); exact mass of $C_{13}H_{17}ClF_3N$: 279.10.

Step 5: 1-(2-chloro-4-nitrophenyl)-4-(3-(trifluoromethyl)benzyl)piperidine

The title compound was prepared by the procedure described in step 5 of Example 9 using 2-chloro-1-fluoro-4-nitrobenzene (1.10 g, 6.29 mmol), potassium carbonate (3.04 g, 22.02 mmol) and 4-(3-(trifluoromethyl)benzyl)piperidine hydrochloride (1.76 g, 6.29 mmol) to give the crude product which was used directly for the next step without further purification. The compound was characterized by the following spectroscopic data:

MS (ESI, pos. ion) m/z: 399.1 (M+1); exact mass of $C_{19}H_{18}ClF_3N_2O_2$: 398.10.

Step 6: 3-chloro-4-(4-(3-(trifluoromethyl)benzyl) piperidin-1-yl)aniline

A solution of 1-(2-chloro-4-nitrophenyl)-4-(3-(trifluoromethyl)benzyl)piperidine (1.60 g, 4.00 mmol) in MeOH (20 mL) was added in activated iron powder (2.24 g, 40.00 mol). The title compound was prepared by the procedure described in step 6 of Example 3 to give a light yellow solid (1.40 g, 94.6%). The compound was characterized by the following spectroscopic data:

MS (ESI, pos. ion) m/z: 369.1 (M+1); exact mass of $C_{19}H_{20}ClF_3N_2$: 368.13.

Step 7: 3-(3-chloro-4-(4-(3-(trifluoromethyl)benzyl) piperidin-1-yl)phenyl)-2,6-dimethylpyrimidin-4 (3H)-one The title compound was prepared by the procedure described in step 3 of Example 2 starting with 3-chloro-4-(4-(3-(trifluoromethyl)benzyl)piperidin-1-yl)aniline (1.40 g, 3.80 mmol), trimethylaluminium (7.6 mL, 15.20 mmol, 2.0 mol/L in toluene) and a solution of methyl 3-acetamidobut-2-enoate (716 mg, 4.56 mmol) in toluene (2 mL) under $N_2$ to give the title compound as a light yellow solid (1.00 g, 55.2%). The compound was characterized by the following spectroscopic data:

MS (ESI, pos. ion) m/z: 476.1 (M+1); exact mass of $C_{25}H_{25}ClF_3N_3O$: 475.16; and $^1$H NMR (400 MHz, DMSO-$d_6$) δ 7.56 (d, J=12.7 Hz, 4H), 7.46 (d, J=1.9 Hz, 1H), 7.28-7.17 (m, 2H), 6.22 (s, 1H), 3.32-3.23 (m, 2H), 2.76-2.55 (m, 4H), 2.19 (s, 3H), 2.06 (s, 3H), 1.69 (t, J=11.5 Hz, 3H), 1.50-1.33 (m, 2H).

Example 15: 3-(3-chloro-4-(4-(2-chlorobenzyl)piperidin-1-yl)phenyl)-2,6-dimethylpyrimidin-4(3H)-one

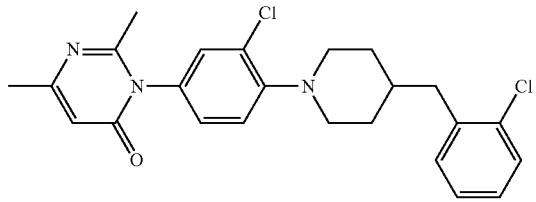 [SMILES: Cc1cc(=O)n(-c2ccc(N3CCC(Cc4ccccc4Cl)CC3)c(Cl)c2)c(C)n1]

Step 1: tert-butyl 4-(2-chlorobenzyl)piperidine-1-carboxylate

A mixture of tert-butyl 4-methylenepiperidine-1-carboxylate (3.00 g, 15.21 mmol) and 9-borabicyclo [3,3,1]nonane (30.0 mL, 15.00 mmol, 0.5 mol/L in THF) was refluxed under $N_2$ for 3 hours. Then the mixture was cooled to room temperature, and to the mixture was added 1-bromo-2-chlorobenzene (2.77 g, 14.45 mmol), Pd(dppf)Cl$_2$ (330 mg, 0.45 mmol), 30 mL of DMF, 5 mL of H$_2$O and potassium carbonate (2.50 g, 18.25 mmol). The resulted mixture was heated to 60° C. overnight. After the reaction was finished, the mixture was cooled to rt, and to the mixture was added H$_2$O (100 mL). The mixture was adjusted to pH 11 with 10% aqueous NaOH solution and extracted with EtOAc (100 mL×2). The combined organic phases were washed with water (100 mL×2) and brine (100 mL) in turn, dried over anhydrous Na$_2$SO$_4$ (20 g), filtered and concentrated in vacuo. The crude was purified by silica column chromatography (PE/EtOAc (v/v)=4/1) to give the title compound as a white solid (4.00 g, 84.9%).

Step 2: 4-(2-chlorobenzyl)piperidine hydrochloride

To a solution of tert-butyl 4-(2-chlorobenzyl)piperidine-1-carboxylate (1.53 g, 5.09 mmol) in EtOAc (30 mL) was added a solution of HCl in EtOAc (4.4 mol/L, 17.6 mL, 77.46 mmol). The reaction mixture was stirred at rt under N$_2$ overnight. After the reaction was finished, the mixture was concentrated in vacuo. The residue was wash with EtOAc (30 mL), dried under vacuum to give the crude product as a white solid (2.00 g, 62.9%) which was used directly for the next step without further purification. The compound was characterized by the following spectroscopic data:

MS (ESI, pos. ion) m/z: 210.1 (M+1-HCl); exact mass of C$_{12}$H$_{17}$Cl$_2$N: 245.07.

Step 3: 1-(2-chloro-4-nitrophenyl)-4-(2-chlorobenzyl)piperidine

To a solution of 2-chloro-1-fluoro-4-nitrobenzene (0.64 g, 3.66 mmol) in EtOAc (20 mL) was added TEA (1.23 g, 12.18 mmol) and 4-(2-chlorobenzyl)piperidine hydrochloride (1.00 g, 4.06 mmol). The reaction mixture was stirred at rt under N$_2$ overnight. After the reaction was finished, the reaction mixture was filtered and the filtrate was concentrated in vacuo. The residue was purified by silica column chromatography (PE/EtOAc (v/v)=8/1) to give the crude product as yellow oil (0.50 g, 33.7%) which was used directly for the next step without further purification. The compound was characterized by the following spectroscopic data:

MS (ESI, pos. ion) m/z: 365.1 (M+1); exact mass of C$_{18}$H$_{18}$Cl$_2$N$_2$O$_2$: 364.07.

Step 4: 3-chloro-4-(4-(2-chlorobenzyl)piperidin-1-yl)aniline

The title compound was prepared by the procedure described in step 6 of Example 3 starting with a solution of 1-(2-chloro-4-nitrophenyl)-4-(2-chlorobenzyl)piperidine (0.50 g, 1.37 mmol) in a mixture of THF and MeOH (v/v=10 mL/10 mL) was added in activated iron power (0.77 g, 13.70 mmol) to give the title compound as a light yellow solid (450 mg, 98.1%). The compound was characterized by the following spectroscopic data:

MS (ESI, pos. ion) m/z: 335.1 (M+1); exact mass of C$_{18}$H$_{20}$Cl$_2$N$_2$: 334.10.

Step 5: 3-(3-chloro-4-(4-(2-chlorobenzyl)piperidin-1-yl)phenyl)-2,6-dimethylpyrimidin-4(3H)-one The title compound was prepared by the procedure described in step 3 of Example 2 starting with 3-chloro-4-(4-(2-chlorobenzyl)piperidin-1-yl)aniline (800 mg, 2.39 mmol), trimethylaluminium (4.8 mL, 9.60 mmol, 2.0 mol/L in toluene) and a solution of methyl 3-acetamidobut-2-enoate (450 mg, 2.86 mmol) in toluene (5 mL) under N$_2$ to give the title compound as a light yellow solid (400 mg, 37.7%). The compound was characterized by the following spectroscopic data:

MS (ESI, pos. ion) m/z: 442.2 (M+1); exact mass of C$_{24}$H$_{25}$Cl$_2$N$_3$O: 441.14; and $^1$H NMR (400 MHz, CDCl$_3$) δ 7.39-7.34 (m, 1H), 7.22-7.18 (m, 3H), 7.18-7.13 (m, 1H), 7.11 (d, J=8.5 Hz, 1H), 7.02 (dd, J=8.5, 2.4 Hz, 1H), 6.28 (s, 1H), 3.43 (dd, J=36.0, 11.2 Hz, 2H), 2.75 (t, J=7.7 Hz, 2H), 2.64 (dtd, J=41.4, 11.6, 2.2 Hz, 2H), 2.29 (d, J=0.4 Hz, 3H), 2.18 (s, 3H), 1.87-1.71 (m, 3H), 1.60-1.50 (m, 2H).

Example 16: 3-(3-chloro-4-(4-(4-chloro-3-fluorobenzyl)piperidin-1-yl)phenyl)-2,6-dimethylpyrimidin-4(3H)-one

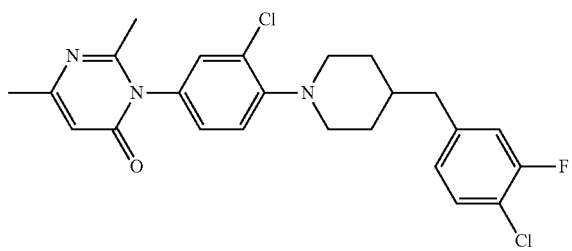 [SMILES: Cc1cc(=O)n(-c2ccc(N3CCC(Cc4ccc(Cl)c(F)c4)CC3)c(Cl)c2)c(C)n1]

Step 1: tert-butyl 4-(4-chloro-3-fluorobenzyl)piperidine-1-carboxylate

The title compound was prepared by the procedure described in step 1 of Example 15 except using tert-butyl 4-methylenepiperidine-1-carboxylate (2.17 g, 11.00 mmol), 9-borabicyclo[3,3,1]nonane (22 mL, 11.00 mmol, 0.5 mol/L in THF), 4-bromo-1-chloro-2-fluorobenzene (2.09 g, 10.00 mmol), Pd(dppf)Cl$_2$ (220 mg, 0.30 mmol) and potassium carbonate (1.80 g, 1.30 mmol) as starting materials to give the title compound as colourless oil (1.35 g, 41.1%). The compound was characterized by the following spectroscopic data:

MS (ESI, pos. ion) m/z: 272.1 (M+1-t-Bu); exact mass of C$_{17}$H$_{23}$ClFNO$_2$: 327.14.

Step 2: 4-(4-chloro-3-fluorobenzyl)piperidine hydrochloride

The title compound was prepared by the procedure described in step 4 of Example 3 using tert-butyl 4-(4-chloro-3-fluorobenzyl)piperidine-1-carboxylate (1.23 g, 3.75 mmol) and a solution of HCl in EtOAc (4.4 mol/L, 4.0 mL, 17.60 mmol) to give the crude product which was used directly for the next step without further purification. The compound was characterized by the following spectroscopic data:

MS (ESI, pos. ion) m/z: 229.1 (M+1-HCl); exact mass of C$_{12}$H$_{16}$Cl$_2$FN: 263.06.

Step 3: 4-(4-chloro-3-fluorobenzyl)-1-(2-chloro-4-nitrophenyl)piperidine

The title compound was prepared by the procedure described in step 5 of Example 4 using 2-chloro-1-fluoro-4-nitrobenzene (598 mg, 3.41 mmol), 4-(4-chloro-3-fluorobenzyl)piperidine hydrochloride (991 mg, 3.75 mmol) and TEA (1.03 g, 10.22 mmol) to give the title compound as yellow oil (1.00 g, 76.6%). The compound was characterized by the following spectroscopic data:

MS (ESI, pos. ion) m/z: 384.1 (M+1); exact mass of $C_{18}H_{17}Cl_2FN_2O_2$: 382.07.

Step 4: 3-chloro-4-(4-(4-chloro-3-fluorobenzyl)piperidin-1-yl)aniline

A solution of 4-(4-chloro-3-fluorobenzyl)-1-(2-chloro-4-nitrophenyl)piperidine (1.00 g, 2.61 mmol) in a mixture of THF and H$_2$O (v/v=15 mL/5 mL) was added in activated iron powder (1.46 g, 26.10 mmol). The title compound was prepared by the procedure described in step 4 of Example 1 to give a yellow solid (820 mg, 89.0%). The compound was characterized by the following spectroscopic data:
MS (ESI, pos. ion) m/z: 354.0 (M+1); exact mass of $C_{18}H_{19}Cl_2FN_2$: 352.09.

Step 5: 3-(3-chloro-4-(4-(4-chloro-3-fluorobenzyl)piperidin-1-yl)phenyl)-2,6-dimethylpyrimidin-4(3H)-one The title compound was prepared by the procedure described in step 3 of Example 2 starting with 3-chloro-4-(4-(4-chloro-3-fluorobenzyl)piperidin-1-yl)aniline (740 mg, 2.09 mmol), trimethylaluminium (4.2 mL, 8.40 mmol, 2.0 mol/L in toluene) and a solution of methyl 3-acetamidobut-2-enoate (494 mg, 3.14 mmol) in toluene (5 mL) under N$_2$ to give the title compound as a yellow solid (669 mg, 69.4%). The compound was characterized by the following spectroscopic data:
MS (ESI, pos. ion) m/z: 460.1 (M+1); exact mass of $C_{24}H_{24}Cl_2FN_3O$: 459.13; and
$^1$H NMR (600 MHz, CDCl$_3$) δ 7.33 (t, J=7.9 Hz, 1H), 7.22 (d, J=2.3 Hz, 1H), 7.14 (d, J=8.5 Hz, 1H), 7.05 (dd, J=8.5, 2.3 Hz, 1H), 7.00 (dd, J=10.0, 1.6 Hz, 1H), 6.95-6.90 (m, 1H), 6.30 (s, 1H), 3.46 (dd, J=53.5, 12.5 Hz, 2H), 2.71 (t, J=10.8 Hz, 1H), 2.66-2.56 (m, 3H), 2.32 (s, 3H), 2.21 (s, 3H), 1.69 (tdd, J=11.0, 7.4, 3.7 Hz, 3H), 1.53 (dd, J=22.3, 10.2 Hz, 2H).

Example 17: 3-(3-chloro-4-(4-(3,4,5-trifluorobenzyl)piperidin-1-yl)phenyl)-2,6-dimethylpyrimidin-4(3H)-one

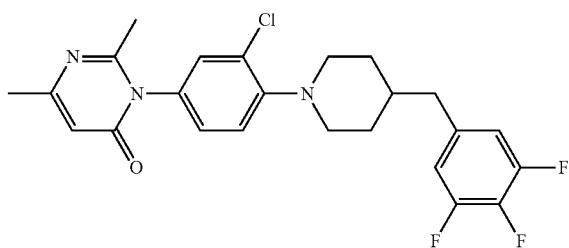 [SMILES: Cc1cc(=O)n(-c2ccc(N3CCC(Cc4cc(F)c(F)c(F)c4)CC3)c(Cl)c2)c(C)n1]

Step 1: diethyl 3,4,5-trifluorobenzylphosphonate

A mixture of triethyl phosphite (1.91 g, 11.50 mmol) and 5-(bromomethyl)-1,2,3-trifluorobenzene (2.25 g, 10.00 mmol) was stirred at 87° C. under N$_2$ overnight. The mixture was cooled to room temperature. The reaction mixture was used directly for the next step without further operation. The compound was characterized by the following spectroscopic data:

MS (ESI, pos. ion) m/z: 283.1 (M+1); exact mass of $C_{11}H_{14}F_3O_3P$: 282.06.

Step 2: tert-butyl 4-(3,4,5-trifluorobenzylidene)piperidine-1-carboxylate

The title compound was prepared by the procedure described in step 2 of Example 3 using 60% NaH (480 mg, 12.00 mmol), diethyl 3,4,5-trifluorobenzylphosphonate (2.82 g, 10.00 mmol), 15-crown-5 (0.1 mL) and tert-butyl 4-oxopiperidine-1-carboxylate (1.99 g, 10.00 mmol) to give the title compound as a white solid (2.04 g, 62.3%). The compound was characterized by the following spectroscopic data:
MS (ESI, pos. ion) m/z: 272.1 (M+1-t-Bu); exact mass of $C_{17}H_{20}F_3NO_2$: 327.14; and
$^1$H NMR (400 MHz, CDCl$_3$) δ 6.78 (dd, J=8.3, 6.7 Hz, 2H), 6.21 (s, 1H), 3.55-3.37 (m, 4H), 2.36 (dt, J=35.8, 5.6 Hz, 4H), 1.48 (s, 9H).

Step 3: tert-butyl 4-(3,4,5-trifluorobenzyl)piperidine-1-carboxylate

The title compound was prepared by the procedure described in step 3 of Example 3 using a solution of tert-butyl 4-(3,4,5-trifluorobenzylidene)piperidine-1-carboxylate (2.76 g, 9.47 mmol) in a mixture solvent of THF and MeOH (v/v=25 mL/25 mL), and 10% Pa/C (0.12 g) to give the title compound as colourless oil (2.02 g, 98.4%).

Step 4: 4-(3,4,5-trifluorobenzyl)piperidine hydrochloride

The title compound was prepared by the procedure described in step 4 of Example 3 using a solution of tert-butyl 4-(3,4,5-trifluorobenzyl)piperidine-1-carboxylate (2.02 g, 6.13 mmol) in 30 mL of EtOAc and a solution of HCl in EtOAc (4.4 mol/L, 10.0 mL, 44.00 mmol) to give the title compound as a white solid (1.63 g, 100%). The compound was characterized by the following spectroscopic data:
MS (ESI, pos. ion) m/z: 230.2 (M+1-HCl); exact mass of $C_{12}H_{15}ClF_3N$: 265.08.

Step 5: 1-(2-chloro-4-nitrophenyl)-4-(3,4,5-trifluorobenzyl)piperidine

The title compound was prepared by the procedure described in step 5 of Example 3 using 2-chloro-1-fluoro-4-nitrobenzene (1.08 g, 6.13 mmol), 4-(3,4,5-trifluorobenzyl)piperidine hydrochloride (1.63 g, 6.13 mmol) and potassium carbonate (3.39 g, 24.54 mmol) to give the title compound as yellow oil (2.11 g, 94.0%). The compound was characterized by the following spectroscopic data:
MS (ESI, pos. ion) m/z: 385.1 (M+1); exact mass of $C_{18}H_{16}ClF_3N_2O_2$: 384.09;
$^1$H NMR (400 MHz, CDCl$_3$) δ 8.23 (d, J=2.6 Hz, 1H), 8.07 (dd, J=9.0, 2.6 Hz, 1H), 7.01 (d, J=9.0 Hz, 1H), 6.84-6.73 (m, 2H), 3.58 (d, J=12.2 Hz, 2H), 2.73 (dd, J=12.0, 10.3 Hz, 2H), 2.57 (d, J=6.9 Hz, 2H), 1.81-1.63 (m, 3H), 1.49 (ddd, J=14.9, 12.2, 4.5 Hz, 2H).

Step 6: 3-chloro-4-(4-(3,4,5-trifluorobenzyl)piperidin-1-yl)aniline

A solution of 1-(2-chloro-4-nitrophenyl)-4-(3,4,5-trifluorobenzyl)piperidine (2.22 g, 5.77 mmol) in a mixture of THF and MeOH (v/v=30 mL/30 mL) was added in activated iron powder (3.22 g, 57.70 mmol). The title compound was prepared by the procedure described in step 6 of Example 3 to give yellow oil (2.02 g, 99.2%). The compound was characterized by the following spectroscopic data:

MS (ESI, pos. ion) m/z: 355.1 (M+1); exact mass of $C_{18}H_{18}ClF_3N_2$: 354.11.

Step 7: 3-(3-chloro-4-(4-(3,4,5-trifluorobenzyl)piperidin-1-yl)phenyl)-2,6-dimethylpyrimidin-4(3H)-one The title compound was prepared by the procedure described in step 3 of Example 2 starting with 3-chloro-4-(4-(3,4,5-trifluorobenzyl)piperidin-1-yl)aniline (2.03 g, 5.72 mmol), trimethylaluminium (12.0 mL, 24.00 mmol, 2.0 mol/L in toluene) and a solution of methyl 3-acetamidobut-2-enoate (1.08 g, 6.87 mmol) in toluene (10 mL) under $N_2$ to give the title compound as a white solid (1.36 g, 51.5%). The compound was characterized by the following spectroscopic data:

MS (ESI, pos. ion) m/z: 462.1 (M+1); exact mass of $C_{24}H_{23}ClF_3N_3O$: 461.15; and
$^1$H NMR (400 MHz, CDCl$_3$) δ 7.20 (d, J=2.4 Hz, 1H), 7.12 (d, J=8.5 Hz, 1H), 7.03 (dd, J=8.5, 2.4 Hz, 1H), 6.83-6.74 (m, 2H), 6.28 (s, 1H), 3.44 (dd, J=33.5, 12.0 Hz, 2H), 2.69 (dd, J=11.5, 9.6 Hz, 1H), 2.64-2.50 (m, 3H), 2.29 (s, 3H), 2.18 (s, 3H), 1.71 (dd, J=17.8, 8.3 Hz, 2H), 1.57-1.42 (m, 3H).

Example 18: 3-(4-(4-(2,5-bis(trifluoromethyl)benzyl)piperidin-1-yl)-3-chlorophenyl)-2,6-dimethylpyrimidin-4(3H)-one

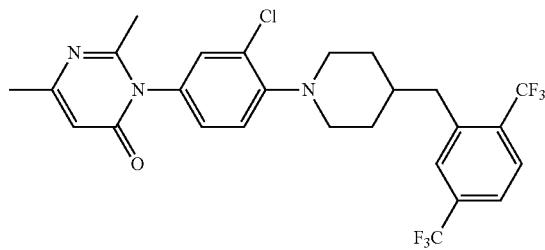 [SMILES: Cc1cc(=O)n(-c2ccc(N3CCC(Cc4cc(C(F)(F)F)ccc4C(F)(F)F)CC3)c(Cl)c2)c(C)n1]

Step 1: diethyl 2,5-bis(trifluoromethyl)benzylphosphonate

A mixture of triethyl phosphite (1.91 g, 11.50 mmol) and 2-(bromomethyl)-1,4-bis(trifluoromethyl)benzene (3.07 g, 10.00 mmol) was stirred at 87° C. under $N_2$ overnight. The mixture was cooled to room temperature. The reaction mixture was used directly for the next step without further operation. The compound was characterized by the following spectroscopic data:

MS (ESI, pos. ion) m/z: 365.1 (M+1); exact mass of $C_{13}H_{15}F_6O_3P$: 364.07.

Step 2: tert-butyl 4-(2,5-bis(trifluoromethyl)benzylidene)piperidine-1-carboxylate The title compound was prepared by the procedure described in step 2 of Example 3 using 60% NaH (480 mg, 12.00 mmol), diethyl 2,5-bis(trifluoromethyl)benzylphosphonate (3.64 g, 10.00 mmol), 15-crown-5 (0.1 mL) and tert-butyl 4-oxopiperidine-1-carboxylate (1.99 g, 10.00 mmol) to give the title compound as a white solid (2.48 g, 60.6%). The compound was characterized by the following spectroscopic data:

MS (ESI, pos. ion) m/z: 354.1 (M+1-t-Bu); exact mass of $C_{19}H_{21}F_6NO_2$: 409.15; and
$^1$H NMR (400 MHz, CDCl$_3$) δ 7.79 (d, J=8.2 Hz, 1H), 7.61 (d, J=8.2 Hz, 1H), 7.47 (s, 1H), 6.49 (s, 1H), 3.59-3.47 (m, 2H), 3.43-3.31 (m, 2H), 2.37 (t, J=5.4 Hz, 2H), 2.24-2.12 (m, 2H), 1.47 (s, 9H).

Step 3: tert-butyl 4-(2,5-bis(trifluoromethyl)benzyl)piperidine-1-carboxylate

The title compound was prepared by the procedure described in step 3 of Example 3 using a solution of tert-butyl 4-(2,5-bis(trifluoromethyl)benzylidene)piperidine-1-carboxylate (2.48 g, 6.06 mmol) in a mixture of THF and MeOH (v/v=25 mL/25 mL), and 10% Pa/C (0.13 g) to give the title compound as colourless oil (2.45 g, 98.3%).

Step 4: 4-(2,5-bis(trifluoromethyl)benzyl)piperidine hydrochloride

The title compound was prepared by the procedure described in step 4 of Example 3 using a solution of tert-butyl 4-(2,5-bis(trifluoromethyl)benzyl)piperidine-1-carboxylate (2.45 g, 5.96 mmol) in 50 mL of EtOAc and a solution of HCl in EtOAc (4.4 mol/L, 10.0 mL, 44.00 mmol) to give the title compound as a white solid (2.13 g, 103%). The compound was characterized by the following spectroscopic data:

MS (ESI, pos. ion) m/z: 312.1 (M+1-HCl); exact mass of $C_{14}H_{16}ClF_6N$: 347.09.

Step 5: 4-(2,5-bis(trifluoromethyl)benzyl)-1-(2-chloro-4-nitrophenyl)piperidine

The title compound was prepared by the procedure described in step 5 of Example 3 using 2-chloro-1-fluoro-4-nitrobenzene (1.08 g, 6.13 mmol), 4-(2,5-bis(trifluoromethyl)benzyl)piperidine hydrochloride (2.13 g, 6.13 mmol) and potassium carbonate (3.39 g, 24.54 mmol) to give the title compound as yellow oil (2.51 g, 87.8%). The compound was characterized by the following spectroscopic data:

MS (ESI, pos. ion) m/z: 467.1 (M+1); exact mass of $C_{20}H_{17}ClF_6N_2O_2$: 466.09; and
$^1$H NMR (400 MHz, CDCl$_3$) δ 8.24 (d, J=2.6 Hz, 1H), 8.08 (dd, J=9.0, 2.6 Hz, 1H), 7.80 (d, J=8.1 Hz, 1H), 7.60 (d, J=9.4 Hz, 2H), 7.01 (d, J=9.0 Hz, 1H), 3.59 (d, J=12.1 Hz, 2H), 2.88 (d, J=6.8 Hz, 2H), 2.73 (t, J=11.3 Hz, 2H), 1.88-1.72 (m, 3H), 1.66-1.57 (m, 2H).

Step 6: 4-(4-(2,5-bis(trifluoromethyl)benzyl)piperidin-1-yl)-3-chloroaniline

To a suspension of a solution of 4-(2,5-bis(trifluoromethyl)benzyl)-1-(2-chloro-4-nitrophenyl)piperidine (2.51 g, 5.38 mmol) in a mixture of THF and MeOH (v/v=25 mL/25 mL) was added in activated iron powder (3.00 g, 53.77 mmol). The title compound was prepared by the procedure described in step 6 of Example 3 to give yellow oil (2.36 g, 100.5%). The compound was characterized by the following spectroscopic data:

MS (ESI, pos. ion) m/z: 437.2 (M+1); exact mass of $C_{20}H_{19}ClF_6N_2$: 436.11.

Step 7: 3-(4-(4-(2,5-bis(trifluoromethyl)benzyl)piperidin-1-yl)-3-chlorophenyl)-2,6-dimethylpyrimidin-4(3H)— one The title compound was prepared by the procedure described in step 3 of Example 2 starting with 4-(4-(2,5-bis(trifluoromethyl)benzyl)piperidin-1-yl)-3-chloroaniline (2.36 g, 5.40 mmol), trimethylaluminium (11.0 mL, 22.00 mmol, 2.0 mol/L in toluene) and a solution of methyl 3-acetamidobut-2-enoate (1.02 g, 6.48 mmol) in toluene (10 mL) under $N_2$ to give the title compound as a light yellow solid (1.60 g, 54.5%). The compound was characterized by the following spectroscopic data:
MS (ESI, pos. ion) m/z: 544.1 (M+1); exact mass of $C_{26}H_{24}ClF_6N_3O$: 543.15; and
$^1H$ NMR (400 MHz, $CDCl_3$) δ 7.79 (d, J=8.7 Hz, 1H), 7.59 (d, J=6.2 Hz, 2H), 7.21 (d, J=2.4 Hz, 1H), 7.12 (d, J=8.5 Hz, 1H), 7.06-7.00 (m, 1H), 6.28 (s, 1H), 3.46 (dd, J=38.3, 12.0 Hz, 2H), 2.87 (d, J=6.6 Hz, 2H), 2.65 (dt, J=43.5, 10.9 Hz, 2H), 2.29 (s, 3H), 2.18 (s, 3H), 1.76 (d, J=10.8 Hz, 3H), 1.62-1.52 (m, 2H).

Example 19: 3-(3-chloro-4-(4-(3-chlorobenzyl)piperidin-1-yl)phenyl)-2,6-dimethylpyrimidin-4(3H)-one

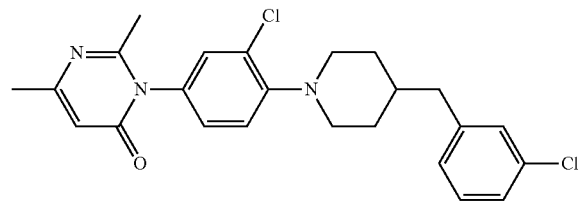 [SMILES: Cc1cc(=O)n(-c2ccc(N3CCC(Cc4cccc(Cl)c4)CC3)c(Cl)c2)c(C)n1]

Step 1: tert-butyl 4-(3-chlorobenzyl)piperidine-1-carboxylate

The title compound was prepared by the procedure described in step 1 of Example 15 using tert-butyl 4-methylenepiperidine-1-carboxylate (4.00 g, 20.28 mmol), 9-borabicyclo[3,3,1]nonane (40.0 mL, 20.00 mmol, 0.5 mol/L in THF), 1-bromo-3-chlorobenzene (3.69 g, 19.26 mmol), $Pd(dppf)Cl_2$ (445 mg, 0.60 mmol) and potassium carbonate (3.35 g, 24.30 mmol) to give the title compound as colourless oil (3.73 g, 59.4%). The compound was characterized by the following spectroscopic data:
MS (ESI, pos. ion) m/z: 254.1 (M+1-t-Bu); exact mass of $C_{17}H_{24}ClNO_2$: 309.15.

Step 2: 4-(3-chlorobenzyl)piperidine hydrochloride

The title compound was prepared by the procedure described in step 2 of Example 15 using tert-butyl 4-(3-chlorobenzyl)piperidine-1-carboxylate (3.00 g, 9.68 mmol) and a solution of HCl in EtOAc (4.4 mol/L, 13.2 mL, 58.1 mmol) to give the title compound as a white solid (2.0 g, 84.0%).

Step 3: 1-(2-chloro-4-nitrophenyl)-4-(3-chlorobenzyl)piperidine

The title compound was prepared by the procedure described in step 3 of Example 15 using 2-chloro-1-fluoro-4-nitrobenzene (1.28 g, 7.31 mmol), TEA (2.47 g, 24.30 mmol) and 4-(3-chlorobenzyl)piperidine hydrochloride (2.00 g, 8.12 mmol) to give the title compound as yellow oil (2.20 g, 74.0%). The compound was characterized by the following spectroscopic data:
MS (ESI, pos. ion) m/z: 365.2 (M+1); exact mass of $C_{18}H_{18}Cl_2N_2O_2$: 364.07.

Step 4: 3-chloro-4-(4-(3-chlorobenzyl)piperidin-1-yl)aniline

The title compound was prepared by the procedure described in step 6 of Example 3 starting with a solution of 1-(2-chloro-4-nitrophenyl)-4-(3-chlorobenzyl)piperidine (2.20 g, 6.02 mmol) in a mixture of THF and $H_2O$ (v/v=10 mL/10 mL) was added in activated iron powder (3.36 g, 60.20 mmol) to give the title compound as yellow oil (1.90 g, 94.0%). The compound was characterized by the following spectroscopic data:
MS (ESI, pos. ion) m/z: 335.0 (M+1); exact mass of $C_{18}H_{20}Cl_2N_2$: 334.10.

Step 5: 3-(3-chloro-4-(4-(3-chlorobenzyl)piperidin-1-yl)phenyl)-2,6-dimethylpyrimidin-4(3H)-one The title compound was prepared by the procedure described in step 3 of Example 2 starting with 3-chloro-4-(4-(3-chlorobenzyl)piperidin-1-yl)aniline (1.90 g, 5.67 mmol), trimethylaluminium (8.5 mL, 17.00 mmol, 2.0 mol/L in toluene) and a solution of methyl 3-acetamidobut-2-enoate (1.07 g, 6.80 mmol) in toluene (10 mL) under $N_2$ to give the title compound as a white solid (1.90 g, 52.0%). The compound was characterized by the following spectroscopic data:
MS (ESI, pos. ion) m/z: 442.2 (M+1); exact mass of $C_{24}H_{25}Cl_2N_3O$: 441.14; and
$^1H$ NMR (400 MHz, $CDCl_3$) δ 7.27-7.20 (m, 2H), 7.20-7.16 (m, 2H), 7.11 (d, J=8.5 Hz, 1H), 7.06 (d, J=7.2 Hz, 1H), 7.02 (dd, J=8.5, 2.4 Hz, 1H), 6.28 (s, 1H), 3.44 (dd, J=36.2, 11.4 Hz, 2H), 2.74-2.63 (m, 1H), 2.63-2.53 (m, 3H), 2.29 (s, 3H), 2.18 (s, 3H), 1.75 (d, J=12.5 Hz, 2H), 1.71-1.68 (m, 1H), 1.51 (qd, J=11.7, 3.7 Hz, 2H).

Example 20: 3-(4-(4-(benzo[c][1,2,5]oxadiazol-5-ylmethyl)piperidin-1-yl)-3-chlorophenyl)-2,6-dimethylpyrimidin-4(3H)-one

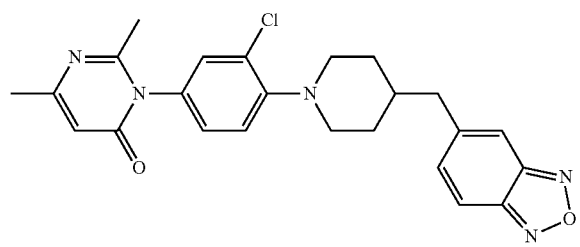 [SMILES: Cc1cc(=O)n(-c2ccc(N3CCC(Cc4ccc5nonc5c4)CC3)c(Cl)c2)c(C)n1]

Step 1: diethyl (benzo[c][1,2,5]oxadiazol-5-ylmethyl)phosphonate

A mixture of triethyl phosphite (1.91 g, 11.50 mmol) and 5-(bromomethyl)benzo[c][1,2,5]oxadiazole (2.13 g, 10.00 mmol) was stirred at 87° C. under $N_2$ overnight. The mixture was cooled to room temperature. The reaction mixture was used directly for the next step without further operation. The compound was characterized by the following spectroscopic data:

MS (ESI, pos. ion) m/z: 271.0 (M+1); exact mass of $C_{11}H_{15}N_2O_4P$: 270.08.

Step 2: tert-butyl 4-(benzo[c][1,2,5]oxadiazol-5-ylmethylene)piperidine-1-carboxylate The title compound was prepared by the procedure described in step 2 of Example 3 using 60% NaH (480 mg, 12.00 mmol), diethyl (benzo[c][1,2,5]oxadiazol-5-ylmethyl) phosphonate (2.70 g, 10.00 mmol), 15-crown-5 (0.1 mL) and tert-butyl 4-oxopiperidine-1-carboxylate (1.99 g, 10.00 mmol) to give the title compound as a white solid (2.69 g, 85.3%). The compound was characterized by the following spectroscopic data:

MS (ESI, pos. ion) m/z: 260.1 (M+1-t-Bu); exact mass of $C_{17}H_{21}N_3O_3$: 315.16; and
$^1$H NMR (400 MHz, CDCl$_3$) δ 7.77 (dt, J=7.2, 3.6 Hz, 1H), 7.55 (d, J=1.0 Hz, 1H), 7.29-7.22 (m, 1H), 6.36 (s, 1H), 3.59-3.51 (m, 2H), 3.44 (dd, J=13.9, 8.1 Hz, 2H), 2.51 (t, J=5.5 Hz, 2H), 2.40 (t, J=5.5 Hz, 2H), 1.49 (s, 9H).

Step 3: tert-butyl 4-(benzo[c][1,2,5]oxadiazol-5-ylmethyl)piperidine-1-carboxylate The title compound was prepared by the procedure described in step 3 of Example 3 using a solution of tert-butyl 4-(benzo[c][1,2,5]oxadiazol-5-ylmethylene)piperidine-1-carboxylate (2.69 g, 8.53 mmol) in a mixture of THF and H$_2$O (v/v=25 mL/25 mL), and 10% Pa/C (0.14 g) to give the title compound as white solid (670 mg, 24.8%). The compound was characterized by the following spectroscopic data:

MS (ESI, pos. ion) m/z: 262.2 (M+1-t-Bu); exact mass of $C_{17}H_{23}N_3O_3$: 317.17.

Step 4: 5-(piperidin-4-ylmethyl)benzo[c][1,2,5]oxadiazole hydrochloride

The title compound was prepared by the procedure described in step 4 of Example 3 using tert-butyl 4-(benzo[c][1,2,5]oxadiazol-5-ylmethyl)piperidine-1-carboxylate (670 mg, 2.11 mmol) and a solution of HCl in EtOAc (4.4 mol/L, 5.0 mL, 22.00 mmol) to give the title compound as a white solid (551 mg, 103%). The compound was characterized by the following spectroscopic data:

MS (ESI, pos. ion) m/z: 218.1 (M+1-HCl); exact mass of $C_{12}H_{16}ClN_3O$: 253.10.

Step 5: 5-((1-(2-chloro-4-nitrophenyl)piperidin-4-yl)methyl)benzo[c][1,2,5]oxadiazole The title compound was prepared by the procedure described in step 5 of Example 3 using 2-chloro-1-fluoro-4-nitrobenzene (457 mg, 2.61 mmol), 5-(piperidin-4-ylmethyl)benzo[c][1,2,5]oxadiazole hydrochloride (551 mg, 2.17 mmol) and potassium carbonate (900 mg, 6.51 mmol) to give the title compound as a yellow solid (731 mg, 90.3%). The compound was characterized by the following spectroscopic data:

$^1$H NMR (400 MHz, CDCl$_3$) δ 8.24 (d, J=2.6 Hz, 1H), 8.07 (dd, J=8.9, 2.6 Hz, 1H), 7.79 (d, J=9.3 Hz, 1H), 7.57 (s, 1H), 7.28 (d, J=6.7 Hz, 1H), 7.01 (d, J=9.0 Hz, 1H), 3.59 (d, J=12.1 Hz, 2H), 2.82-2.70 (m, 4H), 1.82 (d, J=13.1 Hz, 3H), 1.66-1.56 (m, 2H).

Step 6: 4-(4-(benzo[c][1,2,5]oxadiazol-5-ylmethyl)piperidin-1-yl)-3-chloroaniline A solution of 5-((1-(2-chloro-4-nitrophenyl)piperidin-4-yl)methyl)benzo[c][1,2,5]oxadiazole (731 mg, 1.96 mmol) in a mixture of THF and MeOH (v/v=25 mL/25 mL) was added in activated iron powder (1.10 g, 19.61 mmol). The title compound was prepared by the procedure described in step 6 of Example 3 to give yellow oil (662 mg, 98.5%). The compound was characterized by the following spectroscopic data:

MS (ESI, pos. ion) m/z: 343.2 (M+1); exact mass of $C_{18}H_{19}ClN_4O$: 342.12.

Step 7: 3-(4-(4-(benzo[c][1,2,5]oxadiazol-5-ylmethyl)piperidin-1-yl)-3-chlorophenyl)-2,6-dimethylpyrimidin-4(3H)-one The title compound was prepared by the procedure described in step 3 of Example 2 starting with 4-(4-(benzo[c][1,2,5]oxadiazol-5-ylmethyl)piperidin-1-yl)-3-chloroaniline (662 mg, 1.93 mmol), trimethylaluminium (4.8 mL, 9.60 mmol, 2.0 mol/L in toluene) and a solution of methyl 3-acetamidobut-2-enoate (364 mg, 2.32 mmol) in toluene (2 mL) under N$_2$ to give the title compound as a light yellow solid (397 mg, 45.7%). The compound was characterized by the following spectroscopic data:

MS (ESI, pos. ion) m/z: 450.1 (M+1); exact mass of $C_{24}H_{24}ClN_5O_2$: 449.16; and
$^1$H NMR (400 MHz, CDCl$_3$) δ 7.78 (d, J=9.0 Hz, 1H), 7.57 (s, 1H), 7.32-7.27 (m, 1H), 7.21 (d, J=2.4 Hz, 1H), 7.12 (d, J=8.6 Hz, 1H), 7.03 (dd, J=8.5, 2.4 Hz, 1H), 6.28 (s, 1H), 3.51 (d, J=12.4 Hz, 1H), 3.41 (d, J=11.6 Hz, 1H), 2.77-2.56 (m, 4H), 2.29 (s, 3H), 2.18 (s, 3H), 1.80 (d, J=8.7 Hz, 3H), 1.66-1.57 (m, 2H).

Example 21: 3-(3-chloro-4-(4-(3-fluoro-4-methoxybenzyl)piperidin-1-yl)phenyl)-2,6-dimethylpyrimidin-4(3H)-one

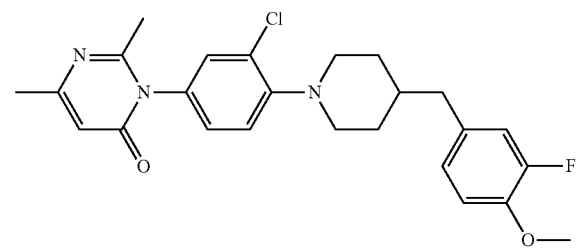

Step 1: diethyl 3-fluoro-4-methoxybenzylphosphonate

A mixture of triethyl phosphite (1.91 g, 11.50 mmol) and 4-(bromomethyl)-2-fluoro-1-methoxybenzene (2.19 g, 10.00 mmol) was stirred at 87° C. under N$_2$ overnight. The mixture was cooled to room temperature. The reaction mixture was used directly for the next step without further operation.

Step 2: tert-butyl 4-(3-fluoro-4-methoxybenzylidene)piperidine-1-carboxylate The title compound was prepared by the procedure described in step 2 of Example 3 using 60% NaH (480 mg, 12.00 mmol), diethyl 3-fluoro-4-methoxybenzylphosphonate (2.76 g, 10.00 mmol), 15-crown-5 (0.1 mL) and tert-butyl 4-oxopiperidine-1-carboxylate (1.99 g, 10.00 mmol) to give the title compound as a white solid (1.45 g, 45.0%). The compound was characterized by the following spectroscopic data:

MS (ESI, pos. ion) m/z: 266.2 (M+1-t-Bu); exact mass of $C_{18}H_{24}FNO_3$: 321.17.

Step 3: tert-butyl 4-(3-fluoro-4-methoxybenzyl)piperidine-1-carboxylate

The title compound was prepared by the procedure described in step 3 of Example 3 using a solution of tert-butyl 4-(3-fluoro-4-methoxybenzylidene)piperidine-1-carboxylate (1.45 g, 4.50 mmol) in a mixture of THF and MeOH (v/v=20 mL/30 mL), and 10% Pa/C (0.13 g) to give the title compound as a light yellow oil (1.08 g, 74.0%). The compound was characterized by the following spectroscopic data:

MS (ESI, pos. ion) m/z: 268.1 (M+1-t-Bu); exact mass of $C_{18}H_{26}FNO_3$: 323.19.

Step 4: 4-(3-fluoro-4-methoxybenzyl)piperidine hydrochloride

The title compound was prepared by the procedure described in step 2 of Example 15 using tert-butyl 4-(3-fluoro-4-methoxybenzyl)piperidine-1-carboxylate (1.08 g, 3.33 mmol) in EtOAc (50 mL) and a solution of HCl in EtOAc (4.4 mol/L, 4.0 mL, 17.6 mmol) to give the title compound as a white solid (845 mg, 97.7%).

Step 5: 1-(2-chloro-4-nitrophenyl)-4-(3-fluoro-4-methoxybenzyl)piperidine

The title compound was prepared by the procedure described in step 5 of Example 3 using 2-chloro-1-fluoro-4-nitrobenzene (571 mg, 3.25 mmol), 4-(3-fluoro-4-methoxybenzyl)piperidine hydrochloride (845 mg, 3.25 mmol) and potassium carbonate (2.25 g, 16.27 mmol) to give the title compound as yellow oil (1.16 g, 94.1%).

Step 6: 3-chloro-4-(4-(3-fluoro-4-methoxybenzyl)piperidin-1-yl)aniline

A solution of 1-(2-chloro-4-nitrophenyl)-4-(3-fluoro-4-methoxybenzyl)piperidine (1.16 g, 3.06 mmol) in a mixture of THF and MeOH (25 mL/25 mL) was added in activated iron powder (1.71 g, 30.62 mmol). The title compound was prepared by the procedure described in step 6 of Example 3 to give yellow oil (1.12 g, 104.8%). The compound was characterized by the following spectroscopic data:

MS (ESI, pos. ion) m/z: 349.2 (M+1); exact mass of $C_{19}H_{22}ClFN_2O$: 348.14.

Step 7: 3-(3-chloro-4-(4-(3-fluoro-4-methoxybenzyl)piperidin-1-yl)phenyl)-2,6-dimethylpyrimidin-4(3H)-one The title compound was prepared by the procedure described in step 3 of Example 2 starting with 3-chloro-4-(4-(3-fluoro-4-methoxybenzyl)piperidin-1-yl)aniline (1.12 g, 3.21 mmol), trimethylaluminium (6.5 mL, 13.0 mmol, 2.0 mol/L in toluene) and a solution of methyl 3-acetamidobut-2-enoate (606 mg, 3.85 mmol) in toluene (5 mL) under $N_2$ to give the title compound as a light yellow solid (239 mg, 16.3%). The compound was characterized by the following spectroscopic data:

MS (ESI, pos. ion) m/z: 456.3 (M+1); exact mass of $C_{25}H_{27}ClFN_3O_2$: 455.18; and $^1$H NMR (400 MHz, CDCl$_3$) δ 7.19 (d, J=2.4 Hz, 1H), 7.12 (d, J=8.5 Hz, 1H), 7.02 (dd, J=8.5, 2.4 Hz, 1H), 6.95-6.83 (m, 3H), 6.29 (s, 1H), 3.88 (s, 3H), 3.48 (d, J=12.9 Hz, 1H), 3.38 (s, 1H), 2.63 (d, J=38.3 Hz, 2H), 2.55 (d, J=7.0 Hz, 2H), 2.31 (s, 3H), 2.21 (s, 3H), 1.76-1.70 (m, 3H), 1.65 (s, 2H).

Example 22: 3-(3-chloro-4-(4-(quinolin-8-ylmethyl)piperidin-1-yl)phenyl)-2,6-dimethylpyrimidin-4(3H)-one

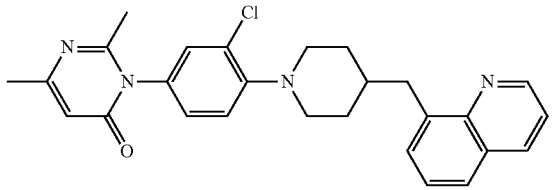 [SMILES: Cc1cc(=O)n(-c2ccc(N3CCC(Cc4cccc5cccnc45)CC3)c(Cl)c2)c(C)n1]

Step 1: diethyl (quinolin-8-ylmethyl)phosphonate

A mixture of triethyl phosphite (1.73 g, 10.40 mmol) and 8-(bromomethyl)quinoline (2.00 g, 9.00 mmol) was stirred at 87° C. under $N_2$ overnight. The mixture was cooled to room temperature. The reaction mixture was used directly for the next step without further operation. The compound was characterized by the following spectroscopic data:

MS (ESI, pos. ion) m/z: 280.2 (M+1); exact mass of $C_{14}H_{18}NO_3P$: 279.10.

Step 2: tert-butyl 4-(quinolin-8-ylmethylene)piperidine-1-carboxylate

The title compound was prepared by the procedure described in step 2 of Example 3 using diethyl (quinolin-8-ylmethyl)phosphonate (2.50 g, 9.00 mmol), tert-butyl 4-oxopiperidine-1-carboxylate (1.44 g, 7.20 mmol) and potassium tert-butanolate (1.97 g, 17.55 mmol) to give the title compound as brown oil (2.33 g, 100%). The compound was characterized by the following spectroscopic data:

MS (ESI, pos. ion) m/z: 325.3 (M+1); exact mass of $C_{20}H_{24}N_2O_2$: 324.18.

Step 3: tert-butyl 4-(quinolin-8-ylmethyl)piperidine-1-carboxylate

The title compound was prepared by the procedure described in step 3 of Example 3 using a solution of tert-butyl 4-(quinolin-8-ylmethylene)piperidine-1-carboxylate (2.33 g, 7.20 mmol) in a mixture of THF and MeOH (v/v=25 mL/25 mL), and 10% Pa/C (0.20 g) to give the title compound as yellow oil (2.00 g, 85.8%). The compound was characterized by the following spectroscopic data:

MS (ESI, pos. ion) m/z: 327.3 (M+1); exact mass of $C_{20}H_{26}N_2O_2$: 326.20.

Step 4: 8-(piperidin-4-ylmethyl)quinoline hydrochloride

The title compound was prepared by the procedure described in step 4 of Example 3 using tert-butyl 4-(quinolin-8-ylmethyl)piperidine-1-carboxylate (2.00 g, 7.70 mmol) and a solution of HCl in EtOAc (4.45 mol/L, 17.5 mL, 77.9 mmol) to give the title compound as a yellow solid (without desiccation) (2.30 g, 113.7%).

Step 5: 8-((1-(2-chloro-4-nitrophenyl)piperidin-4-yl)methyl)quinoline

The title compound was prepared by the procedure described in step 5 of Example 9 using 8-(piperidin-4-ylmethyl)quinoline hydrochloride (2.30 g, 8.80 mmol), potassium carbonate (4.26 g, 30.88 mmol) and 2-chloro-1-fluoro-4-nitrobenzene (1.55 g, 8.80 mmol) to give the title compound as yellow oil (2.95 g, 87.8%). The compound was characterized by the following spectroscopic data:
MS (ESI, pos. ion) m/z: 382.1 (M+1); exact mass of $C_{21}H_{20}ClN_3O_2$: 381.12.

Step 6: 3-chloro-4-(4-(quinolin-8-ylmethyl)piperidin-1-yl)aniline

A solution of 8-((1-(2-chloro-4-nitrophenyl)piperidin-4-yl)methyl)quinoline (2.95 g, 7.80 mmol) in a mixture of THF and MeOH (v/v=20 mL/20 mL) was added in activated iron powder (2.62 g, 46.80 mol). The title compound was prepared by the procedure described in step 4 of Example 1 to give the title compound as a white solid (0.60 g, 21.9%). The compound was characterized by the following spectroscopic data:
MS (ESI, pos. ion) m/z: 352.1 (M+1); exact mass of $C_{21}H_{22}ClN_3$: 351.15.

Step 7: 3-(3-chloro-4-(4-(quinolin-8-ylmethyl)piperidin-1-yl)phenyl)-2,6-dimethylpyrimidin-4(3H)-one The title compound was prepared by the procedure described in step 3 of Example 2 starting with 3-chloro-4-(4-(quinolin-8-ylmethyl)piperidin-1-yl)aniline (0.60 g, 1.71 mmol), trimethylaluminium (3.5 mL, 7.0 mmol, 2.0 mol/L in toluene) and a solution of methyl 3-acetamidobut-2-enoate (295 mg, 1.88 mmol) in toluene (5 mL) under $N_2$ to give the title compound as a white solid (0.10 g, 18.9%). The compound was characterized by the following spectroscopic data:
MS (ESI, pos. ion) m/z: 459.1 (M+1); exact mass of $C_{27}H_{27}ClN_4O$: 458.19; and
$^1$H NMR (400 MHz, CDCl$_3$) δ 8.96 (dd, J=4.1, 1.6 Hz, 1H), 8.16 (d, J=7.0 Hz, 1H), 7.71 (d, J=7.0 Hz, 1H), 7.56 (d, J=5.9 Hz, 1H), 7.52-7.45 (m, 1H), 7.41 (dd, J=8.2, 4.2 Hz, 1H), 7.18 (d, J=2.4 Hz, 1H), 7.09 (d, J=8.5 Hz, 1H), 7.00 (dd, J=8.5, 2.4 Hz, 1H), 6.27 (s, 1H), 3.51-3.33 (m, 2H), 3.32-3.22 (m, 2H), 2.62 (ddd, J=47.7, 11.7, 9.3 Hz, 2H), 2.28 (s, 3H), 2.17 (s, 3H), 1.85-1.71 (m, 2H), 1.44-1.20 (m, 3H).

Example 23: 3-(3-chloro-4-(4-(pyridin-3-ylmethyl)piperidin-1-yl)phenyl)-2,6-dimethylpyrimidin-4(3H)-one

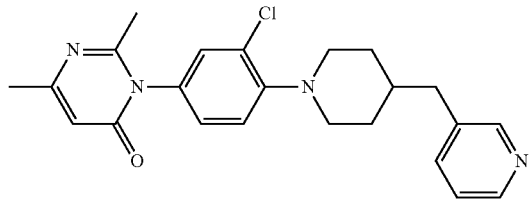 [SMILES: Cc1cc(=O)n(-c2ccc(N3CCC(Cc4cccnc4)CC3)c(Cl)c2)c(C)n1]

Step 1: tert-butyl 4-(pyridin-3-ylmethyl)piperidine-1-carboxylate

The title compound was prepared by the procedure described in step 1 of Example 15 using tert-butyl 4-methylenepiperidine-1-carboxylate (4.00 g, 20.28 mmol), 9-borabicyclo[3,3,1]nonane (40.0 mL, 20.00 mmol, 0.5 mol/L in THF), 3-bromopyridine (3.52 g, 22.30 mmol), Pd(dppf)Cl$_2$ (445 mg, 0.60 mmol) and potassium carbonate (3.35 g, 24.30 mmol) to give the title compound as colourless oil (2.56 g, 45.7%). The compound was characterized by the following spectroscopic data:
MS (ESI, pos. ion) m/z: 277.1 (M+1); exact mass of $C_{16}H_{24}N_2O_2$: 276.18.

Step 2: 3-(piperidin-4-ylmethyl)pyridine hydrochloride

The title compound was prepared by the procedure described in step 4 of Example 3 using tert-butyl 4-(pyridin-3-ylmethyl)piperidine-1-carboxylate (2.56 g, 9.26 mmol) and a solution of HCl in EtOAc (4.4 mol/L, 10.4 mL, 45.8 mmol) to give the crude product as a white solid which was used directly for the next step without further purification.

Step 3: 3-((1-(2-chloro-4-nitrophenyl)piperidin-4-yl)methyl)pyridine

The title compound was prepared by the procedure described in step 5 of Example 4 using 2-chloro-1-fluoro-4-nitrobenzene (1.97 g, 9.26 mmol), TEA (2.81 g, 27.78 mmol) and 3-(piperidin-4-ylmethyl)pyridine hydrochloride (1.63 g, 9.26 mmol) to give the title compound as a yellow solid (1.02 g, 33.2%). The compound was characterized by the following spectroscopic data:
MS (ESI, pos. ion) m/z: 332.1 (M+1); exact mass of $C_{17}H_{18}ClN_3O_2$: 331.11.

Step 4: 3-chloro-4-(4-(pyridin-3-ylmethyl)piperidin-1-yl)aniline

A solution of 3-((1-(2-chloro-4-nitrophenyl)piperidin-4-yl)methyl)pyridine (1.02 g, 3.07 mmol) in a mixture of THF and H$_2$O (v/v=20 mL/30 mL) was added in activated iron powder (1.72 g, 30.70 mmol). The title compound was prepared by the procedure described in step 6 of Example 3 to give the crude product (0.75 g, 80.8%) which was used directly for the next step without further purification. The compound was characterized by the following spectroscopic data:

MS (ESI, pos. ion) m/z: 302.1 (M+1); exact mass of $C_{17}H_{20}ClN_3$: 301.13.

Step 5: 3-(3-chloro-4-(4-(pyridin-3-ylmethyl)piperidin-1-yl)phenyl)-2,6-dimethylpyrimidin-4(3H)-one The title compound was prepared by the procedure described in step 3 of Example 2 starting with 3-chloro-4-(4-(pyridin-3-ylmethyl)piperidin-1-yl)aniline (0.72 g, 2.48 mmol), trimethylaluminium (3.73 mL, 7.45 mmol, 2.0 mol/L in toluene) and a solution of methyl 3-acetamidobut-2-enoate (0.59 g, 3.73 mmol) in toluene (10 mL) under $N_2$ to give the title compound as a yellow solid (306 mg, 30.0%). The compound was characterized by the following spectroscopic data:

MS (ESI, pos. ion) m/z: 409.1 (M+1); exact mass of $C_{23}H_{25}ClN_4O$: 408.17; and $^1$H NMR (400 MHz, CDCl$_3$) δ 8.47 (d, J=3.7 Hz, 2H), 7.51 (d, J=7.8 Hz, 1H), 7.25-7.22 (m, 1H), 7.20 (d, J=2.4 Hz, 1H), 7.11 (d, J=8.5 Hz, 1H), 7.03 (dd, J=8.5, 2.4 Hz, 1H), 6.28 (s, 1H), 3.44 (dd, J=35.9, 11.8 Hz, 2H), 2.73-2.53 (m, 4H), 2.29 (s, 3H), 2.18 (s, 3H), 1.79-1.65 (m, 3H), 1.58-1.50 (m, 2H).

Example 24: 3-(3-chloro-4-(4-(pyridin-2-ylmethyl)piperidin-1-yl)phenyl)-2,6-dimethylpyrimidin-4(3H)-one

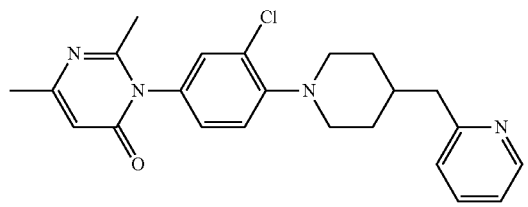 [SMILES: Cc1cc(=O)n(-c2ccc(N3CCC(Cc4ccccn4)CC3)c(Cl)c2)c(C)n1]

Step 1: tert-butyl 4-(pyridin-2-ylmethyl)piperidine-1-carboxylate

The title compound was prepared by the procedure described in step 1 of Example 15 using tert-butyl 4-methylenepiperidine-1-carboxylate (4.00 g, 20.28 mmol), 9-borabicyclo[3,3,1]nonane (40.0 mL, 20.00 mmol, 0.5 mol/L in THF), 2-bromopyridine (3.52 g, 22.30 mmol), Pd(dppf)Cl$_2$ (445 mg, 0.60 mmol) and potassium carbonate (3.35 g, 24.30 mmol) to give the title compound as colourless oil (4.30 g, 76.8%). The compound was characterized by the following spectroscopic data:

MS (ESI, pos. ion) m/z: 277.3 (M+1); exact mass of $C_{16}H_{24}N_2O_2$: 276.18.

Step 2: 2-(piperidin-4-ylmethyl)pyridine hydrochloride

The title compound was prepared by the procedure described in step 2 of Example 15 using a solution of tert-butyl 4-(pyridin-2-ylmethyl)piperidine-1-carboxylate (4.30 g, 15.56 mmol) in 20 mL of EtOAc and a solution of HCl in EtOAc (4.4 mol/L, 21.2 mL, 93.3 mmol) to give the title compound as a white solid (2.14 g, 64.6%). The compound was characterized by the following spectroscopic data:

MS (ESI, pos. ion) m/z: 177.2 (M+1-HCl); exact mass of $C_{11}H_{17}ClN_2$: 212.11.

Step 3: 2-((1-(2-chloro-4-nitrophenyl)piperidin-4-yl)methyl)pyridine

The title compound was prepared by the procedure described in step 3 of Example 15 using 2-chloro-1-fluoro-4-nitrobenzene (1.56 g, 8.88 mmol), TEA (3.00 g, 29.62 mmol) and 2-(piperidin-4-ylmethyl)pyridine hydrochloride (2.10 g, 9.87 mmol) as starting materials to give the title compound as a yellow solid (2.50 g, 76.2%). The compound was characterized by the following spectroscopic data:

MS (ESI, pos. ion) m/z: 332.1 (M+1); exact mass of $C_{17}H_{18}ClN_3O_2$: 331.11.

Step 4: 3-chloro-4-(4-(pyridin-2-ylmethyl)piperidin-1-yl)aniline

A solution of 2-((1-(2-chloro-4-nitrophenyl)piperidin-4-yl)methyl)pyridine (2.20 g, 6.63 mmol) in a mixture of THF and H$_2$O (20 mL/20 mL) was added in activated iron powder (3.70 g, 66.30 mmol). The title compound was prepared by the procedure described in step 6 of Example 3 to give yellow oil (1.75 g, 87.5%). The compound was characterized by the following spectroscopic data:

MS (ESI, pos. ion) m/z: 302.1 (M+1); exact mass of $C_{17}H_{20}ClN_3$: 301.13.

Step 5: 3-(3-chloro-4-(4-(pyridin-2-ylmethyl)piperidin-1-yl)phenyl)-2,6-dimethylpyrimidin-4(3H)-one The title compound was prepared by the procedure described in step 3 of Example 2 starting with 3-chloro-4-(4-(pyridin-2-ylmethyl)piperidin-1-yl)aniline (1.74 g, 5.77 mmol), trimethylaluminium (11.5 mL, 23.00 mmol, 2.0 mol/L in toluene) and a solution of methyl 3-acetamidobut-2-enoate ((1.09 g, 6.92 mmol) in toluene (10 mL) under $N_2$ to give the title compound as a light yellow solid (1.00 g, 43.5%). The compound was characterized by the following spectroscopic data:

MS (ESI, pos. ion) m/z: 409.1 (M+1); $C_{23}H_{25}ClN_4O$: 408.17; and $^1$H NMR (400 MHz, CDCl$_3$) δ 8.57 (d, J=4.8 Hz, 1H), 7.61 (td, J=7.7, 1.8 Hz, 1H), 7.19 (d, J=2.4 Hz, 1H), 7.17-7.08 (m, 3H), 7.02 (dd, J=8.5, 2.4 Hz, 1H), 6.27 (s, 1H), 3.43 (dd, J=30.6, 11.5 Hz, 2H), 2.79 (d, J=7.2 Hz, 2H), 2.67 (dtd, J=25.5, 11.5, 2.0 Hz, 2H), 2.29 (s, 3H), 2.17 (s, 3H), 1.98 (ddd, J=11.2, 7.2, 3.5 Hz, 1H), 1.76 (t, J=12.5 Hz, 2H), 1.63-1.51 (m, 2H).

Example 25: 3-(3-fluoro-4-(4-(4-fluorobenzyl)piperidin-1-yl)phenyl)-2,6-dimethylpyrimidin-4(3H)-one

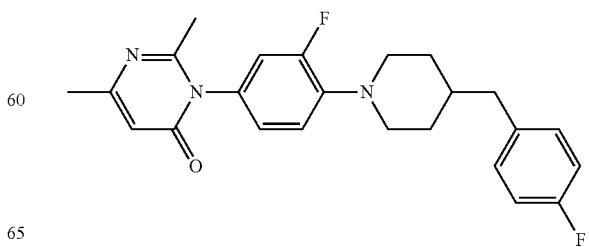

Step 1: 1-(2-fluoro-4-nitrophenyl)-4-(4-fluorobenzyl)piperidine

The title compound was prepared by the procedure described in step 5 of Example 4 using 1,2-difluoro-4-nitrobenzene (741 mg, 4.66 mmol), TEA (2.36 g, 23.29 mmol) and 4-(4-fluorobenzyl)piperidine hydrochloride (1.07 g, 4.66 mmol) to give the title compound as a yellow solid (1.54 g, 99.5%). The compound was characterized by the following spectroscopic data:
MS (ESI, pos. ion) m/z: 333.1 (M+1); exact mass of $C_{18}H_{18}F_2N_2O_2$: 332.13.

Step 2: 3-fluoro-4-(4-(4-fluorobenzyl)piperidin-1-yl)aniline

The title compound was prepared by the procedure described in step 2 of Example 2 using a solution of 1-(2-fluoro-4-nitrophenyl)-4-(4-fluorobenzyl)piperidine (1.54 g, 4.63 mmol) in a mixture of THF and MeOH (v/v=25 mL/25 mL), and 10% Pa/C (0.15 g) to give the title compound as a white solid (945 mg, 67.5%). The compound was characterized by the following spectroscopic data:
MS (ESI, pos. ion) m/z: 303.2 (M+1); exact mass of $C_{18}H_{20}F_2N_2$: 302.16; and
$^1$H NMR (400 MHz, CDCl$_3$) δ 7.11 (dd, J=8.6, 5.5 Hz, 2H), 6.97 (t, J=7.7 Hz, 2H), 6.83-6.74 (m, 1H), 6.39 (ddd, J=11.6, 11.0, 3.0 Hz, 2H), 3.51 (s, 2H), 3.23 (s, 2H), 2.63-2.46 (m, 4H), 1.70 (dd, J=12.5, 1.3 Hz, 2H), 1.57-1.52 (m, 1H), 1.52-1.40 (m, 2H).

Step 3: 3-(3-fluoro-4-(4-(4-fluorobenzyl)piperidin-1-yl)phenyl)-2,6-dimethylpyrimidin-4(3H)-one The title compound was prepared by the procedure described in step 3 of Example 2 starting with 3-fluoro-4-(4-(4-fluorobenzyl)piperidin-1-yl)aniline (945 mg, 3.13 mmol), trimethylaluminium (6.5 mL, 13.00 mmol, 2.0 mol/L in toluene) and a solution of methyl 3-acetamidobut-2-enoate (590 mg, 3.75 mmol) in toluene (2 mL) under N$_2$ to give the title compound as a light yellow solid (362 mg, 28.3%). The compound was characterized by the following spectroscopic data:
MS (ESI, pos. ion) m/z: 410.2 (M+1); exact mass of $C_{24}H_{25}F_2N_3O$: 409.20; and
$^1$H NMR (400 MHz, CDCl$_3$) δ 7.12 (dd, J=8.5, 5.5 Hz, 2H), 7.00 (dt, J=15.3, 8.7 Hz, 3H), 6.91-6.84 (m, 2H), 6.28 (s, 1H), 3.54 (d, J=12.2 Hz, 1H), 3.45 (d, J=12.1 Hz, 1H), 2.76-2.60 (m, 2H), 2.58 (d, J=7.0 Hz, 2H), 2.29 (s, 3H), 2.18 (s, 3H), 1.75 (d, J=12.9 Hz, 2H), 1.70-1.61 (m, 1H), 1.50-1.43 (m, 2H).

Example 26: 3-(3-fluoro-4-(4-(naphthalen-1-ylmethyl)piperidin-1-yl)phenyl)-2,6-dimethylpyrimidin-4(3H)-one

Step 1: 1-(2-fluoro-4-nitrophenyl)-4-(naphthalen-1-ylmethyl)piperidine

The title compound was prepared by the procedure described in step 5 of Example 4 using 1,2-difluoro-4-nitrobenzene (227 mg, 1.42 mmol), TEA (721 mg, 7.12 mmol) and 4-(naphthalen-1-ylmethyl)piperidine hydrochloride (373 mg, 1.42 mmol) to give the title compound as a yellow solid (645 mg, 124.2%). The compound was characterized by the following spectroscopic data:
MS (ESI, pos. ion) m/z: 365.2 (M+1); exact mass of $C_{22}H_{21}FN_2O_2$: 364.16.

Step 2: 3-fluoro-4-(4-(naphthalen-1-ylmethyl)piperidin-1-yl)aniline

The title compound was prepared by the procedure described in step 2 of Example 2 using a solution of 1-(2-fluoro-4-nitrophenyl)-4-(naphthalen-1-ylmethyl)piperidine (645 mg, 1.77 mmol) in a mixture of THF and MeOH (v/v=25 mL/25 mL), and 10% Pa/C (65 mg) to give the title compound as a white solid (309 mg, 52.2%). The compound was characterized by the following spectroscopic data:
MS (ESI, pos. ion) m/z: 335.2 (M+1); exact mass of $C_{22}H_{23}FN_2$: 334.18.

Step 3: 3-(3-fluoro-4-(4-(naphthalen-1-ylmethyl)piperidin-1-yl)phenyl)-2,6-dimethylethylpyrimidin-4(3H)-one The title compound was prepared by the procedure described in step 3 of Example 2 starting with 3-fluoro-4-(4-(naphthalen-1-ylmethyl)piperidin-1-yl)aniline (309 mg, 0.92 mmol), trimethylaluminium (2.0 mL, 4.00 mmol, 2.0 mol/L in toluene) and a solution of methyl 3-acetamidobut-2-enoate (174 mg, 1.11 mmol) in toluene (2 mL) under N$_2$ to give the title compound as a white solid (111 mg, 27.0%). The compound was characterized by the following spectroscopic data:
MS (ESI, pos. ion) m/z: 442.2 (M+1); exact mass of $C_{28}H_{28}FN_3O$: 441.22; and
$^1$H NMR (600 MHz, CDCl$_3$) δ 8.07 (d, J=8.4 Hz, 1H), 7.90 (d, J=8.0 Hz, 1H), 7.77 (d, J=8.2 Hz, 1H), 7.58-7.54 (m, 1H), 7.52 (t, J=7.0 Hz, 1H), 7.48-7.40 (m, 1H), 7.34 (d, J=6.8 Hz, 1H), 7.08-6.98 (m, 1H), 6.93-6.85 (m, 2H), 6.30 (s, 1H), 3.52 (dd, J=52.7, 12.2 Hz, 2H), 3.14-3.03 (m, 2H), 2.74-2.59 (m, 2H), 2.31 (s, 3H), 2.20 (s, 3H), 1.96-1.87 (m, 1H), 1.82 (d, J=13.0 Hz, 2H), 1.63 (td, J=12.2, 3.5 Hz, 2H).

Example 27: 3-(3-chloro-4-(4-(3-fluorophenoxy)piperidin-1-yl)phenyl)-2,6-dimethylpyrimidin-4(3H)-one

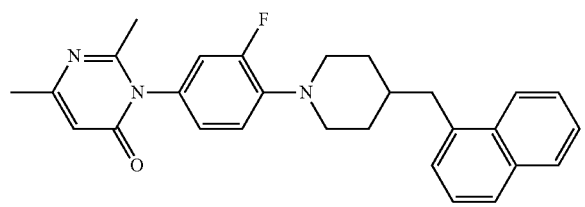 [SMILES: Cc1cc(=O)n(-c2ccc(N3CCC(Cc4cccc5ccccc45)CC3)c(F)c2)c(C)n1]

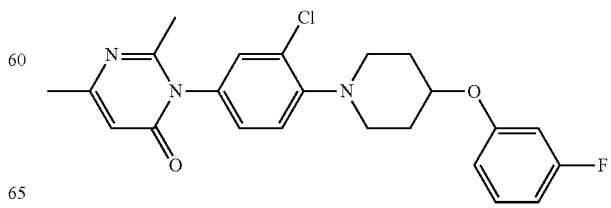

Step 1: 1-(2-chloro-4-nitrophenyl)piperidin-4-ol

A mixture of 2-chloro-1-fluoro-4-nitrobenzene (104.00 g, 592.44 mmol), piperidin-4-ol (71.91 g, 710.93 mmol), TEA (179.85 g, 1.78 mol) and EtOAc (500 mL) was heated at 50° C. for 50 hours. After the reaction was finished, the mixture was cooled to rt, and filtered. The filtrate was concentrated in vacuo. The residue was dissolved in 250 mL of DCM. The resulted mixture was washed with 1 mol/L aqueous hydrochloric acid solution (240 mL×2). The organic phase was dried over anhydrous $Na_2SO_4$ (25 g), filtered and concentrated in vacuo. The residue was dried under vacuum to give the crude product as a yellow solid (143.61 g, 94.4%). The crude product was used directly for the next step without purification.

Step 2: 1-(2-chloro-4-nitrophenyl)piperidin-4-yl 4-methylbenzenesulfonate

To a mixture of 1-(2-chloro-4-nitrophenyl)piperidin-4-ol (143.61 g, 559.48 mmol) and TEA (565.07 g, 5.59 mol) was added tosyl chloride (106.00 g, 559.48 mmol) and 4-dimethylaminopyridine (13.67 g, 111.90 mmol). The resulted mixture was heated at 50° C. for 4 hours. After the reaction was finished, the mixture was cooled to rt and concentrated in vacuo. The residue was dissolved in 2000 mL of DCM. The resulted mixture was washed with water (1000 mL×2) and brine (1000 mL) in turn. The separated organic phase was dried over $Na_2SO_4$ (200 g), filtered and concentrated in vacuo. The residue was dried under vacuum to give the crude product as a yellow solid (135.21 g, 58.8%). The crude product was used directly for the next step without purification.

Step 3: 1-(2-chloro-4-nitrophenyl)-4-(3-fluorophenoxy)piperidine

To a suspension of 60% NaH (584 mg, 14.60 mmol) in DMF (20 mL) was added 3-fluorophenol (655 mg, 5.84 mmol) dropwise at rt. After the addition, the mixture was stirred at rt for 30 minutes. Then the mixture was added a solution of 1-(2-chloro-4-nitrophenyl)piperidin-4-yl 4-methylbenzenesulfonate (2.00 g, 4.87 mmol) in DMF (20 mL) dropwise. After the addition, the mixture was stirred at 80° C. overnight. After the reaction was finished, the mixture was cooled to rt, quenched with water (30 mL), and diluted with EtOAc (100 mL). The resulted mixture was washed with water (100 mL×3) and saturated brine (100 mL). The organic phase was dried over $Na_2SO_4$ (10 g), filtered and concentrated in vacuo. The crude was purified by silica column chromatography (PE/EtOAc (v/v)=20/1) to give the title compound as yellow oil (0.91 g, 53.4%). The compound was characterized by the following spectroscopic data:

MS (ESI, pos. ion) m/z: 351.1 (M+1); exact mass of $C_{17}H_{16}ClFN_2O_3$: 350.08.

Step 4: 3-chloro-4-(4-(3-fluorophenoxy)piperidin-1-yl)aniline

A solution of 1-(2-chloro-4-nitrophenyl)-4-(3-fluorophenoxy)piperidine (1.14 g, 3.26 mmol) in a mixture of THF and $H_2O$ (v/v=20 mL/20 mL) was added in activated iron powder (1.82 g, 32.60 mmol). The title compound was prepared by the procedure described in step 6 of Example 3 to give yellow oil (0.83 g, 79.5%).

Step 5: 3-(3-chloro-4-(4-(3-fluorophenoxy)piperidin-1-yl)phenyl)-2,6-dimethylpyrimidin-4(3H)-one The title compound was prepared by the procedure described in step 3 of Example 2 starting with 3-chloro-4-(4-(3-fluorophenoxy)piperidin-1-yl)aniline (831 mg, 2.59 mmol), trimethylaluminium (5.0 mL, 10.00 mmol, 2.0 mol/L in toluene) and a solution of methyl 3-acetamidobut-2-enoate (610 mg, 3.88 mmol) in toluene (5 mL) under $N_2$ to give the title compound as a yellow solid (762 mg, 68.8%). The compound was characterized by the following spectroscopic data:

MS (ESI, pos. ion) m/z: 428.1 (M+1); exact mass of $C_{23}H_{23}ClFN_3O_2$: 427.15; and $^1$H NMR (400 MHz, CDCl$_3$) δ 7.25-7.21 (m, 2H), 7.18 (d, J=8.5 Hz, 1H), 7.06 (dd, J=8.5, 2.4 Hz, 1H), 6.75-6.71 (m, 1H), 6.66 (ddd, J=5.8, 4.5, 2.1 Hz, 2H), 6.28 (s, 1H), 4.50 (tt, J=6.9, 3.6 Hz, 1H), 3.44-3.24 (m, 2H), 3.12-2.93 (m, 2H), 2.29 (s, 3H), 2.19 (s, 3H), 2.18-2.11 (m, 2H), 2.07-1.98 (m, 2H).

Example 28: 3-(3-fluoro-4-(4-(3-fluorophenoxy)piperidin-1-yl)phenyl)-2,6-dimethylpyrimidin-4(3H)-one

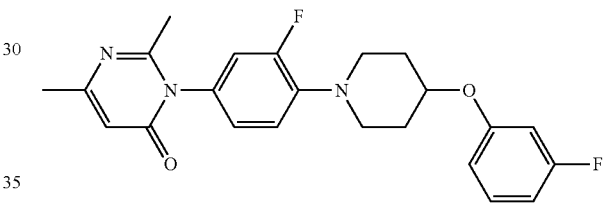

Step 1: 1-(2-fluoro-4-nitrophenyl)piperidin-4-ol

To a solution of 1,2-difluoro-4-nitrobenzene (4.77 g, 30.00 mmol) in EtOAc (50 mL) was added TEA (9.11 g, 90.00 mmol) and piperidin-4-ol (3.64 g, 36.00 mmol). The mixture was stirred at rt under $N_2$ overnight. After the completion of the reaction, the mixture was filtered and the filtrate was concentrated in vacuo. The crude was purified by silica column chromatography (PE/EtOAc (v/v)=4/1) to give the title compound as a yellow solid (4.00 g, 55.5%). The compound was characterized by the following spectroscopic data:

MS (ESI, pos. ion) m/z: 241.1 (M+1); exact mass of $C_{11}H_{13}FN_2O_3$: 240.09.

Step 2: 1-(2-fluoro-4-nitrophenyl)piperidin-4-yl 4-methylbenzenesulfonate

To a solution of 1-(2-fluoro-4-nitrophenyl)piperidin-4-ol (4.00 g, 16.60 mmol) in EtOAc (20 mL) was added TEA (1.68 g, 16.60 mmol) and tosyl chloride (3.81 g, 20.00 mmol). The resulted mixture was stirred at rt under $N_2$ overnight. After the completion of the reaction, the mixture was concentrated in vacuo. The crude was purified by silica column chromatography (PE/EtOAc (v/v)=8/1) to give the title compound as a yellow solid (2.50 g, 38.2%). The compound was characterized by the following spectroscopic data:

MS (ESI, pos. ion) m/z: 395.1 (M+1); exact mass of $C_{18}H_{19}FN_2O_5S$: 394.10.

Step 3: 1-(2-fluoro-4-nitrophenyl)-4-(3-fluorophenoxy)piperidine

To a solution of 1-(2-fluoro-4-nitrophenyl)piperidin-4-yl 4-methylbenzenesulfonate (2.50 g, 6.34 mmol) in DMF (20 mL) was added 3-fluorophenol (0.85 g, 7.58 mmol) and cesium carbonate (4.13 g, 21.40 mmol). The mixture was heated at 100° C. under $N_2$ overnight. After the completion of the reaction, the mixture was cooled to rt, and poured into DCM (100 mL), and then the resulted mixture was washed with water (100 mL×2) and brine (100 mL×2). The organic phase was dried over anhydrous $Na_2SO_4$ (15 g), filtered and concentrated in vacuo. The crude was purified by silica column chromatography (PE/EtOAc (v/v)=4/1) to give the title compound as yellow oil (0.60 g, 28.3%). The compound was characterized by the following spectroscopic data:
MS (ESI, pos. ion) m/z: 335.2 (M+1); exact mass of $C_{17}H_{16}F_2N_2O_3$: 334.11.

Step 4: 3-fluoro-4-(4-(3-fluorophenoxy)piperidin-1-yl)aniline

To a solution of 1-(2-fluoro-4-nitrophenyl)-4-(3-fluorophenoxy)piperidine (0.60 g, 1.79 mmol) in MeOH (20 mL) was added 10% Pa/C (0.06 g). The resulted mixture was stirred at rt under $H_2$ overnight. After the reaction was finished, the mixture was filtered and the filtrate was concentrated in vacuo. The crude was purified by silica column chromatography (PE/EtOAc (v/v)=4/1) to give the title compound as yellow oil (501 mg, 92.0%). The compound was characterized by the following spectroscopic data:
MS (ESI, pos. ion) m/z: 305.2 (M+1); exact mass of $C_{17}H_{18}F_2N_2O$: 304.14.

Step 5: N-(3-fluoro-4-(4-(3-fluorophenoxy)piperidin-1-yl)phenyl)-3-oxobutanamide The title compound was prepared by the procedure described in step 5 of Example 1 using 3-fluoro-4-(4-(3-fluorophenoxy)piperidin-1-yl)aniline (700 mg, 2.30 mmol) and 4-methyleneoxetan-2-one (414 mg, 4.92 mmol) to give the title compound as yellow oil (653 mg, 73.1%). The compound was characterized by the following spectroscopic data:
MS (ESI, pos. ion) m/z: 389.2 (M+1); exact mass of $C_{21}H_{22}F_2N_2O_3$: 388.16.

Step 6: 3-amino-N-(3-fluoro-4-(4-(3-fluorophenoxy)piperidin-1-yl)phenyl)but-2-enamide The title compound was prepared by the procedure described in step 6 of Example 1 starting with a solution of N-(3-fluoro-4-(4-(3-fluorophenoxy)piperidin-1-yl)phenyl)-3-oxobutanamide (700 mg, 1.80 mmol) in MeOH (10 mL) and ammonium hydroxide (10 mL) to give the crude product which was used directly for the next step without further purification.

Step 7 3-(3-fluoro-4-(4-(3-fluorophenoxy)piperidin-1-yl)phenyl)-2,6-dimethylpyrimidin-4(3H)-one The title compound was prepared by the procedure described in step 7 of Example 1 starting with a solution of 3-amino-N-(3-fluoro-4-(4-(3-fluorophenoxy)piperidin-1-yl)phenyl)but-2-enamide (500 mg, 1.28 mmol) in triethyl orthoacetate (10 mL) to give the title compound as a light yellow solid (348 mg, 66.0%). The compound was characterized by the following spectroscopic data:
MS (ESI, pos. ion) m/z: 412.2 (M+1); exact mass of $C_{23}H_{23}F_2N_3O_2$: 411.18; and
$^1$H NMR (400 MHz, CDCl$_3$) δ 7.21 (d, J=2.4 Hz, 1H), 7.17 (d, J=8.5 Hz, 1H), 7.08-7.01 (m, 2H), 6.36 (dd, J=8.2, 1.3 Hz, 1H), 6.31-6.25 (m, 3H), 4.46 (tt, J=6.7, 3.4 Hz, 1H), 3.38 (dd, J=13.8, 5.3 Hz, 1H), 3.32-3.25 (m, 1H), 3.11-2.91 (m, 2H), 2.29 (s, 3H), 2.18 (s, 3H), 2.16-2.07 (m, 2H), 2.03-1.90 (m, 2H).

Example 29: 3-((1-(2-chloro-4-(2,4-dimethyl-6-oxopyrimidin-1 (6H)-yl)phenyl)piperidin-4-yl)oxy)benzonitrile

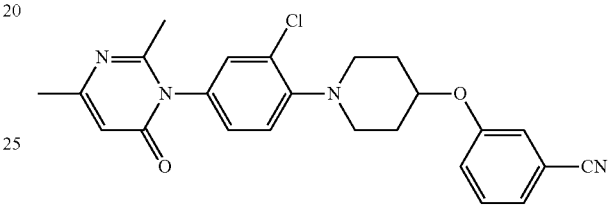

Step 1: 3-((1-(2-chloro-4-nitrophenyl)piperidin-4-yl)oxy)benzonitrile

The title compound was prepared by the procedure described in step 3 of Example 28 using 1-(2-chloro-4-nitrophenyl)piperidin-4-yl 4-methylbenzenesulfonate (4.93 g, 12.00 mmol), 3-hydroxybenzonitrile (1.19 g, 10.00 mmol) and cesium carbonate (6.52 g, 20.00 mmol) as starting materials to give the title compound as yellow oil (2.71 g, 75.7%). The compound was characterized by the following spectroscopic data:
MS (ESI, pos. ion) m/z: 358.10 (M+1); exact mass of $C_{18}H_{16}ClN_3O_3$: 357.09.

Step 2: 3-((1-(4-amino-2-chlorophenyl)piperidin-4-yl)oxy)benzonitrile

A solution of 3-((1-(2-chloro-4-nitrophenyl)piperidin-4-yl)oxy)benzonitrile (2.71 g, 7.57 mmol) in a mixture of THF and MeOH (v/v=30 mL/30 mL) was added in activated iron powder (4.23 g, 75.70 mmol). The title compound was prepared by the procedure described in step 6 of Example 3 to give the crude product (1.85 g, 77.5%). The compound was characterized by the following spectroscopic data:
MS (ESI, pos. ion) m/z: 328.2 (M+1); exact mass of $C_{18}H_{18}ClN_3O$: 327.11.

Step 3: 3-((1-(2-chloro-4-(2,4-dimethyl-6-oxopyrimidin-1(6H)-yl)phenyl)piperidin-4-yl)oxy)benzonitrile The title compound was prepared by the procedure described in step 3 of Example 2 starting with 3-((1-(4-amino-2-chlorophenyl)piperidin-4-yl)oxy)benzonitrile (1.85 g, 5.64 mmol), trimethylaluminium (8.5 mL, 17.00 mmol, 2.0 mol/L in toluene) and a solution of methyl 3-acetamidobut-2-enoate (1.35 g, 8.47 mmol) in toluene (10 mL) under N₂ to give the title compound as a yellow solid (0.86 g, 35.0%). The compound was characterized by the following spectroscopic data:

MS (ESI, pos. ion) m/z: 435.1 (M+1); exact mass of $C_{24}H_{23}ClN_4O_2$: 434.15; and $^1$H NMR (400 MHz, CDCl₃) δ 7.39 (t, J=7.9 Hz, 1H), 7.26-7.22 (m, 2H), 7.18 (d, J=8.7 Hz, 3H), 7.07 (dd, J=8.5, 2.4 Hz, 1H), 6.29 (s, 1H), 4.54 (s, 1H), 3.35 (d, J=32.1 Hz, 2H), 3.13-2.96 (m, 2H), 2.30 (s, 3H), 2.19 (s, 3H), 2.17-2.11 (m, 1H), 2.04 (d, J=4.7 Hz, 3H).

Example 30: 3-(3-chloro-4-(4-((3-fluorophenoxy)methyl)piperidin-1-yl)phenyl)-2,6-dimethylpyrimidin-4(3H)-one

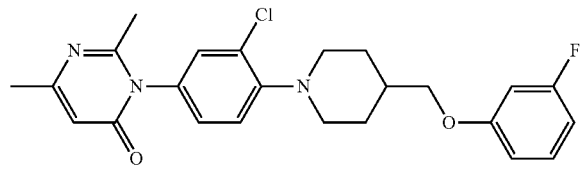

Step 1: (1-(2-chloro-4-nitrophenyl)piperidin-4-yl)methanol

The title compound was prepared by the procedure described in step 1 of Example 27 using 2-chloro-1-fluoro-4-nitrobenzene (3.51 g, 20.00 mmol), piperidin-4-ylmethanol (2.53 g, 22.00 mmol) and TEA (7.29 g, 72.00 mmol) to give the title compound as a yellow solid (4.78 g, 88.3%).

Step 2: (1-(2-chloro-4-nitrophenyl)piperidin-4-yl)methyl 4-methylbenzenesulfonate The title compound was prepared by the procedure described in step 2 of Example 27 using (1-(2-chloro-4-nitrophenyl)piperidin-4-yl)methanol (4.78 g, 17.70 mmol), TEA (17.88 g, 177.00 mmol) and tosyl chloride (4.04 g, 21.20 mmol) to give the title compound as a yellow solid (6.75 g, 90.0%).

Step 3: 1-(2-chloro-4-nitrophenyl)-4-((3-fluorophenoxy)methyl)piperidine

The title compound was prepared by the procedure described in step 3 of Example 27 using 60% NaH (1.91 g, 47.66 mmol), 3-fluorophenol (2.14 g, 19.06 mmol) and a solution of (1-(2-chloro-4-nitrophenyl)piperidin-4-yl)methyl 4-methylbenzenesulfonate (6.75 g, 15.89 mmol) in 10 mL of DMF to give the title compound as a yellow solid (6.01 g, 104%).

Step 4: 3-chloro-4-(4-((3-fluorophenoxy)methyl)piperidin-1-yl)aniline

To a mixture of 1-(2-chloro-4-nitrophenyl)-4-((3-fluorophenoxy)methyl)piperidine (6.01 g, 16.50 mmol), THF (60 mL), MeOH (60 mL) and H₂O (30 mL) was added iron powder (4.59 g, 82.20 mmol) and ammonium chloride (1.76 g, 32.90 mmol). The mixture was stirred at 60° C. overnight. After the reaction was finished, the mixture was cooled to rt, and adjusted to pH 10 with TEA. Then the mixture was filtered. The filtrate was concentrated in vacuo. The residue was dissolved in EtOAc (100 mL) and the resulted mixture was washed with water (40 mL×3) and saturated brine (50 mL). The organic phase was dried over anhydrous Na₂SO₄ (10 g), filtered and concentrated in vacuo. The crude was purified by silica column chromatography (PE/EtOAc (v/v)=4/1) to give the title compound as a yellow solid (3.14 g, 57.0%). The compound was characterized by the following spectroscopic data:

MS (ESI, pos. ion) m/z: 335.1 (M+1); exact mass of $C_{18}H_{20}ClFN_2O$: 334.12.

Step 5: 3-(3-chloro-4-(4-((3-fluorophenoxy)methyl)piperidin-1-yl)phenyl)-2,6-dimethylpyrimidin-4(3H)-one The title compound was prepared by the procedure described in step 3 of Example 2 starting with 3-chloro-4-(4-((3-fluorophenoxy)methyl)piperidin-1-yl)aniline (1.00 g, 3.00 mmol), trimethylaluminium (5.3 mL, 10.60 mmol, 2.0 mol/L in toluene) and a solution of methyl 3-acetamidobut-2-enoate (707 mg, 4.50 mmol) in toluene (5 mL) under N₂ to give the product as a white solid (989 mg, 74.6%). The compound was characterized by the following spectroscopic data:

MS (ESI, pos. ion) m/z: 442.2 (M+1); exact mass of $C_{24}H_{25}ClFN_3O_2$: 441.16; and $^1$H NMR (400 MHz, CDCl₃) δ 7.29-7.20 (m, 2H), 7.16 (d, J=8.5 Hz, 1H), 7.05 (dd, J=8.5, 2.4 Hz, 1H), 6.74-6.56 (m, 3H), 6.28 (s, 1H), 3.87 (d, J=7.8 Hz, 2H), 3.51 (dd, J=34.8, 11.5 Hz, 2H), 2.75 (dt, J=23.8, 12.7 Hz, 2H), 2.29 (s, 3H), 2.19 (s, 3H), 2.06-1.90 (m, 3H), 1.64 (td, J=12.4, 3.7 Hz, 2H).

Example 31: 3-(3-chloro-4-(4-(3-methoxyphenoxy)piperidin-1-yl)phenyl)-2,6-dimethylpyrimidin-4(3H)-one

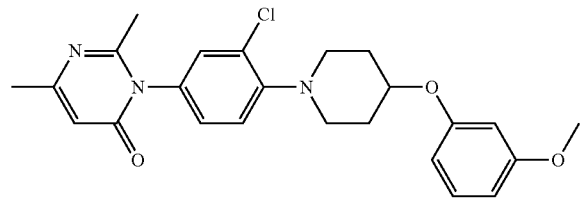

Step 1: 1-(2-chloro-4-nitrophenyl)-4-(3-methoxyphenoxy)piperidine

The title compound was prepared by the procedure described in step 3 of Example 28 using 1-(2-chloro-4-nitrophenyl)piperidin-4-yl 4-methylbenzenesulfonate (4.93 g, 12.00 mmol), 3-methoxyphenol (1.24 g, 10.00 mmol) and cesium carbonate (6.52 g, 20.00 mmol) to give the title compound as yellow oil (1.94 g, 53.5%). The compound was characterized by the following spectroscopic data:

MS (ESI, pos. ion) m/z: 363.10 (M+1); exact mass of $C_{18}H_{19}ClN_2O_4$: 362.10.

Step 2: 3-chloro-4-(4-(3-methoxyphenoxy)piperidin-1-yl)aniline

A solution of 1-(2-chloro-4-nitrophenyl)-4-(3-methoxyphenoxy)piperidine (1.94 g, 5.35 mmol) in a mixture of THF and H₂O (v/v=30 mL/30 mL) was added in activated iron powder (2.99 g, 53.47 mmol). The title compound was prepared by the procedure described in step 6 of Example 3 to give the crude product (1.38 g, 77.5%). The compound was characterized by the following spectroscopic data:

MS (ESI, pos. ion) m/z: 333.1 (M+1); exact mass of $C_{18}H_{21}ClN_2O_2$: 332.13.

Step 3: 3-(3-chloro-4-(4-(3-methoxyphenoxy)piperidin-1-yl)phenyl)-2,6-dimethylpyrimidin-4(3H)-one The title compound was prepared by the procedure described in step 3 of Example 2 starting with 3-chloro-4-(4-(3-methoxyphenoxy)piperidin-1-yl)aniline (1.38 g, 4.15 mmol), trimethylaluminium (6.0 mL, 12.00 mmol, 2.0 mol/L in toluene) and a solution of methyl 3-acetamidobut-2-enoate (0.99 g, 6.22 mmol) in toluene (10 mL) under N₂ to give the title compound as a yellow solid (1.44 g, 78.9%). The compound was characterized by the following spectroscopic data:

MS (ESI, pos. ion) m/z: 440.1 (M+1); exact mass of $C_{24}H_{26}ClN_3O_3$: 439.17; and $^1$H NMR (400 MHz, CDCl₃) δ 7.20 (dd, J=16.3, 5.6 Hz, 3H), 7.05 (dd, J=8.5, 2.4 Hz, 1H), 6.59-6.49 (m, 3H), 6.28 (s, 1H), 4.57-4.42 (m, 1H), 3.80 (s, 3H), 3.39 (s, 1H), 3.29 (d, J=7.8 Hz, 1H), 3.12-2.93 (m, 2H), 2.29 (s, 3H), 2.19 (s, 3H), 2.15 (s, 2H), 2.04 (d, J=4.2 Hz, 2H).

Example 32: 3-(3-chloro-4-(4-((3-fluorobenzyl)oxy)piperidin-1-yl)phenyl)-2,6-dimethylpyrimidin-4(3H)-one

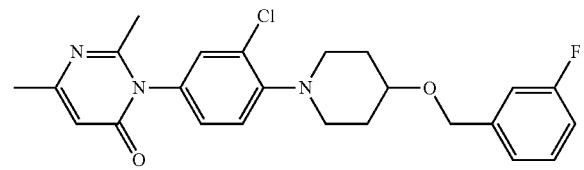 [SMILES: Cc1cc(=O)n(-c2ccc(N3CCC(COc4cccc(F)c4)CC3)c(Cl)c2)c(C)n1]

Step 1: tert-butyl 4-((3-fluorobenzyl)oxy)piperidine-1-carboxylate

To a suspension of 60% NaH (185 mg, 7.70 mmol) in 10 mL of anhydrous DMF was added dropwise a solution of tert-butyl 4-hydroxypiperidine-1-carboxylate (2.01 g, 1.00 mmol) in 10 mL of anhydrous DMF under ice bath and under N₂. After addition, the mixture was stirred at rt for 30 minutes. Then the mixture was cooled under ice bath again and added dropwise a solution of 1-(bromomethyl)-3-fluorobenzene (2.08 g, 1.10 mmol) in 10 mL of anhydrous DMF. After addition, the mixture was stirred at rt overnight. After the reaction was finished, the mixture was quenched with water (100 mL), and extracted with EtOAc (50 mL×3). The combined organic phases were washed with water (50 mL×2) and saturated brine (50 mL), dried over anhydrous Na₂SO₄ (15 g), filtered and concentrated in vacuo to give the crude product as yellow oil (3.00 g, 88.2%) which was used directly for the next step without further purification. The compound was characterized by the following spectroscopic data:

MS (ESI, pos. ion) m/z: 254.1 (M+1-t-Bu); exact mass of $C_{17}H_{24}FNO_3$: 309.17.

Step 2: 4-((3-fluorobenzyl)oxy)piperidine hydrochloride

The title compound was prepared by the procedure described in step 4 of Example 3 using tert-butyl 4-((3-fluorobenzyl)oxy)piperidine-1-carboxylate (3.00 g, 9.70 mmol) and a solution of HCl in EtOAc (4.45 mol/L, 22 mL, 97.9 mmol) to give the title compound as a colourless solid (2.29 g, 96.2%).

Step 3: 1-(2-chloro-4-nitrophenyl)-4-((3-fluorobenzyl)oxy)piperidine

The title compound was prepared by the procedure described in step 5 of Example 4 using 4-((3-fluorobenzyl)oxy)piperidine hydrochloride (650 mg, 2.64 mmol), 2-chloro-1-fluoro-4-nitrobenzene (948 mg, 5.40 mmol) and TEA (3 mL, 2.15 mmol) to give the title compound as yellow oil (650 mg, 67.5%).

Step 4: 3-chloro-4-(4-((3-fluorobenzyl)oxy)piperidin-1-yl)aniline

A solution of 1-(2-chloro-4-nitrophenyl)-4-((3-fluorobenzyl)oxy)piperidine (650 mg, 1.78 mmol) in MeOH (20 mL) was added in activated iron powder (994 mg, 17.80 mol). The title compound was prepared by the procedure described in step 6 of Example 3 to give the title compound as brown oil (192 mg, 32.2%). The compound was characterized by the following spectroscopic data:

MS (ESI, pos. ion) m/z: 335.1 (M+1); exact mass of $C_{18}H_{20}ClFN_2O$: 334.12.

Step 5: 3-(3-chloro-4-(4-((3-fluorobenzyl)oxy)piperidin-1-yl)phenyl)-2,6-dimethylpyrimidin-4(3H)-one The title compound was prepared by the procedure described in step 3 of Example 2 starting with 3-chloro-4-(4-((3-fluorobenzyl)oxy)piperidin-1-yl)aniline (192 mg, 0.57 mmol), trimethylaluminium (1.0 mL, 2.00 mmol, 2.0 mol/L in toluene) and a solution of methyl 3-acetamidobut-2-enoate (943 mg, 6.00 mmol) in toluene (6 mL) under N₂ to give the title compound as a light yellow solid (80 mg, 31.6%). The compound was characterized by the following spectroscopic data:

MS (ESI, pos. ion) m/z: 442.1 (M+1); exact mass of $C_{24}H_{25}ClFN_3O_2$: 441.16; and $^1$H NMR (400 MHz, DMSO-d₆) δ 7.48 (d, J=1.4 Hz, 1H), 7.44-7.34 (m, 1H), 7.30-7.15 (m, 4H), 7.14-7.05 (m, 1H), 6.23 (s, 1H), 4.59 (s, 2H), 3.60 (td, J=8.3, 4.2 Hz, 1H), 3.29-3.18 (m, 2H), 2.86 (dt, J=21.1, 9.2 Hz, 2H), 2.19 (s, 3H), 2.06 (s, 3H), 2.02 (s, 2H), 1.72 (d, J=9.8 Hz, 2H).

Example 33: 3-(4-(4-(2-allylphenoxy)piperidin-1-yl)-3-chlorophenyl)-2,6-dimethylpyrimidin-4(3H)-one

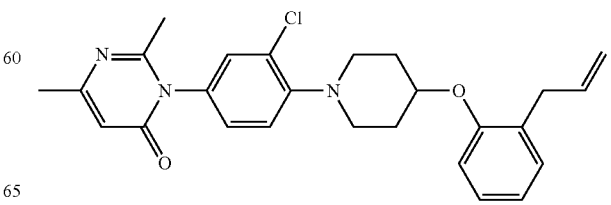

Step 1: 4-(2-allylphenoxy)-1-(2-chloro-4-nitrophenyl)piperidine

To a suspension of 60% NaH (0.28 g, 11.68 mmol) in anhydrous DMF (10 mL) was added a solution of 2-allylphenol (0.58 g, 4.28 mmol) in anhydrous DMF (10 mL) dropwise at ice bath under $N_2$. After addition, the mixture was stirred at rt for 30 minutes. Then the mixture was cooled at ice bath again, and to the mixture was added a solution of 1-(2-chloro-4-nitrophenyl)piperidin-4-yl 4-methylbenzenesulfonate (1.60 g, 3.89 mmol) in anhydrous DMF (20 mL). After addition, the mixture was stirred at rt overnight, then diluted with water (20 mL), and extracted with EtOAc (30 mL×2). The combined organic phases were washed with water (30 mL×2) and saturated brine (30 mL), dried over anhydrous $Na_2SO_4$ (10 g), filtered and concentrated in vacuo. The crude product was purified by silica column chromatography (PE/EtOAc (v/v)=8/1) to give the title compound as yellow oil (0.50 g, 34.5%). The compound was characterized by the following spectroscopic data:

MS (ESI, pos. ion) m/z: 373.0 (M+1); exact mass of $C_{20}H_{21}ClN_2O_3$: 372.12.

Step 2: 4-(4-(2-allylphenoxy)piperidin-1-yl)-3-chloroaniline

The title compound was prepared by the procedure described in step 6 of Example 3 starting with a solution of 4-(2-allylphenoxy)-1-(2-chloro-4-nitrophenyl)piperidine (0.80 g, 2.15 mmol) in a mixture of THF and MeOH (v/v=10 mL/10 mL) was added in activated iron power (1.20 g, 21.50 mmol) to give the title compound as a light yellow solid (370 mg, 50.3%). The compound was characterized by the following spectroscopic data:

MS (ESI, pos. ion) m/z: 343.0 (M+1); exact mass of $C_{20}H_{23}ClN_2O$: 342.15.

Step 3: 3-(4-(4-(2-allylphenoxy)piperidin-1-yl)-3-chlorophenyl)-2,6-dimethylpyrimidin-4(3H)-one The title compound was prepared by the procedure described in step 3 of Example 2 except starting with 4-(4-(2-allylphenoxy)piperidin-1-yl)-3-chloroaniline (370 mg, 1.08 mmol), trimethylaluminium (2.2 mL, 4.40 mmol, 2.0 mol/L in toluene) and methyl 3-acetamidobut-2-enoate (203 mg, 1.29 mmol) in toluene (5 mL) under $N_2$ to give the title compound as a light yellow solid (150 mg, 31.0%). The compound was characterized by the following spectroscopic data:

MS (ESI, pos. ion) m/z: 450.2 (M+1); exact mass of $C_{26}H_{28}ClN_3O_2$: 449.19; and $^1$H NMR (400 MHz, CDCl$_3$) δ 7.22 (d, J=2.4 Hz, 1H), 7.18 (dd, J=7.7, 5.5 Hz, 3H), 7.06 (dd, J=8.5, 2.4 Hz, 1H), 6.91 (t, J=7.2 Hz, 2H), 6.29 (s, 1H), 6.01 (ddt, J=16.7, 10.0, 6.6 Hz, 1H), 5.13-5.00 (m, 2H), 4.62-4.50 (m, 1H), 3.44 (d, J=6.6 Hz, 2H), 3.40-3.23 (m, 2H), 3.16-2.96 (m, 2H), 2.30 (s, 3H), 2.19 (s, 3H), 2.14 (dt, J=17.1, 8.5 Hz, 2H), 2.06 (ddd, J=13.4, 6.6, 3.3 Hz, 2H).

Example 34: 3-(4-(4-(3-aminophenoxy)piperidin-1-yl)-3-chlorophenyl)-2,6-dimethylpyrimidin-4(3H)-one

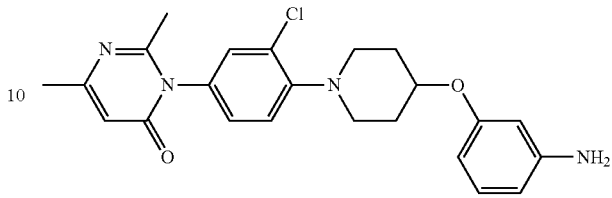

Step 1: tert-butyl (3-hydroxyphenyl)carbamate

To a mixture of 3-aminophenol (1.09 g, 10.00 mmol) in THF (60 mL) was added (Boc)$_2$O (2.51 g, 11.50 mmol) in THF (25 mL). The reaction mixture was heated to 66° C. for 7 hours. The mixture was cooled to rt and dissolved in EtOAc (100 mL). The resulted mixture was washed with 0.5 mol/L hydrochloric acid (100 mL×2), aqueous saturated sodium bicarbonate solution (100 mL×2) and saturated brine (100 mL) in turn, dried over anhydrous $Na_2SO_4$ (10 g), filtered and concentrated in vacuo to give the crude product as yellow oil (2.20 g, 105.3%) which was used directly for the next step without purification. The compound was characterized by the following spectroscopic data:

MS (ESI, pos. ion) m/z: 210.2 (M+1); exact mass of $C_{11}H_{15}NO_3$: 209.11.

Step 2: tert-butyl (3-((1-(2-chloro-4-nitrophenyl)piperidin-4-yl)oxy)phenyl)carbamate The title compound was prepared by the procedure described in step 3 of Example 28 using 1-(2-chloro-4-nitrophenyl)piperidin-4-yl 4-methylbenzenesulfonate (2.51 g, 6.10 mmol), tert-butyl (3-hydroxyphenyl)carbamate (1.60 g, 7.60 mmol) and cesium carbonate (4.96 g, 15.30 mmol) to give the title compound as yellow oil (657 mg, 25.1%). The compound was characterized by the following spectroscopic data:

MS (ESI, pos. ion) m/z: 448.2 (M+1); exact mass of $C_{22}H_{26}ClN_3O_5$: 447.16.

Step 3: tert-butyl (3-((1-(4-amino-2-chlorophenyl)piperidin-4-yl)oxy)phenyl)carbamate To a solution of tert-butyl (3-((1-(2-chloro-4-nitrophenyl)piperidin-4-yl)oxy)phenyl)carbamate (1.24 g, 2.77 mmol) in a mixture of THF and MeOH (v/v=15 mL/15 mL) was added in activated iron powder (1.55 g, 27.70 mmol). The title compound was prepared by the procedure described in step 6 of Example 3 to give a yellow solid (1.34 g, 115.9%).

Step 4: 3-(4-(4-(3-aminophenoxy)piperidin-1-yl)-3-chlorophenyl)-2,6-dimethylpyrimidin-4(3H)-one The title compound was prepared by the procedure described in step 3 of Example 2 starting with tert-butyl (3-((1-(4-amino-2-chlorophenyl)piperidin-4-yl)oxy)phenyl) carbamate (1.34 g, 3.21 mmol), trimethylaluminium (6.4 mL, 12.80 mmol, 2.0 mol/L in toluene) and a solution of methyl 3-acetamidobut-2-enoate (655 mg, 4.17 mmol) in toluene (2 mL) under $N_2$ to give the title compound as a light yellow solid (310 mg, 22.8%). The compound was characterized by the following spectroscopic data:

MS (ESI, pos. ion) m/z: 425.1 (M+1); exact mass of $C_{24}H_{26}ClN_3O_2$: 423.17; and $^1$H NMR (400 MHz, CDCl$_3$) δ 7.21 (d, J=2.4 Hz, 1H), 7.17 (d, J=8.5 Hz, 1H), 7.08-7.01 (m, 2H), 6.36 (dd, J=8.2, 1.3 Hz, 1H), 6.31-6.25 (m, 3H), 4.46 (tt, J=6.7, 3.4 Hz, 1H), 3.42-3.23 (m, 2H), 3.11-2.91 (m, 2H), 2.29 (s, 3H), 2.18 (s, 3H), 2.16-2.07 (m, 2H), 2.03-1.90 (m, 2H), 1.25 (t, J=7.1 Hz, 2H).

Example 35: 3-(3-chloro-4-(4-(2-(trifluoromethoxy)phenoxy)piperidin-1-yl)phenyl)-2,6-dimethylpyrimidin-4(3H)-one

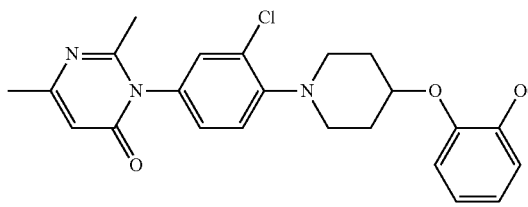

Step 1: 1-(2-chloro-4-nitrophenyl)-4-(2-(trifluoromethoxy)phenoxy)piperidine

The title compound was prepared by the procedure described in step 3 of Example 28 using 1-(2-chloro-4-nitrophenyl)piperidin-4-yl 4-methylbenzenesulfonate (2.00 g, 11.30 mmol), 2-(trifluoromethyl)phenol (3.90 g, 9.50 mmol) and cesium carbonate (6.19 g, 19.00 mmol) to give the title compound as yellow oil (2.65 g, 67.1%). The compound was characterized by the following spectroscopic data:

MS (ESI, pos. ion) m/z: 417.0 (M+1); exact mass of $C_{18}H_{16}ClF_3N_2O_4$: 416.08.

Step 2: 3-chloro-4-(4-(2-(trifluoromethoxy)phenoxy)piperidin-1-yl)aniline

The title compound was prepared by the procedure described in step 6 of Example 3 starting with a solution of 1-(2-chloro-4-nitrophenyl)-4-(2-(trifluoromethoxy)phenoxy)piperidine (2.65 g, 6.40 mmol) in a mixture of THF and MeOH (30 mL/15 mL) was added in activated iron power (2.14 g, 38.40 mmol) to give the title compound as yellow oil (2.75 g, 111.0%). The compound was characterized by the following spectroscopic data:

MS (ESI, pos. ion) m/z: 387.0 (M+1); exact mass of $C_{18}H_{18}ClF_3N_2O_2$: 386.10.

Step 3: 3-(3-chloro-4-(4-(2-(trifluoromethoxy)phenoxy)piperidin-1-yl)phenyl)-2,6-dimethylpyrimidin-4(3H)-one The title compound was prepared by the procedure described in step 3 of Example 2 starting with 3-chloro-4-(4-(2-(trifluoromethoxy)phenoxy)piperidin-1-yl)aniline (2.75 g, 7.11 mmol), trimethylaluminium (12.53 mL, 28.44 mmol, 2.0 mol/L in toluene) and a solution of methyl 3-acetamidobut-2-enoate (1.23 mg, 7.82 mmol) in toluene (5 mL) under N$_2$ to give the title compound as a white solid (446 mg, 12.7%). The compound was characterized by the following spectroscopic data:

MS (ESI, pos. ion) m/z: 495.1 (M+1); exact mass of $C_{24}H_{23}ClF_3N_3O_3$: 493.14; and $^1$H NMR (400 MHz, CDCl$_3$) δ 7.23 (dd, J=12.9, 4.5 Hz, 3H), 7.18 (d, J=8.5 Hz, 1H), 7.08-7.01 (m, 2H), 6.99-6.92 (m, 1H), 6.28 (s, 1H), 4.61-4.51 (m, 1H), 3.33 (ddd, J=19.9, 17.0, 8.4 Hz, 2H), 3.13-2.97 (m, 2H), 2.29 (s, 3H), 2.19 (s, 3H), 2.10 (ddd, J=22.7, 10.6, 5.6 Hz, 4H).

Example 36: 3-(3-chloro-4-(4-(2-(methylamino)phenoxy)piperidin-1-yl)phenyl)-2,6-dimethylpyrimidin-4(3H)-one

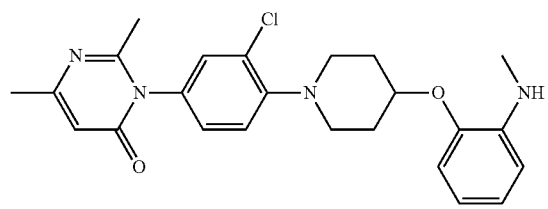 [SMILES: CNc1ccccc1OC1CCN(c2ccc(-n3c(C)nc(C)cc3=O)cc2Cl)CC1]

Step 1: 2-((1-(2-chloro-4-nitrophenyl)piperidin-4-yl)oxy)-N-methylaniline

The title compound was prepared by the procedure described in step 3 of Example 28 using 1-(2-chloro-4-nitrophenyl)piperidin-4-yl 4-methylbenzenesulfonate (8.00 g, 19.49 mmol), 2-(methylamino)phenol (2.00 g, 16.24 mmol) and cesium carbonate (10.58 g, 32.48 mmol) to give the title compound as a yellow solid (2.30 g, 39.0%). The compound was characterized by the following spectroscopic data:

MS (ESI, pos. ion) m/z: 362.1 (M+1); exact mass of $C_{18}H_{20}ClN_3O_3$: 361.12.

Step 2: 2-((1-(4-amino-2-chlorophenyl)piperidin-4-yl)oxy)-N-methylaniline

The title compound was prepared by the procedure described in step 6 of Example 3 starting with a solution of 2-((1-(2-chloro-4-nitrophenyl)piperidin-4-yl)oxy)-N-methylaniline (2.30 g, 6.36 mmol) in a mixture of THF and MeOH (v/v=10 mL/10 mL) was added in activated iron power (3.55 g, 63.6 mmol) to give the title compound as a light yellow solid (1.84 g, 87.6%). The compound was characterized by the following spectroscopic data:

MS (ESI, pos. ion) m/z: 332.0 (M+1); exact mass of $C_{18}H_{22}ClN_3O$: 331.15.

Step 3: 3-(3-chloro-4-(4-(2-(methylamino)phenoxy)piperidin-1-yl)phenyl)-2,6-dimethylpyrimidin-4(3H)-one The title compound was prepared by the procedure described in step 3 of Example 2 using a solution of 2-((1-(4-amino-2-chlorophenyl)piperidin-4-yl)oxy)-N-methylaniline (1.70 g, 5.12 mmol) in methylbenzene (20 mL), trimethylaluminium (10.25 mL, 20.50 mmol) and a solution of methyl 3-acetamidobut-2-enoate (966 mg, 6.15 mmol) in toluene (10 mL) under N$_2$ to give the title compound as a light yellow solid (1.50 g, 67.0%). The compound was characterized by the following spectroscopic data:

MS (ESI, pos. ion) m/z: 439.1 (M+1); exact mass of $C_{24}H_{27}ClN_4O_2$: 438.18; and $^1$H NMR (400 MHz, CDCl$_3$) δ 7.22 (d, J=2.4 Hz, 1H), 7.17 (d, J=8.5 Hz, 1H), 7.05 (dd, J=8.5, 2.4 Hz, 1H), 6.92 (td, J=7.7, 1.2 Hz, 1H), 6.85-6.80 (m, 1H), 6.65 (ddd, J=7.8, 5.6, 1.7 Hz, 2H), 6.28 (s, 1H), 4.50 (dt, J=10.8, 3.6 Hz, 1H), 4.34 (s, 1H), 3.45-3.25 (m, 2H), 3.12-2.92 (m, 2H), 2.88 (s, 3H), 2.29 (s, 3H), 2.23-2.12 (m, 5H), 2.09-1.98 (m, 2H).

Example 37: 3-(3-chloro-4-(4-(2-chloro-4-methyl-phenoxy)piperidin-1-yl)phenyl)-2,6-dimethylpyrimidin-4(3H)-one

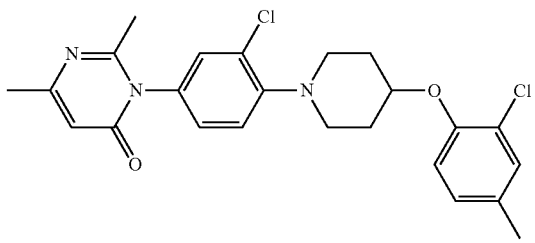

Step 1: 4-(2-chloro-4-methylphenoxy)-1-(2-chloro-4-nitrophenyl)piperidine

The title compound was prepared by the procedure described in step 3 of Example 28 using 1-(2-chloro-4-nitrophenyl)piperidin-4-yl 4-methylbenzenesulfonate (10.37 g, 25.25 mmol), 2-chloro-4-methylphenol (3.00 g, 21.04 mmol) and cesium carbonate (13.70 g, 42.08 mmol) to give the title compound as a yellow solid (4.00 g, 50.0%).

MS (ESI, pos. ion) m/z: 381.0 (M+1); exact mass of $C_{18}H_{18}Cl_2N_2O_3$: 380.07.

Step 2: 3-chloro-4-(4-(2-chloro-4-methylphenoxy)piperidin-1-yl)aniline

To a solution of 4-(2-chloro-4-methylphenoxy)-1-(2-chloro-4-nitrophenyl)piperidine (4.00 g, 10.49 mmol) in a mixture of THF and MeOH (v/v=15 mL/15 mL) was added in activated iron powder (5.86 g, 104.90 mmol). The title compound was prepared by the procedure described in step 6 of Example 3 to give a yellow solid (3.60 g, 97.0%). The compound was characterized by the following spectroscopic data:

MS (ESI, pos. ion) m/z: 351.0 (M+1); exact mass of $C_{18}H_{20}Cl_2N_2O$: 350.10.

Step 3: 3-(3-chloro-4-(4-(2-chloro-4-methylphenoxy)piperidin-1-yl)phenyl)-2,6-dimethylpyrimidin-4(3H)-one The title compound was prepared by the procedure described in step 3 of Example 2 starting with 3-chloro-4-(4-(2-chloro-4-methylphenoxy)piperidin-1-yl)aniline (3.50 g, 9.96 mmol), trimethylaluminium (20 mL, 40.00 mmol, 2.0 mol/L in toluene) and methyl 3-acetamidobut-2-enoate (1.88 g, 11.96 mmol) in toluene (10 mL) under N$_2$ to give the title compound as a yellow solid (2.80 g, 61.3%). The compound was characterized by the following spectroscopic data:

MS (ESI, pos. ion) m/z: 458.0 (M+1); exact mass of $C_{24}H_{25}Cl_2N_3O_2$: 457.13; and $^1$H NMR (400 MHz, CDCl$_3$) δ 7.20 (dd, J=11.0, 5.5 Hz, 3H), 7.05 (dd, J=8.5, 2.4 Hz, 1H), 7.00 (dd, J=8.3, 1.5 Hz, 1H), 6.90 (d, J=8.3 Hz, 1H), 6.28 (s, 1H), 4.55-4.47 (m, 1H), 3.45-3.29 (m, 2H), 3.11-2.95 (m, 2H), 2.29 (s, 3H), 2.28 (s, 3H), 2.19 (s, 3H), 2.16-2.05 (m, 4H).

Example 38: 3-(3-chloro-4-(4-(4-fluoro-2-methylphenoxy)piperidin-1-yl)phenyl)-2,6-dimethylpyrimidin-4(3H)-one

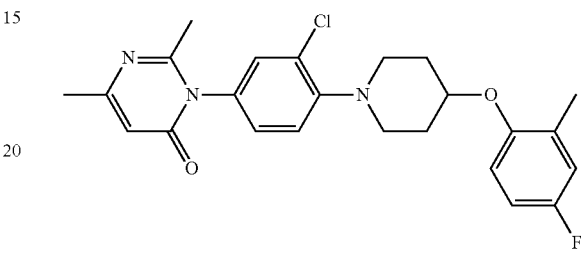

Step 1: 1-(2-chloro-4-nitrophenyl)-4-(4-fluoro-2-methylphenoxy)piperidine

The title compound was prepared by the procedure described in step 3 of Example 28 using 1-(2-chloro-4-nitrophenyl)piperidin-4-yl 4-methylbenzenesulfonate (2.50 g, 19.90 mmol), 4-fluoro-2-methylphenol (6.82 g, 16.60 mmol) and cesium carbonate (10.82 g, 33.20 mmol) to give the title compound as yellow oil (4.20 g, 69.4%). The compound was characterized by the following spectroscopic data:

MS (ESI, pos. ion) m/z: 365.0 (M+1); exact mass of $C_{18}H_{18}ClFN_2O_3$: 364.10.

Step 2: 3-chloro-4-(4-(4-fluoro-2-methylphenoxy)piperidin-1-yl)aniline

A solution of 1-(2-chloro-4-nitrophenyl)-4-(4-fluoro-2-methylphenoxy)piperidine (4.20 g, 11.50 mmol) in a mixture of THF and MeOH (v/v=40 mL/20 mL) was added in activated iron powder (3.86 g, 69.00 mmol). The title compound was prepared by the procedure described in step 2 of Example 29 to give yellow oil (2.61 g, 67.8%). The compound was characterized by the following spectroscopic data:

MS (ESI, pos. ion) m/z: 335.1 (M+1); exact mass of $C_{18}H_{20}ClFN_2O$: 334.12.

Step 3: 3-(3-chloro-4-(4-(4-fluoro-2-methylphenoxy)piperidin-1-yl)phenyl)-2,6-dimethylpyrimidin-4(3H)-one The title compound was prepared by the procedure described in step 3 of Example 2 starting with 3-chloro-4-(4-(4-fluoro-2-methylphenoxy)piperidin-1-yl)aniline (1.77 g, 5.30 mmol), trimethylaluminium (10.6 mL, 21.20 mmol, 2.0 mol/L in toluene) and a solution of methyl 3-acetamidobut-2-enoate (928 mg, 5.90 mmol) in toluene (5 mL) under N$_2$ to give the title compound as a light yellow solid (294 mg, 12.6%). The compound was characterized by the following spectroscopic data:

MS (ESI, pos. ion) m/z: 442.3 (M+1); exact mass of $C_{24}H_{25}ClFN_3O_2$: 441.16; and $^1$H NMR (400 MHz, CDCl$_3$) δ 7.29-7.20 (m, 2H), 7.18 (d, J=8.5 Hz, 1H), 7.06 (dd, J=8.5, 2.3 Hz, 1H), 6.88 (d, J=8.5 Hz, 1H), 6.84-6.76 (m, 2H), 6.28 (s, 1H), 4.43 (d, J=3.2 Hz, 1H), 3.43-3.23 (m, 2H), 3.11-2.94 (m, 2H), 2.29 (s, 3H), 2.26 (s, 3H), 2.19 (s, 3H), 2.14 (dd, J=10.3, 6.4 Hz, 2H), 2.04 (s, 2H).

Example 39: 3-(3-chloro-4-(4-(2,6-dichloro-4-methylphen oxy)piperidin-1-yl)phenyl)-2,6-dimethylpyrimidin-4(3H)— one

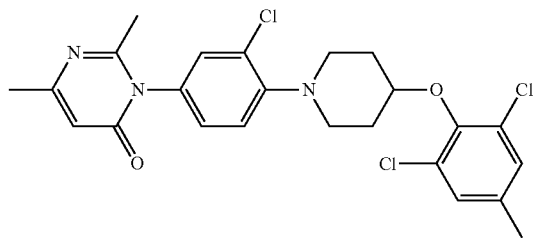

Step 1: 1-(2-chloro-4-nitrophenyl)-4-(2,6-dichloro-4-methylphenoxy)piperidine

The title compound was prepared by the procedure described in step 3 of Example 28 using 1-(2-chloro-4-nitrophenyl)piperidin-4-yl 4-methylbenzenesulfonate (2.80 g, 5.65 mmol), 2,6-dichloro-4-methylphenol (1.00 g, 5.65 mmol) and cesium carbonate (3.68 g, 11.30 mmol) to give the title compound as yellow oil (1.52 g, 64.7%).

Step 2: 3-chloro-4-(4-(2,6-dichloro-4-methylphenoxy)piperidin-1-yl)aniline

A solution of 1-(2-chloro-4-nitrophenyl)-4-(2,6-dichloro-4-methylphenoxy)piperidine (1.52 g, 3.66 mmol) in a mixture of THF and MeOH (v/v=10 mL/10 mL) was added in activated iron powder (2.04 g, 36.56 mmol). The title compound was prepared by the procedure described in step 6 of Example 3 to give a yellow solid (1.42 g, 100.7%). The compound was characterized by the following spectroscopic data:

MS (ESI, pos. ion) m/z: 385.1 (M+1); exact mass of $C_{18}H_{19}Cl_3N_2O$: 384.06.

Step 3: 3-(3-chloro-4-(4-(2,6-dichloro-4-methylphen oxy)piperidin-1-yl)phenyl)-2,6-dimethylpyrimidin-4 (3H)— one The title compound was prepared by the procedure described in step 3 of Example 2 starting with 3-chloro-4-(4-(2,6-dichloro-4-methylphenoxy)piperidin-1-yl)aniline (1.42 g, 3.68 mmol), trimethylaluminium (7.4 mL, 14.80 mmol, 2.0 mol/L in toluene) and a solution of methyl 3-acetamidobut-2-enoate (694 mg, 4.42 mmol) in toluene (2 mL) under N$_2$ to give the title compound as a light yellow solid (1.31 g, 72.2%). The compound was characterized by the following spectroscopic data:

MS (ESI, pos. ion) m/z: 491.1 (M+1); exact mass of $C_{25}H_{25}Cl_3N_2O_2$: 490.10; and $^1$H NMR (400 MHz, CDCl$_3$) δ 7.21 (d, J=2.3 Hz, 1H), 7.16 (d, J=8.5 Hz, 1H), 7.12 (s, 2H), 7.04 (dd, J=8.5, 2.4 Hz, 1H), 6.27 (s, 1H), 4.39 (dd, J=7.9, 3.7 Hz, 1H), 3.57-3.37 (m, 2H), 3.01-2.81 (m, 2H), 2.28 (s, 3H), 2.28 (s, 3H), 2.18 (s, 3H), 2.17-2.07 (m, 4H).

Example 40: 4-((1-(2-chloro-4-(2,4-dimethyl-6-oxopyrimidin-1 (6H)-yl)phenyl)piperidin-4-yl)oxy)-2-fluorobenzonitrile

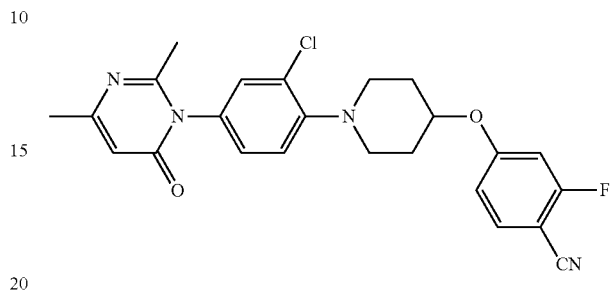

Step 1: 4-((1-(2-chloro-4-nitrophenyl)piperidin-4-yl)oxy)-2-fluorobenzonitrile

The title compound was prepared by the procedure described in step 3 of Example 28 using 1-(2-chloro-4-nitrophenyl)piperidin-4-yl 4-methylbenzenesulfonate (2.05 g, 5.00 mmol), 2-fluoro-4-hydroxybenzonitrile (0.57 g, 4.17 mmol) and cesium carbonate (2.72 g, 8.33 mmol) to give the title compound as a yellow solid (1.57 g, 100%). The compound was characterized by the following spectroscopic data:

MS (ESI, pos. ion) m/z: 376.1 (M+1); exact mass of $C_{18}H_{15}ClFN_3O_3$: 375.08.

Step 2: 4-((1-(4-amino-2-chlorophenyl)piperidin-4-yl)oxy)-2-fluorobenzonitrile

The title compound was prepared by the procedure described in step 6 of Example 3 starting with a solution of 4-((1-(2-chloro-4-nitrophenyl)piperidin-4-yl)oxy)-2-fluorobenzonitrile (1.57 g, 4.18 mmol) in MeOH (30 mL) was added in activated iron power (1.57 g, 41.78 mmol) to give the title compound as a yellow solid (0.81 g, 56.1%). The compound was characterized by the following spectroscopic data:

MS (ESI, pos. ion) m/z: 346.1 (M+1); exact mass of $C_{18}H_{17}ClFN_3O$: 345.10.

Step 3: 4-((1-(2-chloro-4-(2,4-dimethyl-6-oxopyrimidin-1 (6H)-yl)phenyl)piperidin-4-yl)oxy)-2-fluorobenzonitrile The title compound was prepared by the procedure described in step 3 of Example 2 starting with 4-((1-(4-amino-2-chlorophenyl)piperidin-4-yl)oxy)-2-fluorobenzonitrile (0.81 g, 2.34 mmol), trimethylaluminium (3.5 mL, 7.0 mmol, 2.0 mol/L, 2.0 mol/L in toluene) and a solution of methyl 3-acetamidobut-2-enoate (0.56 g, 3.51 mmol) in toluene (10 mL) under N$_2$ to give the title compound as a yellow solid (0.40 g, 37.7%). The compound was characterized by the following spectroscopic data:

MS (ESI, pos. ion) m/z: 453.1 (M+1); exact mass of $C_{24}H_{22}ClFN_4O_2$: 452.14; and $^1$H NMR (400 MHz, CDCl$_3$) δ 7.58-7.49 (m, 1H), 7.24 (d, J=2.4 Hz, 1H), 7.18 (d, J=8.5 Hz, 1H), 7.07 (dd, J=8.5, 2.5

Hz, 1H), 6.78 (ddd, J=13.3, 9.8, 2.2 Hz, 2H), 6.29 (s, 1H), 4.58 (d, J=3.6 Hz, 1H), 3.33 (d, J=33.6 Hz, 2H), 3.15-2.98 (m, 2H), 2.30 (s, 3H), 2.21 (d, J=11.8 Hz, 5H), 2.05 (s, 2H).

Example 41: 3-(3-chloro-4-(4-((2-chloropyridin-4-yl)oxy)piperidin-1-yl)phenyl)-2,6-dimethylpyrimidin-4(3H)-one

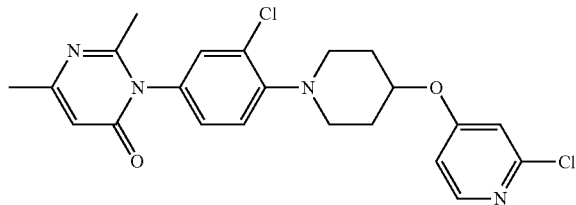 [SMILES: Cc1cc(=O)n(-c2ccc(N3CCC(Oc4ccnc(Cl)c4)CC3)c(Cl)c2)c(C)n1]

Step 1: 2-chloro-4-((1-(2-chloro-4-nitrophenyl)piperidin-4-yl)oxy)pyridine

The title compound was prepared by the procedure described in step 3 of Example 28 using 1-(2-chloro-4-nitrophenyl)piperidin-4-yl 4-methylbenzenesulfonate (8.22 g, 20.00 mmol), 2-chloropyridin-4-ol (2.16 g, 16.67 mmol) and cesium carbonate (13.03 g, 40.00 mmol) to give the title compound as yellow oil (5.35 g, 87.2%). The compound was characterized by the following spectroscopic data:
MS (ESI, pos. ion) m/z: 370.1 (M+1); exact mass of $C_{16}H_{15}Cl_2N_3O_3$: 367.05.

Step 2: 3-chloro-4-(4-((2-chloropyridin-4-yl)oxy)piperidin-1-yl)aniline

The title compound was prepared by the procedure described in step 6 of Example 3 starting with a solution of 2-chloro-4-((1-(2-chloro-4-nitrophenyl)piperidin-4-yl)oxy)pyridine (5.35 g, 14.53 mmol) in MeOH (30 mL) was added in activated iron power (13.41 g, 145.30 mmol) to give the title compound as a yellow solid (4.91 g, 100.0%). The compound was characterized by the following spectroscopic data:
MS (ESI, pos. ion) m/z: 339.1 (M+1); exact mass of $C_{16}H_{17}Cl_2N_3O$: 337.07.

Step 3: N-(3-chloro-4-(4-((2-chloropyridin-4-yl)oxy)piperidin-1-yl)phenyl)-3-oxobutanamide The title compound was prepared by the procedure described in step 5 of Example 1 using 3-chloro-4-(4-((2-chloropyridin-4-yl)oxy)piperidin-1-yl)aniline (4.91 g, 14.53 mmol) and 4-methyleneoxetan-2-one (1.83 g, 21.78 mmol) to give the title compound as yellow oil (2.29 g, 37.4%). The compound was characterized by the following spectroscopic data:
MS (ESI, pos. ion) m/z: 423.1 (M+1); exact mass of $C_{20}H_{21}Cl_2N_3O_3$: 421.10.

Step 4: (Z)-3-amino-N-(3-chloro-4-(4-((2-chloropyridin-4-yl)oxy)piperidin-1-yl)phenyl)but-2-enamide The title compound was prepared by the procedure described in step 8 of Example 12 using N-(3-chloro-4-(4-((2-chloropyridin-4-yl)oxy)piperidin-1-yl)phenyl)-3-oxobutanamide (2.29 g, 5.42 mmol) and a solution of $NH_3$ in MeOH (7 mol/L, 2.5 mL, 16.20 mmol) to give the title compound as a light yellow solid (2.29 g, 37.4%).

Step 5: 3-(3-chloro-4-(4-((2-chloropyridin-4-yl)oxy)piperidin-1-yl)phenyl)-2,6-dimethylpyrimidin-4(3H)-one The title compound was prepared by the procedure described in step 7 of Example 1 starting with (Z)-3-amino-N-(3-chloro-4-(4-((2-chloropyridin-4-yl)oxy)piperidin-1-yl)phenyl)but-2-enamide (2.29 g, 5.41 mmol) and triethyl orthoacetate (15 mL) to give the title compound as a yellow solid (0.92 g, 38.2%). The compound was characterized by the following spectroscopic data:
MS (ESI, pos. ion) m/z: 446.2 (M+1); exact mass of $C_{22}H_{22}Cl_2N_4O_2$: 444.11; and
$^1$H NMR (400 MHz, CDCl$_3$) δ 8.21 (d, J=5.8 Hz, 1H), 7.24 (d, J=2.3 Hz, 1H), 7.18 (d, J=8.5 Hz, 1H), 7.07 (dd, J=8.5, 2.4 Hz, 1H), 6.87 (d, J=2.1 Hz, 1H), 6.78 (dd, J=5.8, 2.2 Hz, 1H), 6.29 (s, 1H), 4.62 (s, 1H), 3.32 (dd, J=30.5, 8.6 Hz, 2H), 3.15-2.98 (m, 2H), 2.30 (s, 3H), 2.19 (s, 5H), 2.07 (d, J=17.1 Hz, 2H).

Example 42: 3-(3-chloro-4-(4-((3-fluorophenyl)amino)piperidin-1-yl)phenyl)-2,6-dimethylpyrimidin-4(3H)-one

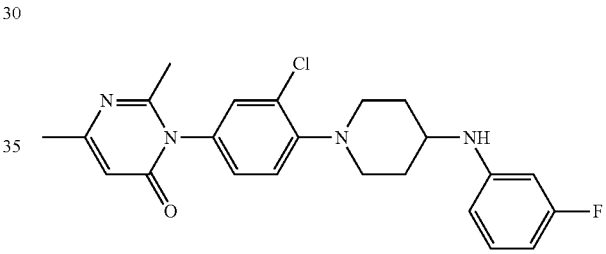

Step 1: tert-butyl 4-((3-fluorophenyl)amino)piperidine-1-carboxylate

To a mixture of tert-butyl 4-oxopiperidine-1-carboxylate (4.00 g, 20.08 mmol), 3-fluoroaniline (2.68 g, 24.09 mmol), acetic acid glacial (7.23 g, 120.5 mmol) and DCM (30 mL) was added sodium triacetoxyborohydride (6.38 g, 30.11 mmol) dropwise at ice bath. After the addition, the mixture was stirred at rt for 2 hours, and then to the mixture was added aqueous NaOH solution (100 mL, 3.3 mol/L). The resulted mixture was extracted with DCM (50 mL×3). The combined organic phases were dried over anhydrous Na$_2$SO$_4$ (20 g), filtered and concentrated in vacuo. The crude was purified by silica column chromatography (PE/EtOAc (v/v)=5/1) to give the title compound as a white solid (5.8 g, 98.1%).

Step 2: N-(3-fluorophenyl)piperidin-4-amine hydrochloride

The title compound was prepared by the procedure described in step 4 of Example 3 using tert-butyl 4-((3-fluorophenyl)amino)piperidine-1-carboxylate (5.81 g, 19.70 mmol) and a solution of HCl in EtOAc (4.4 mol/L, 27 mL, 118.80 mmol) to give the crude product as a white solid (4.40 g, 97.0%) which was used directly for the next step without further purification. The compound was characterized by the following spectroscopic data:

MS (ESI, pos. ion) m/z: 195.2 (M+1-HCl); exact mass of $C_{11}H_{16}ClFN_2$: 230.10.

Step 3: 1-(2-chloro-4-nitrophenyl)-N-(3-fluorophenyl)piperidin-4-amine

The title compound was prepared by the procedure described in step 5 of Example 4 using 2-chloro-1-fluoro-4-nitrobenzene (2.94 g, 16.77 mmol), TEA (9.43 g, 93.19 mmol) and N-(3-fluorophenyl)piperidin-4-amine hydrochloride (4.30 g, 18.64 mmol) to give the title compound as yellow oil (3.00 g, 46.0%). The compound was characterized by the following spectroscopic data:

MS (ESI, pos. ion) m/z: 350.1 (M+1); exact mass of $C_{17}H_{17}ClFN_3O_2$: 349.10.

Step 4: 1-(4-amino-2-chlorophenyl)-N-(3-fluorophenyl)piperidin-4-amine

A solution of 1-(2-chloro-4-nitrophenyl)-N-(3-fluorophenyl)piperidin-4-amine (3.00 g, 8.58 mmol) in a mixture of THF and MeOH (v/v=10 mL/5 mL) was added in activated iron powder (4.79 g, 85.77 mol). The title compound was prepared by the procedure described in step 6 of Example 3 to give a light yellow solid (2.20 g, 81.0%). The compound was characterized by the following spectroscopic data:

MS (ESI, pos. ion) m/z: 320.2 (M+1); exact mass of $C_{17}H_{19}ClFN_3$: 319.13.

Step 5: 3-(3-chloro-4-(4-((3-fluorophenyl)amino)piperidin-1-yl)phenyl)-2,6-dimethylpyrimidin-4(3H)-one The title compound was prepared by the procedure described in step 3 of Example 2 starting with 1-(4-amino-2-chlorophenyl)-N-(3-fluorophenyl)piperidin-4-amine (1.00 g, 3.13 mmol), trimethylaluminium (6.3 mL, 12.60 mmol, 2.0 mol/L in toluene) and a solution of methyl 3-acetamidobut-2-enoate (590 mg, 3.75 mmol) in toluene (5 mL) under $N_2$ to give the title compound as a light yellow solid (800 mg, 60.0%). The compound was characterized by the following spectroscopic data:

MS (ESI, pos. ion) m/z: 427.2 (M+1); exact mass of $C_{23}H_{24}ClFN_4O$: 426.16; and $^1$H NMR (400 MHz, CDCl$_3$) δ 7.22 (d, J=2.4 Hz, 1H), 7.16 (d, J=8.5 Hz, 1H), 7.13-7.03 (m, 2H), 6.42-6.35 (m, 2H), 6.33 (dd, J=11.7, 2.1 Hz, 1H), 6.29 (s, 1H), 3.79 (s, 1H), 3.53-3.35 (m, 3H), 2.98-2.74 (m, 2H), 2.29 (s, 3H), 2.21 (d, J=16.3 Hz, 5H), 1.77-1.60 (m, 2H).

Example 43: 3-(3-chloro-4-(4-((3-(trifluoromethyl)phenyl)amino)piperidin-1-yl)phenyl)-2,6-dimethylpyrimidin-4(3H)-one

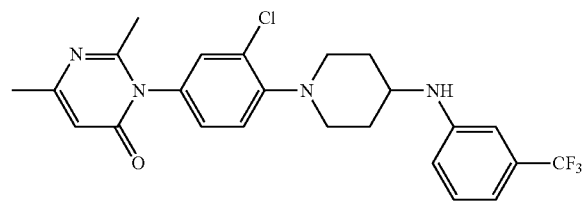

Step 1: tert-butyl 4-((3-(trifluoromethyl)phenyl)amino)piperidine-1-carboxylate The title compound was prepared by the procedure described in step 1 of Example 42 using tert-butyl 4-oxopiperidine-1-carboxylate (4.00 g, 20.08 mmol), 3-(trifluoromethyl)aniline (3.88 g, 24.09 mmol), acetic acid glacial (7.23 g, 120.45 mmol) and sodium triacetoxyborohydride (6.38 g, 30.11 mmol) to give the title compound as a white solid (6.80 g, 97.0%). The compound was characterized by the following spectroscopic data:

MS (ESI, pos. ion) m/z: 289.1 (M+1-t-Bu); exact mass of $C_{17}H_{23}F_3N_2O_2$: 344.17.

Step 2: N-(3-(trifluoromethyl)phenyl)piperidin-4-amine hydrochloride

The title compound was prepared by the procedure described in step 4 of Example 3 using tert-butyl 4-((3-(trifluoromethyl)phenyl)amino)piperidine-1-carboxylate (6.80 g, 19.75 mmol) and solution of HCl in EtOAc (4.4 mol/L, 27 mL, 118.50 mmol) to give the title compound as a white solid (5.50 g, 95.0%). The compound was characterized by the following spectroscopic data:

MS (ESI, pos. ion) m/z: 245.2 (M+1-HCl); exact mass of $C_{12}H_{16}F_3N_2$: 280.10.

Step 3: 1-(2-chloro-4-nitrophenyl)-N-(3-(trifluoromethyl)phenyl)piperidin-4-amine The title compound was prepared by the procedure described in step 5 of Example 4 using 2-chloro-1-fluoro-4-nitrobenzene (3.10 g, 17.63 mmol), TEA (9.91 g, 97.96 mmol) and N-(3-(trifluoromethyl)phenyl)piperidin-4-amine hydrochloride (5.50 g, 19.59 mmol) to give the title compound as yellow oil (2.20 g, 28.0%). The compound was characterized by the following spectroscopic data:

MS (ESI, pos. ion) m/z: 400.1 (M+1); exact mass of $C_{18}H_{17}ClF_3N_3O_2$: 399.10.

Step 4: 1-(4-amino-2-chlorophenyl)-N-(3-(trifluoromethyl)phenyl)piperidin-4-amine A solution of 1-(2-chloro-4-nitrophenyl)-N-(3-(trifluoromethyl)phenyl)piperidin-4-amine (2.20 g, 5.50 mmol) in a mixture of THF and MeOH (v/v=10 mL/10 mL) was added in activated iron powder (3.07 g, 55.00 mmol). The title compound was prepared by the procedure described in step 6 of Example 3 to give mahogany oil (1.00 g, 50.0%). The compound was characterized by the following spectroscopic data:

MS (ESI, pos. ion) m/z: 370.1 (M+1); exact mass of $C_{18}H_{19}ClF_3N_3$: 369.12.

Step 5: 3-(3-chloro-4-(4-((3-(trifluoromethyl)phenyl)amino)piperidin-1-yl)phenyl)-2,6-dimethylpyrimidin-4(3H)-one The title compound was prepared by the procedure described in step 3 of Example 2 starting with 1-(4-amino-2-chlorophenyl)-N-(3-(trifluoromethyl)phenyl)piperidin-4-amine (0.95 g, 2.57 mmol), trimethylaluminium (5.2 mL, 10.40 mmol, 2.0 mol/L in toluene) and a solution of methyl 3-acetamidobut-2-enoate (485 mg, 3.08 mmol) in toluene (5 mL) under $N_2$ to give the title compound as a light yellow solid (800 mg, 65.0%). The compound was characterized by the following spectroscopic data:

MS (ESI, pos. ion) m/z: 477.2 (M+1); exact mass of $C_{24}H_{24}ClF_3N_4O$: 476.16; and $^1$H NMR (400 MHz, CDCl$_3$) δ 7.27 (d, J=6.4 Hz, 1H), 7.25-7.21 (m, 1H), 7.17 (d, J=8.5 Hz, 1H), 7.06 (dd, J=8.5, 2.4 Hz, 1H), 6.93 (d, J=7.5 Hz, 1H), 6.82 (s, 1H), 6.77 (d, J=8.1 Hz, 1H), 6.29 (s, 1H), 3.51 (t, J=10.4 Hz, 2H), 3.42 (d, J=11.8 Hz, 1H), 2.99-2.79 (m, 2H), 2.30 (s, 3H), 2.19 (s, 5H), 1.69 (dt, J=15.0, 7.4 Hz, 2H).

Example 44: 3-(3-chloro-4-(4-(3,4-difluorobenzyl) piperidin-1-yl)phenyl)-2,6-dimethylpyrimidin-4 (3H)-one

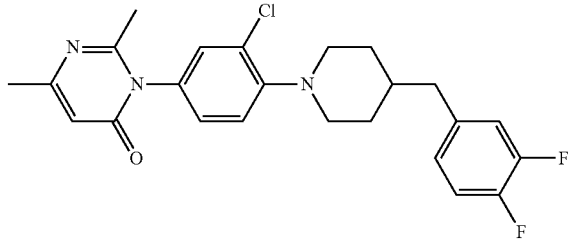 [SMILES: Cc1cc(=O)n(-c2ccc(N3CCC(Cc4ccc(F)c(F)c4)CC3)c(Cl)c2)c(C)n1]

Step 1: diethyl 3,4-difluorobenzylphosphonate

A mixture of triethyl phosphite (2.57 g, 15.30 mmol) and 4-(bromomethyl)-1,2-difluorobenzene (2.75 g, 13.30 mmol) was stirred at 110° C. overnight. After the reaction was finished, the mixture was cooled to room temperature to give yellow oil (3.30 g, 94.3%) which was used directly for the next step without further operation. The compound was characterized by the following spectroscopic data:

MS (ESI, pos. ion) m/z: 265.1 (M+1); exact mass of $C_{11}H_{15}F_2O_3P$: 264.07.

Step 2: tert-butyl 4-(3,4-difluorobenzylidene)piperidine-1-carboxylate

The title compound was prepared by the procedure described in step 2 of Example 7 using diethyl 3,4-difluorobenzylphosphonate (3.30 g, 12.60 mmol), tert-butyl 4-oxopiperidine-1-carboxylate (2.00 g, 10.10 mmol) and potassium tert-butanolate (1.02 g, 9.08 mmol) to give the title compound as yellow oil (2.69 g, 86.2%). The compound was characterized by the following spectroscopic data:

MS (ESI, pos. ion) m/z: 254.1 (M+1-t-Bu); exact mass of $C_{17}H_{21}F_2NO_2$: 309.15.

Step 3: tert-butyl 4-(3,4-difluorobenzyl)piperidine-1-carboxylate

The title compound was prepared by the procedure described in step 3 of Example 3 using tert-butyl 4-(3,4-difluorobenzylidene)piperidine-1-carboxylate (2.69 g, 8.69 mmol) and 10% Pa/C (0.20 g) to give the title compound as yellow oil (2.20 g, 81.8%). The compound was characterized by the following spectroscopic data:

MS (ESI, pos. ion) m/z: 256.3 (M+1-t-Bu); exact mass of $C_{17}H_{23}F_2NO_2$: 311.17.

Step 4: 4-(3,4-difluorobenzyl)piperidine hydrochloride

The title compound was prepared by the procedure described in step 4 of Example 3 using tert-butyl 4-(3,4-difluorobenzyl)piperidine-1-carboxylate (1.53 g, 5.09 mmol) and a solution of HCl in EtOAc (4.45 mol/L, 16 mL, 71.00 mmol) to give the title compound as a white solid (1.50 g, 85.2%). The compound was characterized by the following spectroscopic data:

MS (ESI, pos. ion) m/z: 212.2 (M+1-HCl); exact mass of $C_{12}H_{16}ClF_2N$: 247.09.

Step 5: 1-(2-chloro-4-nitrophenyl)-4-(3,4-difluorobenzyl)piperidine

The title compound was prepared by the procedure described in step 5 of Example 9 using 4-(3,4-difluorobenzyl)piperidine hydrochloride (1.50 g, 6.10 mmol), potassium carbonate (2.95 g, 21.35 mmol) and 2-chloro-1-fluoro-4-nitrobenzene (1.07 g, 6.10 mmol) to give the title compound as yellow oil (2.14 g, 95.5%). The compound was characterized by the following spectroscopic data:

MS (ESI, pos. ion) m/z: 367.1 (M+1); exact mass of $C_{18}H_{17}ClF_2N_2O_2$: 366.09.

Step 6: 3-chloro-4-(4-(3,4-difluorobenzyl)piperidin-1-yl)aniline

The title compound was prepared by the procedure described in step 6 of Example 3 starting with a solution of 1-(2-chloro-4-nitrophenyl)-4-(3,4-difluorobenzyl)piperidine (2.14 g, 5.90 mmol) in a mixture of THF and MeOH (v/v=16 mL/8 mL) was added in activated iron powder (1.98 g, 35.40 mol) to give the title compound as yellow oil (0.80 g, 40.2%). The compound was characterized by the following spectroscopic data:

MS (ESI, pos. ion) m/z: 337.1 (M+1); exact mass of $C_{18}H_{19}ClF_2N_2$: 336.12.

Step 7: 3-(3-chloro-4-(4-(3,4-difluorobenzyl)piperidin-1-yl)phenyl)-2,6-dimethylpyrimidin-4(3H)-one The title compound was prepared by the procedure described in step 3 of Example 2 starting with 3-chloro-4-(4-(3,4-difluorobenzyl)piperidin-1-yl)aniline (0.80 g, 2.38 mmol), trimethylaluminium (4.8 mL, 9.6 mmol, 2.0 mol/L in toluene) and a solution of methyl 3-acetamidobut-2-enoate (411 mg, 2.62 mmol) in toluene (6 mL) under N$_2$ to give the title compound as a white solid (0.20 g, 18.9%). The compound was characterized by the following spectroscopic data:

MS (ESI, pos. ion) m/z: 444.1 (M+1); exact mass of $C_{24}H_{24}ClF_2N_3O$: 443.16; and $^1$H NMR (400 MHz, CDCl$_3$) δ 7.20 (d, J=2.4 Hz, 1H), 7.11 (d, J=8.5 Hz, 1H), 7.07 (dd, J=8.4, 1.9 Hz, 1H), 7.05-7.02 (m, 1H), 7.02-7.00 (m, 1H), 6.99-6.94 (m, 1H), 6.28 (s, 1H), 3.44 (dd, J=34.8, 11.8 Hz, 2H), 2.73-2.53 (m, 4H), 2.29 (s, 3H), 2.18 (s, 3H), 1.74 (d, J=12.6 Hz, 2H), 1.70-1.63 (m, 1H), 1.51 (dt, J=19.7, 7.6 Hz, 2H).

Example 45: 3-(3-chloro-4-(4-(4-(trifluoromethoxy)benzyl)piperidin-1-yl)phenyl)-2,6-dimethylpyrimidin-4(3H)-one

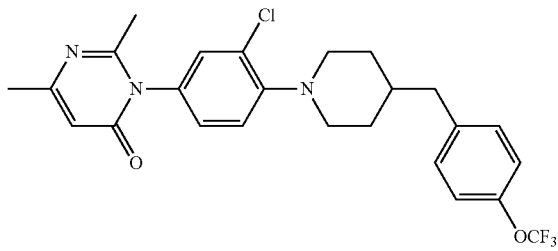 [SMILES: Cc1cc(=O)n(-c2ccc(N3CCC(Cc4ccc(OC(F)(F)F)cc4)CC3)c(Cl)c2)c(C)n1]

Step 1: diethyl 4-(trifluoromethoxy)benzylphosphonate

A mixture of triethyl phosphite (1.51 g, 9.10 mmol) and 1-(bromomethyl)-4-(trifluoromethoxy)benzene (2.00 g, 7.90 mmol) was stirred at 105° C. under $N_2$ overnight. After the reaction was finished, the mixture was cooled to room temperature to give yellow oil (2.34 g, 95.0%) which was used directly for the next step without further operation. The compound was characterized by the following spectroscopic data:

MS (ESI, pos. ion) m/z: 313.1 (M+1); exact mass of $C_{12}H_{16}F_3O_4P$: 312.07.

Step 2: tert-butyl 4-(4-(trifluoromethoxy)benzylidene)piperidine-1-carboxylate The title compound was prepared by the procedure described in step 2 of Example 7 using diethyl 4-(trifluoromethoxy)benzylphosphonate (2.34 g, 7.50 mmol), tert-butyl 4-oxopiperidine-1-carboxylate (1.20 g, 6.02 mmol) and potassium tert-butanolate (1.01 g, 8.99 mmol) to give the title compound as yellow oil (2.55 g, 95.2%). The compound was characterized by the following spectroscopic data:

MS (ESI, pos. ion) m/z: 303.1 (M+1-t-Bu); exact mass of $C_{18}H_{22}F_3NO_3$: 357.16.

Step 3: 4-(4-(trifluoromethoxy)benzylidene)piperidine hydrochloride

The title compound was prepared by the procedure described in step 4 of Example 3 using tert-butyl 4-(4-(trifluoromethoxy)benzylidene)piperidine-1-carboxylate (2.50 g, 7.00 mmol) and a solution of HCl in EtOAc (4.45 mol/L, 16 mL, 71.2 mmol) to give the title compound as a colourless solid (2.00 g, 96.6%). The compound was characterized by the following spectroscopic data:

MS (ESI, pos. ion) m/z: 258.1 (M+1-HCl); exact mass of $C_{13}H_{15}ClF_3NO$: 293.08.

Step 4: 4-(4-(trifluoromethoxy)benzyl)piperidine hydrochloride

The title compound was prepared by the procedure described in step 3 of Example 3 using 4-(4-(trifluoromethoxy)benzylidene)piperidine hydrochloride (1.85 g, 6.40 mmol) in a mixture of THF and MeOH (v/v=10 mL/10 mL) and 10% Pa/C (0.07 g) to give the title compound as a whited solid (2.00 g, 96.8%). The compound was characterized by the following spectroscopic data:

MS (ESI, pos. ion) m/z: 260.2 (M+1-HCl); exact mass of $C_{13}H_{17}ClF_3NO$: 295.10.

Step 5: 1-(2-chloro-4-nitrophenyl)-4-(4-(trifluoromethoxy)benzyl)piperidine

The title compound was prepared by the procedure described in step 5 of Example 9 using 4-(4-(trifluoromethoxy)benzyl)piperidine hydrochloride (1.94 g, 7.40 mmol), potassium carbonate (3.58 g, 25.9. mmol) and 2-chloro-1-fluoro-4-nitrobenzene (1.30 g, 7.40 mmol) to give the title compound as yellow oil (1.62 g, 52.8%). The compound was characterized by the following spectroscopic data:

MS (ESI, pos. ion) m/z: 415.0 (M+1); $C_{19}H_{18}ClF_3N_2O_3$: 414.10.

Step 6: 3-chloro-4-(4-(4-(trifluoromethoxy)benzyl)piperidin-1-yl)aniline

A solution of 1-(2-chloro-4-nitrophenyl)-4-(4-(trifluoromethoxy)benzyl)piperidine (1.62 g, 3.90 mmol) in a mixture of THF and MeOH (v/v=20 mL/10 mL) was added in activated iron powder (1.30 g, 23.28 mol). The title compound was prepared by the procedure described in step 6 of Example 3 to give yellow oil (1.20 g, 80.0%). The compound was characterized by the following spectroscopic data:

MS (ESI, pos. ion) m/z: 385.1 (M+1); exact mass of $C_{19}H_{20}ClF_3N_2O$: 384.12.

Step 7: 3-(3-chloro-4-(4-(4-(trifluoromethoxy)benzyl)piperidin-1-yl)phenyl)-2,6-dimethylpyrimidin-4(3H)-one The title compound was prepared by the procedure described in step 3 of Example 2 starting with 3-chloro-4-(4-(4-(trifluoromethoxy)benzyl)piperidin-1-yl)aniline (1.20 g, 3.20 mmol), trimethylaluminium (6.4 mL, 12.80 mmol, 2.0 mol/L in toluene) and a solution of methyl 3-acetamidobut-2-enoate (566 mg, 3.60 mmol) in toluene (8 mL) under $N_2$ to give the title compound as a white solid (137 mg, 8.73%). The compound was characterized by the following spectroscopic data:

MS (ESI, pos. ion) m/z: 492.2 (M+1); exact mass of $C_{25}H_{25}ClF_3N_3O_2$: 491.16; and $^1$H NMR (400 MHz, CDCl$_3$) δ 7.20 (dd, J=5.5, 3.1 Hz, 3H), 7.13 (dd, J=12.7, 8.4 Hz, 3H), 7.02 (dd, J=8.5, 2.4 Hz, 1H), 6.28 (s, 1H), 3.44 (dd, J=35.8, 11.5 Hz, 2H), 2.74-2.53 (m, 4H), 2.29 (s, 3H), 2.18 (s, 3H), 1.69 (d, J=7.1 Hz, 3H), 1.56-1.47 (m, 2H).

Example 46: 3-(3-chloro-4-(4-((4-chloropyridin-2-yl)methoxy)piperidin-1-yl)phenyl)-2,6-dimethylpyrimidin-4(3H)-one

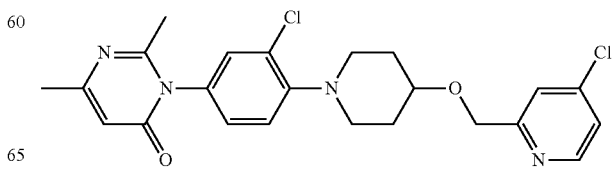

Step 1: 4-chloro-2-(chloromethyl)pyridine

To a mixture of (4-chloropyridin-2-yl)methanol (0.45 g, 3.14 mmol) and DCM (5 mL) was added $SOCl_2$ (0.56 g, 4.70 mmol) dropwise at ice bath. After addition, the reaction mixture was stirred at rt for 5.5 hours. After the reaction was finished, the mixture was added saturated aqueous natrium carbonate solution (50 mL) and DCM (25 mL). The separated organic phase was dried over anhydrous $NaSO_4$ (5 g), filtered and concentrated in vacuo to give the title compound as light yellow oil (0.50 g, 98.2%) which was used directly for the next step without further operation. The compound was characterized by the following spectroscopic data:

MS (ESI, pos. ion) m/z: 162.1 (M+1); exact mass of $C_6H_5Cl_2N$: 160.98.

Step 2: tert-butyl 4-((4-chloropyridin-2-yl)methoxy)piperidine-1-carboxylate A mixture of tert-butyl 4-hydroxypiperidine-1-carboxylate (0.59 g, 2.93 mmol), potassium tert-butanolate (0.38 g, 3.39 mmol) and anhydrous THF (5 mL) was stirred at rt for 5 minutes. Then to the mixture was added a solution of 4-chloro-2-(chloromethyl)pyridine (0.50 g, 3.09 mmol) in THF (5 mL). The reaction mixture was heated to 60° C. overnight. After the reaction was finished, the mixture was cooled to rt and concentrated in vacuo. The residue was dissolved in DCM (100 mL), and the resulted mixture was washed with water (100 mL×2) and brine (100 mL). The organic phase was dried over anhydrous $Na_2SO_4$ (10 g), filtered and concentrated in vacuo to give the title compound as yellow oil (960 mg, 95.1%) which was used directly for the next step without further operation. The compound was characterized by the following spectroscopic data:

MS (ESI, pos. ion) m/z: 327.1 (M+1); exact mass of $C_{16}H_{23}ClN_2O_3$: 326.14.

Step 3: 4-chloro-2-((piperidin-4-yloxy)methyl)pyridine hydrochloride

The title compound was prepared by the procedure described in step 4 of Example 3 using tert-butyl 4-((4-chloropyridin-2-yl)methoxy)piperidine-1-carboxylate (0.96 g, 2.94 mmol) and a solution of HCl in EtOAc (4.45 mol/L, 6.6 mL, 29.37 mmol) as starting materials to give the title compound as a white solid (0.77 g, 99.5%).

Step 4: 4-chloro-2-(((1-(2-chloro-4-nitrophenyl)piperidin-4-yl)oxy)methyl)pyridine The title compound was prepared by the procedure described in step 5 of Example 9 using 4-chloro-2-((piperidin-4-yloxy)methyl)pyridine hydrochloride (0.77 g, 2.93 mmol), potassium carbonate (1.42 g, 12.26 mmol) and 2-chloro-1-fluoro-4-nitrobenzene (1.07 g, 6.10 mmol) as starting materials to give the title compound as yellow oil (0.33 g, 29.5%). The compound was characterized by the following spectroscopic data:

MS (ESI, pos. ion) m/z: 382.1 (M+1); exact mass of $C_{17}H_{17}Cl_2N_3O_3$: 381.06.

Step 5: 3-chloro-4-(4-((4-chloropyridin-2-yl)methoxy)piperidin-1-yl)aniline

A solution of 4-chloro-2-(((1-(2-chloro-4-nitrophenyl)piperidin-4-yl)oxy)methyl)pyridine (1.46 g, 3.90 mmol) in a mixture of THF and MeOH (v/v=20 mL/10 mL) was added in activated iron powder (1.30 g, 23.40 mmol). The title compound was prepared by the procedure described in step 6 of Example 3 to give yellow oil (1.02 g, 74.5%). The compound was characterized by the following spectroscopic data:

MS (ESI, pos. ion) m/z: 352.1 (M+1); exact mass of $C_{17}H_{19}Cl_2N_3O$: 351.09.

Step 6: 3-(3-chloro-4-(4-((4-chloropyridin-2-yl)methoxy)piperidin-1-yl)phenyl)-2,6-dimethylpyrimidin-4(3H)-one The title compound was prepared by the procedure described in step 3 of Example 2 starting with 3-chloro-4-(4-((4-chloropyridin-2-yl)methoxy)piperidin-1-yl)aniline (1.02 g, 2.90 mmol), trimethylaluminium (5.8 mL, 11.6 mmol, 2.0 mol/L in toluene) and a solution of methyl 3-acetamidobut-2-enoate (503 mg, 3.20 mmol) in toluene (8 mL) under $N_2$ to give the title compound as a white solid (160 mg, 12.0%). The compound was characterized by the following spectroscopic data:

MS (ESI, pos. ion) m/z: 459.2 (M+1); exact mass of $C_{23}H_{24}Cl_2N_4O_2$: 458.13; and $^1$H NMR (400 MHz, CDCl$_3$) δ 8.45 (d, J=5.3 Hz, 1H), 7.54 (d, J=10.8 Hz, 1H), 7.22 (d, J=2.5 Hz, 2H), 7.16 (d, J=8.5 Hz, 1H), 7.04 (dd, J=8.5, 2.4 Hz, 1H), 6.28 (s, 1H), 4.70 (s, 2H), 3.74-3.62 (m, 1H), 3.46-3.25 (m, 2H), 2.94 (ddd, J=38.1, 14.5, 5.7 Hz, 2H), 2.29 (s, 3H), 2.19 (s, 3H), 2.11 (dt, J=14.0, 7.1 Hz, 2H), 1.93 (ddd, J=12.1, 8.5, 4.2 Hz, 2H).

Example 47: 3-(3-chloro-4-(4-((4-fluorophenoxy)methyl)piperidin-1-yl)phenyl)-2,6-dimethylpyrimidin-4(3H)-one

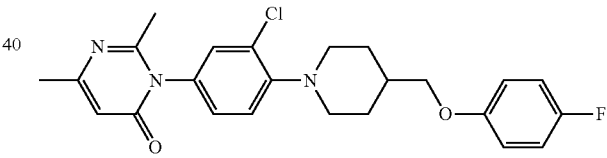

Step 1: (1-(2-chloro-4-nitrophenyl)piperidin-4-yl)methanol

The title compound was prepared by the procedure described in step 1 of Example 27 using 2-chloro-1-fluoro-4-nitrobenzene (3.51 g, 20.00 mmol), piperidin-4-ylmethanol (2.30 g, 20.00 mmol) and TEA (6.07 g, 60.00 mmol) to give the title compound as a yellow solid (3.12 g, 57.8%). The compound was characterized by the following spectroscopic data:

MS (ESI, pos. ion) m/z: 271.0 (M+1); $C_{12}H_{15}ClN_2O_3$: 270.08.

Step 2: (1-(2-chloro-4-nitrophenyl)piperidin-4-yl)methyl 4-methylbenzenesulfonate The title compound was prepared by the procedure described in step 2 of Example 27 using (1-(2-chloro-4-nitrophenyl)piperidin-4-yl)methanol (3.12 g, 11.53 mmol), tosyl chloride (3.30 g, 17.29 mmol), DMAP (0.28 g, 2.31 mmol) and TEA (3.50 g, 34.58 mmol) to give the title compound as a yellow solid (3.22 g, 65.8%) The compound was characterized by the following spectroscopic data:

MS (ESI, pos. ion) m/z: 425.2 (M+1); exact mass of $C_{19}H_{21}ClN_2O_5S$: 424.09.

Step 3: 1-(2-chloro-4-nitrophenyl)-4-((4-fluorophenoxy)methyl)piperidine

The title compound was prepared by the procedure described in step 3 of Example 28 using (1-(2-chloro-4-nitrophenyl)piperidin-4-yl)methyl 4-methylbenzenesulfonate (1.62 g, 3.81 mmol), 4-fluorophenol (0.52 g, 4.58 mmol) and caesium carbonate (2.48 g, 7.63 mmol) to give the title compound as yellow oil (1.36 g, 97.8%). The compound was characterized by the following spectroscopic data:

MS (ESI, pos. ion) m/z: 365.1 (M+1); exact mass of $C_{18}H_{18}ClFN_2O_3$: 364.10.

Step 4: 3-chloro-4-(4-((4-fluorophenoxy)methyl)piperidin-1-yl)aniline

A solution of 1-(2-chloro-4-nitrophenyl)-4-((4-fluorophenoxy)methyl)piperidine (1.36 g, 3.73 mmol) in a mixture of THF and MeOH (v/v=10 mL/10 mL) was added in activated iron powder (2.08 g, 37.30 mmol). The title compound was prepared by the procedure described in step 6 of Example 3 to give a light yellow solid (0.78 g, 62.3%). The compound was characterized by the following spectroscopic data:

MS (ESI, pos. ion) m/z: 335.1 (M+1); exact mass of $C_{18}H_{20}ClFN_2O$: 334.12.

Step 5: 3-(3-chloro-4-(4-((4-fluorophenoxy)methyl)piperidin-1-yl)phenyl)-2,6-dimethylpyrimidin-4(3H)-one The title compound was prepared by the procedure described in step 3 of Example 2 starting with 3-chloro-4-(4-((4-fluorophenoxy)methyl)piperidin-1-yl)aniline (0.78 g, 2.32 mmol), trimethylaluminium (3.5 mL, 7.00 mmol, 2.0 mol/L in toluene) and methyl 3-acetamidobut-2-enoate (0.55 g, 3.49 mmol) in toluene (10 mL) under $N_2$ to give the title compound as a yellow solid (0.58 g, 56.5%). The compound was characterized by the following spectroscopic data:

MS (ESI, pos. ion) m/z: 442.1 (M+1); exact mass of $C_{24}H_{25}ClFN_3O_2$: 441.16; and
$^1$H NMR (400 MHz, CDCl$_3$) δ 7.21 (d, J=2.3 Hz, 1H), 7.16 (d, J=8.5 Hz, 1H), 7.05 (dd, J=8.5, 2.4 Hz, 1H), 6.98 (t, J=8.6 Hz, 2H), 6.88-6.81 (m, 2H), 6.28 (s, 1H), 3.85 (d, J=4.7 Hz, 2H), 3.51 (dd, J=34.1, 10.9 Hz, 2H), 3.10 (d, J=7.3 Hz, 1H), 2.83-2.65 (m, 2H), 2.29 (s, 3H), 2.19 (s, 3H), 1.97 (t, J=10.8 Hz, 4H).

Example 48: 3-(3-chloro-4-(4-((naphthalen-2-yloxy)methyl)piperidin-1-yl)phenyl)-2,6-dimethylpyrimidin-4(3H)-one

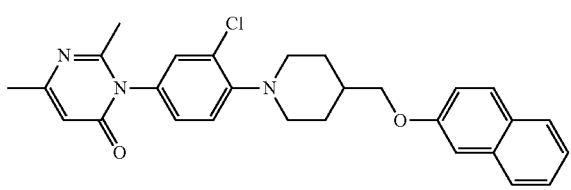 [SMILES: Cc1cc(=O)n(-c2ccc(N3CCC(COc4ccc5ccccc5c4)CC3)c(Cl)c2)c(C)n1]

Step 1: 1-(2-chloro-4-nitrophenyl)-4-((naphthalen-2-yloxy)methyl)piperidine

The title compound was prepared by the procedure described in step 3 of Example 27 using 60% NaH (170 mg, 4.24 mmol), naphthalen-2-ol (265 mg, 1.84 mmol) and (1-(2-chloro-4-nitrophenyl)piperidin-4-yl)methyl 4-methylbenzenesulfonate (600 mg, 1.41 mmol) in 10 mL of DMF to give the title compound as yellow oil (107 mg, 19.1%). The compound was characterized by the following spectroscopic data:

MS (ESI, pos. ion) m/z: 397.1 (M+1); exact mass of $C_{22}H_{21}ClN_2O_3$: 396.12.

Step 2: 3-chloro-4-(4-((naphthalen-2-yloxy)methyl)piperidin-1-yl)aniline

A solution of 1-(2-chloro-4-nitrophenyl)-4-((naphthalen-2-yloxy)methyl)piperidine (107 mg, 0.27 mmol) in a mixture of THF and MeOH (v/v=10 mL/10 mL) was added in activated iron powder (151 mg, 2.70 mmol). The title compound was prepared by the procedure described in step 6 of Example 3 to give a yellow solid (123 mg, 124.4%). The compound was characterized by the following spectroscopic data:

MS (ESI, pos. ion) m/z: 367.2 (M+1); exact mass of $C_{22}H_{23}ClN_2O$: 366.15.

Step 3: 3-(3-chloro-4-(4-((naphthalen-2-yloxy)methyl)piperidin-1-yl)phenyl)-2,6-dimethylpyrimidin-4(3H)-one The title compound was prepared by the procedure described in step 3 of Example 2 starting with 3-chloro-4-(4-((naphthalen-2-yloxy)methyl)piperidin-1-yl)aniline (123 mg, 0.34 mmol), trimethylaluminium (0.68 mL, 1.36 mmol, 2.0 mol/L in toluene) and a solution of methyl 3-acetamidobut-2-enoate (79 mg, 0.50 mmol) in toluene (3 mL) under $N_2$ to give the title compound as a yellow solid (114 mg, 70.7%). The compound was characterized by the following spectroscopic data:

MS (ESI, pos. ion) m/z: 474.1 (M+1); exact mass of $C_{28}H_{28}ClN_3O_2$: 473.19; and
$^1$H NMR (400 MHz, CDCl$_3$) δ 7.75 (dd, J=14.8, 7.2 Hz, 3H), 7.44 (t, J=7.3 Hz, 1H), 7.36-7.30 (m, 1H), 7.22 (d, J=2.2 Hz, 1H), 7.17 (d, J=9.3 Hz, 3H), 7.05 (d, J=6.4 Hz, 1H), 6.29 (s, 1H), 4.02 (d, J=3.9 Hz, 2H), 3.53 (dd, J=35.8, 11.5 Hz, 2H), 2.78 (dt, J=40.4, 11.2 Hz, 2H), 2.30 (s, 3H), 2.19 (s, 3H), 2.04 (t, J=13.0 Hz, 5H).

Example 49: 3-(3-chloro-4-(4-((6-methoxynaphthalen-2-yl)methyl)piperidin-1-yl)phenyl)-2,6-dimethylpyrimidin-4(3H)-one

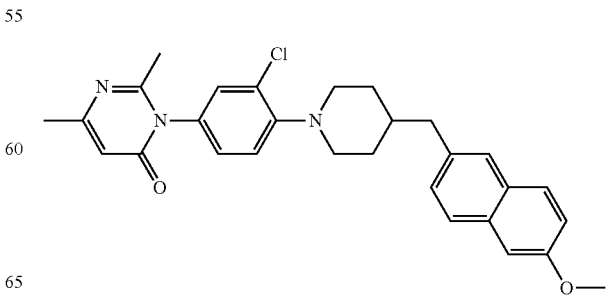

Step 1: tert-butyl 4-((6-methoxynaphthalen-2-yl)methyl)piperidine-1-carboxylate The title compound was prepared by the procedure described in step 1 of Example 15 using tert-butyl 4-methylenepiperidine-1-carboxylate (3.00 g, 15.20 mmol), 9-borabicyclo[3,3,1]nonane (30.4 mL, 15.20 mmol, 0.5 mol/L in THF), 2-bromo-6-methoxynaphthalene (3.28 g, 13.80 mmol), Pd(dppf)Cl$_2$ (0.51 g, 0.69 mmol) and potassium carbonate (2.86 g, 20.70 mmol) as starting materials to give the title compound as a white solid (4.00 g, 81.6%). The compound was characterized by the following spectroscopic data:

MS (ESI, pos. ion) m/z: 300.3 (M+1-t-Bu); exact mass of C$_{22}$H$_{29}$NO$_3$: 355.21.

Step 2: 4-((6-methoxynaphthalen-2-yl)methyl)piperidine hydrochloride

The title compound was prepared by the procedure described in step 4 of Example 3 using tert-butyl 4-((6-methoxynaphthalen-2-yl)methyl)piperidine-1-carboxylate (4.20 g, 11.90 mmol) and a solution of HCl in EtOAc (5.1 mol/L, 24 mL, 122.4 mmol) to give the title compound as a white solid (2.16 g, 62.3%). The compound was characterized by the following spectroscopic data:

MS (ESI, pos. ion) m/z: 256.1 (M+1-HCl); exact mass of C$_{17}$H$_{22}$ClNO: 291.14.

Step 3: 1-(2-chloro-4-nitrophenyl)-4-((6-methoxynaphthalen-2-yl)methyl)piperidine The title compound was prepared by the procedure described in step 5 of Example 9 except using 4-((6-methoxynaphthalen-2-yl)methyl)piperidine hydrochloride (2.16 g, 7.40 mmol), potassium carbonate (3.58 g, 25.90 mmol) and 2-chloro-1-fluoro-4-nitrobenzene (1.30 g, 7.40 mmol) as starting materials to give the title compound as an orangered solid (2.12 g, 69.7%). The compound was characterized by the following spectroscopic data:

MS (ESI, pos. ion) m/z: 411.2 (M+1); exact mass of C$_{23}$H$_{23}$ClN$_2$O$_3$: 410.14.

Step 4: 3-chloro-4-(4-((6-methoxynaphthalen-2-yl)methyl)piperidin-1-yl)aniline The title compound was prepared by the procedure described in step 6 of Example 3 starting with a solution of 1-(2-chloro-4-nitrophenyl)-4-((6-methoxynaphthalen-2-yl)methyl)piperidine (2.12 g, 5.20 mmol) in a mixture of THF and MeOH (v/v=20 mL/10 mL) was added in activated iron powder (1.75 g, 31.20 mmol). The title compound was prepared by the procedure described in step 6 of Example 3 to give a white solid (2.06 g, 104%). The compound was characterized by the following spectroscopic data:

MS (ESI, pos. ion) m/z: 381.1 (M+1); exact mass of C$_{23}$H$_{25}$ClN$_2$O: 380.17.

Step 5: 3-(3-chloro-4-(4-((6-methoxynaphthalen-2-yl)methyl)piperidin-1-yl)phenyl)-2,6-dimethylpyrimidin-4(3H)-one The title compound was prepared by the procedure described in step 3 of Example 2 starting with 3-chloro-4-(4-((6-methoxynaphthalen-2-yl)methyl)piperidin-1-yl)aniline (0.80 g, 2.38 mmol), trimethylaluminium (10.8 mL, 21.60 mmol, 2.0 mol/L in toluene) and a solution of methyl 3-acetamidobut-2-enoate (943 mg, 6.00 mmol) in toluene (6 mL) under N$_2$ to give the title compound as a hoary solid (0.55 g, 20.9%). The compound was characterized by the following spectroscopic data:

MS (ESI, pos. ion) m/z: 488.1 (M+1); exact mass of C$_{29}$H$_{30}$ClN$_3$O$_2$: 487.20; and $^1$H NMR (400 MHz, CDCl$_3$) δ 7.72-7.65 (m, 2H), 7.55 (s, 1H), 7.30 (dd, J=8.4, 1.6 Hz, 1H), 7.19 (d, J=2.4 Hz, 1H), 7.15-7.08 (m, 3H), 7.01 (dd, J=8.5, 2.4 Hz, 1H), 6.27 (s, 1H), 3.92 (s, 3H), 3.44 (dd, J=37.6, 11.4 Hz, 2H), 2.77-2.53 (m, 4H), 2.29 (s, 3H), 2.17 (s, 3H), 1.85-1.69 (m, 3H), 1.62-1.46 (m, 2H).

Example 50: 3-(3-chloro-4-(4-((7-methoxynaphthalen-2-yl)methyl)piperidin-1-yl)phenyl)-2,6-dimethylpyrimidin-4(3H)-one

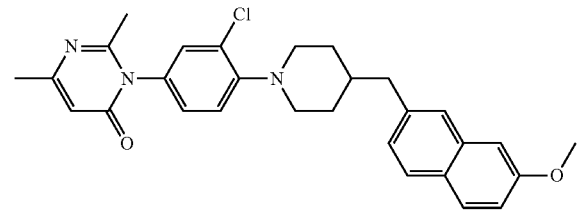

Step 1: 2-bromo-7-methoxynaphthalene

To a suspension of 60% NaH (888 mg, 22.20 mmol) in 30 mL of DMF was added 7-bromonaphthalen-2-ol (4.50 g, 20.20 mmol) dropwise under N$_2$ at ice bath. After the addition, the mixture was stirred at rt for 30 minutes. Then the mixture was cooled at ice bath again, and to the mixture was added iodomethane (4.30 g, 30.30 mmol) dropwise. After the addition, the mixture was stirred at rt overnight, quenched with water (100 mL), and extracted with EtOAc (50 mL×2). The combined organic phases were washed with water (50 mL×2) and saturated brine (100 mL), dried over anhydrous Na$_2$SO$_4$ (10 g), filtered and concentrated in vacuo. The crude was purified by silica column chromatography (PE/EtOAc (v/v)=100/1) to give the title compound as a white solid (4.57 g, 95.4%).

Step 2: tert-butyl 4-((7-methoxynaphthalen-2-yl)methyl)piperidine-1-carboxylate The title compound was prepared by the procedure described in step 1 of Example 15 using tert-butyl 4-methylenepiperidine-1-carboxylate (3.80 g, 19.28 mmol), 9-borabicyclo[3,3,1]nonane (38.6 mL, 19.30 mmol, 0.5 mol/L in THF), 2-bromo-7-methoxynaphthalene (4.57 g, 19.28 mmol), Pd(dppf)Cl$_2$ (705 mg, 0.96 mmol) and potassium carbonate (4.80 g, 34.70 mmol) to give the title compound as a white solid (3.55 g, 51.8%). The compound was characterized by the following spectroscopic data:

MS (ESI, pos. ion) m/z: 300.1 (M+1-t-Bu); exact mass of C$_{22}$H$_{29}$NO$_3$: 355.21.

Step 3: 4-((7-methoxynaphthalen-2-yl)methyl)piperidine hydrochloride

The title compound was prepared by the procedure described in step 4 of Example 3 using tert-butyl 4-((7-methoxynaphthalen-2-yl)methyl)piperidine-1-carboxylate (3.55 g, 9.99 mmol) and a solution of HCl in EtOAc (5.16 mol/L, 9.7 mL, 50.00 mmol) to give the title compound as a white solid (2.40 g, 82.3%). The compound was characterized by the following spectroscopic data:

MS (ESI, pos. ion) m/z: 256.2 (M+1-HCl); exact mass of $C_{17}H_{22}ClNO$: 291.14.

Step 4: 1-(2-chloro-4-nitrophenyl)-4-((7-methoxynaphthalen-2-yl)methyl)piperidine The title compound was prepared by the procedure described in step 5 of Example 3 using 2-chloro-1-fluoro-4-nitrobenzene (1.44 g, 8.22 mmol), 4-((7-methoxynaphthalen-2-yl)methyl)piperidine hydrochloride (2.40 g, 8.22 mmol) and potassium carbonate (4.00 g, 28.80 mmol) to give the title compound as yellow oil (1.85 g, 54.8%).

Step 5: 3-chloro-4-(4-((7-methoxynaphthalen-2-yl)methyl)piperidin-1-yl)aniline A solution of 1-(2-chloro-4-nitrophenyl)-4-((7-methoxynaphthalen-2-yl)methyl)piperidine (1.00 g, 2.61 mmol) in a mixture of THF and MeOH (v/v=15 mL/15 mL) was added in activated iron powder (1.46 g, 26.10 mmol). The title compound was prepared by the procedure described in step 6 of Example 3 to give yellow oil (1.67 g, 97.1%). The compound was characterized by the following spectroscopic data:

MS (ESI, pos. ion) m/z: 381.1 (M+1); exact mass of $C_{23}H_{25}ClN_2O$: 380.17.

Step 6: 3-(3-chloro-4-(4-((7-methoxynaphthalen-2-yl)methyl)piperidin-1-yl)phenyl)-2,6-dimethylpyrimidin-4(3H)-one The title compound was prepared by the procedure described in step 3 of Example 2 starting with 3-chloro-4-(4-((7-methoxynaphthalen-2-yl)methyl)piperidin-1-yl)aniline (1.67 g, 4.38 mmol), trimethylaluminium (8.8 mL, 17.60 mmol, 2.0 mol/L in toluene) and a solution of methyl 3-acetamidobut-2-enoate (826 mg, 5.25 mmol) in toluene (10 mL) under $N_2$ to give the title compound as a yellow solid (1.36 g, 63.6%). The compound was characterized by the following spectroscopic data:

MS (ESI, pos. ion) m/z: 489.3 (M+1); exact mass of $C_{29}H_{30}ClN_3O_2$: 487.20; and $^1$H NMR (400 MHz, CDCl$_3$) δ 7.70 (d, J=9.0 Hz, 2H), 7.52 (s, 1H), 7.19 (dd, J=6.0, 3.5 Hz, 2H), 7.13-7.06 (m, 3H), 7.01 (dd, J=8.5, 2.4 Hz, 1H), 6.27 (s, 1H), 4.12 (q, J=7.1 Hz, 1H), 3.43 (dd, J=35.5, 11.4 Hz, 2H), 2.82-2.72 (m, 2H), 2.72-2.49 (m, 2H), 2.28 (s, 3H), 2.17 (s, 3H), 2.04 (s, 1H), 1.79 (d, J=10.5 Hz, 3H), 1.71 (s, 2H), 1.56 (q, J=12.5 Hz, 2H).

Example 51: 3-(3-chloro-4-(4-((6-fluoronaphthalen-2-yl)methyl)piperidin-1-yl)phenyl)-2,6-dimethylpyrimidin-4(3H)-one

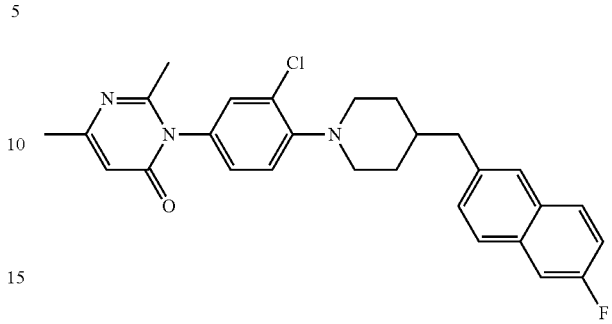

Step 1: tert-butyl 4-((6-fluoronaphthalen-2-yl)methyl)piperidine-1-carboxylate The title compound was prepared by the procedure described in step 1 of Example 15 using tert-butyl 4-methylenepiperidine-1-carboxylate (2.63 g, 13.30 mmol), 9-borabicyclo[3,3,1]nonane (26.6 mL, 13.30 mmol, 0.5 mol/L in THF), 2-bromo-6-fluoronaphthalene (3.00 g, 13.30 mmol), Pd(dppf)Cl$_2$ (486 mg, 0.67 mmol) and potassium carbonate (3.32 g, 24.00 mmol) to give the title compound as yellow oil (2.83 g, 62.0%). The compound was characterized by the following spectroscopic data:

MS (ESI, pos. ion) m/z: 288.1 (M+1-t-Bu); exact mass of $C_{21}H_{26}FNO_2$: 343.19.

Step 2: 4-((6-fluoronaphthalen-2-yl)methyl)piperidine hydrochloride

The title compound was prepared by the procedure described in step 4 of Example 3 using tert-butyl 4-((6-fluoronaphthalen-2-yl)methyl)piperidine-1-carboxylate (2.83 g, 8.24 mmol) and a solution of HCl in EtOAc (5.16 mol/L, 8.0 mL, 41.28 mmol) to give the title compound as a white solid (2.45 g, 106.3%). The compound was characterized by the following spectroscopic data:

MS (ESI, pos. ion) m/z: 244.2 (M+1-HCl); exact mass of $C_{16}H_{19}ClFN$: 279.12.

Step 3: 1-(2-chloro-4-nitrophenyl)-4-((6-fluoronaphthalen-2-yl)methyl)piperidine The title compound was prepared by the procedure described in step 5 of Example 9 using 2-chloro-1-fluoro-4-nitrobenzene (1.54 g, 8.76 mmol), 4-((6-fluoronaphthalen-2-yl)methyl)piperidine hydrochloride (2.45 g, 8.76 mmol) and potassium carbonate (4.24 g, 30.66 mmol) to give the title compound as yellow oil (2.39 g, 68.4%). The compound was characterized by the following spectroscopic data:

MS (ESI, pos. ion) m/z: 399.2 (M+1); exact mass of $C_{22}H_{20}ClFN_2O_2$: 398.12.

Step 4: 3-chloro-4-(4-((6-fluoronaphthalen-2-yl)methyl)piperidin-1-yl)aniline A solution of 1-(2-chloro-4-nitrophenyl)-4-((6-fluoronaphthalen-2-yl)methyl)piperidine (2.39 g, 5.99 mmol) in a mixture of THF and MeOH (v/v=15 mL/15 mL) was added in activated iron powder (3.35 g, 59.90 mmol). The title compound was prepared by the procedure described in step 6 of Example 3 to give the title compound as yellow oil (2.11 g, 95.5%). The compound was characterized by the following spectroscopic data:

MS (ESI, pos. ion) m/z: 369.2 (M+1); exact mass of $C_{22}H_{22}ClFN_2$: 368.15.

Step 5: 3-(3-chloro-4-(4-((6-fluoronaphthalen-2-yl)methyl)piperidin-1-yl)phenyl)-2,6-dimethylpyrimidin-4(3H)-one The title compound was prepared by the procedure described in step 3 of Example 2 starting with 3-chloro-4-(4-((6-fluoronaphthalen-2-yl)methyl)piperidin-1-yl)aniline (2.11 g, 5.72 mmol), trimethylaluminium (11.4 mL, 22.80 mmol, 2.0 mol/L in toluene) and a solution of methyl 3-acetamidobut-2-enoate (1.08 g, 6.86 mmol) in toluene (10 mL) under $N_2$ to give the title compound as a yellow solid (1.81 g, 66.5%). The compound was characterized by the following spectroscopic data:

MS (ESI, pos. ion) m/z: 476.3 (M+1); exact mass of $C_{28}H_{27}ClFN_3O$: 475.18; and $^1$H NMR (400 MHz, CDCl$_3$) δ 7.81-7.70 (m, 2H), 7.61 (s, 1H), 7.43 (dd, J=9.9, 2.3 Hz, 1H), 7.36 (d, J=8.3 Hz, 1H), 7.23 (dd, J=8.7, 2.5 Hz, 1H), 7.19 (d, J=2.4 Hz, 1H), 7.11 (d, J=8.5 Hz, 1H), 7.01 (dd, J=8.5, 2.4 Hz, 1H), 6.27 (s, 1H), 3.44 (dd, J=36.0, 11.1 Hz, 2H), 2.77 (d, J=6.6 Hz, 2H), 2.64 (dt, J=38.2, 10.9 Hz, 2H), 2.28 (s, 3H), 2.17 (s, 3H), 1.78 (d, J=11.4 Hz, 3H), 1.56 (dd, J=22.9, 11.4 Hz, 2H).

Example 52: 6-((1-(2-chloro-4-(2,4-dimethyl-6-oxopyrimidin-1 (6H)-yl)phenyl)piperidin-4-yl)methyl)-2-naphthonitrile

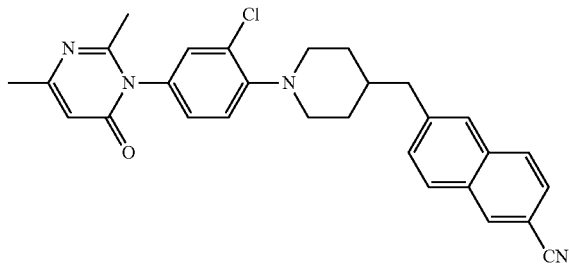 [SMILES: Cc1cc(=O)n(-c2ccc(N3CCC(Cc4ccc5cc(C#N)ccc5c4)CC3)c(Cl)c2)c(C)n1]

Step 1: 6-cyanonaphthalen-2-yl trifluoromethanesulfonate

To a mixture of 6-hydroxy-2-naphthonitrile (2.13 g, 12.59 mmol), pyridine (1.29 g, 16.37 mmol) and DCM (30 mL) was added trifluoromethanesulfonic anhydride (3.91 g, 13.85 mmol) via syringe in 10 minutes. The reaction mixture was stirred at rt overnight. After the reaction was finished, the reaction mixture was quenched with water (20 mL), and the mixture was poured into DCM (100 mL). The resulting mixture was washed with water (100 mL×2) and saturated brine (100 mL). The organic phase was dried over anhydrous $Na_2SO_4$ (15 g), filtered and concentrated in vacuo. The crude was purified by silica column chromatography (PE/EtOAc (v/v)=4/1) to give the title compound as a white solid (3.00 g, 79.1%).

Step 2: tert-butyl 4-((6-cyanonaphthalen-2-yl)methyl)piperidine-1-carboxylate

The title compound was prepared by the procedure described in step 1 of Example 15 using tert-butyl 4-methylenepiperidine-1-carboxylate (1.91 g, 9.57 mmol), 9-borabicyclo[3,3,1]nonane (19.2 mL, 9.57 mmol, 0.5 mol/L in THF), 6-cyanonaphthalen-2-yl trifluoromethanesulfonate (2.62 g, 8.70 mmol), Pd(dppf)Cl$_2$ (0.21 g, 0.29 mmol) and potassium carbonate (1.44 g, 10.44 mmol) to give the title compound as colourless oil (2.54 g, 83.3%). The compound was characterized by the following spectroscopic data:

MS (ESI, pos. ion) m/z: 295.20 (M+1-t-Bu); exact mass of $C_{22}H_{26}N_2O_2$: 350.20.

Step 3: 6-(piperidin-4-ylmethyl)-2-naphthonitrile hydrochloride

The title compound was prepared by the procedure described in step 2 of Example 23 using tert-butyl 4-((6-cyanonaphthalen-2-yl)methyl)piperidine-1-carboxylate (2.54 g, 7.25 mmol) in EtOAc (30 mL) and a solution of HCl in EtOAc (4.4 mol/L, 8.2 mL, 36.08 mmol) to give the title compound as a white solid (1.15 g, 55.3%).

Step 4: 6-((1-(2-chloro-4-nitrophenyl)piperidin-4-yl)methyl)-2-naphthonitrile

The title compound was prepared by the procedure described in step 3 of Example 15 using 2-chloro-1-fluoro-4-nitrobenzene (0.71 g, 4.01 mmol), EtOAc (30 mL), TEA (1.22 g, 12.03 mmol) and 6-(piperidin-4-ylmethyl)-2-naphthonitrile hydrochloride (1.15 g, 4.01 mmol) to give the title compound as a yellow solid (1.17 g, 71.9%). The compound was characterized by the following spectroscopic data:

MS (ESI, pos. ion) m/z: 406.10 (M+1); $C_{23}H_{20}ClN_3O_2$: 405.12.

Step 5: 6-((1-(4-amino-2-chlorophenyl)piperidin-4-yl)methyl)-2-naphthonitrile

A solution of 6-((1-(2-chloro-4-nitrophenyl)piperidin-4-yl)methyl)-2-naphthonitrile (1.17 g, 2.88 mmol) in a mixture of THF and MeOH (v/v=10 mL/10 mL) was added in activated iron power (1.61 g, 28.80 mmol). The title compound was prepared by the procedure described in step 6 of Example 3 to give the title compound as a light yellow solid (1.08 g, 100%). The compound was characterized by the following spectroscopic data:

MS (ESI, pos. ion) m/z: 376.3 (M+1); exact mass of $C_{23}H_{22}ClN_3$: 375.15.

Step 6: 6-((1-(2-chloro-4-(2,4-dimethyl-6-oxopyrimidin-1 (6H)-yl)phenyl)piperidin-4-yl)methyl)-2-naphthonitrile The title compound was prepared by the procedure described in step 3 of Example 2 starting with 6-((1-(4-amino-2-chlorophenyl)piperidin-4-yl)methyl)-2-naphthonitrile (1.08 g, 2.87 mmol), trimethylaluminium (4.31 mL, 8.62 mmol, 2.0 mol/L in toluene) and a solution of methyl 3-acetamidobut-2-enoate (0.68 g, 4.31 mmol) in toluene (10 mL) under $N_2$ to give the title compound as a light yellow solid (132 mg, 9.51%). The compound was characterized by the following spectroscopic data:

MS (ESI, pos. ion) m/z: 483.3 (M+1); exact mass of $C_{29}H_{27}ClN_4O$: 482.19; and ¹H NMR (400 MHz, CDCl₃) δ 8.21 (s, 1H), 7.85 (t, J=8.3 Hz, 2H), 7.67 (s, 1H), 7.59 (dd, J=8.5, 1.5 Hz, 1H), 7.47 (dd, J=8.4, 1.5 Hz, 1H), 7.19 (d, J=2.4 Hz, 1H), 7.11 (d, J=8.5 Hz, 1H), 7.02 (dd, J=8.5, 2.4 Hz, 1H), 6.27 (s, 1H), 3.44 (dd, J=35.9, 10.8 Hz, 2H), 2.82 (d, J=6.9 Hz, 2H), 2.64 (dt, J=21.7, 9.6 Hz, 2H), 2.29 (s, 3H), 2.17 (s, 3H), 1.79 (t, J=11.5 Hz, 3H), 1.56-1.50 (m, 2H).

Example 53: 3-(3-chloro-4-(4-((3-(trifluoromethyl)phen oxy)methyl)piperidin-1-yl)phenyl)-2,6-dimethylpyrimidin-4(3H)-one

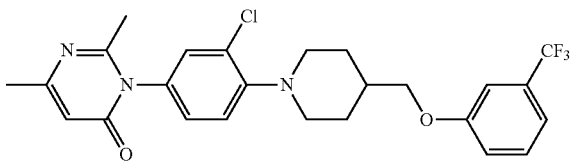 [SMILES: Cc1cc(=O)n(-c2ccc(N3CCC(COc4cccc(C(F)(F)F)c4)CC3)c(Cl)c2)c(C)n1]

Step 1: 1-(2-chloro-4-nitrophenyl)-4-((3-(trifluoromethyl)phenoxy)methyl)piperidine The title compound was prepared by the procedure described in step 3 of Example 28 using (1-(2-chloro-4-nitrophenyl)piperidin-4-yl)methyl 4-methylbenzenesulfonate (1.62 g, 3.81 mmol), 3-(trifluoromethyl)phenol (0.74 g, 4.58 mmol) and cesium carbonate (2.48 g, 7.63 mmol) to give the title compound as yellow oil (1.32 g, 83.5%). The compound was characterized by the following spectroscopic data:
MS (ESI, pos. ion) m/z: 415.1 (M+1); exact mass of C₁₉H₁₈ClF₃N₂O₃: 414.10.

Step 2: 3-chloro-4-(4-((3-(trifluoromethyl)phenoxy)methyl)piperidin-1-yl)aniline A solution of 1-(2-chloro-4-nitrophenyl)-4-((3-(trifluoromethyl)phenoxy)methyl)piperidine (1.32 g, 3.18 mmol) in a mixture of THF and MeOH (v/v=10 mL/10 mL) was added in activated iron power (1.78 g, 31.80 mmol). The title compound was prepared by the procedure described in step 6 of Example 3 to give the title compound as yellow oil (1.22 g, 99.6%). The compound was characterized by the following spectroscopic data:
MS (ESI, pos. ion) m/z: 385.1 (M+1); exact mass of C₁₉H₂₀ClF₃N₂O: 384.12.

Step 3: 3-(3-chloro-4-(4-((3-(trifluoromethyl)phen oxy)methyl)piperidin-1-yl)phenyl)-2,6-dimethylpyrimidin-4(3H)-one The title compound was prepared by the procedure described in step 3 of Example 2 starting with 3-chloro-4-(4-((3-(trifluoromethyl)phenoxy)methyl)piperidin-1-yl)aniline (1.22 g, 3.17 mmol), trimethylaluminium (4.75 mL, 9.50 mmol, 2.0 mol/L in toluene) and a solution of methyl 3-acetamidobut-2-enoate (0.74 g, 4.76 mmol) in toluene (10 mL) under N₂ to give the title compound as a light yellow solid (0.99 g, 63.5%). The compound was characterized by the following spectroscopic data:
MS (ESI, pos. ion) m/z: 492.1 (M+1); exact mass of C₂₅H₂₅ClF₃N₃O₂: 491.16; and
¹H NMR (400 MHz, CDCl₃) δ 7.40 (t, J=8.0 Hz, 1H), 7.24-7.18 (m, 2H), 7.16 (d, J=8.6 Hz, 2H), 7.12-7.02 (m, 2H), 6.28 (s, 1H), 3.92 (d, J=4.3 Hz, 2H), 3.52 (dd, J=35.4, 11.4 Hz, 2H), 2.85-2.67 (m, 2H), 2.29 (s, 3H), 2.19 (s, 3H), 2.00 (dd, J=22.2, 10.8 Hz, 3H), 1.65 (d, J=9.0 Hz, 2H).

Example 54: 3-(3-chloro-4-(4-((6-fluoroquinolin-8-yl)methyl)piperidin-1-yl)phenyl)-2,6-dimethylpyrimidin-4(3H)-one

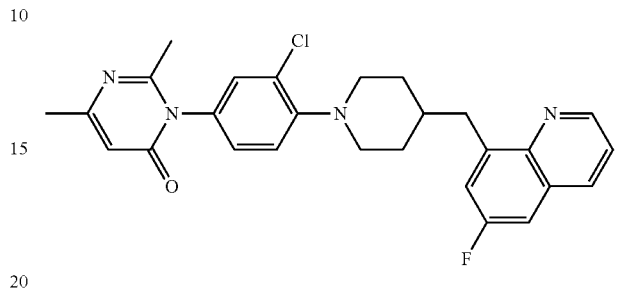

Step 1: 8-bromo-6-fluoroquinoline

To a mixture of 2-bromo-4-fluoroaniline (7.00 g, 36.84 mmol), glycerinum (7.00 g, 76.00 mmol) and sodium 3-nitrobenzenesulfonate (12.44 g, 55.30 mmol) was added 70% sulfuric acid (26 mL) slowly. After addition, the reaction mixture was heated to 150° C. for 20 hours. Then the reaction mixture was cooled to rt, and poured into water, and then adjusted to pH 7 with aqueous sodium hydroxide solution. The resulting mixture was filtered and the filter cake was dissolved in EtOAc. The mixture was stirred at rt for a while and filtered. The filtrate was concentrated in vacuo. The crude was purified by silica column chromatography (PE/EtOAc (v/v)=15/1) to give the title compound as a white solid (8.08 g, 97.0%). The compound was characterized by the following spectroscopic data:
MS (ESI, pos. ion) m/z: 226.0 (M+1), 228.0 (M+3); exact mass of C₉H₅BrFN: 224.96.

Step 2: tert-butyl 4-((6-fluoroquinolin-8-yl)methyl)piperidine-1-carboxylate The title compound was prepared by the procedure described in step 1 of Example 15 using tert-butyl 4-methylenepiperidine-1-carboxylate (2.17 g, 11.00 mmol), 9-borabicyclo[3,3,1]nonane (22 mL, 11.00 mmol, 0.5 mol/L in THF), 8-bromo-6-fluoroquinoline (2.26 g, 10.00 mmol), Pd(dppf)Cl₂ (220 mg, 0.30 mmol) and potassium carbonate (1.80 g, 13.00 mmol) to give the title compound as yellow oil (1.47 g, 42.7%). The compound was characterized by the following spectroscopic data:
MS (ESI, pos. ion) m/z: 345.3 (M+1); exact mass of C₂₀H₂₅FN₂O₂: 344.19.

Step 3: 6-fluoro-8-(piperidin-4-ylmethyl)quinoline hydrochloride

The title compound was prepared by the procedure described in step 4 of Example 3 except using tert-butyl 4-((6-fluoroquinolin-8-yl)methyl)piperidine-1-carboxylate (1.47 g, 4.27 mmol) and a solution of HCl in EtOAc (5.2 mol/L, 5 mL, 26.00 mmol) to give the crude product which was used directly for the next step without further purification.

Step 4: 8-((1-(2-chloro-4-nitrophenyl)piperidin-4-yl)methyl)-6-fluoroquinoline

The title compound was prepared by the procedure described in step 5 of Example 4 using 2-chloro-1-fluoro-4-nitrobenzene (625 mg, 3.56 mmol), 6-fluoro-8-(piperidin-4-ylmethyl)quinoline hydrochloride (1.20 g, 4.27 mmol) and TEA (1.08 g, 10.68 mmol) to give the title compound as a yellow solid (1.09 g, 76.3%).

Step 5: 3-chloro-4-(4-((6-fluoroquinolin-8-yl)methyl)piperidin-1-yl)aniline

A solution of 8-((1-(2-chloro-4-nitrophenyl)piperidin-4-yl)methyl)-6-fluoroquinoline (1.09 g, 2.73 mmol) in a mixture of THF and H₂O (20 mL/20 mL) was added in activated iron power (1.52 g, 27.30 mmol). The title compound was prepared by the procedure described in step 6 of Example 3 to give a yellow solid (619 mg, 61.4%).

Step 6: 3-(3-chloro-4-(4-((6-fluoroquinolin-8-yl)methyl)piperidin-1-yl)phenyl)-2,6-dimethylpyrimidin-4(3H)-one The title compound was prepared by the procedure described in step 3 of Example 2 starting with 3-chloro-4-(4-((6-fluoroquinolin-8-yl)methyl)piperidin-1-yl)aniline (619 mg, 1.67 mmol), trimethylaluminium (3.4 mL, 6.80 mmol, 2.0 mol/L in toluene) and a solution of methyl 3-acetamidobut-2-enoate (395 mg, 2.51 mmol) in toluene (3 mL) under N₂ to give the title compound as a white solid (366 mg, 45.8%). The compound was characterized by the following spectroscopic data:

MS (ESI, pos. ion) m/z: 477.1 (M+1); exact mass of $C_{27}H_{26}ClFN_4O$: 476.18; and $^1$H NMR (400 MHz, CDCl₃) δ 8.90 (dd, J=4.1, 1.7 Hz, 1H), 8.09 (dd, J=8.3, 1.7 Hz, 1H), 7.42 (dd, J=8.3, 4.1 Hz, 1H), 7.32 (tt, J=14.0, 4.1 Hz, 2H), 7.19 (d, J=2.4 Hz, 1H), 7.10 (d, J=8.5 Hz, 1H), 7.01 (dd, J=8.5, 2.4 Hz, 1H), 6.27 (s, 1H), 3.43 (dd, J=36.9, 11.5 Hz, 2H), 3.27 (t, J=10.3 Hz, 2H), 2.63 (dtd, J=25.6, 11.4, 2.1 Hz, 2H), 2.28 (s, 3H), 2.17 (s, 3H), 1.83-1.55 (m, 5H).

Example 55: 3-(3-chloro-4-(4-((5-fluoroquinolin-8-yl)methyl)piperidin-1-yl)phenyl)-2,6-dimethylpyrimidin-4(3H)-one

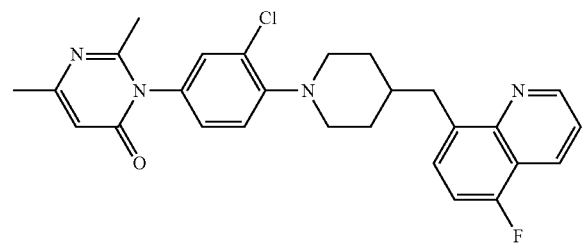

Step 1: 8-bromo-5-fluoroquinoline

The title compound was prepared by the procedure described in step 1 of Example 54 using 2-bromo-5-fluoroaniline (7.00 g, 36.84 mmol), glycerinum (7.00 g, 76.00 mmol), sodium 3-nitrobenzenesulfonate (12.44 g, 55.30 mmol) and 70% sulfuric acid (26 mL) to give the title compound as a white solid (6.52 g, 78.3%). The compound was characterized by the following spectroscopic data:

MS (ESI, pos. ion) m/z: 226.0 (M+1), 228.0 (M+3); exact mass of $C_9H_5BrFN$: 224.96.

Step 2: tert-butyl 4-((5-fluoroquinolin-8-yl)methyl)piperidine-1-carboxylate

The title compound was prepared by the procedure described in step 1 of Example 15 using tert-butyl 4-methylenepiperidine-1-carboxylate (2.17 g, 11.00 mmol), 9-borabicyclo[3,3,1]nonane (22 mL, 11.00 mmol, 0.5 mol/L in THF), 8-bromo-5-fluoroquinoline (2.26 g, 10.00 mmol), Pd(dppf)Cl₂ (220 mg, 0.30 mmol) and potassium carbonate (1.80 g, 13.00 mmol) to give the title compound as yellow oil (1.40 g, 40.7%). The compound was characterized by the following spectroscopic data:

MS (ESI, pos. ion) m/z: 345.2 (M+1); exact mass of $C_{20}H_{25}FN_2O_2$: 344.19.

Step 3: 5-fluoro-8-(piperidin-4-ylmethyl)quinoline hydrochloride

The title compound was prepared by the procedure described in step 4 of Example 3 using tert-butyl 4-((5-fluoroquinolin-8-yl)methyl)piperidine-1-carboxylate (1.40 g, 4.06 mmol) and a solution of HCl in EtOAc (5.2 mol/L, 5 mL, 26.00 mmol) to give the crude product which was used directly for the next step without purification.

Step 4: 8-((1-(2-chloro-4-nitrophenyl)piperidin-4-yl)methyl)-5-fluoroquinoline

The title compound was prepared by the procedure described in step 5 of Example 4 using 2-chloro-1-fluoro-4-nitrobenzene (594 mg, 3.38 mmol), 5-fluoro-8-(piperidin-4-ylmethyl)quinoline hydrochloride (1.14 g, 4.06 mmol) and TEA (1.03 g, 10.15 mmol) to give the title compound as a yellow solid (1.09 g, 80.2%).

Step 5: 3-chloro-4-(4-((5-fluoroquinolin-8-yl)methyl)piperidin-1-yl)aniline

A solution of 8-((1-(2-chloro-4-nitrophenyl)piperidin-4-yl)methyl)-5-fluoroquinoline (1.09 g, 2.73 mmol) in a mixture of THF and MeOH (v/v=20 mL/20 mL) was added in activated iron power (1.52 g, 27.30 mmol). The title compound was prepared by the procedure described in step 6 of Example 4 to give a yellow solid (472 mg, 46.8%). The compound was characterized by the following spectroscopic data:

MS (ESI, pos. ion) m/z: 370.2 (M+1); exact mass of $C_{21}H_{21}ClFN_3$: 369.14.

Step 6: 3-(3-chloro-4-(4-((5-fluoroquinolin-8-yl)methyl)piperidin-1-yl)phenyl)-2,6-dimethylpyrimidin-4(3H)— one The title compound was prepared by the procedure described in step 3 of Example 2 except starting with 3-chloro-4-(4-((5-fluoroquinolin-8-yl)methyl)piperidin-1-yl)aniline (472 mg, 1.28 mmol), trimethylaluminium (2.6 mL, 5.20 mmol, 2.0 mol/L in toluene) and a solution of methyl 3-acetamidobut-2-enoate (301 mg, 1.91 mmol) in toluene (3 mL) under N₂ to give the crude product as a yellow solid which was purified by prepared HPLC to give the title compound as a white solid (255 mg, 41.9%). The compound was characterized by the following spectroscopic data:

MS (ESI, pos. ion) m/z: 477.1 (M+1); exact mass of $C_{27}H_{26}ClFN_4O$: 476.18; and $^1$H NMR (400 MHz, CDCl$_3$) δ 8.99 (dd, J=4.2, 1.8 Hz, 1H), 8.44 (dd, J=8.4, 1.8 Hz, 1H), 7.50-7.42 (m, 2H), 7.21-7.11 (m, 2H), 7.09 (d, J=8.5 Hz, 1H), 7.00 (dd, J=8.5, 2.4 Hz, 1H), 6.27 (s, 1H), 3.42 (dd, J=35.7, 11.4 Hz, 2H), 3.25-3.19 (m, 2H), 2.71-2.50 (m, 2H), 2.28 (s, 3H), 2.17 (s, 3H), 1.99 (ddd, J=15.1, 7.6, 3.8 Hz, 1H), 1.82-1.51 (m, 4H).

Example 56: 3-(3-chloro-4-(4-((5-(trifluoromethyl) quinolin-8-yl)methyl)piperidin-1-yl)phenyl)-2,6-dimethylpyrimidin-4(3H)-one

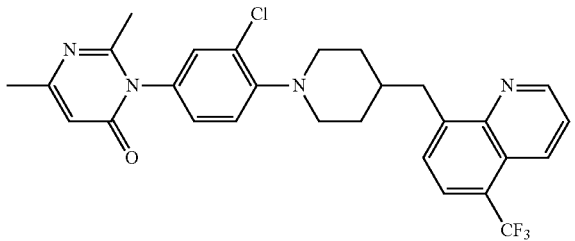 [SMILES: Cc1cc(=O)n(-c2ccc(N3CCC(Cc4ccc(C(F)(F)F)c5cccnc45)CC3)c(Cl)c2)c(C)n1]

Step 1: tert-butyl 4-((5-(trifluoromethyl)quinolin-8-yl)methyl)piperidine-1-carboxylate The title compound was prepared by the procedure described in step 1 of Example 15 using tert-butyl 4-methylenepiperidine-1-carboxylate (1.72 g, 8.69 mmol), 9-borabicyclo[3,3,1]nonane (17.4 mL, 8.70 mmol, 0.5 mol/L in THF), 8-bromo-5-(trifluoromethyl)quinoline (2.00 g, 7.24 mmol), Pd(dppf)Cl$_2$ (265 mg, 0.36 mmol) and aqueous sodium hydroxide solution (3 mol/L, 7.3 mL, 21.90 mmol) to give the title compound as a white solid (820 mg, 28.7%). The compound was characterized by the following spectroscopic data:

MS (ESI, pos. ion) m/z: 395.1 (M+1); exact mass of $C_{21}H_{25}F_3N_2O_2$: 394.19.

Step 2: 8-(piperidin-4-ylmethyl)-5-(trifluoromethyl) quinoline hydrochloride

The title compound was prepared by the procedure described in step 4 of Example 3 using tert-butyl 4-((5-(trifluoromethyl)quinolin-8-yl)methyl)piperidine-1-carboxylate (4.46 g, 11.31 mmol) and a solution of HCl in EtOAc (5.16 mol/L, 8.8 mL, 45.41 mmol) to give the title compound as a white solid (3.76 g, 100.5%).

Step 3: 8-((1-(2-chloro-4-nitrophenyl)piperidin-4-yl) methyl)-5-(trifluoromethyl)quinoline The title compound was prepared by the procedure described in step 3 of Example 15 using 2-chloro-1-fluoro-4-nitrobenzene (2.39 g, 13.64 mmol), 8-(piperidin-4-ylmethyl)-5-(trifluoromethyl)quinoline hydrochloride (3.76 g, 11.37 mmol) and TEA (3.45 g, 34.10 mmol) to give the title compound as yellow oil (2.60 g, 50.8%). The compound was characterized by the following spectroscopic data:

MS (ESI, pos. ion) m/z: 450.1 (M+1); exact mass of $C_{22}H_{19}ClF_3N_3O_2$: 449.11.

Step 4: 3-chloro-4-(4-((5-(trifluoromethyl)quinolin-8-yl)methyl)piperidin-1-yl)aniline The title compound was prepared by the procedure described in step 4 of Example 30 using ammonium chloride (464 mg, 8.67 mmol), a solution of 8-((1-(2-chloro-4-nitrophenyl)piperidin-4-yl)methyl)-5-(trifluoromethyl)quinoline (2.60 g, 5.78 mmol) in EtOH (50 mL) and iron powder (2.10 g, 37.57 mmol) to give the title compound as a yellow solid (2.10 g, 86.5%).

Step 5: 3-(3-chloro-4-(4-((5-(trifluoromethyl)quinolin-8-yl)methyl)piperidin-1-yl)phenyl)-2,6-dimethylpyrimidin-4(3H)-one The title compound was prepared by the procedure described in step 3 of Example 2 starting with 3-chloro-4-(4-((5-(trifluoromethyl)quinolin-8-yl)methyl)piperidin-1-yl)aniline (2.10 g, 5.00 mmol), trimethylaluminium (10.0 mL, 20.00 mmol, 2.0 mol/L in toluene) and a solution of methyl 3-acetamidobut-2-enoate (1.10 g, 7.00 mmol) in toluene (5 mL) under N$_2$ to give the title compound as a yellow solid (747 mg, 28.3%). The compound was characterized by the following spectroscopic data:

MS (ESI, pos. ion) m/z: 527.1 (M+1); exact mass of $C_{28}H_{26}ClF_3N_4O$: 526.17; and $^1$H NMR (400 MHz, CDCl$_3$) δ 8.99 (dd, J=4.1, 1.6 Hz, 1H), 8.50-8.39 (m, 1H), 7.81 (d, J=7.5 Hz, 1H), 7.54 (d, J=7.4 Hz, 1H), 7.49 (dd, J=8.7, 4.1 Hz, 1H), 7.17 (d, J=2.4 Hz, 1H), 7.05 (d, J=8.6 Hz, 1H), 6.98 (dd, J=8.5, 2.4 Hz, 1H), 6.23 (s, 1H), 3.38 (dd, J=30.0, 12.3 Hz, 2H), 3.28 (d, J=7.0 Hz, 2H), 2.58 (dt, J=23.3, 10.5 Hz, 2H), 2.24 (s, 3H), 2.14 (s, 3H), 1.78-1.50 (m, 5H).

Example 57: 3-(3-chloro-4-(4-((5,6-difluoroquinolin-8-yl)methyl)piperidin-1-yl)phenyl)-2,6-dimethylpyrimidin-4(3H)-one

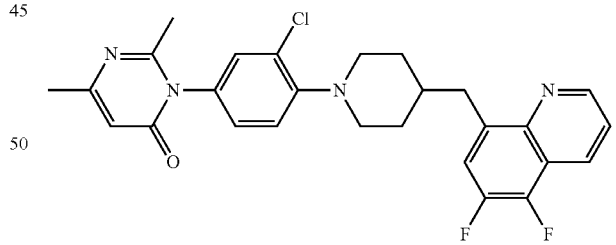

Step 1: tert-butyl 4-((5,6-difluoroquinolin-8-yl) methyl)piperidine-1-carboxylate The title compound was prepared by the procedure described in step 1 of Example 15 using tert-butyl 4-methylenepiperidine-1-carboxylate (2.91 g, 14.75 mmol), 9-borabicyclo[3,3,1]nonane (29.5 mL, 14.75 mmol, 0.5 mol/L in THF), 8-bromo-5,6-difluoroquinoline (3.00 g, 12.29 mmol), Pd(dppf)Cl$_2$ (449 mg, 0.61 mmol) and aqueous sodium hydroxide solution (3 mol/L, 12.3 mL, 36.90 mmol) to give the title compound as a white solid (2.20 g, 49.4%).

Step 2:
5,6-difluoro-8-(piperidin-4-ylmethyl)quinoline hydrochloride

The title compound was prepared by the procedure described in step 2 of Example 15 using tert-butyl 4-((5,6-difluoroquinolin-8-yl)methyl)piperidine-1-carboxylate (2.20 g, 6.07 mmol) and a solution of HCl in EtOAc (5.16 mol/L, 4.5 mL, 23.20 mmol) as starting materials to give the title compound as a white solid (1.60 g, 88.2%).

Step 3: 8-((1-(2-chloro-4-nitrophenyl)piperidin-4-yl)methyl)-5,6-difluoroquinoline The title compound was prepared by the procedure described in step 3 of Example 15 using 2-chloro-1-fluoro-4-nitrobenzene (1.13 g, 6.43 mmol), 5,6-difluoro-8-(piperidin-4-ylmethyl)quinoline hydrochloride (1.60 g, 5.36 mmol) and TEA (1.63 g, 16.07 mmol) to give the title compound as yellow oil (1.10 g, 59.2%).

MS (ESI, pos. ion) m/z: 418.0 (M+1); exact mass of $C_{21}H_{18}ClF_2N_3O_2$: 417.11.

Step 4: 3-chloro-4-(4-((5,6-difluoroquinolin-8-yl)methyl)piperidin-1-yl)aniline

The title compound was prepared by the procedure described in step 4 of Example 30 using ammonium chloride (210 mg, 3.95 mmol), a solution of 8-((1-(2-chloro-4-nitrophenyl)piperidin-4-yl)methyl)-5,6-difluoroquinoline (1.10 g, 2.63 mmol) in EtOH (32 mL) and iron powder (956 mg, 17.11 mmol) to give the title compound as a light yellow solid (980 mg, 96.0%).

Step 5: 3-(3-chloro-4-(4-((5,6-difluoroquinolin-8-yl)methyl)piperidin-1-yl)phenyl)-2,6-dimethylpyrimidin-4(3H)-one The title compound was prepared by the procedure described in step 3 of Example 2 starting with 3-chloro-4-(4-((5,6-difluoroquinolin-8-yl)methyl)piperidin-1-yl)aniline (980 mg, 2.53 mmol), trimethylaluminium (5.1 mL, 10.2 mmol, 2.0 mol/L in toluene) and a solution of methyl 3-acetamidobut-2-enoate (596 mg, 3.79 mmol) in toluene (5 mL) under $N_2$ to give the title compound as a light yellow solid (248 mg, 19.8%). The compound was characterized by the following spectroscopic data:

MS (ESI, pos. ion) m/z: 495.3 (M+1); exact mass of $C_{27}H_{25}ClF_2N_4O$: 494.17; and $^1$H NMR (400 MHz, CDCl$_3$) δ 8.91 (dd, J=4.1, 1.6 Hz, 1H), 8.38 (dd, J=8.5, 1.7 Hz, 1H), 7.46 (dd, J=8.4, 4.1 Hz, 1H), 7.38 (dd, J=11.1, 8.4 Hz, 1H), 7.17 (d, J=2.4 Hz, 1H), 7.07 (d, J=8.6 Hz, 1H), 6.99 (dd, J=8.5, 2.4 Hz, 1H), 6.24 (s, 1H), 3.39 (dd, J=32.4, 11.5 Hz, 2H), 3.20 (d, J=7.2 Hz, 2H), 2.59 (dtd, J=44.3, 11.5, 2.0 Hz, 2H), 2.25 (s, 3H), 2.15 (s, 3H), 1.98-1.88 (m, 1H), 1.73 (t, J=11.4 Hz, 2H), 1.64-1.50 (m, 2H).

Example 58: 3-(3-chloro-4-(4-((4-fluoronaphthalen-1-yl)methyl)piperidin-1-yl)phenyl)-2,6-dimethylpyrimidin-4(3H)-one

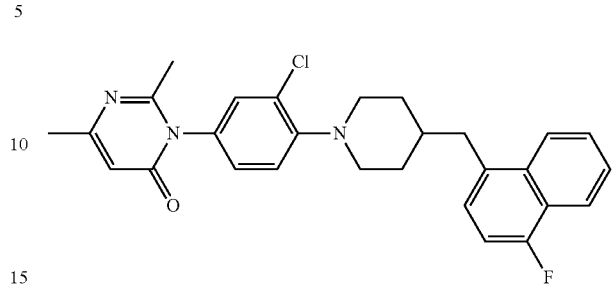

Step 1: tert-butyl 4-((4-fluoronaphthalen-1-yl)methyl)piperidine-1-carboxylate

The title compound was prepared by the procedure described in step 1 of Example 15 using tert-butyl 4-methylenepiperidine-1-carboxylate (3.24 g, 16.42 mmol), 9-borabicyclo[3,3,1]nonane (32.8 mL, 16.40 mmol, 0.5 mol/L in THF), 1-bromo-4-fluoronaphthalene (3.36 g, 14.93 mmol), Pd(dppf)Cl$_2$ (546 mg, 0.75 mmol) and aqueous sodium hydroxide solution (3 mol/L, 14.9 mL, 44.8 mmol) to give the title compound as a white solid (5.08 g, 99.1%). The compound was characterized by the following spectroscopic data:

MS (ESI, pos. ion) m/z: 288.0 (M+1-t-Bu); exact mass of $C_{21}H_{26}FNO_2$: 343.19.

Step 2: 4-((4-fluoronaphthalen-1-yl)methyl)piperidine hydrochloride

The title compound was prepared by the procedure described in step 2 of Example 15 using tert-butyl 4-((4-fluoronaphthalen-1-yl)methyl)piperidine-1-carboxylate (5.08 g, 14.79 mmol) and a solution of HCl in EtOAc (5.16 mol/L, 11.5 mL, 59.2 mmol) to give the title compound as a white solid (4.03 g, 97.4%).

Step 3: 1-(2-chloro-4-nitrophenyl)-4-((4-fluoronaphthalen-1-yl)methyl)piperidine The title compound was prepared by the procedure described in step 5 of Example 3 using 2-chloro-1-fluoro-4-nitrobenzene (2.60 g, 14.83 mmol), 4-((4-fluoronaphthalen-1-yl)methyl)piperidine hydrochloride (4.15 g, 14.83 mmol) and potassium carbonate (6.15 g, 44.50 mmol) to give the title compound as yellow oil (2.08 g, 35.2%).

Step 4: 3-chloro-4-(4-((4-fluoronaphthalen-1-yl)methyl)piperidin-1-yl)aniline

The title compound was prepared by the procedure described in step 4 of Example 30 using ammonium chloride (418 mg, 7.82 mmol), a solution of 1-(2-chloro-4-nitrophenyl)-4-((4-fluoronaphthalen-1-yl)methyl)piperidine (2.08 g, 5.21 mmol) in EtOH (32 mL) and iron powder (1.89 g, 33.90 mmol) to give the title compound as a light yellow solid (1.92 g, 99.8%). The compound was characterized by the following MS (ESI, pos. ion) m/z: 369.1 (M+1); exact mass of C$_{22}$H$_{22}$ClFN$_2$: 368.15.

Step 5: 3-(3-chloro-4-(4-((4-fluoronaphthalen-1-yl)methyl)piperidin-1-yl)phenyl)-2,6-dimethylpyrimidin-4(3H)-on The title compound was prepared by the procedure described in step 3 of Example 2 starting with 3-chloro-4-(4-((4-fluoronaphthalen-1-yl)methyl)piperidin-1-yl)aniline (1.92 g, 5.21 mmol), trimethylaluminium (10.4 mL, 20.8 mmol, 2.0 mol/L in toluene) and a solution of methyl 3-acetamidobut-2-enoate (900 mg, 5.73 mmol) in toluene (5 mL) under N$_2$ to give the title compound as a light yellow solid (1.42 g, 57.3%). The compound was characterized by the following spectroscopic data:

MS (ESI, pos. ion) m/z: 476.3 (M+1); exact mass of C$_{28}$H$_{27}$ClFN$_3$O: 475.18; and
$^1$H NMR (400 MHz, CDCl$_3$) δ 8.14 (d, J=7.8 Hz, 1H), 8.02 (d, J=8.0 Hz, 1H), 7.63-7.49 (m, 2H), 7.22 (dt, J=8.0, 4.1 Hz, 2H), 7.16-7.00 (m, 3H), 6.35 (s, 1H), 3.45 (t, J=11.0 Hz, 2H), 3.02 (d, J=6.9 Hz, 2H), 2.71-2.54 (m, 2H), 2.16 (s, 3H), 2.04 (s, 3H), 1.85 (ddd, J=13.6, 6.9, 3.1 Hz, 1H), 1.79 (d, J=13.6 Hz, 2H), 1.62 (t, J=12.0 Hz, 2H).

Example 59: 3-(6-(4-(3-fluorobenzyl)piperidin-1-yl)pyridin-3-yl)-2,6-dimethylpyrimidin-4(3H)-one

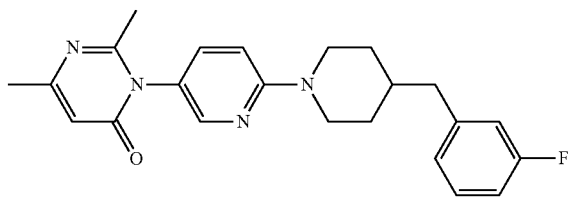 [SMILES: Cc1cc(=O)n(-c2ccc(N3CCC(Cc4cccc(F)c4)CC3)nc2)c(C)n1]

Step 1: 2-(4-(3-fluorobenzyl)piperidin-1-yl)-5-nitropyridine

The title compound was prepared by the procedure described in step 5 of Example 3 using 2-chloro-5-nitropyridine (1.59 g, 10.00 mmol), 4-(3-fluorobenzyl)piperidine hydrochloride (2.76 g, 12.00 mmol) and potassium carbonate (6.91 g, 50.00 mmol) to give the title compound as a yellow solid (3.13 g, 99.3%). The compound was characterized by the following spectroscopic data:

MS (ESI, pos. ion) m/z: 316.2 (M+1); exact mass of C$_{17}$H$_{18}$FN$_3$O$_2$: 315.14.

Step 2: 6-(4-(3-fluorobenzyl)piperidin-1-yl)pyridin-3-amine

A solution of 2-(4-(3-fluorobenzyl)piperidin-1-yl)-5-nitropyridine (3.13 g, 9.93 mmol) in a mixture of THF and MeOH (v/v=30 mL/30 mL) was added in activated iron power (5.54 g, 99.3 mmol). The title compound was prepared by the procedure described in step 6 of Example 3 to give the title compound as red oil (2.13 g, 75.2%). The compound was characterized by the following spectroscopic data:

MS (ESI, pos. ion) m/z: 286.1 (M+1); exact mass of C$_{17}$H$_{20}$FN$_3$: 285.16.

Step 3: 3-(6-(4-(3-fluorobenzyl)piperidin-1-yl)pyridin-3-yl)-2,6-dimethylpyrimidin-4(3H)-one The title compound was prepared by the procedure described in step 3 of Example 2 starting with 6-(4-(3-fluorobenzyl)piperidin-1-yl)pyridin-3-amine (1.00 g, 3.50 mmol), trimethylaluminium (7.0 mL, 14.00 mmol, 2.0 mol/L in toluene) and a solution of methyl 3-acetamidobut-2-enoate (826 mg, 5.26 mmol) in toluene (5 mL) under N$_2$ to give the title compound as a brown solid (320 mg, 23.3%). The compound was characterized by the following spectroscopic data:

MS (ESI, pos. ion) m/z: 393.2 ((M+1); exact mass of C$_{23}$H$_{25}$FN$_4$O: 392.20; and
$^1$H NMR (400 MHz, CDCl$_3$) δ 7.96 (d, J=2.6 Hz, 1H), 7.27 (dd, J=7.9, 3.2 Hz, 2H), 6.99-6.84 (m, 3H), 6.74 (d, J=9.1 Hz, 1H), 6.30 (s, 1H), 4.36 (dd, J=12.2, 10.6 Hz, 2H), 2.86 (q, J=13.7 Hz, 2H), 2.59 (d, J=7.0 Hz, 2H), 2.31 (s, 3H), 2.23 (s, 3H), 1.77 (d, J=12.4 Hz, 3H), 1.31 (dd, J=12.0, 3.6 Hz, 2H).

Example 60: 3-(5-(4-(3-fluorobenzyl)piperidin-1-yl)pyridin-2-yl)-2,6-dimethylpyrimidin-4(3H)-one

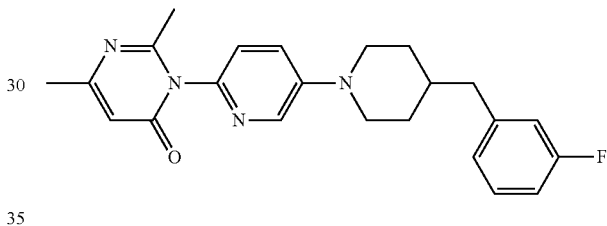

Step 1: 5-(4-(3-fluorobenzyl)piperidin-1-yl)-2-nitropyridine

The title compound was prepared by the procedure described in step 5 of Example 3 using 5-fluoro-2-nitropyridine (1.55 g, 10.92 mmol), 4-(3-fluorobenzyl)piperidine hydrochloride (2.76 g, 12.01 mmol) and potassium carbonate (4.54 g, 32.85 mmol) to give the title compound as yellow oil (2.17 g, 63.0%). The compound was characterized by the following spectroscopic data:

MS (ESI, pos. ion) m/z: 316.2 ((M+1); exact mass of C$_{17}$H$_{18}$FN$_3$O$_2$:315.14.

Step 2: 5-(4-(3-fluorobenzyl)piperidin-1-yl)pyridin-2-amine

A solution of 5-(4-(3-fluorobenzyl)piperidin-1-yl)-2-nitropyridine (2.17 g, 6.88 mmol) in a mixture of THF and MeOH (v/v=50 mL/50 mL) was added in activated iron power (3.84 g, 68.81 mmol). The title compound was prepared by the procedure described in step 6 of Example 3 to give a light yellow solid (1.13 g, 57.6%). The compound was characterized by the following spectroscopic data:

MS (ESI, pos. ion) m/z: 286.2 (M+1); C$_{17}$H$_{20}$FN$_3$: 285.16.

Step 3: N-(5-(4-(3-fluorobenzyl)piperidin-1-yl)pyridin-2-yl)-3-oxobutanamide

The title compound was prepared by the procedure described in step 5 of Example 1 using 5-(4-(3-fluorobenzyl)

piperidin-1-yl)pyridin-2-amine (1.13 g, 3.96 mmol) and 4-methyleneoxetan-2-one (666 mg, 7.92 mmol) to give the title compound as a light yellow solid (1.07 g, 73.1%). The compound was characterized by the following spectroscopic data:

MS (ESI, pos. ion) m/z: 370.2 (M+1); exact mass of $C_{21}H_{24}FN_3O_2$: 369.19.

Step 4: (Z)-3-amino-N-(5-(4-(3-fluorobenzyl)piperidin-1-yl)pyridin-2-yl)but-2-enamide The title compound was prepared by the procedure described in step 8 of Example 12 using N-(5-(4-(3-fluorobenzyl)piperidin-1-yl)pyridin-2-yl)-3-oxobutanamide (1.07 g, 2.90 mmol) and a solution of $NH_3$ in MeOH (7 mol/L, 5.0 mL, 35.00 mmol) to give the title compound as a light yellow solid (1.07 g, 100.3%).

Step 5: 3-(5-(4-(3-fluorobenzyl)piperidin-1-yl)pyridin-2-yl)-2,6-dimethylpyrimidin-4(3H)-one0

The title compound was prepared by the procedure described in step 7 of Example 1 using (Z)-3-amino-N-(5-(4-(3-fluorobenzyl)piperidin-1-yl)pyridin-2-yl)but-2-enamide (1.07 g, 2.90 mmol) and triethyl orthoacetate (35 mL) to give the title compound as a light yellow solid (755 mg, 66.2%). The compound was characterized by the following spectroscopic data:

MS (ESI, pos. ion) m/z: 393.1 (M+1); exact mass of $C_{23}H_{25}FN_4O$: 392.20; and $^1$H NMR (400 MHz, $CD_3OD$) δ 8.25 (d, J=3.0 Hz, 1H), 7.54 (dd, J=8.9, 3.1 Hz, 1H), 7.30 (ddd, J=10.9, 8.3, 5.6 Hz, 2H), 7.03 (d, J=7.6 Hz, 1H), 7.00-6.89 (m, 2H), 6.34 (s, 1H), 3.90 (d, J=12.7 Hz, 2H), 2.86 (t, J=12.4 Hz, 2H), 2.64 (d, J=6.9 Hz, 2H), 2.33 (s, 3H), 2.17 (s, 3H), 1.79 (d, J=11.9 Hz, 3H), 1.48-1.36 (m, 2H).

Example 61: 3-(5-chloro-6-(4-(3-fluorobenzyl)piperidin-1-yl)pyridin-3-yl)-2,6-dimethylpyrimidin-4(3H)-one

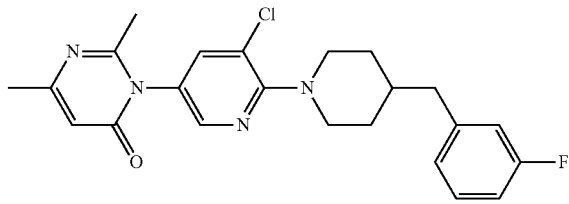 [SMILES: Cc1cc(=O)n(-c2cnc(N3CCC(Cc4cccc(F)c4)CC3)c(Cl)c2)c(C)n1]

Step 1: 3-chloro-2-(4-(3-fluorobenzyl)piperidin-1-yl)-5-nitropyridine

The title compound was prepared by the procedure described in step 5 of Example 3 using 2,3-dichloro-5-nitropyridine (3.00 g, 15.54 mmol), 4-(3-fluorobenzyl)piperidine hydrochloride (4.29 g, 18.67 mmol) and potassium bicarbonate (4.67 g, 46.64 mmol) to give the title compound as a yellow solid (6.42 g, 118.2%). The compound was characterized by the following spectroscopic data:

MS (ESI, pos. ion) m/z: 350.2 (M+1); exact mass of $C_{17}H_{17}ClFN_3O_2$: 349.10.

Step 2: 5-chloro-6-(4-(3-fluorobenzyl)piperidin-1-yl)pyridin-3-amine

A solution of 3-chloro-2-(4-(3-fluorobenzyl)piperidin-1-yl)-5-nitropyridine (6.42 g, 18.35 mmol) in a mixture of THF and MeOH (50 mL/50 mL) was added in activated iron power (10.25 g, 183.54 mmol). The title compound was prepared by the procedure described in step 4 of Example 1 to give brown oil (4.50 g, 77.5%). The compound was characterized by the following spectroscopic data:

MS (ESI, pos. ion) m/z: 320.1 (M+1); exact mass of $C_{17}H_{19}ClFN_3$: 319.13.

Step 3: 3-(5-chloro-6-(4-(3-fluorobenzyl)piperidin-1-yl)pyridin-3-yl)-2,6-dimethylpyrimidin-4(3H)-one The title compound was prepared by the procedure described in step 3 of Example 2 starting with 5-chloro-6-(4-(3-fluorobenzyl)piperidin-1-yl)pyridin-3-amine (1.00 g, 3.13 mmol), trimethylaluminium (6.5 mL, 13.00 mmol, 2.0 mol/L in toluene) and methyl 3-acetamidobut-2-enoate (983 mg, 6.25 mmol) under $N_2$ to give the title compound as a brown solid (704 mg, 52.9%). The compound was characterized by the following spectroscopic data:

MS (ESI, pos. ion) m/z: 427.1 (M+1); exact mass of $C_{23}H_{24}ClFN_4O$: 426.16; and $^1$H NMR (400 MHz, $CDCl_3$) δ 8.00 (d, J=2.4 Hz, 1H), 7.46 (d, J=2.4 Hz, 1H), 7.26 (d, J=7.4 Hz, 1H), 7.00-6.87 (m, 3H), 6.30 (s, 1H), 3.98 (d, J=4.3 Hz, 2H), 2.85 (td, J=12.7, 2.1 Hz, 2H), 2.63 (d, J=6.8 Hz, 2H), 2.32 (s, 3H), 2.24 (s, 3H), 1.79 (t, J=11.3 Hz, 3H), 1.47 (q, J=12.3 Hz, 2H).

Example 62: 3-(6-(4-(4-chloro-3-fluorobenzyl)piperidin-1-yl)pyridin-3-yl)-2,6-dimethylpyrimidin-4(3H)-one

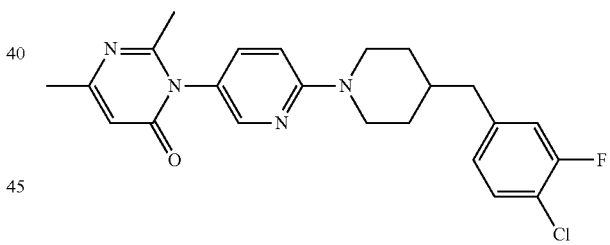

Step 1: 2-(4-(4-chloro-3-fluorobenzyl)piperidin-1-yl)-5-nitropyridine

The title compound was prepared by the procedure described in step 5 of Example 3 using 2-chloro-5-nitropyridine (703 mg, 4.43 mmol), 4-(4-chloro-3-fluorobenzyl)piperidine hydrochloride (1.30 g, 4.92 mmol) and potassium carbonate (2.45 g, 17.70 mmol) to give the title compound as a yellow solid (1.00 g, 64.5%). The compound was characterized by the following spectroscopic data:

MS (ESI, pos. ion) m/z: 350.1 (M+1); exact mass of $C_{17}H_{17}ClFN_3O_2$: 349.10.

Step 2: 6-(4-(4-chloro-3-fluorobenzyl)piperidin-1-yl)pyridin-3-amine

A solution of 2-(4-(4-chloro-3-fluorobenzyl)piperidin-1-yl)-5-nitropyridine (1.00 g, 2.86 mmol) in a mixture of THF and MeOH (v/v=20 mL/20 mL) was added in activated iron power (1.60 g, 28.6 mmol). The title compound was prepared by the procedure described in step 6 of Example 3 to give red oil (564 mg, 61.5%). The compound was characterized by the following spectroscopic data:

MS (ESI, pos. ion) m/z: 320.2 (M+1); exact mass of $C_{17}H_{19}ClFN_3$: 319.13.

Step 3: 3-(6-(4-(4-chloro-3-fluorobenzyl)piperidin-1-yl)pyridin-3-yl)-2,6-dimethylpyrimidin-4(3H)-one The title compound was prepared by the procedure described in step 3 of Example 2 starting with 6-(4-(4-chloro-3-fluorobenzyl)piperidin-1-yl)pyridin-3-amine (564 mg, 1.76 mmol), trimethylaluminium (3.5 mL, 7.00 mmol, 2.0 mol/L in toluene) and a solution of methyl 3-acetamidobut-2-enoate (417 mg, 2.65 mmol) in toluene (5 mL) under $N_2$ to give the title compound as a white solid (400 mg, 53.3%). The compound was characterized by the following spectroscopic data:

MS (ESI, pos. ion) m/z: 427.1 (M+1); exact mass of $C_{23}H_{24}ClFN_4O$: 426.16; and
$^1$H NMR (400 MHz, CDCl$_3$) δ 7.97 (d, J=2.4 Hz, 1H), 7.32 (t, J=7.9 Hz, 1H), 7.30-7.26 (m, 3H), 6.98 (dd, J=10.0, 1.9 Hz, 1H), 6.91 (dd, J=8.1, 1.5 Hz, 1H), 6.75 (d, J=9.0 Hz, 1H), 6.30 (s, 1H), 4.44-4.30 (m, 2H), 2.87 (qd, J=13.1, 2.5 Hz, 2H), 2.57 (d, J=7.0 Hz, 2H), 2.31 (s, 3H), 2.24 (s, 3H), 1.81 (ddd, J=27.3, 15.5, 8.6 Hz, 3H), 1.40-1.30 (m, 2H).

Example 63: 3-(6-(4-(3-fluorophenoxy)piperidin-1-yl)pyridin-3-yl)-2,6-dimethylpyrimidin-4(3H)-one

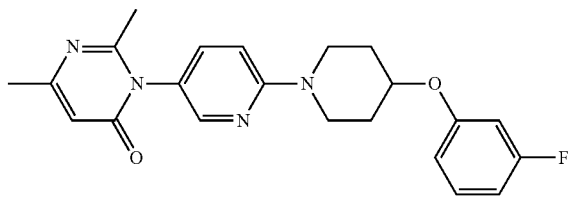 [SMILES: Cc1cc(=O)n(-c2ccc(N3CCC(Oc4cccc(F)c4)CC3)nc2)c(C)n1]

Step 1: 1-(5-nitropyridin-2-yl)piperidin-4-ol

The title compound was prepared by the procedure described in step 5 of Example 3 using 2-chloro-5-nitropyridine (3.17 g, 20.00 mmol), piperidin-4-ol (2.43 g, 24.00 mmol) and potassium bicarbonate (4.00 g, 40.00 mmol) to give the title compound as a yellow solid (4.02 g, 90.0%). The compound was characterized by the following spectroscopic data:

MS (ESI, pos. ion) m/z: 224.2 (M+1); exact mass of $C_{10}H_{13}N_3O_3$: 223.10.

Step 2: 1-(5-nitropyridin-2-yl)piperidin-4-yl 4-methylbenzenesulfonate

To a mixture of 1-(5-nitropyridin-2-yl)piperidin-4-ol (4.02 g, 18.00 mmol), 4-dimethylaminopyridine (440 mg, 3.60 mmol), TEA (5.47 g, 54.00 mmol) and DCM (50 mL) was added tosyl chloride (4.12 g, 21.60 mmol) at rt. The reaction mixture was stirred at rt for 4 hours, and to the mixture was added tosyl chloride (4.12 g, 21.60 mmol). The resulted mixture was stirred at rt for further 72 hours. After the reaction was finished, the mixture was concentrated in vacuo. The crude was purified by silica column chromatography (PE/EtOAc (v/v)=1/1) to give the title compound as a yellow solid (5.78 g, 85.0%). The compound was characterized by the following spectroscopic data:

MS (ESI, pos. ion) m/z: 378.1 (M+1); exact mass of $C_{10}H_{12}TN_3O_3S$: 257.08.

Step 3: 2-(4-(3-fluorophenoxy)piperidin-1-yl)-5-nitropyridine

The title compound was prepared by the procedure described in step 3 of Example 27 using 60% NaH (1.53 g, 38.30 mmol), 3-fluorophenol (2.06 g, 18.40 mmol) and a solution of 1-(5-nitropyridin-2-yl)piperidin-4-yl 4-methylbenzenesulfonate (5.78 g, 15.30 mmol) in 30 mL of DMF to give the title compound as brown oil (1.20 g, 24.7%).

MS (ESI, pos. ion) m/z: 318.2 (M+1); $C_{16}H_{16}FN_3O_3$: 317.12.

Step 4: 6-(4-(3-fluorophenoxy)piperidin-1-yl)pyridin-3-amine

A solution of 2-(4-(3-fluorophenoxy)piperidin-1-yl)-5-nitropyridine (1.20 g, 3.78 mmol) in a mixture of THF and MeOH (v/v=20 mL/20 mL) was added in activated iron power (2.11 g, 37.80 mmol). The title compound was prepared by the procedure described in step 6 of Example 3 to give brown oil (481 mg, 44.2%). The compound was characterized by the following spectroscopic data:

MS (ESI, pos. ion) m/z: 288.1.0 (M+1); exact mass of $C_{16}H_{18}FN_3O$: 287.14.

Step 5: 3-(6-(4-(3-fluorophenoxy)piperidin-1-yl)pyridin-3-yl)-2,6-dimethylpyrimidin-4(3H)-one The title compound was prepared by the procedure described in step 3 of Example 2 starting with 6-(4-(3-fluorophenoxy)piperidin-1-yl)pyridin-3-amine (481 mg, 1.67 mmol), trimethylaluminium (3.5 mL, 7.00 mmol, 2.0 mol/L in toluene) and a solution of methyl 3-acetamidobut-2-enoate (395 mg, 2.51 mmol) in toluene (5 mL) under $N_2$ to give the crude product as brown oil which was purified by prepared HPLC to give the title compound as a yellow solid (71 mg, 10.8%). The compound was characterized by the following spectroscopic data:

MS (ESI, pos. ion) m/z: 395.3 (M+1); exact mass of $C_{22}H_{23}FN_4O_2$: 394.18; and
$^1$H NMR (400 MHz, CDCl$_3$) δ 8.00 (d, J=2.6 Hz, 1H), 7.32 (dd, J=9.0, 2.7 Hz, 1H), 7.25 (t, J=7.6 Hz, 1H), 6.80 (d, J=9.0 Hz, 1H), 6.77-6.72 (m, 1H), 6.72-6.64 (m, 2H), 6.31 (s, 1H), 4.58 (tt, J=7.0, 3.5 Hz, 1H), 3.94 (dd, J=14.0, 7.0 Hz, 2H), 3.73-3.50 (m, 2H), 2.32 (s, 3H), 2.25 (s, 3H), 2.16-2.01 (m, 2H), 1.92 (d, J=7.5 Hz, 2H).

Example 64: 3-(5-chloro-6-(4-(3-fluorophenoxy)piperidin-1-yl)pyridin-3-yl)-2,6-dimethylpyrimidin-4(3H)-one

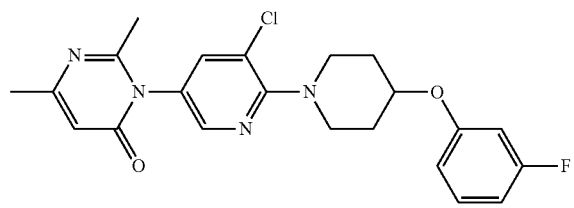 [SMILES: Cc1cc(=O)n(-c2cnc(N3CCC(Oc4cccc(F)c4)CC3)c(Cl)c2)c(C)n1]

Step 1: 1-(3-chloro-5-nitropyridin-2-yl)piperidin-4-ol

The title compound was prepared by the procedure described in step 1 of Example 28 using 2,3-dichloro-5-nitropyridine (1.93 g, 10.0 mmol), piperidin-4-ol (1.11 g, 11.0 mmol) and potassium bicarbonate (2.00 g, 20.0 mmol) to give the title compound as a yellow solid (2.78 g, 108%). The compound was characterized by the following spectroscopic data:

MS (ESI, pos. ion) m/z: 258.0 (M+1); exact mass of $C_{10}H_{12}ClN_3O_3$: 257.06.

Step 2: 1-(3-chloro-5-nitropyridin-2-yl)piperidin-4-yl 4-methylbenzenesulfonate A mixture of 1-(3-chloro-5-nitropyridin-2-yl)piperidin-4-ol (2.78 g, 10.80 mmol), 4-dimethylaminopyridine (264 mg, 2.20 mmol), tosyl chloride (2.47 g, 13.00 mmol) and TEA (50 mL) was heated to 50° C. for 3.5 hours, and then to the mixture was replenished tosyl chloride (2.47 g, 13.00 mmol). The resulted mixture was stirred at 50° C. overnight under $N_2$. The reaction mixture was then cooled to rt and poured into DCM (100 mL). The mixture was stirred at rt for 2 hours, then to the mixture was added 4-dimethylaminopyridine (132 mg, 1.10 mmol). The resulted mixture was stirred for 6 hours, then to the mixture was added tosyl chloride crude (2.47 g, 13.00 mmol). The resulted mixture was stirred for 5 hours, and to the mixture was added tosyl chloride crude (2.47 g, 13.00 mmol) and 4-dimethylaminopyridine (132 mg, 1.10 mmol). The resulted mixture was stirred at rt overnight. After the reaction was finished, the reaction mixture was filtered, and the filtrate was concentrated in vacuo. The crude was purified by silica column chromatography (PE/EtOAc (v/v)=1/1) to give the title compound as a yellow solid (4.06 g, 91.3%). The compound was characterized by the following spectroscopic data:

MS (ESI, pos. ion) m/z: 412.1 (M+1); exact mass of $C_{17}H_{18}ClN_3O_5S$: 411.07.

Step 3: 3-chloro-2-(4-(3-fluorophenoxy)piperidin-1-yl)-5-nitropyridine

A mixture of 1-(3-chloro-5-nitropyridin-2-yl)piperidin-4-yl 4-methylbenzenesulfonate (4.06 g, 9.86 mmol), 3-fluorophenol (1.33 g, 11.83 mmol), potassium carbonate (2.73 g, 19.72 mmol) and DMF (60 mL) was stirred at 70° C. under $N_2$ for 24 hours. The reaction mixture was cooled to rt and stirred at rt overnight. Then the reaction mixture was stirred at 70° C. for further 24 hours, cooled to rt and filtered. The filtrate was concentrated in vacuo, and the crude was purified by silica column chromatography (PE/EtOAc (v/v)=50/1) to give the title compound as yellow oil (1.28 g, 36.9%). The compound was characterized by the following spectroscopic data:

MS (ESI, pos. ion) m/z: 352.0 (M+1); exact mass of $C_{16}H_{15}ClFN_3O_3$: 351.08.

Step 4: 5-chloro-6-(4-(3-fluorophenoxy)piperidin-1-yl)pyridin-3-amine

A solution of 3-chloro-2-(4-(3-fluorophenoxy)piperidin-1-yl)-5-nitropyridine (1.28 g, 3.63 mmol) in a mixture of THF and MeOH (v/v=20 mL/20 mL) was added in activated iron power (2.03 g, 36.30 mmol). The title compound was prepared by the procedure described in step 6 of Example 3 to give brown oil (776 mg, 66.4%). The compound was characterized by the following spectroscopic data:

MS (ESI, pos. ion) m/z: 322.0 (M+1); exact mass of $C_{16}H_{17}ClFN_3O$: 321.10.

Step 5: 3-(5-chloro-6-(4-(3-fluorophenoxy)piperidin-1-yl)pyridin-3-yl)-2,6-dimethylpyrimidin-4(3H)-one The title compound was prepared by the procedure described in step 3 of Example 2 starting with 5-chloro-6-(4-(3-fluorophenoxy)piperidin-1-yl)pyridin-3-amine (776 mg, 2.41 mmol), trimethylaluminium (5.0 mL, 10.00 mmol, 2.0 mol/L in toluene) and a solution of methyl 3-acetamidobut-2-enoate (569 mg, 3.62 mmol) in toluene (5 mL) under $N_2$ to give the title compound as yellow oil (340 mg, 33.0%). The compound was characterized by the following spectroscopic data:

MS (ESI, pos. ion) m/z: 429.1 (M+1); exact mass of $C_{22}H_{22}ClFN_4O_2$: 428.14; and $^1$H NMR (400 MHz, CDCl$_3$) δ 8.02 (d, J=2.2 Hz, 1H), 7.49 (d, J=2.2 Hz, 1H), 7.30-7.18 (m, 1H), 6.74 (d, J=8.7 Hz, 1H), 6.67 (dd, J=8.3, 5.6 Hz, 2H), 6.30 (s, 1H), 4.54 (dd, J=6.8, 3.4 Hz, 1H), 3.73 (dd, J=17.7, 13.3 Hz, 2H), 3.39 (dd, J=8.3, 4.0 Hz, 2H), 2.31 (s, 3H), 2.23 (s, 3H), 2.19-2.09 (m, 2H), 2.03-1.94 (m, 2H).

Example 65: 3-(4-(4-(benzo[d][1,3]dioxol-5-ylmethyl)piperidin-1-yl)-3-chlorophenyl)-2,6-dimethylpyrimidin-4(3H)-one

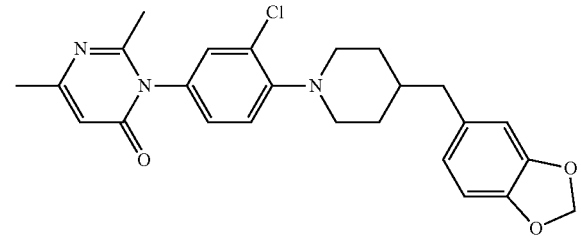 [SMILES: Cc1cc(=O)n(-c2ccc(N3CCC(Cc4ccc5c(c4)OCO5)CC3)c(Cl)c2)c(C)n1]

Step 1: tert-butyl 4-(benzo[d][1,3]dioxol-5-ylmethyl)piperidine-1-carboxylate The title compound was prepared by the procedure described in step 1 of Example 15 using tert-butyl 4-methylenepiperidine-1-carboxylate (2.37 g, 12.00 mmol), 9-borabicyclo [3,3,1]nonane (24.0 mL, 12.0 mmol, 0.5 mol/L in THF), 5-bromobenzo[d][1,3]dioxole (2.01 g, 10.00 mmol), Pd(dppf)Cl$_2$ (220 mg, 0.30 mmol) and aqueous sodium hydroxide solution (3 mol/L, 10.0 mL, 30.0 mmol) to give the title compound as a white solid (1.45 g, 45.4%).

Step 2: 4-(benzo[d][1,3]dioxol-5-ylmethyl)piperidine hydrochloride

The title compound was prepared by the procedure described in step 4 of Example 3 using tert-butyl 4-(benzo[d][1,3]dioxol-5-ylmethyl)piperidine-1-carboxylate (1.45 g, 4.54 mmol) and a solution of HCl in EtOAc (5.2 mol/L, 5.0 mL, 26.00 mmol) to give the crude product which was used directly for the next step without further purification.

Step 3: 4-(benzo[d][1,3]dioxol-5-ylmethyl)-1-(2-chloro-4-nitrophenyl)piperidine The title compound was prepared by the procedure described in step 5 of Example 3 using 2-chloro-1-fluoro-4-nitrobenzene (723 mg, 4.13 mmol), 4-(benzo[d][1,3]dioxol-5-ylmethyl)piperidine hydrochloride (1.16 g, 4.54 mmol) and potassium carbonate (1.71 g, 12.40 mmol) to give the title compound as yellow oil (1.48 g, 95.5%).

Step 4: 4-(4-(benzo[d][1,3]dioxol-5-ylmethyl)piperidin-1-yl)-3-chloroaniline A solution of 4-(benzo[d][1,3]dioxol-5-ylmethyl)-1-(2-chloro-4-nitrophenyl)piperidine (1.48 g, 3.95 mmol) in a mixture of THF and MeOH (v/v=20 mL/20 mL) was added in activated iron power (2.21 g, 39.50 mmol). The title compound was prepared by the procedure described in step 6 of Example 3 to give the crude product which was used directly for the next step without further purification.

Step 5: 3-(4-(4-(benzo[d][1,3]dioxol-5-ylmethyl)piperidin-1-yl)-3-chlorophenyl)-2,6-dimethylpyrimidin-4(3H)-one The title compound was prepared by the procedure described in step 3 of Example 2 starting with 4-(4-(benzo[d][1,3]dioxol-5-ylmethyl)piperidin-1-yl)-3-chloroaniline (1.28 g, 3.71 mmol), trimethylaluminium (7.5 mL, 15.00 mmol, 2.0 mol/L in toluene) and a solution of methyl 3-acetamidobut-2-enoate (875 mg, 5.57 mmol) in toluene (5 mL) under $N_2$ to give the title compound as a yellow solid (768 mg, 45.7%). The compound was characterized by the following spectroscopic data:

MS (ESI, pos. ion) m/z: 452.3 (M+1); exact mass of $C_{25}H_{26}ClN_3O_3$: 451.17; and $^1$H NMR (400 MHz, CDCl$_3$) δ 7.21 (d, J=2.4 Hz, 1H), 7.16-7.10 (m, 1H), 7.04 (dd, J=8.5, 2.4 Hz, 1H), 6.78-6.73 (m, 1H), 6.69 (d, J=1.5 Hz, 1H), 6.64 (dd, J=7.9, 1.6 Hz, 1H), 6.29 (s, 1H), 5.95 (s, 2H), 3.56-3.34 (m, 2H), 2.74-2.58 (m, 2H), 2.54 (dd, J=13.9, 7.0 Hz, 2H), 2.30 (d, J=0.6 Hz, 3H), 2.19 (s, 3H), 1.78 (d, J=13.5 Hz, 2H), 1.65 (dtd, J=14.6, 7.3, 3.7 Hz, 1H), 1.49 (ddt, J=13.3, 10.3, 5.3 Hz, 2H).

Example 66: 3-(4-(4-((1H-indol-1-yl)methyl)piperidin-1-yl)-3-chlorophenyl)-2,6-dimethylpyrimidin-4(3H)-one

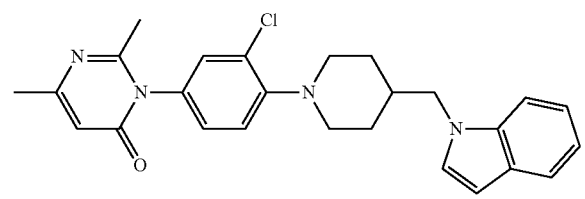 [SMILES: Cc1cc(=O)n(-c2ccc(N3CCC(Cn4ccc5ccccc54)CC3)c(Cl)c2)c(C)n1]

Step 1: 1-((1-(2-chloro-4-nitrophenyl)piperidin-4-yl)methyl)-1H-indole

To a suspension of 60% NaH (290 mg, 12.08 mmol) in anhydrous DMF (5 mL) was added a solution of 1H-indole (610 mg, 5.21 mmol) in anhydrous DMF (3 mL) dropwise at ice bath. After addition, the mixture was stirred at rt for 10 minutes and then to the mixture was added a solution of (1-(2-chloro-4-nitrophenyl)piperidin-4-yl)methyl 4-methylbenzenesulfonate (1.70 g, 4.00 mmol) and potassium iodide (865 mg, 5.21 mmol) in anhydrous DMF (10 mL) dropwise. After addition, the reaction mixture was stirred at 60° C. under $N_2$ overnight and quenched with saturated aqueous ammonia chloride solution (50 mL). The separated water phase was extracted with DCM (50 mL×2). The combined organic phases were washed with saturated brine (100 mL×2), dried over anhydrous $Na_2SO_4$ (20 g), filtered, and concentrated in vacuo. The crude was purified by silica column chromatography (PE/EtOAc (v/v)=4/1) to give the title compound as yellow oil (0.60 g, 40.0%). The compound was characterized by the following spectroscopic data:

MS (ESI, pos. ion) m/z: 370.2 (M+1); exact mass of $C_{20}H_{20}ClN_3O_2$: 369.12.

Step 2: 4-(4-((1H-indol-1-yl)methyl)piperidin-1-yl)-3-chloroaniline

A solution of 1-((1-(2-chloro-4-nitrophenyl)piperidin-4-yl)methyl)-1H-indole (0.60 g, 1.62 mmol) in a mixture of THF and MeOH (5 mL/5 mL) was added in activated iron power (0.90 g, 16.20 mmol). The title compound was prepared by the procedure described in step 6 of Example 3 to give a yellow solid (350 mg, 63.5%). The compound was characterized by the following spectroscopic data:

MS (ESI, pos. ion) m/z: 340.1 (M+1); exact mass of $C_{20}H_{22}ClN_3$: 339.15.

Step 3: 3-(4-(4-((1H-indol-1-yl)methyl)piperidin-1-yl)-3-chlorophenyl)-2,6-dimethylpyrimidin-4(3H)-one The title compound was prepared by the procedure described in step 3 of Example 2 starting with 4-(4-((1H-indol-1-yl)methyl)piperidin-1-yl)-3-chloroaniline (350 mg, 1.03 mmol), trimethylaluminium (2.06 mL, 4.12 mmol, 2.0 mol/L in toluene) and a solution of methyl 3-acetamidobut-2-enoate (195 mg, 1.24 mmol) in toluene (5 mL) under $N_2$ to give the title compound as a light yellow solid (320 mg, 70.0%). The compound was characterized by the following spectroscopic data:

MS (ESI, pos. ion) m/z: 447.1 (M+1); exact mass of $C_{26}H_{27}ClN_4O$: 446.19; and $^1$H NMR (400 MHz, CDCl$_3$) δ 7.67 (d, J=7.9 Hz, 1H), 7.40 (d, J=8.2 Hz, 1H), 7.28-7.20 (m, 2H), 7.17-7.08 (m, 3H), 7.04 (dd, J=8.5, 2.4 Hz, 1H), 6.54 (d, J=2.7 Hz, 1H), 6.30 (s, 1H), 4.13-4.05 (m, 2H), 3.46 (dd, J=32.2, 11.8 Hz, 2H), 2.73-2.55 (m, 2H), 2.31 (s, 3H), 2.20 (s, 3H), 2.12-2.00 (m, 2H), 1.73 (t, J=8.2 Hz, 2H), 1.58 (d, J=9.4 Hz, 1H).

Example 67: 3-(3-chloro-4-(2-((3-fluorophenoxy)methyl)piperidin-1-yl)phenyl)-2,6-dimethylpyrimidin-4(3H)-one

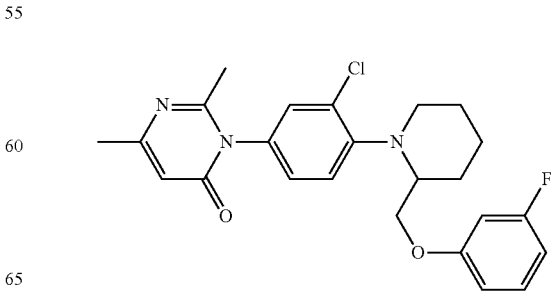

Step 1: (1-(2-chloro-4-nitrophenyl)piperidin-2-yl)methanol

A mixture of 2-chloro-1-fluoro-4-nitrobenzene (7.02 g, 40.00 mmol), piperidin-2-ylmethanol (4.61 g, 40.03 mmol) and dimethyl sulfoxide (50 mL) was stirred at 100° C. under $N_2$ for 24 hours. After the reaction was finished, the mixture was cooled to rt and poured into DCM (100 mL). The resulted mixture was washed with water (100 mL×2) and saturated brine (100 mL), dried over anhydrous $Na_2SO_4$ (20 g), filtered and concentrated in vacuo. The crude was purified by silica column chromatography (PE/EtOAc (v/v)=4/1) to give the title compound as a yellow solid (10.83 g, 50.0%). The compound was characterized by the following spectroscopic data:

MS (ESI, pos. ion) m/z: 271.1 (M+1); exact mass of $C_{12}H_{15}ClN_2O_3$: 270.08.

Step 2: (1-(2-chloro-4-nitrophenyl)piperidin-2-yl)methyl 4-methylbenzenesulfonate The title compound was prepared by the procedure described in step 2 of Example 28 using (1-(2-chloro-4-nitrophenyl)piperidin-2-yl)methanol (5.00 g, 18.47 mmol), TEA (50 mL) and tosyl chloride (5.28 g, 27.70 mmol) as starting materials to give the title compound as a yellow solid (6.72 g, 85.6%). The compound was characterized by the following spectroscopic data:

MS (ESI, pos. ion) m/z: 425.1 (M+1); exact mass of $C_{19}H_{21}ClN_2O_5S$: 424.09.

Step 3: 1-(2-chloro-4-nitrophenyl)-2-((3-fluorophenoxy)methyl)piperidine

The title compound was prepared by the procedure described in step 3 of Example 28 using 3-fluorophenol (1.74 g, 15.53 mmol), 60% NaH (932 mg, 38.83 mmol) and (1-(2-chloro-4-nitrophenyl)piperidin-2-yl)methyl 4-methylbenzenesulfonate (5.50 g, 12.94 mmol) in 10 mL of DMF to give the title compound as yellow oil (3.78 g, 80.0%). The compound was characterized by the following spectroscopic data:

MS (ESI, pos. ion) m/z: 365.1 (M+1); exact mass of $C_{18}H_{18}ClFN_2O_3$: 364.10.

Step 4: 3-chloro-4-(2-((3-fluorophenoxy)methyl)piperidin-1-yl)aniline

A solution of 1-(2-chloro-4-nitrophenyl)-2-((3-fluorophenoxy)methyl)piperidine (3.76 g, 10.31 mmol) in MeOH (50 mL) was added in activated iron power (5.76 g, 103.10 mmol) The title compound was prepared by the procedure described in step 4 of Example 1 to give yellow oil (3.41 g, 98.8%). The compound was characterized by the following spectroscopic data:

MS (ESI, pos. ion) m/z: 335.2 (M+1); exact mass of $C_{18}H_{20}ClFN_2O$: 334.12.

Step 5: N-(5-chloro-4-(2-((3-fluorophenoxy)methyl)piperidin-1-yl)cyclohexa-1,3-dien-1-yl)-3-oxobutanamide The title compound was prepared by the procedure described in step 5 of Example 1 using 3-chloro-4-(2-((3-fluorophenoxy)methyl)piperidin-1-yl)aniline (3.40 g, 10.15 mmol) and 4-methyleneoxetan-2-one (1.71 g, 20.31 mmol) to give the title compound as a yellow solid (2.84 g, 66.7%). The compound was characterized by the following spectroscopic data:

MS (ESI, pos. ion) m/z: 419.2 (M+1); exact mass of $C_{22}H_{24}ClFN_2O_3$: 418.15.

Step 6: (Z)-3-amino-N-(3-chloro-4-(2-((3-fluorophenoxy)methyl)piperidin-1-yl)phenyl)but-2-enamide The title compound was prepared by the procedure described in step 6 of Example 1 using N-(5-chloro-4-(2-((3-fluorophenoxy)methyl)piperidin-1-yl)cyclohexa-1,3-dien-1-yl)-3-oxobutanamide (2.84 g, 6.78 mmol), MeOH (10 mL) and ammonium hydroxide (10 mL) to give the crude product which was used directly for the next step without further purification.

Step 7: 3-(3-chloro-4-(2-((3-fluorophenoxy)methyl)piperidin-1-yl)phenyl)-2,6-dimethylpyrimidin-4(3H)-one The title compound was prepared by the procedure described in step 7 of Example 1 using (Z)-3-amino-N-(3-chloro-4-(2-((3-fluorophenoxy)methyl)piperidin-1-yl)phenyl)but-2-enamide (2.83 g, 6.78 mmol) and triethyl orthoacetate (10 mL) to give the title compound as a white solid (1.61 g, 53.6%). The compound was characterized by the following spectroscopic data:

MS (ESI, pos. ion) m/z: 442.2 (M+1); exact mass of $C_{24}H_{25}ClFN_3O_2$: 441.16; and $^1$H NMR (400 MHz, CDCl$_3$): δ 6.37-7.28 (7H, m), 6.27 (1H, s), 3.97-4.15 (2H, m), 3.91 (1H, m), 3.30 (1H, m), 3.01 (1H, d), 2.28 (3H, s), 2.06 (3H, s), 1.66-1.79 (6H, m).

Example 68: 3-(3-chloro-4-(3-((3-fluorophenoxy)methyl)piperidin-1-yl)phenyl)-2,6-dimethylpyrimidin-4(3H)-one

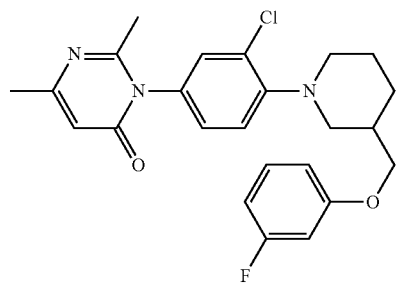 [SMILES: Cc1cc(=O)n(-c2ccc(N3CCCC(COc4cccc(F)c4)C3)c(Cl)c2)c(C)n1]

Step 1: (1-(2-chloro-4-nitrophenyl)piperidin-3-yl)methanol

The title compound was prepared by the procedure described in step 1 of Example 28 using 2-chloro-1-fluoro-4-nitrobenzene (7.62 g, 43.40 mmol) and piperidin-3-ylmethanol (5.00 g, 43.40 mmol) and TEA (13.18 g, 130.24 mmol) to give the title compound as a yellow solid (11.16 g, 95.0%). The compound was characterized by the following spectroscopic data:

MS (ESI, pos. ion) m/z: 271.1 (M+1); exact mass of $C_{12}H_{15}ClN_2O_3$: 270.08.

Step 2: (1-(2-chloro-4-nitrophenyl)piperidin-3-yl)methyl 4-methylbenzenesulfonate The title compound was prepared by the procedure described in step 2 of Example 28 using (1-(2-chloro-4-nitrophenyl)piperidin-3-yl)methanol (5.80 g, 21.42 mmol), TEA (50 mL) and tosyl chloride (6.13 g, 32.14 mmol) to give the title compound as a yellow solid (7.79 g, 85.6%).

Step 3: 1-(2-chloro-4-nitrophenyl)-3-((3-fluorophenoxy)methyl)piperidine

The title compound was prepared by the procedure described in step 3 of Example 27 using 3-fluorophenol (2.44 g, 21.75 mmol), 60% NaH (1.74 g, 72.49 mmol) and (1-(2-chloro-4-nitrophenyl)piperidin-3-yl)methyl 4-methylbenzenesulfonate (7.70 g, 18.12 mmol) in 20 mL of DMF to give the title compound as a yellow solid (5.96 g, 90.1%). The compound was characterized by the following spectroscopic data:

MS (ESI, pos. ion) m/z: 365.2 (M+1); exact mass of $C_{18}H_{18}ClFN_2O_3$: 364.10.

Step 4: 3-chloro-4-(3-((3-fluorophenoxy)methyl)piperidin-1-yl)aniline

A solution of 1-(2-chloro-4-nitrophenyl)-3-((3-fluorophenoxy)methyl)piperidine (3.50 g, 9.59 mmol) in MeOH (50 mL) was added in activated iron power (5.36 g, 95.9 mmol). The title compound was prepared by the procedure described in step 4 of Example 1 to give yellow oil (2.25 g, 70.1%). The compound was characterized by the following spectroscopic data:

MS (ESI, pos. ion) m/z: 335.2 (M+1); exact mass of $C_{18}H_{20}ClFN_2O$: 334.12.

Step 5: N-(3-chloro-4-(3-((3-fluorophenoxy)methyl)piperidin-1-yl)phenyl)-3-oxobutanamide The title compound was prepared by the procedure described in step 5 of Example 1 using 3-chloro-4-(3-((3-fluorophenoxy)methyl)piperidin-1-yl)aniline (2.85 g, 8.51 mmol) and 4-methyleneoxetan-2-one (2.15 g, 25.54 mmol) to give the title compound as a yellow solid (2.33 g, 65.5%). The compound was characterized by the following spectroscopic data:

MS (ESI, pos. ion) m/z: 419.3 (M+1); exact mass of $C_{22}H_{24}ClFN_2O_3$: 418.15.

Step 6: (Z)-3-amino-N-(3-chloro-4-(3-((3-fluorophenoxy)methyl)piperidin-1-yl)phenyl)but-2-enamide The title compound was prepared by the procedure described in step 6 of Example 1 using N-(3-chloro-4-((3-fluorophenoxy)methyl)piperidin-1-yl)phenyl)-3-oxobutanamide (1.00 g, 2.48 mmol), MeOH (10 mL) and ammonium hydroxide (10 mL) to give the crude product which was used directly for the next step without further purification.

Step 7: 3-(3-chloro-4-(3-((3-fluorophenoxy)methyl)piperidin-1-yl)phenyl)-2,6-dimethylpyrimidin-4(3H)-one The title compound was prepared by the procedure described in step 7 of Example 1 using (Z)-3-amino-N-(3-chloro-4-(3-((3-fluorophenoxy)methyl)piperidin-1-yl)phenyl)but-2-enamide (1.00 g, 2.48 mmol) and triethyl orthoacetate (10 mL) to give the title compound as white powder (300 mg, 27.3%). The compound was characterized by the following spectroscopic data:

MS (ESI, pos. ion) m/z: 442.2 (M+1); exact mass of $C_{24}H_{25}ClFN_3O_2$: 441.16; and $^1H$ NMR (400 MHz, CDCl$_3$): δ 7.15-7.22 (m, 3H), 7.03 (m, 1H), 6.60 (m, 3H), 6.28 (s, 1H), 3.91 (m, 2H), 3.26-3.53 (m, 2H), 2.62-2.85 (m, 2H), 2.34 (m, 1H), 2.29 (s, 3H), 2.18 (s, 3H), 1.37 (m, 2H), 1.24 (m, 2H).

Example 69: Cell Experiment Method

1. Cell seeding

HFL1 cells in exponential growth phase were cultured, cells were digested and collected using traditional subculturing when reaching 85-95% fusion and the cells were counted to adjust, the cell density to $5\times10^4$ cells per milliliter, then the cells were seed into 96-well plates, 100 μl/well and incubated in a 5% $CO_2$ incubator at 37° C.

2. Dosing of the Cells

The supernatant of the 96-well plates was removed at 24 hours after the cells adhering to the wall and solutions containing the above compounds with different concentration were added to the wells, with 100 μl/well (the concentration of each compounds are in the range of 0.003-8 mmol/L) each concentration in 3 replicates, and the cells were cultured 48 hours after dosing.

3. Testing the Optical Density

10 μl of CCK-8 solution was added to each well 48 hours after dosing, and incubated for 2 hours. The optical density (A) of each well was determined using a microplate reader at 450 nm wavelength. The cell proliferation inhibition ratio of each compound were calculated based on A using the formula of: cell proliferation inhibition ratio(inhibition ratio, IR)=(1−value of experimental group ($A_i$)/value of control group ($A_o$))×100%, in which IC$_{50}$ of each compound at 48 hours was calculated by data processing software, wherein the control group was the blank group.

| Example | IC50 (mM) | The ratio with PFD (multiple) |
|---|---|---|
| 6 | 0.070 | 121 |
| 9 | 0.080 | 179 |
| 10 | 0.078 | 111 |
| 12 | 0.080 | 112 |
| 13 | 0.070 | 118 |
| 14 | 0.060 | 139 |
| 15 | 0.065 | 151 |
| 16 | 0.070 | 139 |
| 17 | 0.070 | 137 |
| 19 | 0.070 | 137 |
| 22 | 0.090 | 101 |
| 25 | 0.100 | 107 |
| 26 | 0.060 | 137 |
| 29 | 0.090 | 107 |
| 30 | 0.060 | 136 |
| 32 | 0.100 | 107 |
| 33 | 0.070 | 149 |
| 34 | 0.090 | 154 |
| 35 | 0.120 | 119 |
| 37 | 0.080 | 181 |
| 44 | 0.070 | 139 |
| 51 | 0.037 | 618 |
| 53 | 0.038 | 602 |
| 54 | 0.040 | 209 |
| 56 | 0.040 | 209 |
| 57 | 0.060 | 168 |
| 58 | 0.064 | 357 |

The ratio relative to PFD (fold)menas the IC$_{50}$ ratio of Pirfenidone to the compound, and the bigger the fold, the better the vitro inhibitory activity of the compound.

CONCLUSION

Common characteristic of organic fibrosis is the overdeposition of extracellular matrix (ECM) and structural remodeling of organs and tissues, and some cytokines (CK) participate in the process. It was found after screening by in vitro cell test that compounds disclosed herein are more active than Pirfenidone, and some the compounds disclosed herein more active than Pirfenidone by about 200 folds. And compounds disclosed herein can avoid the phototoxic reaction produced by Pirfenidone, which are effective in anti-fibrosis.

It is noted that terms such as "first" and "second" are used herein for purposes of description and are not intended to indicate or imply relative importance or implicitly specified the number of the technical features indicated. Thus the features defined with "first", "second" may be explicitly or implicitly include one or more feathers thereof. Further, in the description of the present disclosure, "more" refers to two or more than two unless expressly described otherwise.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I), or a stereoisomer, a geometric isomer, a tautomer, an N-oxide, a hydrate, a solvate, or a pharmaceutically acceptable salt thereof,

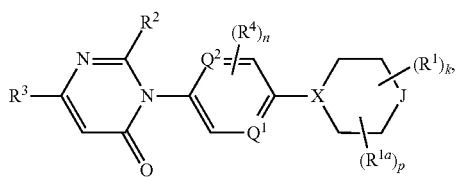

(I)

wherein, each of $Q^1$ and $Q^2$ is independently CH;
X is N;
J is —CH$_2$—;
each R$^1$ is independently —Y—R$^5$, wherein each Y is independently —O—, —(CH$_2$)$_m$—O—, —(CH$_2$)$_m$—N(R$^6$)—, —N(R$^6$)—, or —(CH$_2$)$_m$—;

each R$^{1a}$ is independently H, F, Cl, Br, I, cyano, hydroxy, amino, carboxy, alkyl, haloalkyl, alkoxy, alkylamino, alkylthio, alkenyl, alkynyl, nitro, mercapto, hydroxyalkoxy, hydroxyalkyl, aminoalkoxy, alkyl-O—C(=O)—, aryl, arylalkyl, heteroaryl, heteroarylalkyl, heterocyclyl, heterocyclylalkyl, cycloalkyl, aryloxy, heteroaryloxy, haloalkoxy or cycloalkylalkyl;

each of R$^2$ and R$^3$ is independently H, F, Cl, Br, I, cyano, hydroxy, carboxy, alkyl, haloalkyl, alkoxy, hydroxyalkoxy, hydroxyalkyl, aminoalkoxy, haloalkoxy, aryl, arylalkyl, heteroaryl, heteroarylalkyl, heterocyclyl, heterocyclylalkyl, cycloalkyl or cycloalkylalkyl;

each R$^4$ is independently H, hydroxy, carboxy, amino, F, Cl, Br, I, cyano, nitro, mercapto, alkyl, haloalkyl, alkoxy, alkylamino, alkylthio, aryl, arylalkyl, heteroaryl, heteroarylalkyl, heterocyclyl, heterocyclylalkyl, cycloalkyl or cycloalkylalkyl;

each R$^5$ is independently bridged heterobicyclyl, bridged bicyclyl, fused bicyclyl, fused heterobicyclyl, aryl, arylalkyl, heteroaryl, heteroarylalkyl, heterocyclyl, heterocyclylalkyl, cycloalkyl or cycloalkylalkyl, wherein the aryl is substituted with one or more substituents independently selected from F, Cl, Br, I, alkyl —O—C(=O)—, alkyl, alkenyl, alkynyl, alkoxy, haloalkyl, cyano, nitro, amino, alkylamino, mercapto, alkylthio, aryl, aryloxy, heteroaryl, heteroaryloxy and haloalkoxy;

each R$^6$ is independently H, hydroxy, amino, alkyl, haloalkyl, alkoxy, alkylamino, alkylthio, aryl, arylalkyl or heteroaryl;

each t is independently 0, 1 or 2;
each m is independently 1, 2, 3 or 4;
each of n and p is independently 0, 1, 2, 3 or 4; and
k is 1, 2, 3 or 4;
wherein each of —(CH$_2$)$_m$—O—, —(CH$_2$)$_m$—N(R$^6$)—, —N(R$^6$)—, —(CH$_2$)$_m$—, alkyl, alkenyl, alkynyl, haloalkyl, alkoxy, hydroxyalkoxy, hydroxyalkyl, aminoalkoxy, alkyl-O—C(=O)—, aryl, aryloxy, heteroaryloxy, haloalkoxy, arylalkyl, heteroaryl, heteroarylalkyl, heterocyclyl, heterocyclylalkyl, cycloalkyl, cycloalkylalkyl, bridged heterobicyclyl, bridged bicyclyl, fused bicyclyl, fused heterobicyclyl, alkylamino and alkylthio is independently and optionally substituted with one or more substituents independently selected from oxo (=O), F, Cl, Br, I, alkyl —O—C(=O)—, alkyl, alkenyl, alkynyl, alkoxy, haloalkyl, cyano, nitro, amino, alkylamino, mercapto, alkylthio, aryl, aryloxy, heteroaryl, heteroaryloxy and haloalkoxy.

2. The compound according to claim 1, wherein
each R$^5$ is independently C$_{5-12}$ bridged heterobicyclyl, C$_{5-12}$ bridged bicyclyl, C$_{5-12}$ fused bicyclyl, C$_{5-12}$ fused heterobicyclyl, C$_{6-10}$ aryl, C$_{6-10}$ aryl-C$_{1-4}$-alkyl, C$_{1-9}$ heteroaryl, C$_{1-9}$ heteroaryl-C$_{1-4}$-alkyl, C$_{2-10}$ heterocyclyl, C$_{2-10}$ heterocyclyl-C$_{1-4}$-alkyl, C$_{3-10}$ cycloalkyl or C$_{3-10}$ cycloalkyl-C$_{1-4}$-alkyl, wherein each the aryl is substituted with one or more substituents independently selected from F, Cl, Br, I, C$_{1-4}$ alkyl-O—C(=O)—, C$_{1-4}$ alkyl, C$_{2-4}$ alkenyl, C$_{2-4}$ alkynyl, C$_{1-4}$ alkoxy, C$_{1-4}$ haloalkyl, cyano, nitro, amino, C$_{1-4}$ alkylamino, mercapto, C$_{1-4}$ alkylthio, C$_{6-10}$ aryl, C$_{6-10}$ aryloxy, C$_{1-9}$ heteroaryl, C$_{1-9}$ heteroaryloxy and C$_{1-4}$ haloalkoxy; and
each R$^6$ is independently H, hydroxy, amino, C$_{1-4}$ alkyl, C$_{1-4}$ haloalkyl, C$_{1-4}$ alkoxy, C$_{1-4}$ alkylamino, C$_{1-4}$ alkylthio, C$_{6-10}$ aryl, C$_{6-10}$ aryl-C$_{1-4}$-alkyl or C$_{1-9}$ heteroaryl;

wherein each of $C_{1-4}$ alkyl, $C_{1-4}$ haloalkyl, $C_{1-4}$ alkoxy, $C_{5-12}$ bridged heterobicyclyl, $C_{5-12}$ bridged bicyclyl, $C_{5-12}$ fused bicyclyl, $C_{5-12}$ fused heterobicyclyl, $C_{6-10}$ aryl, $C_{6-10}$ aryl-$C_{1-4}$-alkyl, $C_{1-9}$ heteroaryl, $C_{1-9}$ heteroaryl-$C_{1-4}$-alkyl, $C_{2-10}$ heterocyclyl, $C_{2-10}$ heterocyclyl-$C_{1-4}$-alkyl, $C_{3-10}$ cycloalkyl, $C_{3-10}$ cycloalkyl-$C_{1-4}$-alkyl, $C_{1-4}$ alkylamino and $C_{1-4}$ alkylthio is independently and optionally substituted with one or more substituents independently selected from oxo (=O), F, Cl, Br, I, $C_{1-4}$ alkyl-O—C(=O)—, $C_{1-4}$ alkyl, $C_{2-4}$ alkenyl, $C_{2-4}$ alkynyl, $C_{1-4}$ alkoxy, $C_{1-4}$ haloalkyl, cyano, nitro, amino, $C_{1-4}$ alkylamino, mercapto, $C_{1-4}$ alkylthio, $C_{6-10}$ aryl, $C_{6-10}$ aryloxy, $C_{1-9}$ heteroaryl, $C_{1-9}$ heteroaryloxy and $C_{1-4}$ haloalkoxy.

3. The compound according to claim 1, wherein:

each $R^{1a}$ is independently H, F, Cl, Br, I, cyano, hydroxy, amino, carboxy, $C_{1-4}$ alkyl, $C_{1-4}$ haloalkyl, $C_{1-4}$ alkoxy, $C_{1-4}$ alkylamino, $C_{1-4}$ alkylthio, $C_{2-4}$ alkenyl, $C_{2-4}$ alkynyl, nitro, mercapto, $C_{1-4}$ hydroxyalkoxy, $C_{1-4}$ hydroxyalkyl, $C_{1-4}$ aminoalkyl, $C_{1-4}$ alkyl-O—C(=O)—, $C_{6-10}$ aryl, $C_{6-10}$ aryl-$C_{1-4}$-alkyl, $C_{1-9}$ heteroaryl, $C_{1-9}$ heteroaryl-$C_{1-4}$-alkyl, $C_{2-10}$ heterocyclyl, $C_{2-10}$ heterocyclyl-$C_{1-4}$-alkyl, $C_{3-10}$ cycloalkyl, $C_{6-10}$ aryloxy, $C_{1-9}$ heteroaryloxy, $C_{1-4}$ haloalkoxy or $C_{3-10}$ cycloalkyl-$C_{1-4}$-alkyl;

each of $R^2$ and $R^3$ is independently H, F, Cl, Br, I, cyano, carboxy, hydroxy, $C_{1-6}$ alkyl, $C_{1-6}$ haloalkyl, $C_{1-6}$ alkoxy, $C_{1-6}$ hydroxyalkoxy, $C_{1-6}$ hydroxyalkyl, $C_{1-6}$ aminoalkoxy, $C_{1-6}$ haloalkoxy, $C_{6-10}$ aryl, $C_{6-10}$ aryl-$C_{1-6}$-alkyl, $C_{1-9}$ heteroaryl, $C_{1-9}$ heteroaryl-$C_{1-6}$-alkyl, $C_{2-10}$ heterocyclyl, $C_{2-10}$ heterocyclyl-$C_{1-6}$-alkyl, $C_{3-10}$ cycloalkyl or $C_{3-10}$ cycloalkyl-$C_{1-6}$-alkyl; and each $R^4$ is independently H, hydroxy, carboxyl, amino, F, Cl, Br, I, cyano, nitro, mercapto, $C_{1-4}$ alkyl, $C_{1-6}$ haloalkyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl, $C_{1-9}$ heteroaryl, $C_{1-9}$ heteroaryl-$C_{1-6}$-alkyl, $C_{2-10}$ heterocyclyl, $C_{2-10}$ heterocyclyl-$C_{1-6}$-alkyl, $C_{3-10}$ cycloalkyl or $C_{3-10}$ cycloalkyl-$C_{1-6}$-alkyl.

4. The compound according to claim 1 having formula (II), or a stereoisomer, a geometric isomer, a tautomer, an N-oxide, a hydrate, a solvate, or a pharmaceutically acceptable salt or a prodrug thereof,

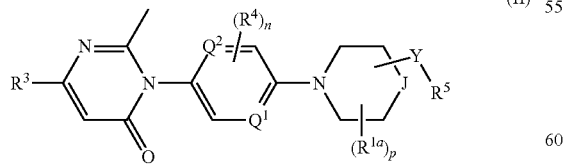

(II)

wherein, each of $Q^1$ and $Q^2$ is independently CH;
J is —$CH_2$—; and
Y is —O—, —$(CH_2)_m$—O—, —$(CH_2)_m$—N($R^6$)—, —N($R^6$)— or —$(CH_2)_m$—.

5. The compound according to claim 1, wherein,
each Y is independently —O—, —$(CH_2)_m$—O—, —$(CH_2)_m$—N($R^6$)—, —N($R^6$)— or —$(CH_2)_m$—;
each $R^5$ is independently

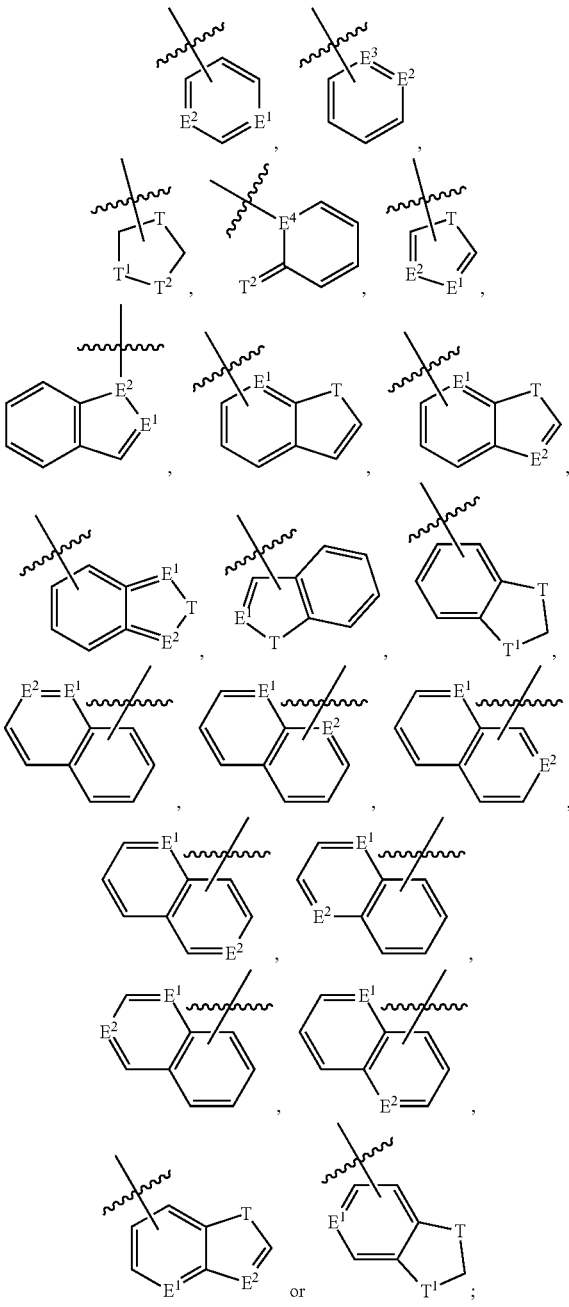

wherein, each $E^1$, $E^3$ and $E^4$ is independently N or $CR^7$;
$E^2$ is N;
each T, $T^1$ and $T^2$ is independently —$NR^8$—, —O—, —S— or —$CR^7R^{7a}$—;
each $R^7$ and $R^{7a}$ is independently H, F, Cl, Br, I, $C_{1-4}$ alkyl-O—C(=O)—, $C_{1-4}$ alkyl, $C_{2-4}$ alkenyl, $C_{2-4}$ alkynyl, $C_{1-4}$ alkoxy, $C_{1-4}$ haloalkyl, cyano, nitro, amino, $C_{1-4}$ alkylamino, mercapto, $C_{1-4}$ alkylthio, $C_{6-10}$ aryl, $C_{6-10}$ aryloxy, $C_{1-9}$ heteroaryl, $C_{1-9}$ heteroaryloxy or $C_{1-4}$ haloalkoxy;

wherein, each R⁵ is independently and optionally substituted with one or more substituents independently selected from oxo (=O), F, Cl, Br, I, $C_{1-4}$ alkyl —O—C(=O)—, $C_{1-4}$ alkyl, $C_{2-4}$ alkenyl, $C_{2-4}$ alkynyl, $C_{1-4}$ alkoxy, $C_{1-4}$ haloalkyl, cyano, nitro, amino, $C_{1-4}$ alkylamino, mercapto, $C_{1-4}$ alkylthio, $C_{6-10}$ aryl, $C_{6-10}$ aryloxy, $C_{1-9}$ heteroaryl, $C_{1-9}$ heteroaryloxy and $C_{1-4}$ haloalkoxy;

each R⁶ is independently H, hydroxy, amino, $C_{1-4}$ alkyl, $C_{1-4}$ haloalkyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl or $C_{1-9}$ heteroaryl; and each R⁸ is independently H, $C_{1-4}$ alkyl-O—C(=O)—, $C_{1-4}$ alkyl, $C_{2-4}$ alkenyl, $C_{2-4}$ alkynyl, $C_{1-4}$ alkoxy, $C_{1-4}$ haloalkyl, amino, $C_{1-4}$ alkylamino, $C_{1-4}$ alkylthio, $C_{6-10}$ aryl or $C_{1-9}$ heteroaryl.

6. The compound according to claim 1, wherein,
each R⁵ is independently

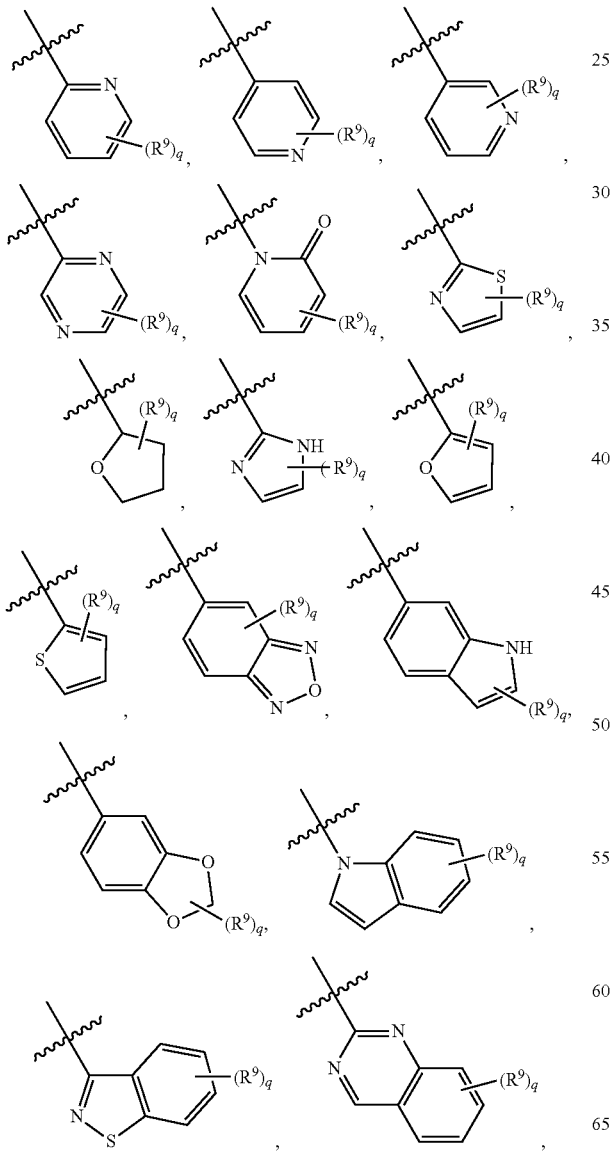

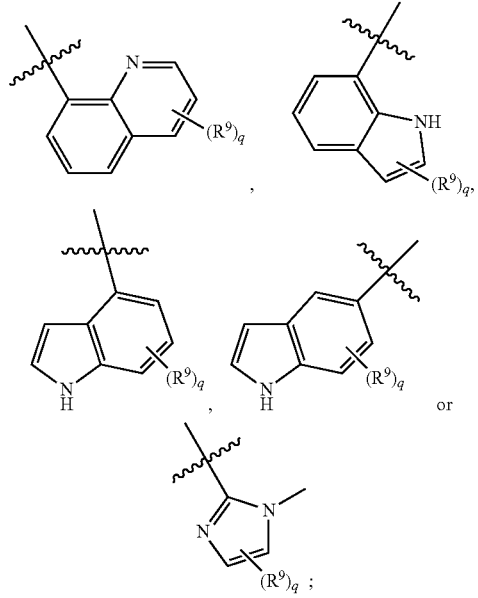

wherein, each R⁹ is independently H, oxo (=O), F, Cl, Br, I, $C_{1-4}$ alkyl-O—C(=O)—, $C_{1-4}$ alkyl, $C_{2-4}$ alkenyl, $C_{2-4}$ alkynyl, $C_{1-4}$ alkoxy, $C_{1-4}$ haloalkyl, cyano, nitro, amino, $C_{1-4}$ alkylamino, mercapto, $C_{1-4}$ alkylthio, $C_{6-10}$ aryl, $C_{6-10}$ aryloxy, $C_{1-9}$ heteroaryl, $C_{1-9}$ heteroaryloxy or $C_{1-4}$ haloalkyloxy; and each q is independently 0, 1, 2, 3, 4, 5, 6 or 7.

7. The compound according to claim 6, wherein,
each R⁹ is independently H, oxo (=O), F, Cl, Br, I, methyl-O—C(=O)—, ethyl-O—C(=O)—, propyl-O—C(=O)—, butyl-O—C(=O)—, tert-butyl —O—C(=O)—, isopropyl-O—C(=O)—, methyl, ethyl, propyl, butyl, tert-butyl, isopropyl, ethenyl, 3-propenyl, propenyl, $C_{2-4}$ alkynyl, methoxy, ethoxy, propoxy, butoxy, trifluoromethyl, chloromethyl, trifluoroethyl, 1-fluoroethyl, cyano, nitro, amino, methylamino, dimethylamino, ethylamino, diethylamino, mercapto, methylthio, ethylthio, propylthio, $C_{6-10}$ aryl, phenoxy, $C_{1-9}$ heteroaryl, $C_{1-9}$ heteroaryloxy, trifluoroethoxy or trifluoromethoxy.

8. The compound according to claim 1, wherein,
each $R^{1a}$ is independently H, F, Cl, Br, I, cyano, hydroxy, amino, carboxyl, methyl, ethyl, propyl, butyl, tert-butyl, isopropyl, trifluoromethyl, trifluoroethyl, 1-fluoromethyl, 1-chloroethyl, methoxy, propoxy, ethoxy, methylamino, ethylamino, dimethylamino, diethylamino, methylthio, ethylthio, $C_{2-4}$ alkenyl, $C_{2-4}$ alkynyl, nitro, mercapto, $C_{1-4}$hydroxyalkoxy, $C_{1-4}$ hydroxyalkyl, $C_{1-4}$aminoalkoxy, $C_{1-4}$ alkyl-O—C(=O)— or phenyl;

each of R² and R³ is independently H, F, Cl, Br, I, cyano, carboxyl, hydroxy, methyl, ethyl, propyl, butyl, tert-butyl, trifluoromethyl, chloromethyl, trifluoroethyl, 1-chloroethyl, methoxy, ethoxy, propoxy, $C_{1-4}$hydroxyalkoxy, $C_{1-4}$ hydroxyalkyl, $C_{1-4}$aminoalkoxy, trifluoromethoxy, 1-chloroethoxy, phenyl or phenyl-$C_{1-4}$-alkyl; and each R⁴ is independently H, F, Cl, Br, I, cyano, carboxyl, hydroxy, methyl, ethyl, propyl, butyl, tert-butyl, trifluoromethyl, chloromethyl, trifluoroethyl, 1-chloroethyl, methoxy, ethoxy, propoxy, $C_{1-4}$ hydroxyalkoxy, $C_{1-4}$ hydroxyalkyl, $C_{1-4}$ aminoalkoxy, trifluoromethoxy, 1-chloroethoxy, phenyl or phenyl-$C_{1-4}$-alkyl.
9. A Compound having one of the following structures:
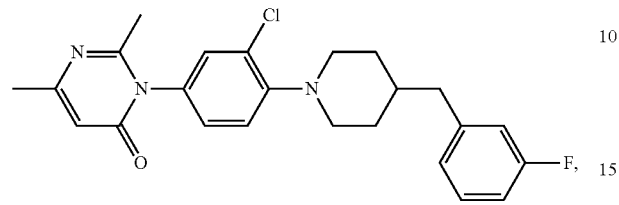
01
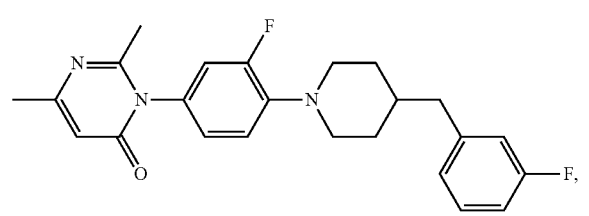
02
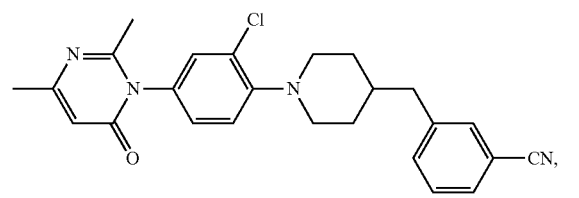
03
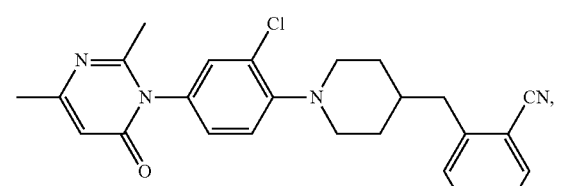
04
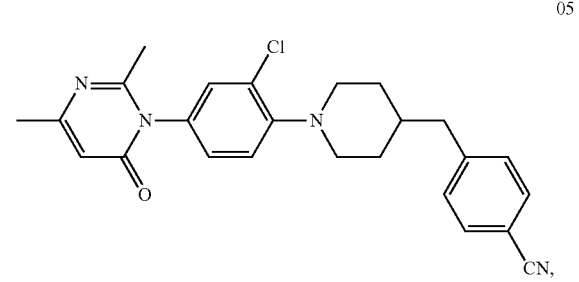
05
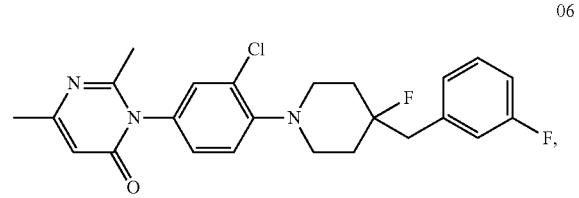
06
-continued
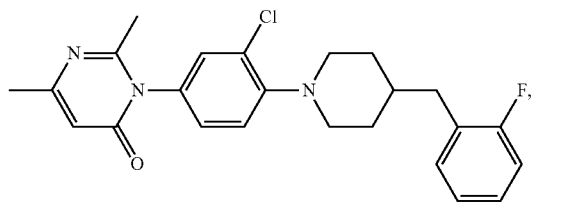
07
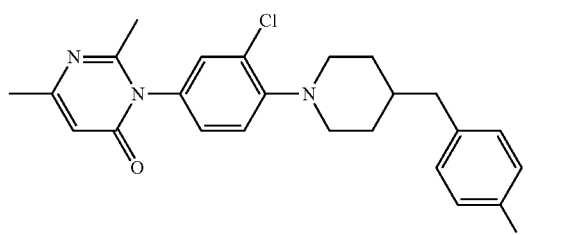
08
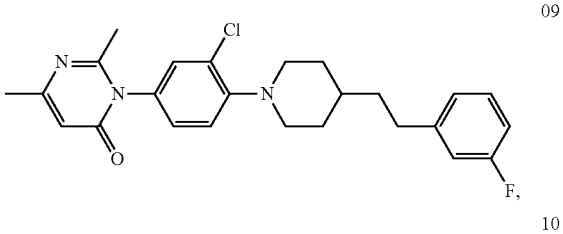
09
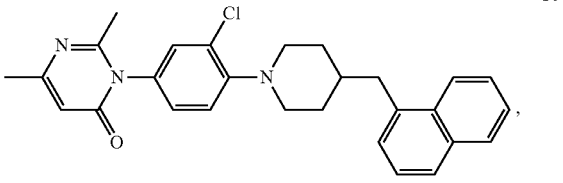
10
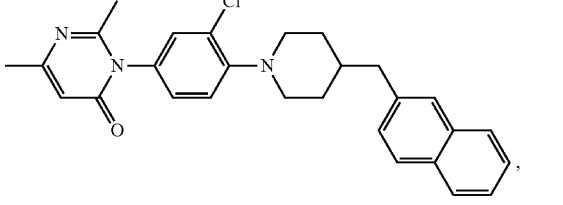
11
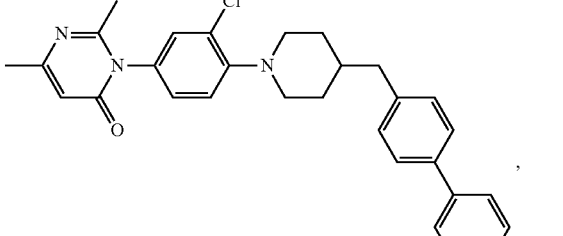
12
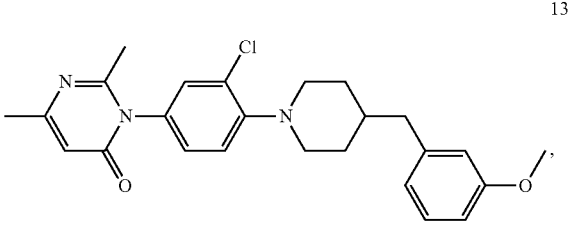
13

14
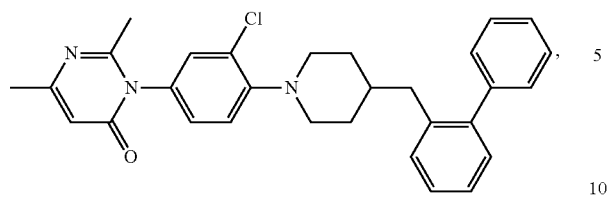
15
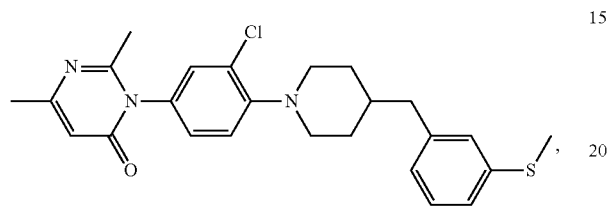
16
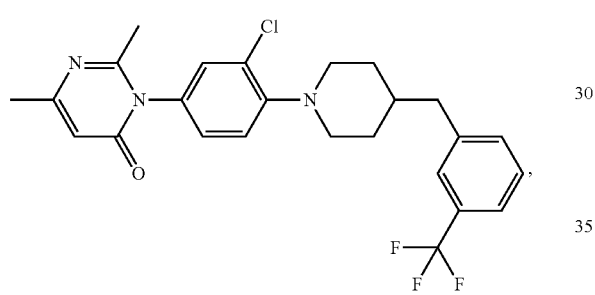
17
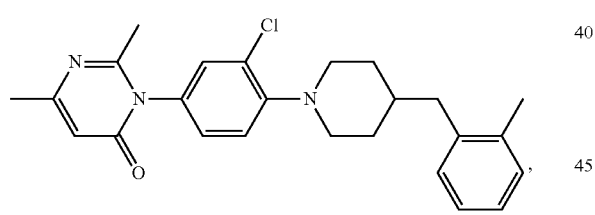
18
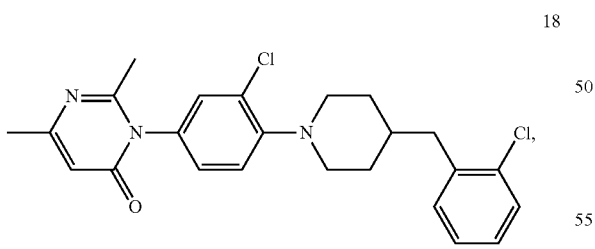
19
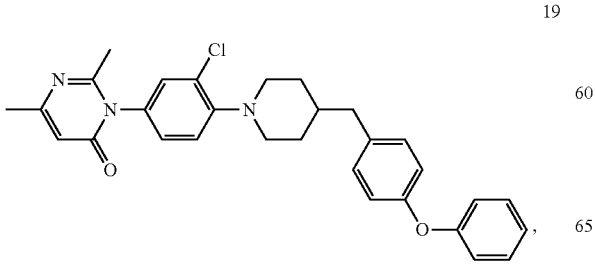
20
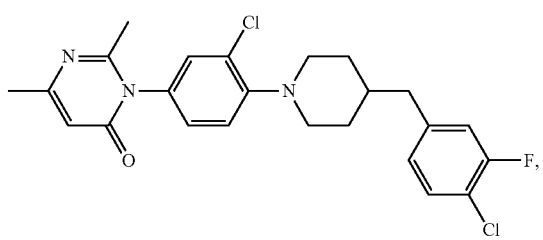
21
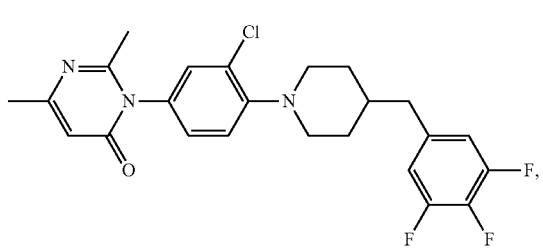
22
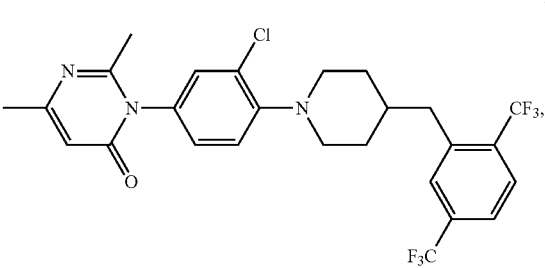
23
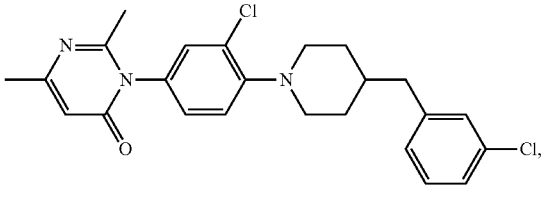
24
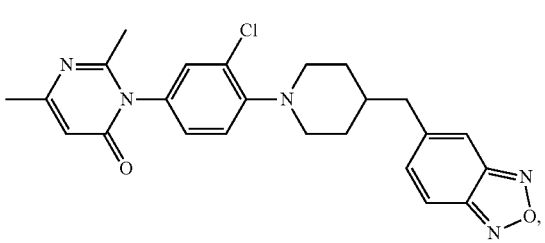
25
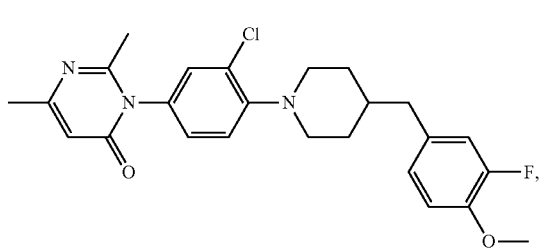

26
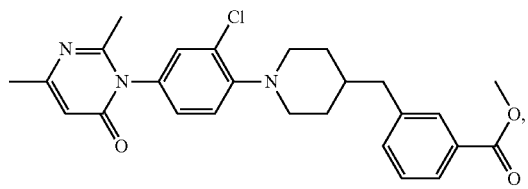
27
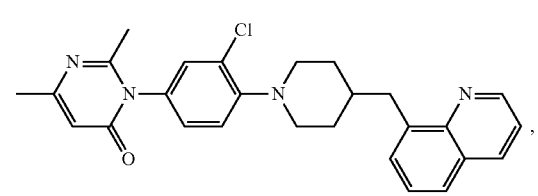
28
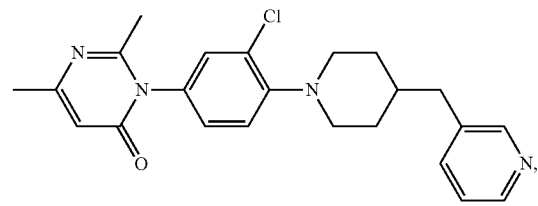
29
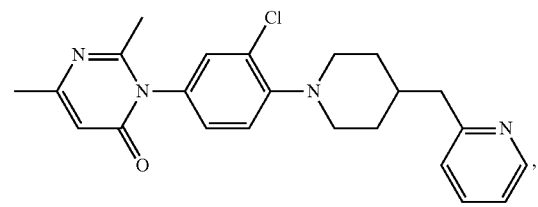
30
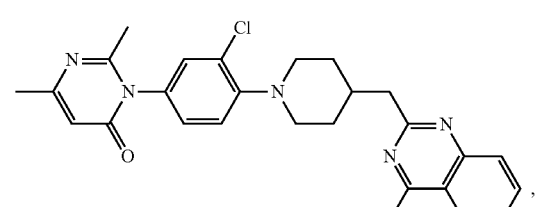
31
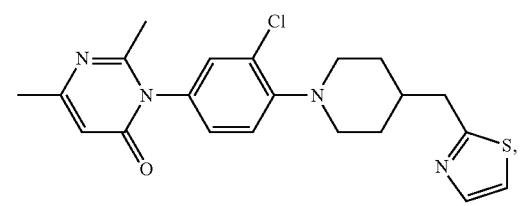
32
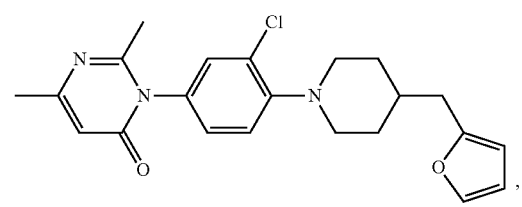
33
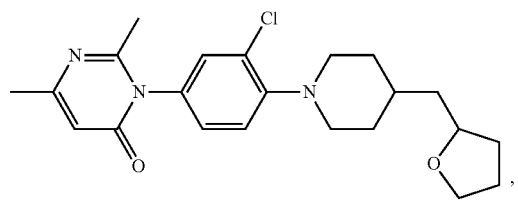
34
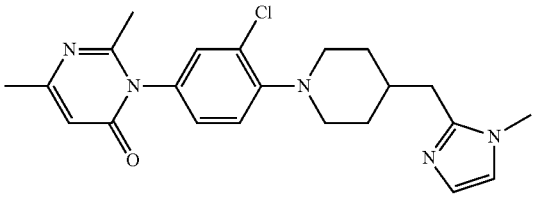
35
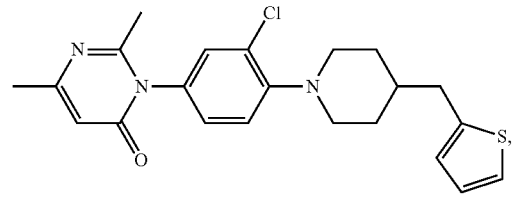
36
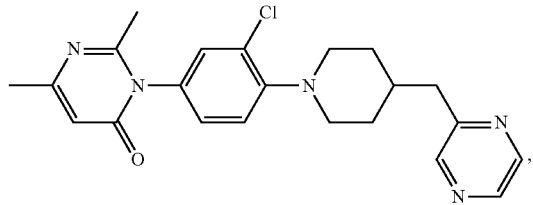
37
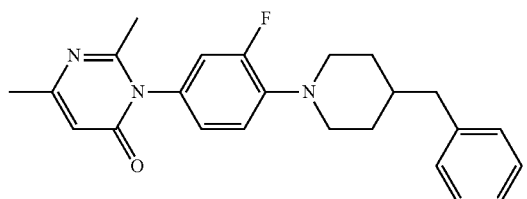
38
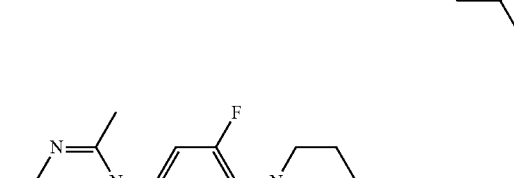
39
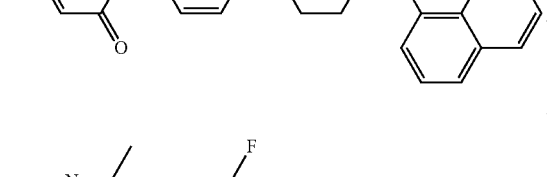

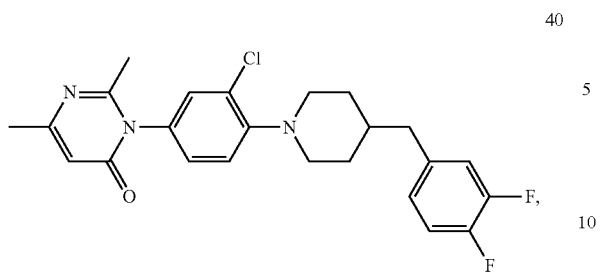
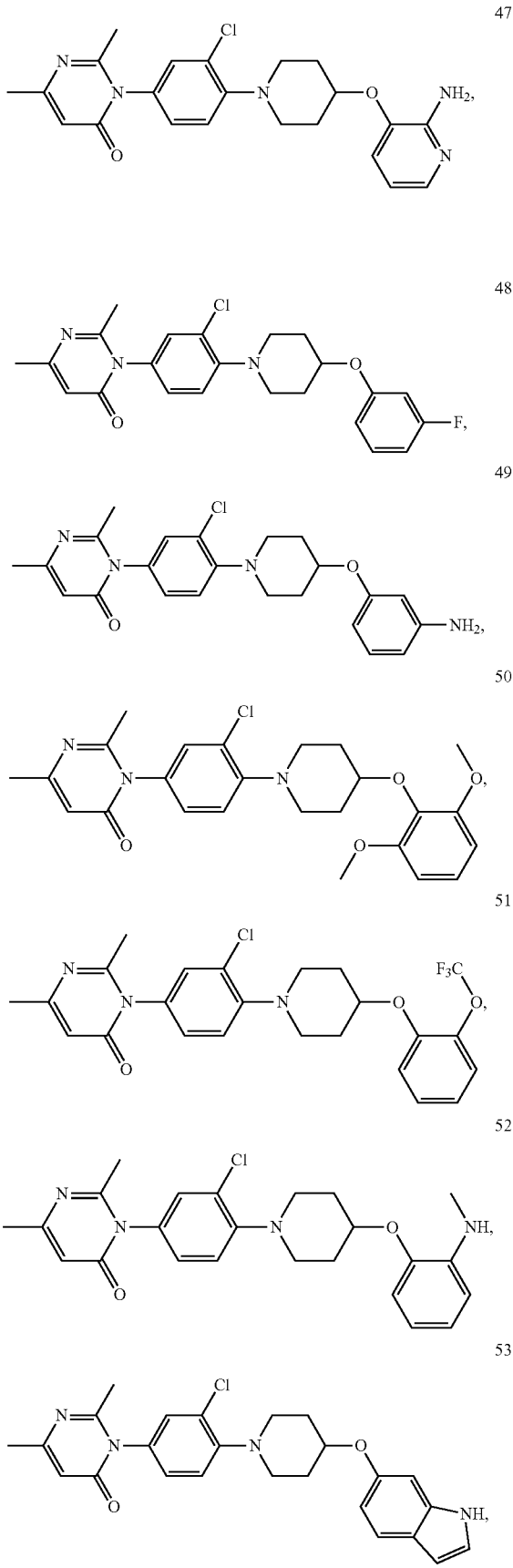

54
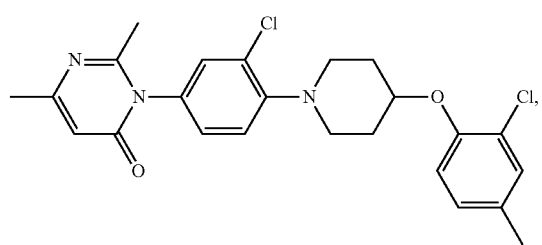
55
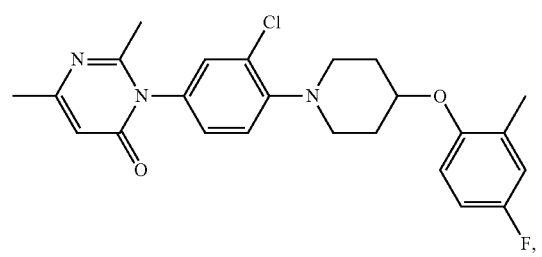
56
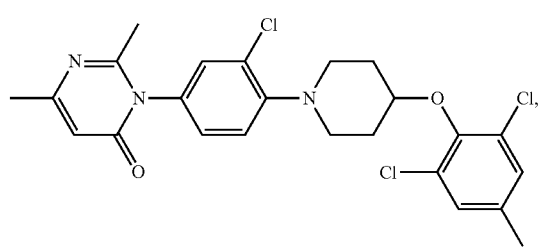
57
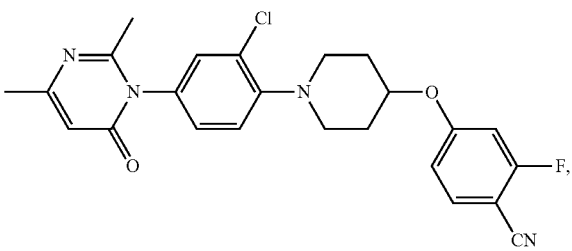
58
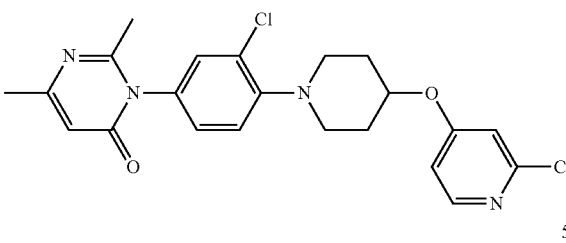
59
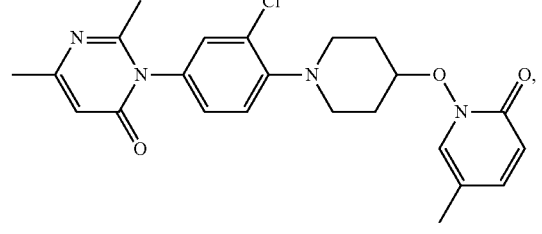
60
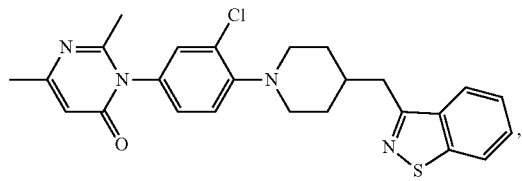
61
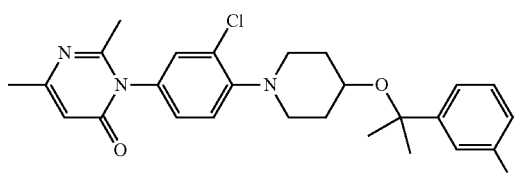
62
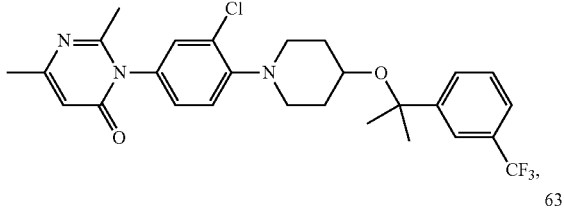
63
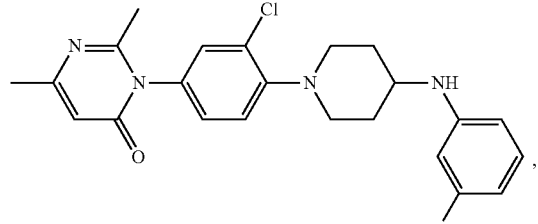
64
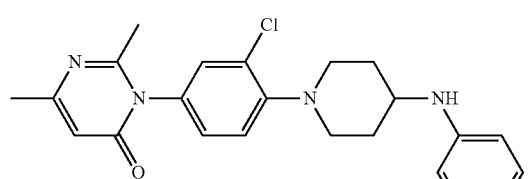
65
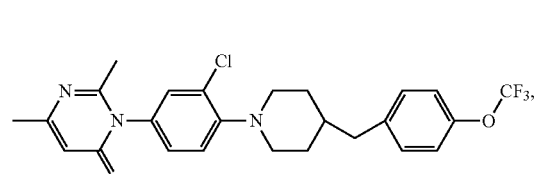
66
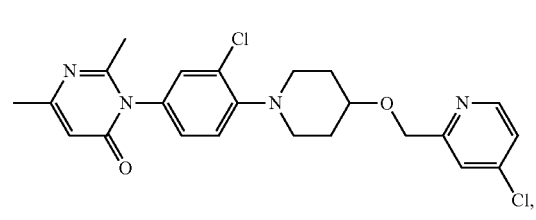

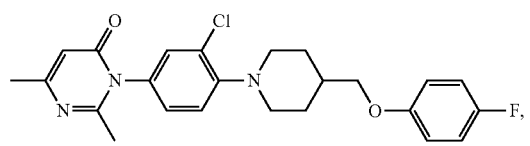
67
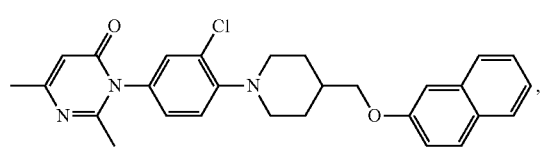
68
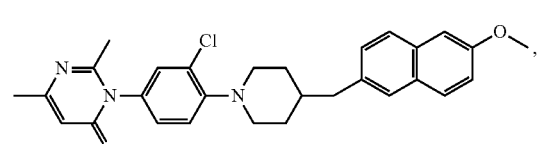
69
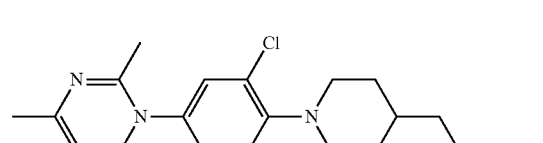
70
71
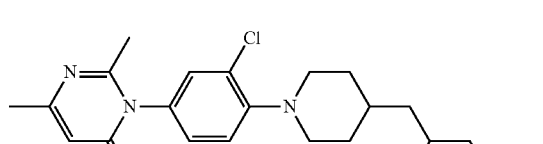
72
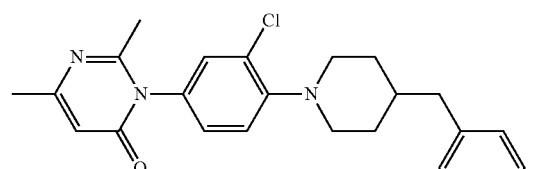
73
74
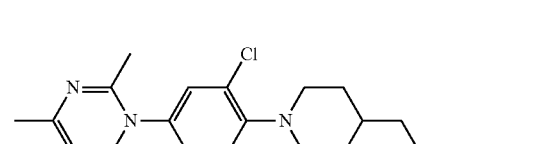
75
76
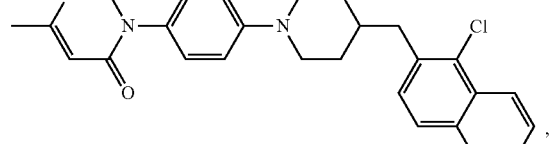
77
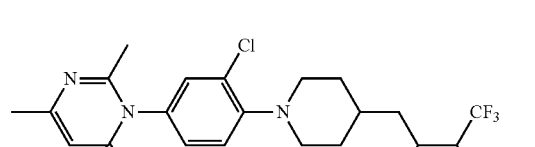
78

-continued or a stereoisomer, a geometric isomer, a tautomer, an N-oxide, a solvate, a hydrate, a ester, or a pharmaceutically acceptable salt thereof.

10. A pharmaceutical composition comprising the compound according to claim 1, and a pharmaceutically acceptable carrier, excipient, diluent, adjuvant, vehicle or a combination thereof.

11. A method of, managing, treating or lessening the severity of tissue or organ fibrosis in a patient comprising administering to the patient with the compound according to claim 1.

12. The method according to claim 11, wherein the tissue or organ fibrosis is renal interstitial fibrosis, glomerulosclerosis, liver fibrosis, pulmonary fibrosis, IPF, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, or vascular fibrosis.

13. A method of, managing, treating or lessening the severity of tissue or organ fibrosis in a patient comprising administering to the patient with the pharmaceutical composition according to claim 10.

14. The method according to claim 13, wherein the tissue or organ fibrosis is renal interstitial fibrosis, glomerulosclerosis, liver fibrosis, pulmonary fibrosis, IPF, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, or vascular fibrosis.

15. The compound according to claim 1, wherein,
each Y is independently —O—, —(CH$_2$)$_m$—O—, —(CH$_2$)$_m$—N(R$^6$)—, —N(R$^6$)— or —(CH$_2$)$_m$—;
each R$^5$ is independently

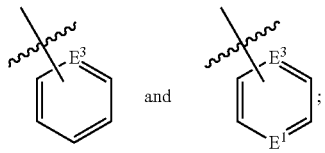

wherein, each E$^1$ and E$^3$ is independently N or CR$^7$;
R$^7$ is H, F, Cl, Br, I, C$_{1-4}$ alkyl-O—C(=O)—, C$_{1-4}$ alkyl, C$_{2-4}$ alkenyl, C$_{2-4}$ alkynyl, C$_{1-4}$ alkoxy, C$_{1-4}$ haloalkyl, cyano, nitro, amino, C$_{1-4}$ alkylamino, mercapto, C$_{1-4}$ alkylthio, C$_{6-10}$ aryl, C$_{6-10}$ aryloxy, C$_{1-9}$ heteroaryl, C$_{1-9}$ heteroaryloxy or C$_{1-4}$ haloalkoxy;

wherein, each R$^5$ is independently substituted with one or more substituents independently selected from F, Cl, Br, I, C$_{1-4}$ alkyl —O—C(=O)—, C$_{1-4}$ alkyl, C$_{2-4}$ alkenyl, C$_{2-4}$ alkynyl, C$_{1-4}$ alkoxy, C$_{1-4}$ haloalkyl, cyano, nitro, amino, C$_{1-4}$ alkylamino, mercapto, C$_{1-4}$ alkylthio, C$_{6-10}$ aryl, C$_{6-10}$ aryloxy, C$_{1-9}$ heteroaryl, C$_{1-9}$ heteroaryloxy and C$_{1-4}$ haloalkoxy;

each R$^6$ is independently H, hydroxy, amino, C$_{1-4}$ alkyl, C$_{1-4}$ haloalkyl, C$_{1-4}$ alkoxy, C$_{1-4}$ alkylamino, C$_{1-4}$ alkylthio, C$_{6-10}$ aryl, C$_{6-10}$ aryl-C$_{1-4}$-alkyl or C$_{1-9}$ heteroaryl; and each m is independently 1, 2, 3 or 4.

16. The compound according to claim 1, wherein,
each R$^5$ is independently

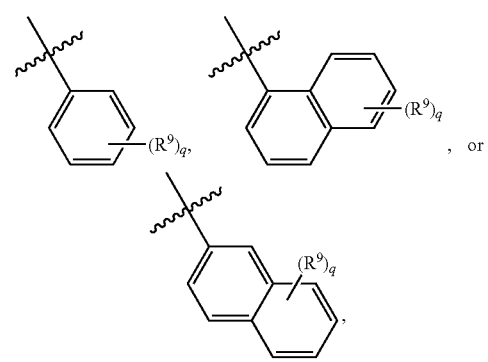

wherein, each R$^9$ is independently F, Cl, Br, I, C$_{1-4}$ alkyl-O—C(=O)—, C$_{1-4}$ alkyl, C$_{2-4}$ alkenyl, C$_{2-4}$ alkynyl, C$_{1-4}$ alkoxy, C$_{1-4}$ haloalkyl, cyano, nitro, amino, C$_{1-4}$ alkylamino, mercapto, C$_{1-4}$ alkylthio, C$_{6-10}$ aryl, C$_{6-10}$ aryloxy, C$_{1-9}$ heteroaryl, C$_{1-9}$ heteroaryloxy or C$_{1-4}$haloalkyloxy; and each q is independently 1, 2, 3, 4, 5, 6 or 7.

* * * * *